US011628276B2

(12) United States Patent
Albany

(10) Patent No.: US 11,628,276 B2
(45) Date of Patent: Apr. 18, 2023

(54) CATHETER SECUREMENT, STABILIZATION, AND ANTIMICROBIAL DEVICE

(71) Applicant: VASONICS, INC., Corona, CA (US)

(72) Inventor: Ramy Albany, Corona, CA (US)

(73) Assignee: Vasonics, Inc., Corona, CA (US)

( * ) Notice: Subject to any disclaimer, the term of this patent is extended or adjusted under 35 U.S.C. 154(b) by 21 days.

(21) Appl. No.: 16/447,684

(22) Filed: Jun. 20, 2019

(65) Prior Publication Data

US 2019/0388652 A1    Dec. 26, 2019

Related U.S. Application Data

(60) Provisional application No. 62/778,230, filed on Dec. 11, 2018, provisional application No. 62/689,543, filed on Jun. 25, 2018.

(51) Int. Cl.
*A61M 25/02* (2006.01)

(52) U.S. Cl.
CPC ..... *A61M 25/02* (2013.01); *A61M 2025/0206* (2013.01); *A61M 2025/028* (2013.01); *A61M 2025/0246* (2013.01); *A61M 2025/0266* (2013.01)

(58) Field of Classification Search
CPC ............ A61M 2025/028; A61M 25/02; A61M 2209/088; A61M 2005/1586; A61M 5/158; A61M 2025/0246; A61M 2025/0266; A61M 2025/024; A61M 2025/0253

See application file for complete search history.

(56) References Cited

U.S. PATENT DOCUMENTS 3,900,026 A     8/1975   Wagner
3,901,226 A     8/1975   Scardenzan
(Continued)

FOREIGN PATENT DOCUMENTS

GB       2046095 A       11/1980
JP       2005-508664     4/2005
(Continued)

OTHER PUBLICATIONS

Search Report and Written Opinion in International Application No. PCT/US2019/038208 dated Oct. 18, 2019, in 26 pages.
(Continued)

*Primary Examiner* — Nathan R Price
*Assistant Examiner* — Mark A Igel
(74) *Attorney, Agent, or Firm* — Knobbe, Martens, Olson & Bear, LLP

(57) ABSTRACT

A catheter housing for securing a catheter device coupled to a catheter. The catheter housing can include a cover and a hub. The catheter housing can additionally include a lock in an interior portion of the cover that secures a portion of the catheter device coupled to the catheter. The catheter housing can additionally include a bridge configured to contact and/or secure a portion of the catheter device and align the catheter device so that the catheter remains inserted at a natural or proper insertion angle relative to a patient's vein. The catheter housing can include one or more wings extending outward from a cover of the housing that can help secure tubing coupled to the catheter device.

18 Claims, 60 Drawing Sheets

(56) References Cited

U.S. PATENT DOCUMENTS

| | | | |
|---|---|---|---|
| 4,224,937 A * | 9/1980 | Gordon | A61M 25/02 |
| | | | 128/DIG. 26 |
| 4,397,647 A * | 8/1983 | Gordon | A61M 25/02 |
| | | | 128/DIG. 26 |
| 4,517,971 A | 5/1985 | Sorbonne | |
| 4,666,434 A | 5/1987 | Kaufman | |
| 4,669,458 A | 6/1987 | Abraham et al. | |
| 4,679,553 A | 7/1987 | Proulx et al. | |
| 4,698,057 A | 10/1987 | Joishy | |
| 4,898,587 A | 2/1990 | Mera | |
| 5,112,313 A * | 5/1992 | Sallee | A61M 25/02 |
| | | | D24/130 |
| 5,304,145 A | 4/1994 | Blair | |
| 6,231,548 B1 | 5/2001 | Bassett | |
| 6,257,240 B1 | 7/2001 | Shesol | |
| 6,361,523 B1 | 3/2002 | Bierman | |
| 6,375,639 B1 | 4/2002 | Duplessie et al. | |
| 6,500,154 B1 | 12/2002 | Hakky et al. | |
| 6,572,240 B2 | 6/2003 | Reinert, Sr. | |
| 6,572,588 B1 | 6/2003 | Bierman et al. | |
| 6,827,707 B2 * | 12/2004 | Wright | A61M 25/02 |
| | | | 604/174 |
| 8,006,699 B2 | 8/2011 | Rozier et al. | |
| 8,123,681 B2 | 2/2012 | Schaeffer | |
| 8,721,606 B2 | 5/2014 | Simmons et al. | |
| 9,044,539 B2 | 6/2015 | Duncan | |
| 9,089,335 B2 | 7/2015 | Okamura | |
| 2002/0092529 A1 | 7/2002 | Lundgaard et al. | |
| 2003/0216686 A1 | 11/2003 | Lynch et al. | |
| 2004/0158209 A1 * | 8/2004 | Wright | A61M 25/02 |
| | | | 604/180 |
| 2004/0204685 A1 * | 10/2004 | Wright | A61M 5/32 |
| | | | 604/174 |
| 2007/0043326 A1 * | 2/2007 | Navarro | A61M 25/02 |
| | | | 604/264 |
| 2007/0060874 A1 | 3/2007 | Nesbitt et al. | |
| 2007/0106222 A1 * | 5/2007 | Bennett | A61M 25/02 |
| | | | 604/174 |
| 2007/0142785 A1 | 6/2007 | Rozier et al. | |
| 2008/0071224 A1 | 3/2008 | Forsyth | |
| 2008/0306454 A1 | 12/2008 | Sikora | |
| 2012/0010572 A1 * | 1/2012 | Bennett | A61M 5/158 |
| | | | 604/174 |
| 2012/0191044 A1 | 7/2012 | Koike | |
| 2012/0197204 A1 | 8/2012 | Helm, Jr. | |
| 2012/0197206 A1 | 8/2012 | Glenn | |
| 2013/0110048 A1 | 5/2013 | Herzog | |
| 2015/0073347 A1 * | 3/2015 | Friedrich | A61M 25/02 |
| | | | 604/180 |
| 2015/0224285 A1 * | 8/2015 | Howell | A61M 25/02 |
| | | | 604/174 |
| 2015/0258309 A1 | 9/2015 | Kyvik et al. | |
| 2016/0256665 A1 | 9/2016 | Doshi et al. | |
| 2017/0143941 A1 | 5/2017 | Augustine et al. | |
| 2018/0177982 A1 | 6/2018 | Albany et al. | |

FOREIGN PATENT DOCUMENTS

| | | |
|---|---|---|
| JP | 2012-152552 | 8/2012 |
| JP | 2013-501595 | 1/2013 |
| JP | 2016-510676 | 4/2016 |
| KR | 101448359 B1 * | 11/2013 |
| KR | 2014-0069877 A | 6/2014 |
| KR | 10-1448359 B1 | 10/2014 |
| KR | 101448359 B1 * | 10/2014 |
| WO | WO 1998/047556 A1 | 10/1998 |
| WO | WO 01/68180 A1 | 9/2001 |
| WO | WO 02/102419 | 12/2002 |
| WO | WO 2007/082093 A3 | 7/2007 |
| WO | WO 2011/019985 | 2/2011 |
| WO | WO 2015/123684 A1 | 8/2015 |
| WO | WO 2016/083806 A1 | 6/2016 |
| WO | WO 2016/141291 A1 | 9/2016 |
| WO | WO 2020/160318 A1 | 8/2020 |

OTHER PUBLICATIONS

International Search Report and Written Opinion for PCT/US2017/068343 dated Apr. 13, 2018 in 16 pages.

European Search Report received in Application No. 17888827.7, dated Aug. 13, 2020.

*2019 Top 10 Patient Safety Concerns: Executive Brief*, ECRI Institute, 2019, 19 pages.

Alekseyev, Sonya, et al. "Prolonging the life of a patient's IV: an integrative review of intravenous securement devices." Medsurg nursing 21.5 (2012).

Bastian, Dallas, "Better dressings needed to curb PIVC failures," Nursing Review, Jul. 27, 2018, 3 pages.

Grau, Delphine, et al. "Complications with peripherally inserted central catheters (PICCs) used in hospitalized patients and outpatients: a prospective cohort study." Antimicrobial Resistance & Infection Control 6.1 (2017): 1-8.

Hedayatinejad, Maryam, et al. "Survey of complications of peripheral venous catheterization at an Intensive Care Unit of (ICU) of Susa city." Jentashapir J Health Res [Internet] (2016).

Helm, Robert E., et al. "Accepted but unacceptable: peripheral IV catheter failure." Journal of Infusion Nursing 38.3 (2015): 189-203.

Marsh, Nicole, et al. "Observational study of peripheral intravenous catheter outcomes in adult hospitalized patients: a multivariable analysis of peripheral intravenous catheter failure." Journal of Hospital Medicine 13.2 (2017): E1-E7.

Piper, Russell, et al. "The mechanistic causes of peripheral intravenous catheter failure based on a parametric computational study." Scientific Reports 8.1 (2018): 1-12.

Rickard, Claire M., et al. "Securing All intravenous devices Effectively in hospitalised patients—the SAVE trial: study protocol for a multicentre randomised controlled trial." BMJ open 5.9 (2015): e008689.

Schneider Jr, Laura Valbousquet, et al. "Evaluation of PICC complications in orthopedic inpatients with bone infection for long-term intravenous antibiotics therapy." The journal of vascular access 16.4 (2015): 299-308.

Takahashi, Toshiaki, et al. "Preventing peripheral intravenous catheter failure by reducing mechanical irritation." Scientific reports 10.1 (2020): 1-13.

Zhang, Li, et al. "Infection risks associated with peripheral vascular catheters." Journal of infection prevention 17.5 (2016): 207-213.

Search Report and Written Opinion received in International Application No. PCT/US2021/064998, dated Apr. 27, 2022, in 19 pages.

Catheter Housing, U.S. Appl. No. 15/853,469, U.S. Pat. No. 10,173,035.

Catheter Housing, U.S. Appl. No. 16/204,689, U.S. Pat. No. 10,960,184.

Catheter Housing, U.S. Appl. No. 17/178,779, 2021/0260342.

* cited by examiner

CATHETER SECUREMENT, STABILIZATION, AND ANTIMICROBIAL DEVICE

INCORPORATION BY REFERENCE TO ANY PRIORITY APPLICATIONS

This application claims the benefit of U.S. Provisional Application No. 62/778,230, filed Dec. 11, 2018, titled CATHETER SECUREMENT, STABILIZATION, AND ANTI-MICROBIAL DEVICE, and U.S. Provisional Application No. 62/689,543, filed Jun. 25, 2018, titled CATHETER SECUREMENT, STABILIZATION, AND DISINFECTION DEVICE. The entire contents of the above-identified patent application are incorporated by reference herein.

TECHNICAL FIELD

In general, the present disclosure relates to catheter securement, stabilization, and securement devices.

BACKGROUND

Intravenous catheter care has been used on patients for hundreds of years. Peripherally Inserted Central Catheters (PICC) or Peripheral Intravenous Catheters (PIVC) (herein referred to collectively as "IV catheter") placement is one of the most common invasive procedures performed on patients. After cleaning a catheter insertion site, a catheter needle is inserted into a vein of a patient. However, traditional methods of cleaning the catheter insertion site (for example, a quick swabbing of the insertion region by an alcohol swab or other antiseptic solution) are inadequate to eliminate risks of contamination or infection. Germs and bacteria commonly inhabit layers of the skin underneath the surface layer. For example, up to 80% of resident microorganisms can inhabit the first 5 layers of the skin's stratum corneum, and up to 20% of the remaining microorganisms can exist in biofilms in the underlying epidermal and dermal layers and sebaceous glands. Traditional techniques of applying one or more adhesive film dressings directly to and/or proximate to a catheter insertion site (for example, by taping a catheter device connected to a catheter cannula to the patient's skin near the insertion site) therefore will cover and incubate such germs at or near the insertion site. Such contamination can lead to various infections and complications, such as blood stream infection and/or phlebitis, among others. Furthermore, traditional adhesive catheter securement techniques inhibit normal skin respiration and/or ventilation processes at or proximate to the insertion site and also raise the humidity and/or temperature levels underneath the adhesive materials at or proximate to the insertion site. This in turn can also promote microorganism growth.

Stabilizing a catheter cannula (also referred to herein as a "catheter") is of critical importance. For example, phlebitis is commonly caused by movement of the catheter relative to a vessel wall. In other examples, catheters can become dislodged from patients due to patient movement or can be pushed further into a patient's arm or other body part, potentially dislodging it from a vein or other tissue and disrupting fluid flow. Moreover, catheters that move in and out of the skin can cause an increased risk of bacterial infection. "Kinking" of a catheter is also a potential issue in typical catheter stabilizing techniques.

Another disadvantage of traditional catheter securement devices and techniques is that firmly fixing a catheter device (coupled to a catheter) to a patient's skin by applying tape directly to the catheter device at or proximate to the catheter insertion site results in a tip of the catheter cannula being improperly angled within the vein and/or vein wall or lumen such that the cannula tip can erode or otherwise cause damage to the vein and/or vein wall or lumen and/or surrounding regions. Such erosion or other damage can be exacerbated when the patient moves or the catheter cannula tip is otherwise altered in its angle or position. In traditional approaches, after inserting a catheter into a patient, a care provider typically applies a series of tapes over and directly around the insertion site in order to stabilize the catheter device coupled to the catheter in an attempt to prevent movement of the catheter. While tapes, adhesive dressings, and adhesive-based catheter stabilizers used to stabilize catheters and/or catheter devices coupled to catheters in this fashion are considered the common standard of care, tapes used in this fashion introduce a number of drawbacks that are solved by the present disclosure. For example, it is difficult to maintain a proper angle of a catheter by taping a catheter device connected to a catheter at or proximate to the insertion site. Tapes, adhesive dressings, and adhesive-based catheter stabilizers can also cause skin trauma (for example with geriatric patients) and irritation to patient skin in and around the catheter insertion site, particularly when worn for an extended period of time. Compounding this problem, tapes can obscure the catheter insertion site and can prevent assessment of IV catheter complications. Tapes can also prevent proper ventilation of areas near and/or surrounding the insertion site, which, among other things, can decrease patient comfort. Moreover, it has been found that tapes on or near the insertion site can introduce and/or incubate bacteria, leading to infections and catheter failure.

Unfortunately, IV catheters applied and/or secured to a patient in this manner can disadvantageously be subject to mechanical failures, occlusion, kinking of the catheter, and/or dislodgement of the catheter. Further, IV catheters applied and/or secured to a patient in this manner can result in infection, phlebitis (inflammation of the vein that can lead to blood clots), and/or infiltration to surrounding tissue. Moreover, commonly accepted practice requires the removal of catheters after a 72-96 hour dwell time. Thus, even under the best circumstances, catheters have a relatively short life span that requires frequent adjustment and/or movement. Catheter failures and frequent catheter movement can result in costly catheter replacements, increased costs due to extended patient care time, and eventually venous depletion. Venous depletion leads to more invasive, risky, and costly venous access devices.

SUMMARY

The present disclosure relates to an IV catheter housing which can provide stabilization, securement, disinfection, local anesthetic, antiseptic, and/or digital monitoring of vital signs. The catheter housing can reduce catheter failure (such as those discussed above) and can solve many problems associated with traditional techniques for securing a catheter device and a catheter coupled to the catheter device to a patient discussed above. The housing discussed herein can also extend catheter dwell time beyond the current standard dwell period.

As used herein, the term "catheter device" refers to a device which connects or couples a catheter cannula (also referred to herein as "catheter") to a fluid tube (also referred to herein as "tube" and "tubing"). For example, as discussed herein, a catheter device can include one or more cylindrical portions that directly connect to a portion of the catheter cannula, a fluid tube, and a male luer connector which connects the one or more cylindrical portions to the fluid tube. The catheter housings (also referred to as "catheter stabilizing devices" "catheter housing devices," "catheter securement device," and "housing" herein) described herein can secure a catheter cannula by securing one or more portions of the catheter device. For example, as discussed below, the catheter housings discussed herein can secure (or at least partially secure) one or more cylindrical portions of a catheter device, a male luer connector of a catheter device (or portions of the male luer connector), and/or a portion of the fluid tube connected to the catheter device. Such securement can thereby secure, align, and/or position a catheter cannula coupled to such catheter device, for example. The "fluid tubes" and "tubing" described herein can deliver fluids (such as medical fluids) to the catheters described herein, and in turn, to the patient.

The catheter housings and methods described herein can include various disinfection or sterilization methods and components. For example, when fully assembled, the catheter housings discussed herein can be supplied with sterilizing inert gas which can suffocate microbes or other contaminants in and around the catheter insertion site, catheter cannula, catheter device coupled to the catheter cannula, and/or a portion of a connected fluid tube. The catheter housings discussed herein (or portions thereof) can be coated with anti-microbial coating to aid with disinfection and/or sterilization near the catheter insertion site and/or in or around the catheter housing. Various components of the catheter housing can be structured to form a hermetic seal, which can advantageously inhibit or prevent microbes or other contaminants from entering portions of the catheter housing. The catheter housing can include a gas line or port which can be used to provide sterilizing gases. Additionally, other gases can be provided in the manner described above, such as local anesthetics and/or antiseptics. For example, soothing, antiseptic, anesthetic, or similar vapor drugs can be provided to the catheter housing in a gaseous form to aid healing or reconstruction in and around the catheter insertion site. The catheter housings discussed herein can include one or more UV SMD ("Surface Mount") LEDs that can provide active sterilization and/or disinfection of areas within the catheter housing, such as areas at or near the catheter insertion site, catheter cannula, catheter device coupled to the catheter cannula, and/or portions of a connected fluid tube. The one or more UV SMD LEDs can also illuminate interior regions within the housing, for example at or near the catheter insertion site. The one or more UV SMD LEDs can also illuminate regions exterior to the housing.

The catheter housings described herein can also include various sensors, including bio-sensors that can measure, gather, and transmit patient medical condition data. The bio-sensors can include a micro-processor. For example, the bio-sensors can include an illuminated LCD monitor for detecting, measuring, storing and/or displaying patient vital functions, including venous and arterial blood pressure, heart beats, blood oxygen levels, general and topical temperature, and local tissue humidity, and/or venous blood current speed, among others. The measurements and/or calculations performed and/or taken by these sensors can be stored on a flash storage memory positioned on the catheter housing. Alternatively, the sensor measurements can be wirelessly transmitted (or be transmitted via a wire) to a patient monitoring system for display to a care provider or user.

The catheter housings and methods described herein can avoid using traditional methods of securing a catheter and/or catheter device connected to a catheter, to a patient's skin at the catheter insertion site such as is described above. The catheter housings and methods described herein can also avoid applying pressure directly to the needle, puncture site, catheter, and/or catheter device. The catheter housings and methods described herein can also avoid kinking of a catheter. For example, as discussed herein, the catheter housing can secure a catheter device connected to a catheter with a lock and/or bridge disposed on an interior of the catheter housing, such as a cover. The catheter housings and methods described herein can dramatically reduce the potential for contamination in and/or around the insertion site. Moreover, because the catheter and/or catheter device can be left uncovered by tape, the insertion area can remain readily visible to a care provider. This visibility allows the care provider to easily, quickly, and repeatedly assess the catheter insertion site for signs of inflammation, failure, or infection, for example. The catheter housings discussed herein can also mechanically isolate the catheter and/or connected portion from patient movement and can hold the catheter and/or connected portion at a proper or natural insertion angle. The catheter housings and methods described herein can also provide a securement system that is highly skin breathable, allowing for patient comfort and reduced skin irritation or skin trauma.

In addition to securing a catheter device connected to a catheter (and/or the catheter) with a portion of the housing (for example, a lock and/or a bridge on an interior of the catheter housing), the catheter housings and methods described herein can utilize anti-slip material and/or methods to secure the catheter housings (or a portion thereof) to a patient around a catheter insertion site. The catheter housings described herein can utilize anti-slip material and/or methods such as an silicon-adhesive, sticky material, rubber compound, biocompatible high-tack coating material, adhesive or other types of material and/or methods that can prevent slipping or movement of the catheter housing on a patient's skin. For example, as discussed herein, the catheter housings discussed herein can have a bottom surface (which can be disposed on a membrane of the catheter housing, for example) that includes anti-slip material, such as a silicon-adhesive. Using some anti-slip materials, such as silicon-adhesive or a rubber compound, may allow for little or no residue (such as adhesive residue) that may be present in traditional tape adhesive materials. Thus, using such type of anti-slip materials to secure a portion of the catheter housing to a patient's skin may not require the use of any alcohol or other liquid to aid the removal of residues.

The catheter housings and methods described herein can provide a number of advantages. For example, the catheter housing discussed herein can include a small number of parts or components which enables convenient assembly and securement of a catheter, catheter device, and/or tubing to a patient. The catheter housings discussed herein can be low-profile. For example, the catheter housings discussed herein can have a total height of approximately 1 cm or less. The catheter housings discussed herein can have a height outside of this value, though (for example, a height greater than 1 cm). The catheter housings discussed herein can be low-weight. For example, the catheter housings discussed herein can have a total weight of no more than several grams. Alternatively, the catheter housings discussed herein can have a total weight of more than several grams. The catheter housings discussed herein can have a small footprint when secured to a patient. The catheter housings discussed herein can have a total volume that is sized and shaped to accommodate various sizes of catheter devices and/or tubing that can be coupled to a catheter cannula. For example, the catheter housings discussed herein can accommodate the volume, shape, size, weight, and/or other characteristics of catheter devices (or portions thereof) and a connected tubes which meet standards set by the International Organization for Standardization (ISO). As discussed below, the catheter housings discussed herein can include a cover that has a detent, recess, or groove that can accommodate a portion of a catheter device (for example, a portion of a male luer connector), which can allow the catheter device to be contained or retained within the catheter housing while also minimizing the total height of the catheter housing. For example, the groove can be a conically-shaped groove that can accommodate a cylindrical (or partially cylindrical) shape of a portion of a catheter device (such as a male luer connector).

The catheter housings discussed herein can optionally include a mechanism to allow the catheter housing to form a hermetic seal around a catheter insertion site. For example, the catheter housings discussed herein can include a cover having a double jacketed wall. For example, the cover can include an outer wall and an inner wall, wherein the inner wall can have a protrusion that can be configured to cooperate with a groove located on a hub of the catheter housing. The protrusion can be a peripheral protrusion around a periphery of the cover, for example, around a periphery of an interior of the cover. The groove can be located on the hub of the catheter housing can be a peripheral groove, for example, around a periphery of an exterior portion of the hub of the catheter housing. Such a hermetic seal is advantageous because it can prevent infection and/or microbial growth in, at, and/or around the catheter insertion site. Such optional hermetic seal can also enclose the gases that can be inserted into the catheter housing and/or around the catheter insertion site, such as sterilizing and/or soothing gases.

As discussed herein, the catheter housing can include a cover having a lock component that can accommodate, secure, and/or secure to, a catheter device. This can, among other things, help to prevent movement of the catheter cannula, the catheter device, and/or tubing connected to the catheter device. Preventing such movement advantageously can reduce the problems described above. The cover can additionally or alternatively include a bridge (also referred to as a "harness bridge") that can help secure, position, align, and/or push down a catheter device (or a portion thereof) to provide an appropriate inclination of the catheter at the insertion site, as discussed herein. The bridge can also prevent the catheter device from flattening out or moving upwards away from the catheter insertion site. The lock can be sized and/or shaped to secure to any type of catheter device (or portion thereof), as discussed herein.

As also discussed herein, the catheter housings can include a cover having one or more openings or slots in a wall of the cover, such as an inner and/or outer wall of the cover. The one or more openings or slots can allow portions of tubing connected to the catheter device and/or portions of the catheter device (for example a stem portion of the male luer connector) to secure, pass, and/or fit therethrough or therein.

As discussed herein, the catheter housings can have one or more strap hoops that can allow fastening straps to pass therethrough, wrap around a portion of the patient, and secure to the catheter housings. The strap hoops and fastening straps can secure the catheter housing to a patient. The one or more strap hoops and/or the one or more fastening straps can be sized and shaped to accommodate any size and/or shape of body part (such as an arm or leg). Additionally or alternatively, the catheter housings can have a hub with a membrane that can have an anti-slip material on a bottom surface that can secure or partially secure the catheter housing to a patient.

Catheter housing devices and methods for securing the same to patients are described in jointly owned, co-pending U.S. application Ser. No. 16/204,689 and U.S. Pat. No. 10,173,035, both of which are incorporated herein in their entirety.

A catheter housing configured to surround a catheter insertion site on a patient can comprise: a hub configured to surround the catheter insertion site on the patient and secure to the patient and a cover configured to at least partially enclose the catheter insertion site and secure to the hub. The hub can include: a membrane configured to contact and secure to the patient's skin, the membrane having an opening configured to surround the catheter insertion site; and a wall, spaced inward from a perimeter of the membrane and extending outward from the membrane and around the catheter insertion site, the wall having an exterior side and an interior side opposite the interior side, the exterior side facing away from the catheter insertion site when the hub is secured to the patient. The wall can include: a first opening sized and shaped to receive a portion of a catheter device; and a groove extending along a portion of an interior side of the wall. The cover can include: a tongue configured to secure to the groove of the wall of the hub; a second opening configured to align with the first opening of the wall of the hub when the cover is secured to the hub; and a lock configured to retain the catheter device within the catheter housing. The cover can comprise a transparent material. The cover can be configured to form a hermetic seal around the catheter insertion site when the tongue of the cover is secured to the groove of the wall of the hub. The tongue can extend outward from an interior surface of the cover. The wall of the hub can comprise a joint proximate the first opening of the wall, the joint configured to be flexibly opened and closed to permit the portion of the catheter device to be inserted into the first opening of the wall. The membrane of the hub can comprise one or more indicators configured to indicate or align with an insertion point of a needle coupled to the catheter device. The cover can further comprise one or more wings extending outward from sides of the cover and configured to secure tubing connected to the catheter device. The one or more wings can curve in a direction towards the membrane of the hub. The cover can comprise a first side and a second side opposite the first side, wherein the one or more wings comprises a first wing located along the first side and a second wing located along the second side. The membrane can be configured to form a hermetic seal around the insertion site when the hub is secured to the patient. The membrane of the hub can comprise a top surface and a bottom surface, wherein the bottom surface can be configured to secure to the patient when the hub is secured to the patient. The bottom surface of the membrane of the hub can comprise an adhesive. The cover can comprise a first port configured to allow gases to flow into of an interior of the catheter housing. The first port can extend along a top exterior surface of the cover, the top exterior surface of the cover facing in a direction opposite the membrane of the hub. The catheter housing can further comprise a second port spaced from the first port, the second port configured to allow gases to flow out of the interior of the catheter housing. The first port can comprise a first opening facing a first direction that is generally parallel to a length of the cover and a second opening facing towards the catheter insertion site, and wherein the first direction can be angled with respect to the second direction. The first direction can be generally perpendicular to the second direction. The cover can further comprise an outer wall and an inner wall inset from the outer wall, wherein the tongue of the cover can extend outward from an outer surface of the inner wall. The cover can further comprise a third opening, and wherein the second opening of the cover can be located on the outer wall and the second opening can be located on the inner wall, and wherein the second and third openings can align with each other. The lock can extend outward from an interior surface of the cover, the interior surface of the cover facing towards the catheter insertion site, and wherein the lock can be spaced inward from the inner wall. The lock can extend outward from an interior surface of the cover. The lock can comprise a first end connected to the interior surface of the cover and a second end opposite the first end. The second end of the lock can comprise a recess sized and shaped to receive a portion of the catheter device. The portion of the catheter device can comprise a cylindrical shape and the recess can be sized and shaped to receive and surround a portion of the cylindrical shape. The recess can comprise a half-circle shape. The recess can be sized and shaped to surround approximately half of a perimeter of the portion of the catheter device. The cover can comprise a bridge extending outwards from the interior surface of the cover and spaced from the lock, and wherein the lock can be configured to secure a first portion of the catheter device and the bridge can be configured to secure a second portion of the catheter device. The lock and the bridge can be spaced inward from a perimeter of the cover. The lock and the bridge can each comprise a first end connected to the interior surface of the cover and a second end opposite the first end, and wherein each of the second ends of the lock and bridge can comprise a recess sized and shaped to retain the first and second portions of the catheter device. The recess of the lock can be larger than the recess of the bridge. The second ends of the bridge and the lock can comprise sloped regions proximate the recesses, and the sloped regions can be configured to help align the first and second portions of the catheter device within the recesses. The lock can extend outward from the interior surface of the cover a first distance and the bridge can extend outward from the interior surface of the cover a second distance, and wherein the second distance can be greater than the second distance. The catheter housing can further comprise a stem wall extending between the bridge and the lock. The stem wall can be integral with the bridge and the lock. The lock can comprise a rectangular cross section having a first width and a first height, the first width extending along a first dimension of the cover and the first height extending along a second dimension of the cover, the first dimension of the cover can be greater than the second dimension of the cover, and wherein the first height can be greater than the first width. The first dimension of the cover can correspond to a first axis and the second dimension of the cover can correspond to a second axis perpendicular to the first axis. The bridge can comprise a rectangular cross section having a second width and a second height, the second width extending along the first dimension of the cover and the second height extending along the second dimension of the cover, the second height being greater than the second width. The first width can be equal to the second width and the first height can be equal to the second height.

A catheter housing configured to surround a catheter insertion site on a patient can comprise: a hub configured to surround the catheter insertion site on the patient and secure to the patient; and a cover configured to enclose the catheter insertion site and secure to the hub. The cover can comprise: an exterior surface, an interior surface opposite the exterior surface and configured to face toward the catheter insertion site, a first wall, and a lock extending outward from the interior surface and toward the catheter insertion site, the lock configured to retain a first portion of a catheter device coupled to a catheter within the catheter housing, wherein the lock is spaced inward from the wall of the cover. The lock can comprise a rectangular cross section having first width and a first height, the first width being smaller than the first height. The lock can comprise a first end connected to the interior surface of the cover and a second end opposite the first end. The second end of the lock can comprise a recess sized and shaped to receive a portion of the catheter device. The second end of the lock can further comprise sloping regions on both sides of the recess, the sloping regions configured to aid alignment of the portion of the catheter device received by the recess. The cover can further comprise a bridge extending outward from the interior surface and toward the catheter insertion site, the bridge spaced from the lock and the wall of the cover, and wherein the bridge can be configured to retain a second portion of the catheter device. The lock can comprise a first end connected to the interior surface of the cover and a second end opposite the first end, the second end comprising a first recess sized and shape to surround and retain the first portion of the catheter device. The bridge can comprise a third end connected to the interior surface of the cover and a fourth end opposite the third end, the fourth end comprising a second recess sized and shape to surround and retain the second portion of the catheter device. The first and second recesses can be rounded. The first and second recesses can comprise a half-circle shape. The first and second recesses can align. The second end of the lock can comprise sloping regions adjacent the first recess, the sloping regions configured to align the first portion of the catheter device within the first recess. The fourth end of the bridge can comprise sloping regions adjacent the second recess, the sloping regions configured to align the second portion of the catheter device within the second recess. The second opening of the cover can align with the first recess of the lock and the second recess of the bridge. The second opening of the cover can be positioned closer to the first recess of the lock than to the second recess of the bridge. The first recess can be greater than the second recess. The lock can comprise a first length between the first and second ends and the bridge can comprise a second length between the third and fourth ends, and wherein the second length of the bridge can be greater than the first length of the lock. The cover can further comprise a stem wall extending outward from the interior surface of the cover and extending between the bridge and the lock. The stem wall can be integral with the bridge and the lock. The stem wall, the bridge, and the lock can form an H-shape. The lock can comprise a rectangular cross section having a first width and a first height, the first width extending along a first dimension of the cover and the first height extending along a second dimension of the cover, the first dimension of the cover greater than the second dimension of the cover, and wherein the first height can be greater than the first width, the first dimension of the cover corresponding to a first axis and the second dimension of the cover corresponding to a second axis perpendicular to the first axis. The bridge can comprise a rectangular cross section having a second width and a second height, the second width extending along the first dimension of the cover and the second height extending along the second dimension of the cover, and the second height can be greater than the second width. The first width and the second width can be equal and wherein the first height and second height can be equal. The hub can comprise: a membrane configured to contact and secure to the patient's skin, the membrane having an opening configured to surround the catheter insertion site; and a wall inset from an exterior edge of the membrane and extending outward from the membrane and around the catheter insertion site. The cover can be configured to secure to the hub by securing to the wall of the hub. The wall of the hub can comprise a groove along at least a portion of an interior facing side of the wall, and wherein the cover can further comprise a tongue configured to secure to the groove of the wall of the hub. The catheter housing can be configured to form a hermetic seal when the tongue of the cover is secured to the groove of the wall of the hub. The wall of the hub can comprise a first opening sized and shaped to receive the portion of the catheter device and wherein the cover comprises a second opening configured to align with the first opening of the wall of the hub when the cover is secured to the hub. The lock can comprise a first end connected to the interior surface of the cover and a second end opposite the first end, and wherein the second end can comprise a recess sized and shaped to retain and surround the first portion of the catheter device. The recess of the lock can be aligned with the first opening of the wall and the second opening of the cover. The recess of the lock can comprise a half-moon shape.

A catheter housing configured to surround a catheter insertion site on a patient can comprise a housing configured to surround and enclose the catheter insertion site, wherein the housing does not touch skin of the patient at the catheter insertion site. The housing can include an opening that is sized and shaped to receive a portion of a catheter device, the housing further comprising a lock extending outward from an interior surface of the housing and towards the catheter insertion site, the lock comprising a first recess sized and shaped to surround and retain a first portion of the catheter device. The lock can comprise a first end connected to the interior surface of the housing and a second end opposite the first end, and wherein the second end comprises the first recess. The lock can be spaced inwards from a perimeter of the housing by a gap. The first recess of the lock can be aligned with the opening in the housing. The housing can further comprise a bridge extending outwards from the interior surface of the housing and spaced from the lock. The bridge can comprise a second recess sized and shaped to surround and retain a second portion of the catheter device. The first recess and the second recess can be aligned with each other. An axis passing through a center of the first recess can be parallel to an axis running through a center of the second recess. The first recess can be larger than the second recess. The first recess and the second recess can be aligned with the opening of the housing. The lock can comprise a rectangular cross section having a first width and a first height, the first width extending along a first dimension of the housing and the first height extending along a second dimension of the housing, the first dimension of the housing greater than the second dimension of the housing, and wherein the first height is greater than the first width, the first dimension of the housing corresponding to a first axis and the second dimension of the housing corresponding to a second axis perpendicular to the first axis. The bridge can comprise a rectangular cross section having a second width and a second height, the second width extending along the first dimension of the housing and the second height extending along the second dimension of the housing, the second height being greater than the second width. The first width and the second width can be equal and wherein the first height and second height can be equal. The housing can comprise a top surface and sides extending in a direction transverse to the top surface, and wherein the interior surface of the housing can be opposite the top surface. The bridge and the lock can be spaced from the sides of the housing by a gap.

A catheter housing configured to surround a catheter insertion site on a patient can comprise a hub configured to surround the catheter insertion site on the patient and secure to the patient and a cover configured to at least partially enclose the catheter insertion site and secure to the hub. The hub can include: a membrane configured to contact and secure to the patient's skin, the membrane having an opening configured to surround the catheter insertion site; a wall, spaced inward from a perimeter of the membrane and extending outward from the membrane and around the catheter insertion site, the wall having an exterior side and an interior side opposite the interior side, the exterior side facing away from the catheter insertion site when the hub is secured to the patient, wherein the wall includes a first opening sized an shaped to receive a tube connected to a catheter device, a groove extending along a portion of an interior side of the wall. The cover can include: a tongue configured to secure to the groove of the wall of the hub; a second opening configured to align with the first opening of the wall of the hub when the cover is secured to the hub; and a lock configured to retain the catheter device within the catheter housing, the lock extending from an interior surface of the cover and spaced inward from a perimeter defined by the cover. The catheter housing can further comprise a UV SMD LED configured to illuminate and sterilize areas within the catheter housing. The UV SMD LED can be electronically coupled to a sensor, and the sensor can be configured to send a signal to the UV SMD LED when the tongue of the cover is secured to the groove of the wall of the hub. The UV SMD LED can be configured to automatically activate when receiving the signal from the sensor. The UV SMD LED can be located on an interior of the cover. The catheter housing can further comprise a physiological sensor configured to measure a physiological parameter of the patient. The physiological sensor can be positioned on a bottom surface of the membrane of the hub. The physiological sensor can be a temperature sensor, a blood pressure sensor, a blood oxygen saturation sensor, a sensor for liquid and blood leakage, or a skin humidity sensor. The catheter housing can be substantially waterproof and/or shockproof. The cover can comprise a material selected from the group consisting of plastic, rubber, and silicon. The cover can comprise a transparent material. The cover can be configured to form a hermetic seal around the catheter insertion site when the tongue of the cover is secured to the groove of the wall of the hub. The cover can comprise a shape selected from the group consisting of trapezoidal, rectangular, square, oval, and circular. The hub can comprise a material selected from the group consisting of plastic, rubber, and silicon. The wall of the hub can be rounded. The tongue can be located along an interior surface of the cover. The wall of the hub can comprise a joint at the second opening of the wall, and the joint can be configured to be flexibly opened and closed to permit the tubing connected to the catheter device to be inserted into the catheter housing. The membrane of the hub can comprise one or more indicators proximate to the insertion site. The cover can further comprise a plurality of strap hoops extending from an outer wall of the cover, and the plurality of strap hoop can be configured to permit one or more fastening straps to pass therethrough and secure the catheter housing to the patient. The cover can further comprise a first side and a second side opposite the first side, wherein the plurality of strap hoops comprises a first strap hoop located along the first side and a second strap hoop located along the second side. The first and second strap hoops can comprise a continuous loop sized and shaped to allow portions of the one or more fastening straps to pass therethrough. The first and second strap hoops can comprise a rounded loop sized and shaped to allow a portions of the one or more fastening straps to pass therethrough, and the rounded loop can comprise a slit configured to allow the one or more fastening straps to be inserted into the rounded loop by feeding a side of the one or more fastening straps therethrough. The wall of the hub can have a first exterior face, a second exterior face opposite the first exterior face, a third exterior face, and a fourth exterior face opposite the third exterior face, and the groove of the wall can extend along the entirety of at least the first exterior face. The membrane can be configured to form a hermetic seal around the insertion site when the hub is secured to the patient. The membrane of the hub can comprise a top surface and a bottom surface, wherein the bottom surface is configured to contact the patient when the hub is secured to the patient. The bottom surface of the membrane of the hub can comprise at least one suction cup configured to at least partially secure to the patient's skin. The bottom surface of the membrane of the hub can comprise a corrugated structure. The bottom surface of the membrane of the hub can comprise an anti-slip material configured to prevent slipping of the hub on the patient's skin. The bottom surface of the membrane of the hub can comprise one or more anti-slip rings configured to secure to the patient. The top surface of the membrane of the hub can comprise Velcro configured to secure to the one or more fastening straps. The catheter housing can comprise at least one light configured to illuminate a region proximate to the catheter housing. The membrane of the hub can have a width greater than an exterior width of the cover, wherein the membrane comprises a top surface and a bottom surface, and the bottom surface is configured to contact the patient when the hub is secured to the patient, and wherein the top surface comprises a Velcro configured to secure to one or more fastening straps. The cover can comprise a bridge positioned within the interior of the cover, wherein the bridge is positioned closer to the insertion site than the lock. The cover can further comprise a plurality of slots in an exterior wall of the cover, wherein the plurality of slots are configured to permit tubing connected to the catheter device to pass therethrough to at least partially secure the tubing to the catheter housing. The plurality of slots in the exterior wall of the cover can comprise a first slot on a first side of the cover and a second slot on a second side of the cover, wherein the tubing connected to the catheter device is permitted to pass through the first opening of the cover and pass through both the first and second slots of the cover to form a J-loop. The cover can further comprise a port extending outward from an exterior wall of the cover, wherein the port is configured to align with a second opening of the wall and permit gas to flow into the catheter housing device. The port of the cover can comprise a port rim configured to secure to a portion of a gas tube in a configuration selected from the group consisting of a snap-fit, a press fit, and a friction fit. The cover can comprise an outer wall and an inner wall inset from the outer wall, wherein the tongue of the cover is located along an inner surface of the inner wall. The cover can further comprise a second slot, wherein the first slot of the cover is located on the outer wall and the second slot is located on the inner wall, and wherein the first and second slots align with each other and permit tubing connected to the catheter device to pass into the catheter housing. The cover can further comprise a plurality of openings in the outer wall of the cover configured to permit the tubing connected to the catheter device to pass therethrough to at least partially secure the tubing to the catheter housing.

A catheter housing configured to surround a catheter insertion site on a patient can include: a cover configured to at least partially enclose the catheter insertion site on the patient, the cover having a first side and a second side opposite the first side; and a lock located on an interior surface of the cover and configured to secure the catheter device within the cover near the insertion site. The cover can include an opening configured to permit tubing connected to the catheter device to pass therethrough to the catheter device and a first slot and a second slot positioned along the first side of the cover, wherein the first and second slots are configured to permit the tubing connected to the catheter device to pass therethrough to at least partially secure the tubing to the cover. The cover can comprise an outer wall and an inner wall inset from the outer wall, wherein the opening in the cover comprises a first opening in the inner wall and a second opening in the outer wall, the first and second openings aligned with each other, wherein the first and second slots located on the outer wall of the cover, the first slot positioned closer to the first and second openings of the cover than the second slot, and wherein, when the catheter device is secured by the lock of the catheter housing, the tubing connected to the catheter device is configured to pass through the first and second openings of the cover and pass through the first and second slots of the outer wall of the cover.

A catheter housing configured to surround a catheter insertion site on a patient can comprise: a hub configured to surround the catheter insertion site on the patient and secure to the patient; and a cover configured to enclose the catheter insertion site and secure to the hub, the cover comprising an exterior surface, an interior surface opposite the exterior surface and configured to face toward the catheter insertion site when the cover is secured to the hub, and a lock extending from on the interior surface and configured to retain a catheter device coupled to a catheter within the catheter housing. The hub can comprise a membrane configured to contact and secure to the patient's skin, and the membrane can have an opening configured to surround the catheter insertion site; and a wall spaced inward from an exterior edge of the membrane and extending above the membrane and around the catheter insertion site. The cover can be configured to secure to the hub by securing to the wall of the hub. The wall of the hub can comprise a groove along at least a portion of an exterior facing side of the wall, and the cover can further comprise a tongue configured to secure to the groove of the wall of the hub. The catheter housing can be configured to form a hermetic seal when the tongue of the cover is secured to the groove of the wall of the hub. The wall can have a first side, a second side opposite the first side, a front side, and a back side opposite the front side, and wherein the groove of the wall extends along the entirety of at least the first side. The lock extending from the interior surface of the cover can be spaced interior to a perimeter of the cover. The lock extending from the interior surface of the cover can be separated from a perimeter of the cover by a gap.

A method of securing a catheter device near a catheter insertion site and sealing the catheter insertion site from contamination can comprise: placing a hub around the catheter insertion site on the patient, the hub including a membrane and a wall extending outward from the membrane and spaced inward from a perimeter of the membrane, the membrane having an opening configured to surround the catheter insertion site; placing a cover around the hub to enclose the catheter insertion site; and securing the catheter device with a lock positioned on an interior surface of the cover; and securing the cover to the patient. The catheter device can be connected to a catheter. The method can further comprise securing the cover to the hub to form a hermetic seal around the insertion site. The cover can be secured to the hub by securing a tongue on an interior of the cover to a groove of the hub. The membrane can comprise a top surface and a bottom surface, wherein the bottom surface is configured to contact the patient when the hub is placed around the insertion site on the patient, and wherein the bottom surface comprises an anti-slip material configured to secure the hub to the patient. The cover can comprise a plurality of strap hoops extending from the cover, and the plurality of strap hoops can be configured to permit one or more fastening straps to pass therethrough and secure the cover to the patient. The method can further comprise placing tubing connected to the catheter device through an opening in the hub before placing the cover around the hub. The cover can include a port, and the method can further comprise attaching a gas line to the port and permitting gas to flow from the gas line through the port and to the catheter insertion site. The gas permitted to flow can be sterilizing gas, ethylene oxide gas, nitrogen gas, hydrogen peroxide gas, and/or anesthetic gas. The cover can include a first port and a second port, and the method can further comprise attaching a first gas line to the first port and permitting gas to flow from the gas line through the first port and to the insertion site, and attaching a second gas line to the second port and permitting gas to flow from the second gas line through the second port and to the insertion site. The gas provided to the first gas line can be anesthetic gas and the gas provided to the second gas line can be sterilizing gas.

A method of securing a catheter device to a patient near an insertion site and measuring a physiological parameter of the patient can comprise: placing a catheter housing around the insertion site on the patient, the catheter housing configured to surround and stabilize the catheter device in order to reduce the likelihood of movement of a catheter connected to the catheter device when the catheter is inserted into the insertion site, the catheter housing including at least one sensor; securing the catheter device with the catheter housing; attaching the catheter housing to the patient; and measuring at least one physiological parameter of the patient with the at least one sensor. The at least one physiological parameter can be measured by a physiological parameter selected from the group consisting of blood pressure, heartbeat, blood oxygen level, temperature, and humidity. The catheter device can be connected to a catheter and the catheter can be configured for insertion into a vein of the patient. The method can further comprise wirelessly transmitting the measured at least one physiological parameter to a patient monitoring system. The method can further comprise storing the measured at least one physiological parameter on a flash storage memory unit located on the catheter housing. The method can further comprise storing the measured at least one physiological parameter on a flash storage memory unit located on the catheter housing, and wirelessly transmitting the measured at least one physiological parameter to a patient monitoring system. The method can further comprise illuminating a region proximate to the catheter housing and/or the insertion site with a light source. The light source can be an LED. The light source can be UV.

A catheter device configured to surround a catheter insertion site on a patient, can comprise a housing configured to surround and enclose the catheter insertion site, wherein the housing does not touch skin of the patient at the catheter insertion site, the housing including a wall having an opening that allows a tube connected to a catheter device to be inserted into an interior space defined by the outer wall of the housing, the housing further comprising, a lock configured to secure the catheter, the lock extending from an interior surface of the wall and extending towards the catheter insertion site. The housing can comprise: a membrane configured to contact and secure to the patient's skin, wherein the membrane has an opening configured to be positioned around the catheter insertion site; and a cover configured to at least partially enclose the catheter insertion site. The membrane can be configured to form a hermetic seal around the insertion site when the catheter housing is secured to the patient. The membrane can comprise a top surface and a bottom surface, wherein the bottom surface is configured to contact the patient when the membrane is secured to the patient. The bottom surface of the membrane can comprise at least one suction cup configured to at least partially secure to the patient's skin. The bottom surface of the membrane can comprise a corrugated structure. The bottom surface of the membrane can at least partially comprise an anti-slip material configured to secure to the patient. The bottom surface of the membrane can comprise one or more anti-slip rings configured to secure to the patient. The housing can further comprise a port configured to permit gas to flow into an interior of the housing. The port can comprise a port rim configured to secure to a portion of a gas tube in a configuration selected from the group consisting of a snap-fit, a press fit, and a friction fit. The port can be configured to permit gas selected from the group consisting of ethylene oxide gas, nitrogen, and anesthetic gas. The lock can secure the catheter by securing to a catheter device connected to the catheter. The catheter housing can further comprise a UV SMD LED configured to illuminate and sterilize areas within the catheter housing. The catheter housing can further comprise a physiological sensor configured to measure a physiological parameter of the patient. The physiological sensor can be a temperature sensor, a blood pressure sensor, a blood oxygen saturation sensor, a sensor for liquid and blood leakage, or a skin humidity sensor. The housing can be substantially waterproof and/or shockproof. The housing can comprise a material selected from the group consisting of plastic, rubber, and silicon. The housing can comprise a transparent material. The housing can be configured to form a hermetic seal around the catheter insertion site. The housing can comprise a plurality of strap hoops extending from an exterior portion of the housing, and the plurality of strap hoops can be configured to permit one or more fastening straps to pass therethrough and secure the housing to the patient. The housing can have a first side and a second side opposite the first side, and the plurality of strap hoops can comprise a first strap hoop located along the first side and a second strap hoop located along the second side. The housing can comprise a shape selected from the group consisting of trapezoidal, rectangular, square, oval, and circular.

A method of securing a catheter device to a patient near an insertion site can comprise: inserting a needle into the patient at the insertion site; inserting a catheter into the insertion site, wherein the catheter is connected to the catheter device; placing a catheter housing over the insertion site; securing the catheter device with a lock located within an interior of the catheter housing, wherein the lock is configured to stabilize the catheter device and reduce the likelihood of catheter movement. The catheter device can be secured with the lock by placing tubing connected to the catheter device within a recess of a first wall of the lock and placing the catheter device between a second wall and a third wall of the lock, wherein the second wall and the third wall are approximately parallel to each other and approximately perpendicular to the first wall. The method can further comprise placing a portion of the catheter device in a bridge positioned within the interior of the catheter housing, wherein the bridge is positioned closer to the insertion site than the lock, and wherein the bridge is configured to prevent the catheter device and the catheter from straightening out when the catheter is inserted into the patient.

A method of stabilizing a catheter device near a catheter insertion site can comprise: placing a catheter housing on the patient wherein the catheter housing surrounds and encloses the catheter insertion site, the catheter housing including an opening and a catheter stabilizing component located within an interior of the catheter housing, wherein the opening is configured to allow catheter tubing to pass through the catheter housing and to the catheter stabilizing component; securing the catheter device connected to the catheter with the catheter stabilizing component; and securing the catheter housing to the patient. The catheter housing can further include an anti-slip material on a bottom surface of the catheter housing, and the securing the catheter housing to the patient can comprise applying pressure to the catheter housing. The catheter housing can further include a first strap loop and a second strap loop, and the first and second strap loops can extend from an exterior of the catheter housing, and the method can further comprise: passing a first end of a fastening strap through the first strap loop and securing the first end of the fastening strap to a first Velcro portion of the fastening strap; wrapping the fastening strap around a portion of the patient's body; and passing a second end of the fastening strap through the second strap loop and securing the second end of the fastening strap to a second Velcro portion of the fastening strap. The first and second strap loops can be rounded and can comprise a slit configured to allow the fastening strap to be inserted into the rounded strap loops by feeding a side of the fastening strap therethrough.

A catheter configured to surround a catheter insertion site on a patient can comprise a hub configured to surround the catheter insertion site on the patient and secure to the patient and a cover configured to at least partially enclose the catheter insertion site and secure to the hub. The hub can comprise: a membrane configured to contact and secure to the patient's skin, the membrane having an opening configured to surround the catheter insertion site; and a wall, spaced inward from a perimeter of the membrane and extending outward from the membrane and around the catheter insertion site. The wall can include: a first opening sized and shaped to receive a tube connected to a catheter device coupled to a catheter; and a first inlet configured to permit gas to flow to into the catheter housing; and a groove extending outward from an along a portion of an interior side of the wall. The cover can comprise: an outer wall and an inner wall spaced inward from the outer wall; a port extending at least partially outward from an exterior surface of the outer wall of the cover and extending through the exterior surface of the outer wall and through an exterior surface of the inner wall, the port configured to align with the first inlet of the wall and permit gas to flow into the catheter housing; a tongue located along an exterior surface of the inner wall and configured to secure to the groove of the wall of the hub, the exterior surface of the inner wall facing the outer wall; a second opening located on the outer wall and a third opening located on the inner wall, wherein the second and third openings align with each other and are sized and shaped to receive the tube connected to the catheter device; a lock configured to retain the catheter device within the catheter housing; a plurality of slots in the outer wall of the cover configured to permit the tubing connected to the catheter device to pass therethrough to at least partially secure the tubing to the catheter housing; and a plurality of strap hoops extending from the outer wall of the cover, the plurality of strap hoops configured to permit one or more fastening straps to pass therethrough and secure the catheter housing to the patient. The catheter housing can further comprise a UV SMD LED configured to illuminate and sterilize areas within the catheter housing. The UV SMD LED can be electronically coupled to a sensor, and the sensor can be configured to send a signal to the UV SMD LED when the tongue of the cover is secured to the groove of the wall of the hub. The UV SMD LED can be configured to automatically activate when receiving the signal from the sensor. The UV SMD LED can be located on an interior of the cover. The catheter housing can further comprise a physiological sensor configured to measure a physiological parameter of the patient. The physiological sensor can be positioned on a bottom surface of the membrane of the hub. The physiological sensor can be a temperature sensor, a blood pressure sensor, a blood oxygen saturation sensor, a sensor for liquid and blood leakage, or a skin humidity sensor. The catheter housing can be substantially waterproof and/or shockproof. The cover can comprise a material selected from the group consisting of plastic, rubber, and silicon. The cover can comprise a transparent material. The cover can be configured to form a hermetic seal around the catheter insertion site when the tongue of the cover is secured to the groove of the wall of the hub. The cover can comprise a shape selected from the group consisting of trapezoidal, rectangular, square, oval, and circular. The hub can comprise a material selected from the group consisting of plastic, rubber, and silicon. The wall of the hub can be rounded. The cover can have a first side and a second side opposite the first side, and the plurality of slots in the outer wall of the cover can comprise a first slot on the first side of the cover and a second slot on the second side of the cover, and the tubing connected to the catheter device can be permitted to pass through the first and second openings of the cover and pass through both the first and second slots of the cover to form a J-loop. The wall of the hub can comprise a joint at the first opening of the wall, the joint configured to be flexibly opened and closed to permit the tubing connected to the catheter device to be inserted into the catheter housing. The membrane of the hub can comprise one or more indicators proximate to the insertion site. The cover can have a first side and a second side opposite the first side, wherein the plurality of strap hoops comprises a first strap hoop located along the first side and a second strap hoop located along the second side. The first and second strap hoops can comprise a rounded loop sized and shaped to allow a portions of one or more fastening straps to pass therethrough. The membrane can be configured to form a hermetic seal around the insertion site when the hub is secured to the patient. The membrane of the hub can comprise a top surface and a bottom surface, wherein the bottom surface is configured to contact the patient when the hub is secured to the patient. The bottom surface of the membrane of the hub can comprise at least one suction cup configured to at least partially secure to the patient's skin. The bottom surface of the membrane of the hub can comprise a corrugated structure. The bottom surface of the membrane of the hub can at least partially comprise an anti-slip material configured to secure to the patient. The bottom surface can comprise one or more anti-slip rings configured to secure to the patient. The top surface of the membrane of the hub can comprise Velcro configured to secure to one or more fastening straps. The catheter housing can further comprise at least one light configured to illuminate a region proximate to the catheter housing device. The membrane of the hub can have a width greater than an exterior width of the cover, and the membrane can comprise a top surface and a bottom surface, the bottom surface configured to contact the patient when the hub is secured to the patient, and wherein the top surface comprises a Velcro configured to secure to one or more fastening straps. The port of the cover can comprise a port rim configured to secure to a portion of a gas tube in a configuration selected from the group consisting of a snap-fit, a press fit, and a friction fit. The wall of the hub can be a stadium wall. The wall of the hub can be rectangular, oval, and/or circular.

A catheter housing which covers a catheter insertion site on a patient can comprise: a hub configured to surround the catheter insertion site on the patient and secure to the patient and a cover configured to at least partially enclose the catheter insertion site and secure to the hub. The hub can include: a membrane configured to contact and secure to the patient's skin, the membrane having an opening configured to surround the catheter insertion site; and a wall, inset from an exterior edge of the membrane and extending above the membrane and around the catheter insertion site. The wall of the hub can include: a first opening configured to permit tubing connected to a catheter device coupled to a catheter to pass into the catheter housing; a first inlet configured to permit gas to flow to into the catheter housing; and a groove along at least a portion of an exterior facing side of the wall. The cover of the catheter housing can include: a main body; a port extending outward from the main body, the port configured to align with the first inlet of the wall and permit gas to flow into the catheter housing; a tongue located along an interior surface of the main body and configured to secure to the groove of the wall of the hub; a first opening in the main body, the first opening configured to permit the tubing connected to the catheter device to pass into the catheter housing; a lock configured to retain the catheter device within the catheter housing; and one or more wings extending outward from sides of the main body and curving in a direction towards the membrane of the hub, the one or more wings configured to secure the tubing connected to the catheter device. The catheter housing can further comprise a bridge positioned within the interior of the cover, the bridge configured to contact a portion of the catheter device and incline the catheter device. The bridge can be positioned closer to the catheter insertion site than the lock. The bridge can extend from an interior surface of the main body of the cover and comprise a recess sized and shaped to conform to a shape of a portion of the catheter device. The bridge can further comprise a stem and side walls extending away from the stem, wherein the stem comprises a recess sized and shaped to conform to a shape of a portion of the catheter device and the side walls comprise ends with surfaces inclined toward the recess of the stem. The catheter housing can further comprise a UV SMD LED configured to illuminate and sterilize areas within the catheter housing. The UV SMD LED can be electronically coupled to a sensor, the sensor configured to send a signal to the UV SMD LED when the tongue of the cover is secured to the groove of the wall of the hub. The UV SMD LED can be configured to automatically activate when receiving the signal from the sensor. The UV SMD LED can be located on an interior of the main body of the cover. The catheter housing can further comprise a physiological sensor configured to measure a physiological parameter of the patient. The physiological sensor can be positioned on a bottom surface of the membrane of the hub. The physiological sensor can be selected from the group consisting of a temperature sensor, a blood pressure sensor, a blood oxygen saturation sensor, a sensor for liquid and blood leakage, and a skin humidity sensor. The catheter housing can be substantially waterproof and shockproof. The cover can comprise a material selected from the group consisting of plastic, rubber, and silicon. The cover can comprise a transparent material. The cover can be configured to form a hermetic seal around the catheter insertion site when the tongue of the cover is secured to the groove of the wall of the hub. The cover can comprise a shape selected from the group consisting of trapezoidal, rectangular, square, oval, and circular. The hub can comprise a material selected from the group consisting of plastic, rubber, and silicon. The wall of the hub can be rounded. The main body of the cover can have a first side and a second side opposite the first side, and wherein the one or more wings comprise a first wing on the first side of the main body and a second wing on the second side of the main body. The wall of the hub can comprise a joint proximate to the first opening of the wall, the joint configured to be flexibly opened and closed to permit the tubing connected to the catheter device to be inserted into the catheter housing. The membrane of the hub can comprise one or more indicators proximate to the catheter insertion site. The membrane can be configured to form a hermetic seal around the insertion site when the hub is secured to the patient. The membrane of the hub can comprise a top surface and a bottom surface, wherein the bottom surface is configured to contact the patient when the hub is secured to the patient. The bottom surface of the membrane of the hub can at least partially comprise an anti-slip material configured to secure to the patient. The bottom surface of the membrane of the hub can comprise a lip extending outward from the bottom surface and configured to contact skin of the patient. The catheter housing can further comprise at least one light configured to illuminate a region proximate to the catheter housing device. The port of the cover can comprise a threaded portion configured to secure to a gas tube. The wall of the hub can be a stadium wall. The lock can comprise a recess shaped to receive a portion of the catheter device. The lock can be arch-shaped. The hub can comprise a front portion and a back portion opposite to the front portion, and wherein the front portion has a height that is greater than a height of the back portion. The height of the hub can taper from a front portion of the hub to a back portion of the hub. The cover can comprise a front portion and a back portion opposite to the front portion, and wherein the front portion has a height that is greater than a height of the back portion. The height of the cover can taper from a front portion of the hub to a back portion of the cover.

While certain aspects, advantages and novel features of embodiments of the invention are described herein, it is to be understood that not necessarily all such advantages can be achieved in accordance with any particular embodiment of the invention disclosed herein. Thus, the invention disclosed herein can be embodied or carried out in a manner that achieves or selects one advantage or group of advantages as taught herein without necessarily achieving other advantages as can be taught or suggested herein.

BRIEF DESCRIPTION OF THE DRAWINGS

Embodiments disclosed herein are described below with reference to the drawings. Throughout the drawings, reference numbers are re-used to indicate correspondence between referenced elements. The drawings are provided to illustrate embodiments of the inventions described herein and not to limit the scope thereof.

DETAILED DESCRIPTION

Figure 1A:
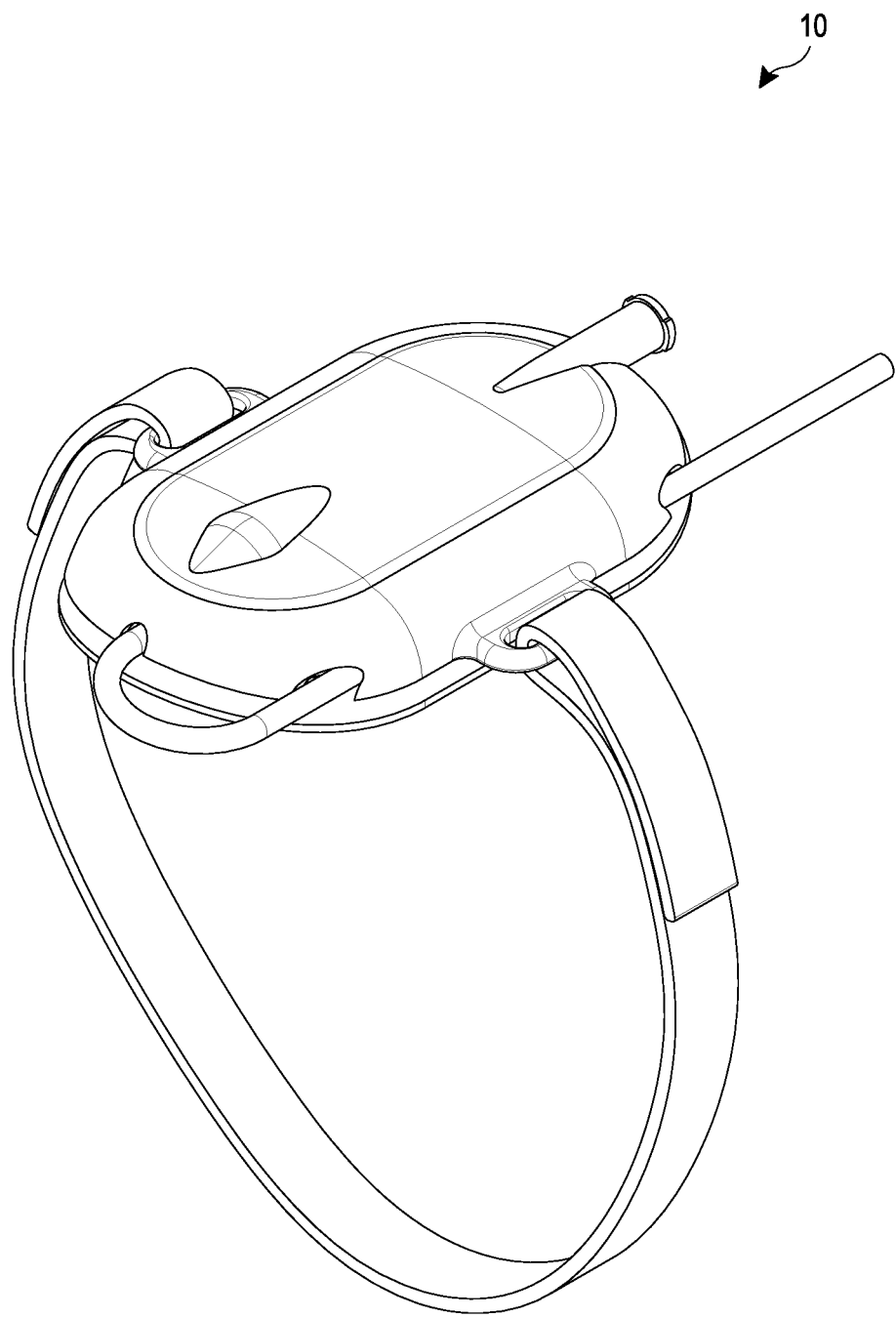
FIG. 1A illustrates a perspective view of an assembly of a catheter housing in accordance with aspects of this disclosure.

Although certain embodiments and examples are disclosed herein, inventive subject matter extends beyond the examples in the specifically disclosed embodiments to other alternative embodiments and/or uses, and to modifications and equivalents thereof. Thus, the scope of the disclosure is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures, systems, and/or devices described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

The catheter housings described herein can stabilize a catheter device coupled to a catheter, a catheter, and/or tubing connected to the catheter device, without applying adhesive directly to the catheter, catheter device, and/or tubing. As discussed above, this can advantageously prevent potential contamination that often results from the use of tapes or other adhesives in such manner. Moreover, because the catheter, catheter device coupled to the catheter, and/or tubing connected to the catheter device can be stabilized by the housings discussed herein without covering the same with tape, the catheter insertion area can remain readily visible to a caregiver. As discussed above, such visibility allows the care giver to easily, quickly, and repeatedly assess the insertion site for signs of inflammation, failure, and/or or infection.

The catheter housings described herein can physically and/or mechanically isolate the catheter, catheter device coupled to the catheter, and/or tubing connected to the catheter device from patient movement and can hold the catheter (and/or catheter device and/or tubing) at a proper insertion angle and/or limit the angling of the catheter device coupled to the catheter. The disclosed catheter housings can also provide a securement system that is highly breathable, allowing for patient comfort and reduced skin irritation and/or skin trauma, for example. The catheter housings described herein can stabilize catheter, catheter device coupled to the catheter, and/or tubing connected to the catheter device, without applying pressure directly to the catheter, catheter device coupled to the catheter, and/or tubing connected to the catheter device. As discussed above, this can advantageously prevent damage to a vein when a catheter is positioned therewithin and/or damage to regions proximate to the catheter insertion site.

FIG. 1A illustrates a perspective view of a fully assembled catheter housing 10 that can be placed on and/or over any portion of a human body. For example, the catheter housing 10 can be secured to an arm or leg of a patient, and can be secured to the arm or leg with the use of an anti-slip material on a bottom surface of the catheter housing 10 (or hub or membrane of the hub) around the insertion site and/or with the use of one or more fastening straps as discussed below.

Figure 1B:
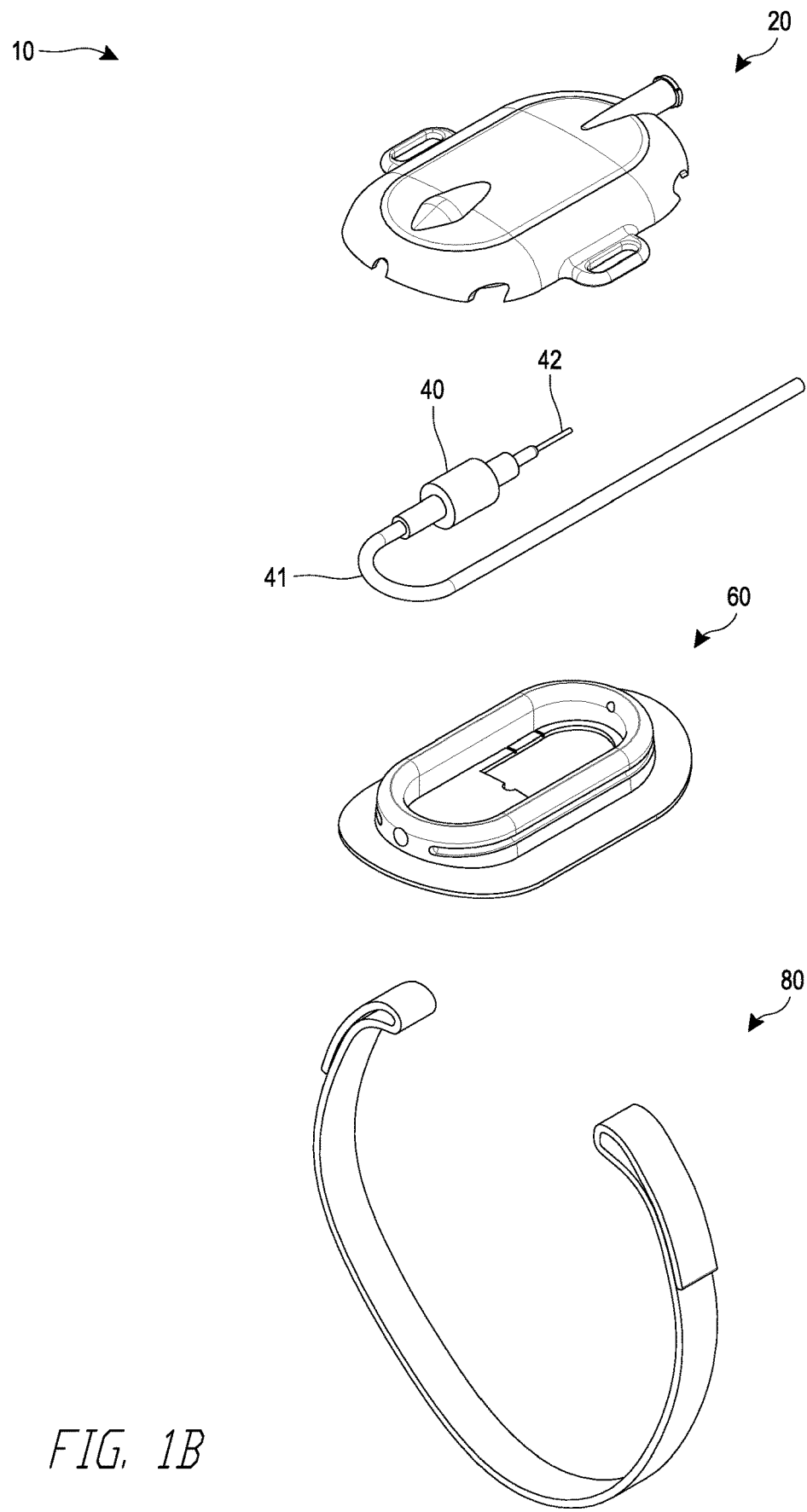
FIG. 1B illustrates an exploded view of the catheter housing of FIG. 1A in accordance with aspects of this disclosure.

FIG. 1B illustrates an exploded view of the catheter housing 10 of FIG. 1A. The catheter housing 10 can have a cover 20 and a hub 60. The cover 20 of the catheter housing 10 can have structure that enables one or more fastening straps 80 to couple with and/or secure to the cover 20 while also securing to a portion of a patient's body. As discussed herein, the catheter housing 10 can secure a catheter, catheter device coupled to the catheter, and/or tubing connected to the catheter device. For example, the catheter housing 10 can secure a catheter 42, catheter device 40 (also referred to herein as "catheter device 40") coupled to the catheter, and/or tubing 41 connected to the catheter device 40. One advantage of the catheter housing 10 is that it can comprise of small number of components or parts, which allow for simple assembly and securement of any type of catheter, catheter device, and/or tubing connected to a catheter device. While the catheter housing 10 discussed herein can include the cover 20 and hub 60 as separate components, the cover 20 and the hub 60 can comprise a unitary structure, and one of skill in the art will recognize that the features discussed herein with respective to the cover 20 and the hub 60 can be incorporated in some, many, or all respects into a unitary catheter housing. The catheter device 40 discussed herein can be any device that couples to a catheter cannula 42 and/or a fluid tube 41. The catheter device 40 can include one or more cylindrical portions which can directly couple to a catheter cannula 42 and/or a male luer connector. Such male luer connector can include a cylindrical ring which connects to the one or more cylindrical portions (for example, by surrounding an end of such portions) and a stem portion that secures to and/or surrounds an end of fluid tube 41, for example. Catheter housing 10 (and components thereof) can secure and/or interact with various sizes or styles of catheter devices 40 and portions thereof, such as those that are typical or commonplace in the field.

Figure 1C:
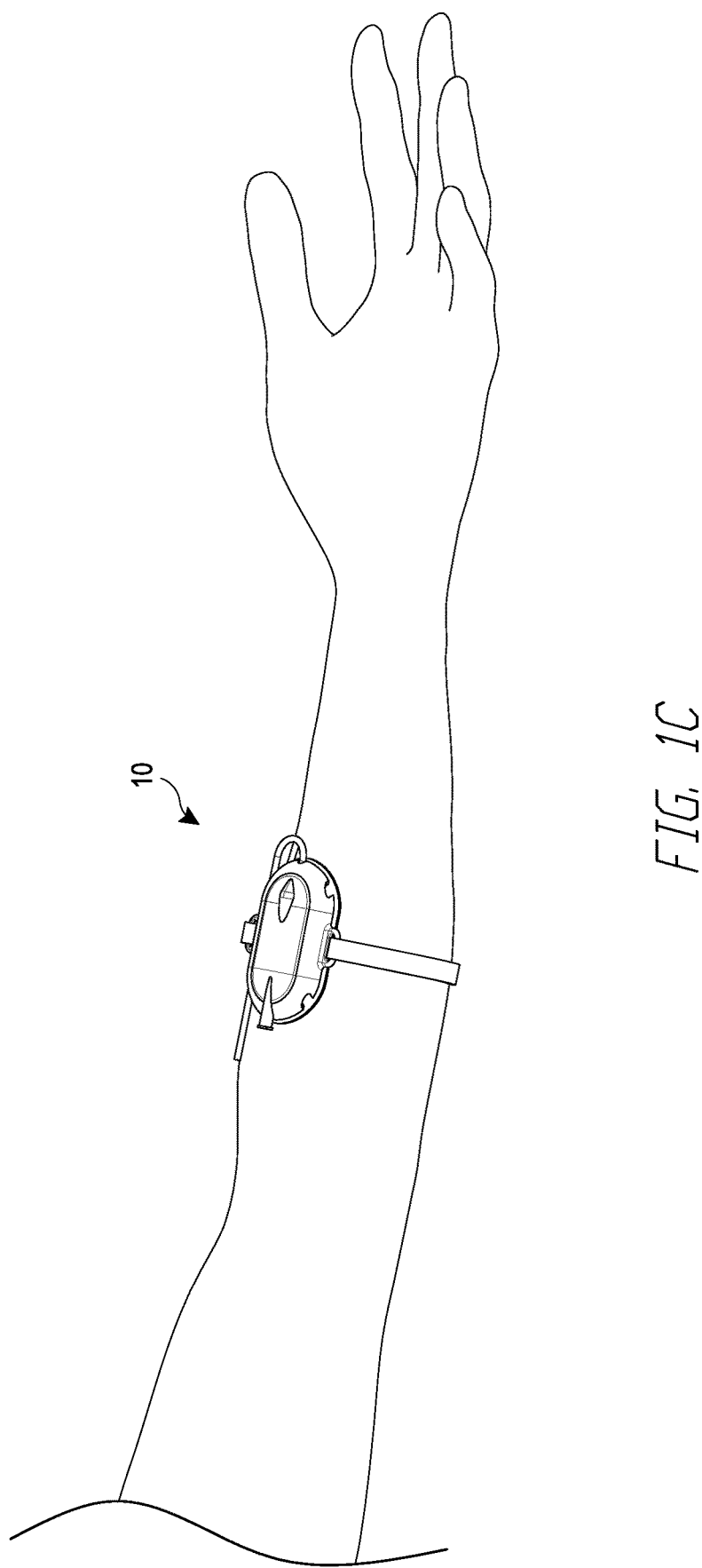
FIG. 1C illustrates a perspective view of the catheter housing of FIG. 1A in an assembled form on a human arm.

As discussed below, cover 20 can be secured to hub 60 and/or hub 60 can be secured to cover 20. As illustrated in FIGS. 1A and 1C, when catheter housing 10 is assembled, cover 20 can substantially surround or enclose hub 60 and/or a portion thereof. The hub 60 can have an opening in a wall of the hub 60 that allows catheter device 40 and/or tubing 41 to pass therethrough, fit within, and/or be inserted into an interior of the 60. The hub 60 can also have an opening in a membrane of hub 60 that allows a catheter 42 to be inserted into a patient while a catheter device 40 coupled to catheter 42 is secured to at least a portion of the catheter housing 10, such as the cover 20. The catheter housing 10 can secure to a patient with the use of an anti-slip surface, mechanism, ring, or protrusion on a bottom surface of the membrane of hub 60, as discussed below. Alternatively or additionally, catheter housing 10 can be secured to the patient using one or more fastening straps 80, as also discussed below. The catheter housing 10 can be integrally formed with one or more fastening straps 80. For example, the cover 20 can be integrally formed with one or more fastening straps 80, and/or the hub 60 can be integrally formed with one or more fastening straps 80. Alternatively, fastening straps 80 can be non-integral with cover 20.

FIG. 1C illustrates a perspective view of an assembled catheter housing 10 secured to a human arm. As discussed above, catheter housing 10 can also be attached to other locations on a human body, such as on a thigh, foot, calf, ankle, arm, leg, hand, and/or neck, among other body parts. For example, catheter housing 10 can be attached to various body parts and surround catheter insertion sites located in different regions on a human body, such as a portion of an underside of an arm, among other areas. The catheter housing 10 can be positioned and/or secured at and/or near any location where an IV can be inserted into a patient. While one or more fastening straps 80 can be used to secure the catheter housing 10 to a patient (for example, in cases where the fastening straps 80 are used to wrap around an arm), catheter housing 10 can secured to a portion of a patient's body without the use of a fastening strap 80. As discussed above, catheter housing 10 can include an anti-slip surface, mechanism, ring, or protrusion on a portion of the catheter housing 10 that can contact a patient.

As discussed herein, catheter housing 10 can be secured to a patient with the use of one or more fastening straps 80. For example, catheter housing 10 can have one, two, three, four, five, six, seven, eight, nine, or ten fastening straps 80. The one or more fastening straps 80 discussed herein can be made from a variety of material or combination of materials. For example, fastening straps 80 can comprise silicone, plastic, rubber, and/or fabric. Alternatively, fastening straps 80 can comprise appropriate biocompatible materials. Alternatively, fastening straps 80 can comprise medical grade soft silicone material. Additionally, fastening straps 80 can be substantially waterproof, durable, and/or washable. The one or more fastening straps 80 can contain information regarding a patient, such as name, birthdate, and other information. Information contained on the one or more fastening straps 80 can also be, for example, information relating to the catheter insertion and/or information relating to inspection by a caregiver. The one or more fastening straps 80 can include various securement means. For example, the one or more fastening straps 80 can comprise hook and loop fasteners, clips, buckles, fungi-like attachment, or other known attachment systems, or a combination of these attachment systems. For example, the one or more fastening straps 80 can include Velcro on a portion of the one or more fastening straps 80. Additionally or alternatively, the one or more fastening straps 80 can comprise an adhesive attachment system. For example, the one or more fastening straps 80 can secure to themselves via an adhesive material.

The various securement means of the one or more fastening straps 80 can allow the one or more fastening straps 80 to secure catheter housing 10 to a patient. For example, a fastening strap 80 can secure to itself and/or catheter housing 10. As discussed below, cover 20, 120 can include one or more strap hoops 22, 122 that can facilitate securement of the catheter housing 10 to a patient using the fastening straps 80. The cover 20, 120 can include, for example, one, two, three, four, five, or six strap hoops. For example, the cover 20 can include a first strap hoop on a first side of cover 20, 120 and a second strap hoop on a second side of cover 20, 120 opposite the first side. A fastening strap 80 can pass through the first strap hoop, secure to itself, wrap around a portion of a patient (such as an arm), pass through the second strap hoop and secure again to itself, using for example Velcro (see FIGS. 1A and 1C). Additionally or alternatively, the cover can have just one strap hoop and/or the fastening strap can secure to a portion of catheter housing 10 instead of having to loop through a second strap hoop of cover 20, 120. For example, the fastening strap 80 can pass through the first strap hoop, secure to itself, wrap around a portion of a patient, and secure to the hub 60, thus securing the catheter housing 10 to a patient. For example, the fastening strap 80 can be sized and or shaped depending on the patient's characteristics (for example, arm thickness).

Figure 2A:
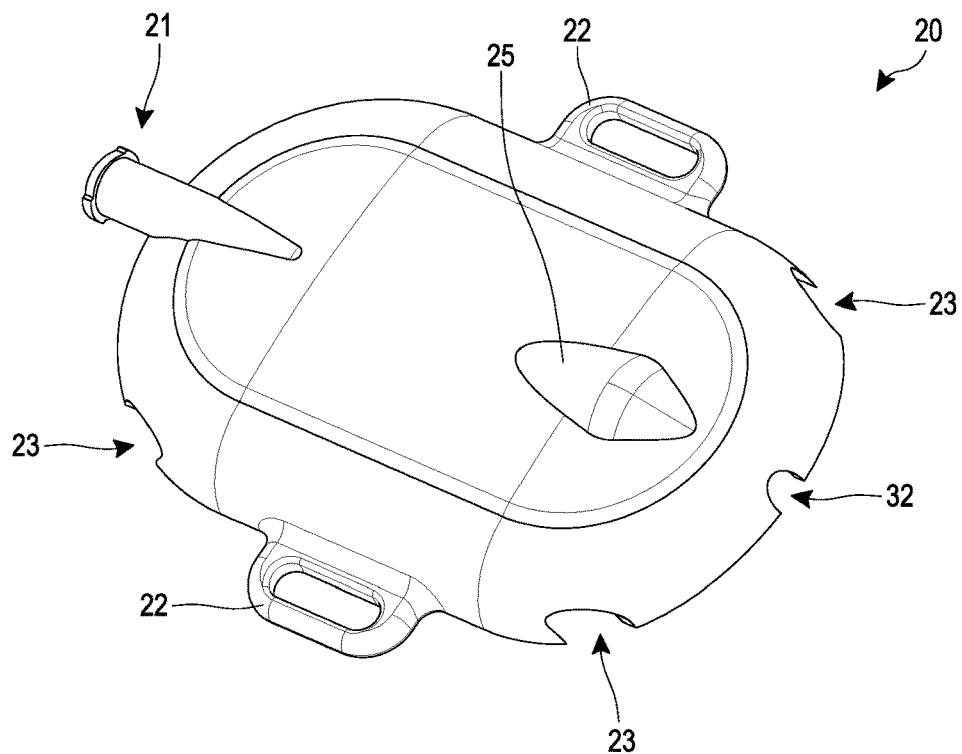
FIG. 2A illustrates a perspective view of a cover of the catheter housing of FIG. 1A.
Figure 2B:
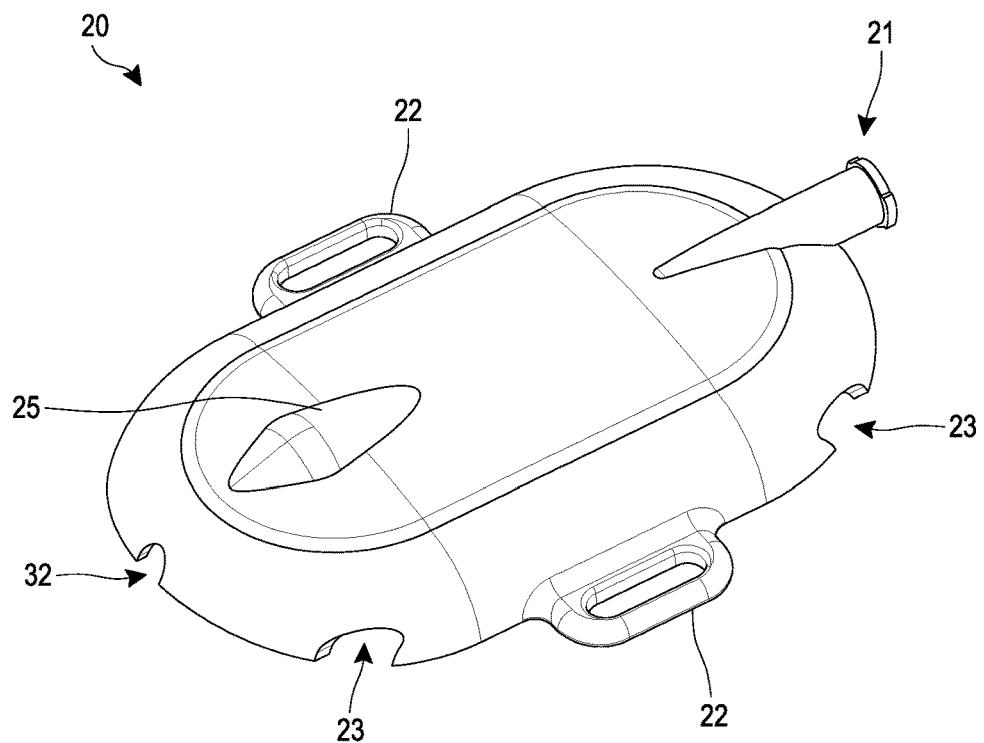
FIG. 2B illustrates another perspective view of the cover of FIG. 2A.

FIGS. 2A-2B illustrate various perspective views of cover 20. As discussed herein, cover 20 can be secured to the hub 60. The cover 20 can be made of transparent material. Alternatively, the cover 20 can be made of nontransparent material. Additionally, cover 20 can comprise both transparent and nontransparent material. For example, the portions of cover 20 can be made of transparent material where it is advantageous to be able to see through the cover in order to observe the other components of catheter housing 10, and/or observe, access, and/or inspect the puncture site without removing the catheter housing 10 or components thereof. The cover 20 can be made of substantially shockproof and/or durable material. This is advantageous because the catheter housing 10 and/or the cover 20 can be subjected to impact during installation or use. The cover 20 can also be made of substantially waterproof material. This is advantageous because the catheter housing 10 and/or the cover 20 can be subjected to water or other liquids when the device is in use. The cover 20 can comprise plastic, rubber, and/or silicone, among other materials, or a combination of such materials. The cover 20 can comprise of a soft, pliable material, such as medical grade silicone. Alternatively, the cover 20 can comprise harder silicone, or rubber can be used.

The cover 20 can be configured to form a closed environment over a site where an intravenous catheter is inserted into a patient. Such a closed environment can aid in keeping the site free from contamination, as discussed herein. As discussed above, the cover 20 can be made of at least partially transparent material so as to allow a caregiver or other person to examine the catheter insertion site and/or other portions of the catheter housing 10 (for example, the hub 60) while the cover 20 is secured to the hub 60.

The cover 20 can include one or more openings 32 to permit tubing 41 to fit within and/or pass through the cover 20 and into and interior of the cover 20, such as one or more, two or more, three or more, four or more, five or more, or six or more openings 32. For example, as discussed herein, such openings can align with one or more openings in the hub 60 (such as opening 65) that can allow tubing 41 to pass through the housing 10 and to a catheter device 40 when the catheter device 40 is secured to lock 26 of cover 20. The cover 20 can have a rounded shape. Alternatively, the cover 20 can have a non-round shape, for example, a rectangular shape. Alternatively, the cover 20 can be approximately trapezoidal, rectangular, square, oval and/or circular in shape, among other shapes. For example, where the catheter housing 10 includes a hub 60 and a wall 61 of the hub 60 shaped like a stadium, the cover 20 can have a shape that accommodates the stadium shape of wall 61. The cover 20 can comprise a single, continuous piece. Alternatively, the cover 20 can comprise more than one piece.

As illustrated in at least FIGS. 2A-2D, the cover 20 can have one or more ports 21, which can be used to insert sterilizing and/or anesthetic gas into the catheter housing 10. For example, the cover 20 can have one, two, three, four, five, six, seven, eight, nine, ten, eleven or more ports 21. The one or more ports 21 can be located on a side of the cover 20. Alternatively, the one or more ports 21 can be located on a top portion of the cover 20. The one or more ports 21 can be used to provide sterilization and/or antiseptic gases (among others), such as ethylene oxide gas, nitrogen gas, or other sterilizing, antiseptic, and/or anesthetic gases. For example, the cover 20 can include a port 21 for providing sterilizing gases, and a separate port for providing anesthetic gases. The one or more ports 21 can comprise an opening and a port rim. The opening of the port 21 can extend outwardly from the cover 20. The port rim can extend radially outward from the opening of the port 21. The port rim can be configured to secure to a portion of a gas tube in a snap-fit, a press fit, and/or a friction fit configuration. For example, the port rim can comprise a female Luer connector.

Figure 2C:
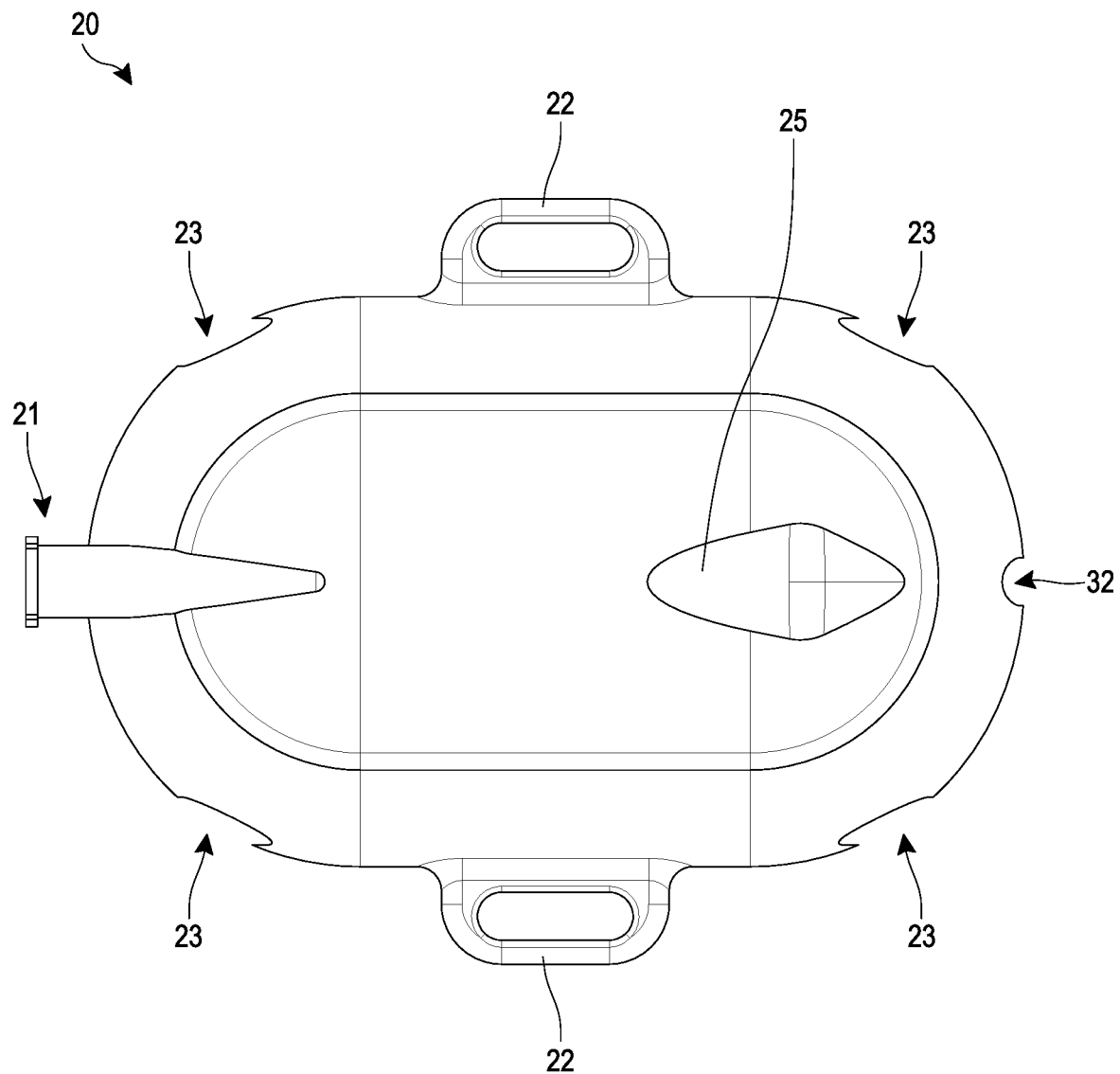
FIG. 2C illustrates a top view of the cover of FIG. 2A.
Figure 2D:
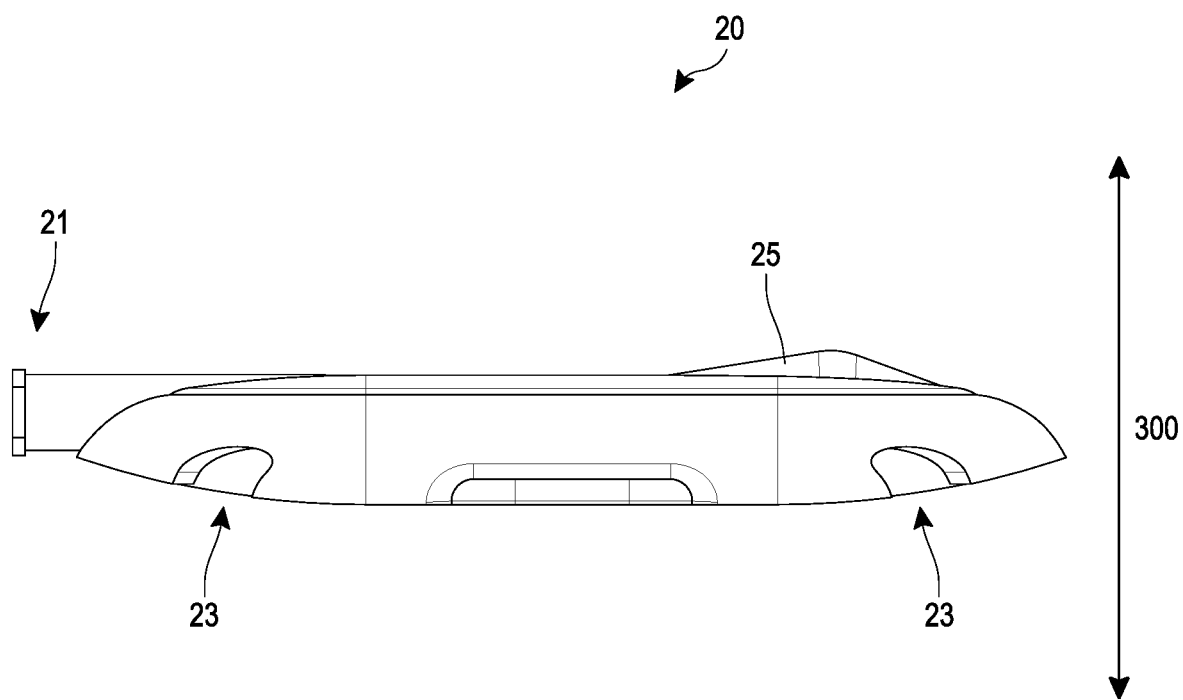
FIG. 2D illustrates a side view of the cover of FIG. 2A.

The one or more ports 21 can be substantially cylindrical, rectangular, or another shape. The one or more ports 21 can include a gas opening which permits sterilizing gas, anesthetic gas, or other gases, to flow into the catheter housing 10. The one or more ports 21 can include a port rim that extends at least partially around an exterior portion of the one or more ports 21. The port rim can extend radially outward from the one or more ports 21. The port rim can be located at an end of the one or more ports 21 (as shown in FIG. 2C) or, alternatively, at another region along the one or more ports 21. The one or more ports 21 can extend outwardly from the cover 20. The port rim can be configured to secure to gas tubes or other devices that provide gas to the catheter housing 10. For example, the port rim can contain one or more threads by which a gas tube or other device can screw into. Alternatively, the port rim can comprise a snap mechanism that can secure to a gas tube or other device, whereby a portion of such tube or other device can be configured to snap into or around the snap mechanism of the port rim. Other alternative methods of securing a gas tube or other device to the port rim of the one or more ports 21 exist. The one or more ports 21 can also include one or more valves, such as a control valve and/or a multi-valve.

Figure 4A:
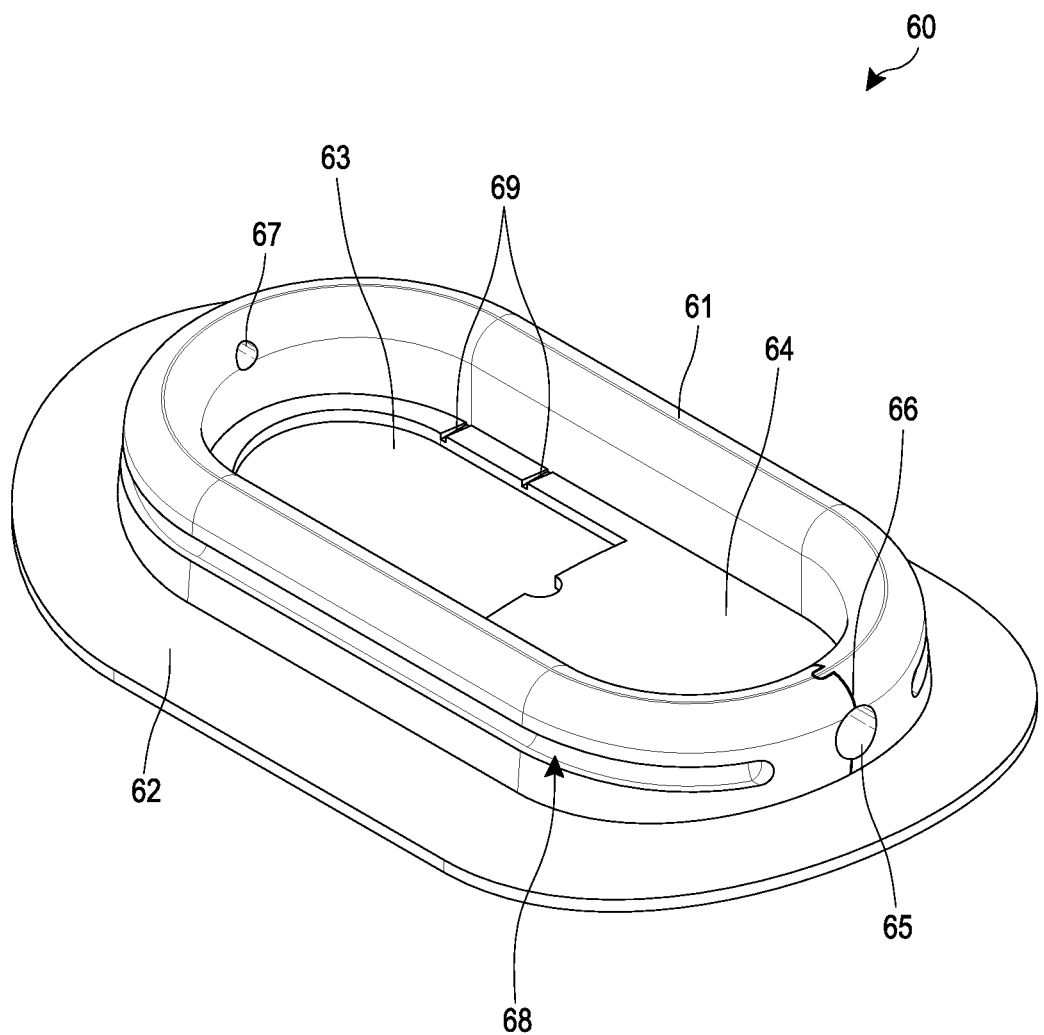
FIG. 4A illustrates a perspective view of a hub of the catheter housing of FIG. 1A.

The one or more ports 21 of the cover 20 can be configured to align with a gas inlet 67 of the hub 60 (see FIG. 4A). For example, when the cover 20 is secured to the hub 60, the one or more ports 21 of the cover 20 can align with the gas inlet 67 of a wall 61 of the hub 60 to allow gases to flow into the interior of the hub 60 and/or to the catheter insertion site.

The catheter housing 10, including the hub 60 and cover 20 discussed herein, can be coated with anti-microbial coating to aid with disinfection and/or sterilization near the catheter insertion site and/or in or around the catheter housing.

The cover 20 can include one or more slots 23 that can allow tubing 41 connected to the catheter device 40 to pass therethrough and be secured to a portion of the catheter housing 10. For example, as shown in at least FIG. 2J, when a catheter 42 and catheter device 40 are secured to the catheter housing 10 by, for example, the cover 20, tubing 41 connected to the catheter device 40 can pass through an opening in the cover 20, curve around a portion of the cover 20 and pass through one or more slots 23 in the cover. Such configuration can form a J-loop, for example, where the tubing 41 curves around a portion of the cover 40 after exiting an opening in the cover and passes through one or more slots on a side of the cover 20. In the configuration illustrated in FIG. 2J, the tubing 41 exits an opening in the cover 20, curves at an approximate 180 degree angle, passes through two slots 23 on the cover 20 and exits out in a direction opposite to the direction that the tubing 41 initially exited the cover 20. However, the cover 20 can have more than two slots 23, for example, the cover 20 can have four slots 23. In such cases, the tubing 41 can be configured to pass though more all four slots, wrap around substantially all of a portion of the cover 20 and, for example, exit out in a the same direction as the tubing 41 initially exited the cover 20. As discussed herein, the cover 20 can have one or more walls, such as an inner wall 29 and an outer wall 28. The one or more slots 23 can be disposed on the outer wall 28. In such configurations, the space between the inner wall 29 and the outer wall 28 can define an interior passage for the tubing 41 to pass through and/or be housed within. Placing a portion of the tubing 40 through such interior passage can provide the benefits discussed herein, such as mechanically decoupling the tubing 41 from the insertion site and/or the catheter device 40, for example.

Regardless of the placement and/or amount of the one or more slots 23, the one or more slots 23 can allow a caregiver to conveniently and safely wrap and/or secure the tubing 41 to the catheter housing 10. This can provide a number of advantages. The one or more slots 23 can allow the insertion site or portions of the catheter housing (such as the lock) to be mechanically decoupled from the tubing 41. Thus, if the tubing 41 gets pulled, caught, or snagged, the force will not affect the insertion site, catheter 42, catheter device 40, and/or portions of the catheter housing 10 (such as the lock 26). Such wrapping and/or securement of the tubing 41 to the catheter housing 10 can also reduce the likelihood that the tubing will get pulled or caught on clothing or other items. Such wrapping and/or securement can also prevent the tubing 41 from sticking out in a direction and/or area that is inconvenient for caregivers or physicians. For example, where a patient is undergoing surgery, many medical tools devices may be used during the surgery and doctors and nurses may be moving in and around areas nearby a catheter insertion site. In such cases, the one or more slots 23 can significantly reduce the "footprint" of the catheter housing 10 and/or tubing 41. This can reduce the likelihood that the tubing 41 will get tangled or will interfere with activities by such caregivers working in proximity to the catheter insertion site, even within a few feet from the site. The wrapping and/or securement of the tubing 41 to the catheter housing 10 can allow the tubing 41 to be essentially unified with the catheter housing 10, and can eliminate the need for a caregiver to secure the tubing 41 in a J-loop configuration with an adhesive applied directly to the patient's skin. The one or more slots 23 can provide securement for the tubing 41 without having the tubing 41 touch the patient's skin, increasing patient comfort and potential rashes or other skin irritation issues resulting from such contact. The one or more slots 23 also can provide securement to the tubing 41 which prevents the tubing 41 from getting pulled out and/or from impacting the securement of the catheter 42 and/or catheter device 40. For example, the one or more slots 23 can resist forces applied if the tubing 41 is moved and can significantly reduce or entirely eliminate the force applied to the catheter device 40 and/or catheter 42 if such movement occurs. This provides a significant advantage since significant damage can occur at the vein and/or the catheter insertion site in traditional devices and methods of catheter securement.

As illustrated in at least FIGS. 2A-2B and as discussed above, the cover 20 can include one more strap hoops 22 that can facilitate securement of the catheter housing 10 to a patient using the fastening straps 80. The cover 20 can include, for example, one, two, three, four, five, or six strap hoops. For example, the cover 20 can include a first strap hoop on a first side of the cover 20 and a second strap hoop on a second side of the cover 20 opposite the first side. A fastening strap 80 can pass through the first strap hoop, secure to itself, wrap around a portion of a patient (such as an arm), pass through the second strap hoop and secure again to itself, using for example Velcro (see FIGS. 1A and 1C). Additionally or alternatively, the cover can have just one strap hoop and/or the fastening strap can secure to a portion of the catheter housing 10 instead of having to loop through a second strap hoop of the cover 20. For example, the fastening strap 80 can pass through the first strap hoop, secure to itself, wrap around a portion of a patient, and secure to the hub 60, thus securing the catheter housing 10 to a patient.

The one or more strap hoops 22 can be sized and shaped to received a portion of a fastening strap 80. The one or more strap hoops 22 can comprise a loop, such as a rounded loop. The one or more strap hoops 22 can be circular, trapezoidal, rectangular, square, and/or oval. The one or more strap hoops 22 can have a width that is sized to accommodate a width of the fastening strap 80 and can have a depth that is sized to accommodate a thickness of the fastening strap 80. The one or more strap hoops 22 can have one or more slits configured to allow a fastening strap 80 to be inserted into the one or more strap hoops 22 by feeding a side of the one or more fastening straps 80 therethrough.

The cover 20 can have, for example, a first strap hoop 22 on a first side of the cover 20 and a second strap hoop 22 on a second side of the cover 20 that is opposite to the first side. The first strap hoop 22 can be aligned with the second strap hoop 22. The one or more fastening straps 80 can include an adhesive and/or a non-adhesive attachment that enables them to secure to themselves and/or to the catheter housing 10.

As discussed herein, the one or more strap hoops 22 and the one or more fastening straps 80 can be used to provide securement of the catheter housing 10 to the patient. The one or more strap hoops 22 and the one or more fastening straps 80 can fully seal the catheter housing 10 so that the catheter housing 10 is difficult if not impossible to take off by the patient. For example, depending on the location of the catheter housing 10 on the patient's body, the patient may only be able to utilize one hand in attempting to remove the catheter housing 10. In some situations, it can be advantageous to prevent a patient from removing a catheter from themselves. For example, patient's often wake up in a drowsy or non-cognizant state and attempt to remove catheters out of fear or confusion. Thus, utilizing the one or more strap hoops 22 and the one or more fastening straps 80 can advantageously prevent such behavior.

Figure 2E:
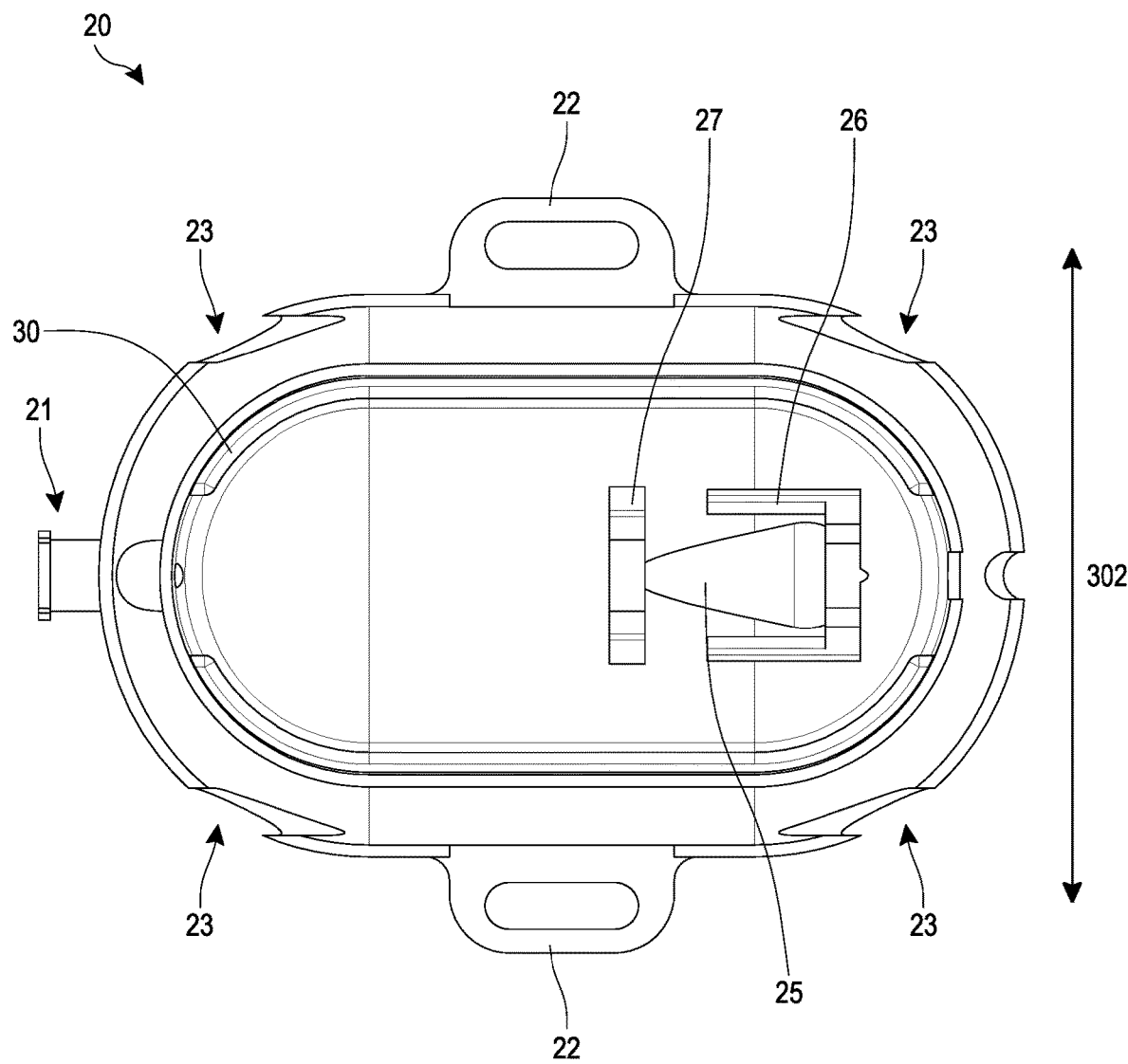
FIG. 2E illustrates a bottom view of the cover of FIG. 2A.
Figure 2F:
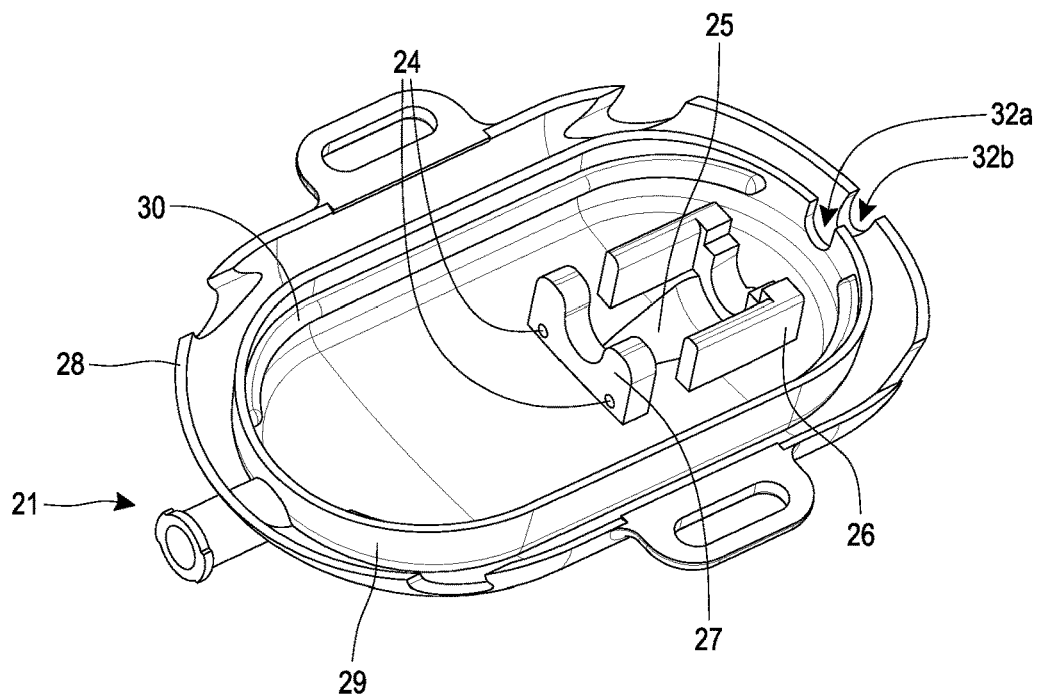
FIG. 2F illustrates a bottom perspective view of the cover of FIG. 2A.
Figure 2G:
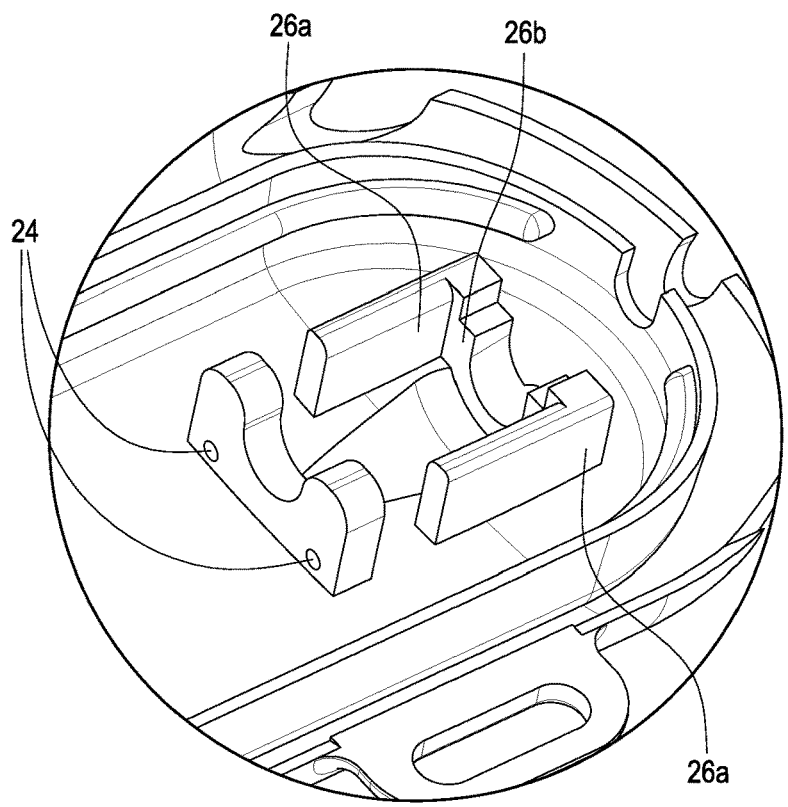
FIG. 2G illustrates a close-up bottom perspective view of the cover of FIG. 2A.
Figure 2H:
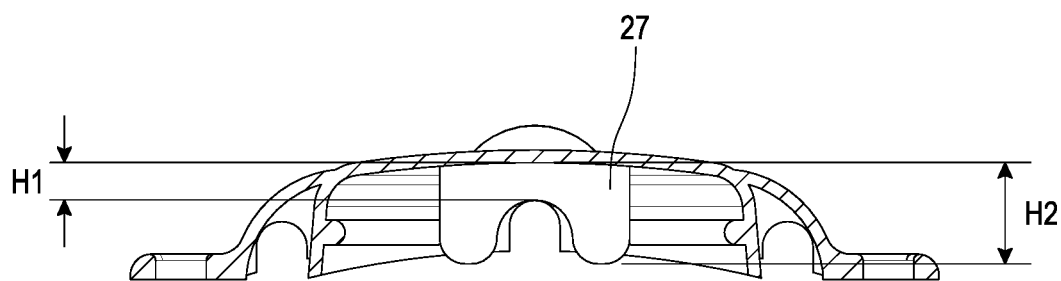
FIG. 2H illustrates a bridge of the cover of FIG. 2A.
Figure 2I:
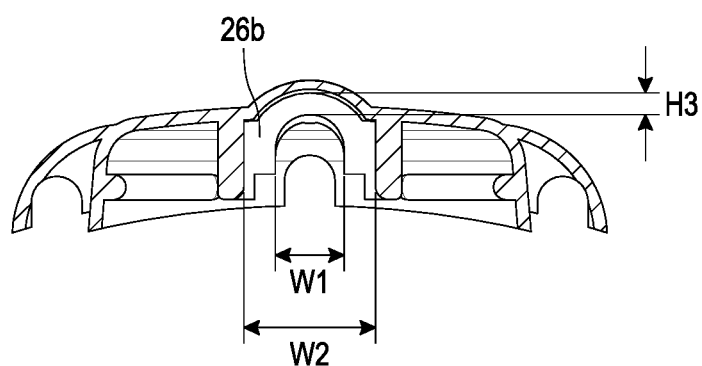
FIG. 2I illustrates a lock of the cover of FIG. 2A.
Figure 2J:
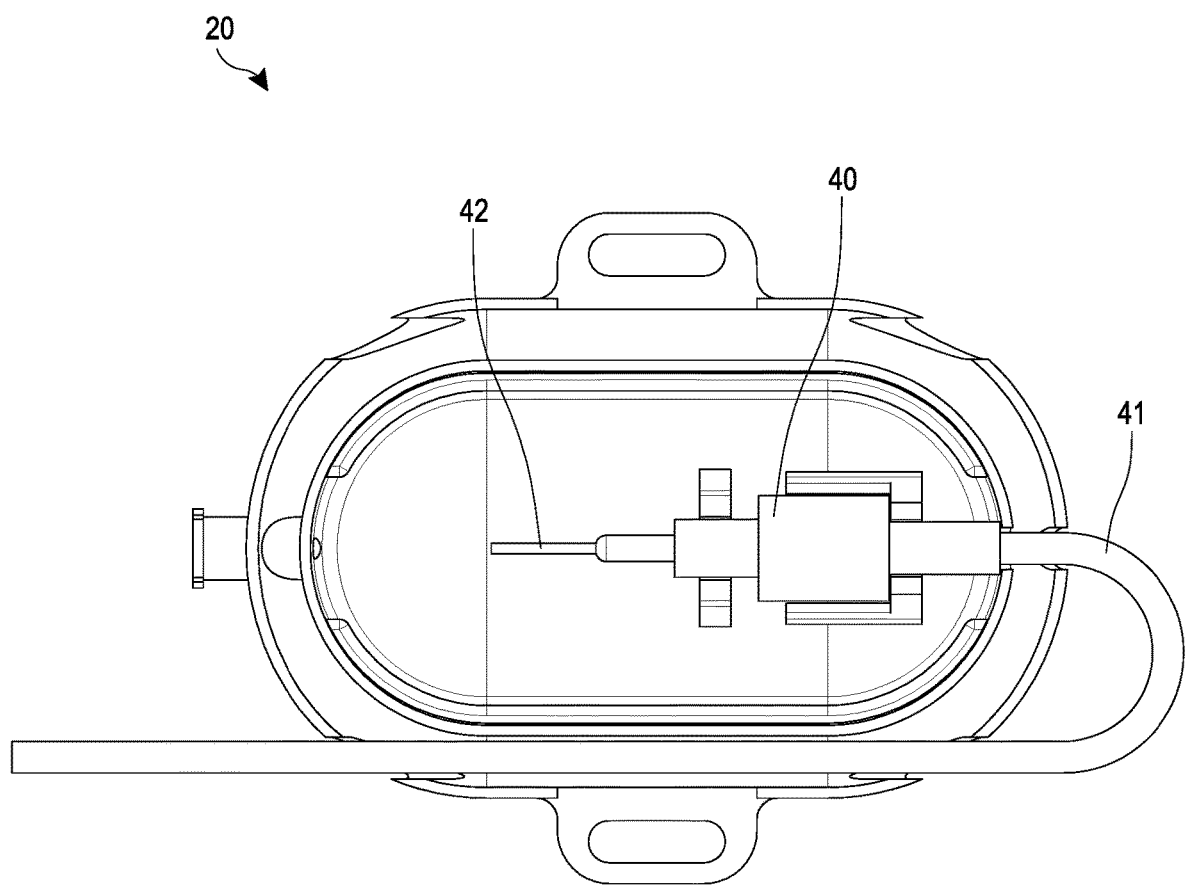
FIG. 2J illustrates a bottom view of the cover of FIG. 2A where a catheter device is secured to the lock of the cover of FIG. 2A in accordance with aspects of this disclosure.

As shown in FIGS. 2E-2F, the cover 20 can include one or more protrusions 30 (also referred herein as "tongues 30"). For example, the cover 20 can include one, two, three, four, or five or more protrusions 30. The one or more protrusions 30 can extend along an interior portion of the cover 20, for example. The one or more protrusions 30 can be located at a lower interior portion of the cover 20, or alternatively, the protrusion 30 can be located at a middle or higher interior portion of the cover 20. The one or more protrusions 30 can be substantially continuous, or alternatively, can be non-continuous, intermittent or exist in sections. The one or more protrusions 30 can extend from an interior of the cover 20. The one or more protrusions 30 can extending along substantially all of an interior of the cover 20. The one or more protrusions 30 can extend around an interior of the cover 20 and be continuous except at and/or near openings in the cover 20. For example, as shown in FIGS. 2E and 2J, the one or more protrusions 30 can comprise two protrusions 30 that extend along an interior of a first side of the cover 20 and an interior of a second side of the cover 20 and extend partially along a front side of the cover proximate to the region where tubing 41 exits the cover 20 when a catheter 41 and/or catheter device 40 is secured to the cover (for example with the lock 26) and extend partially along a back side of the cover 20 proximate to a port 21. Having the one or more protrusions 30 arranged in the configuration can provide strong securement between the cover 20 and the hub 60 when the protrusion 30 are secured to the groove 68 of the hub 60, while also not interfering with the operation and/or use of the lock 26, tubing 41, and/or port 21.

The one or more protrusions 30 can be configured to secure to a portion of the hub 60. For example, such securement can occur when the cover 20 is placed over and/or secure to the hub 60, whereby the one or more protrusions 30 can secure to one or more grooves 68 of the hub 60 (see FIG. 4A). The one or more protrusions 30 can secure to the one or more grooves 68 by a snap-fit, press fit, friction-fit, and/or other configuration for securely connecting the cover 20 to the hub 60. The surface of the one or more protrusions 30 can be rounded (see FIG. 2F). Such a rounded shape can advantageously help the one or more protrusions slide into the one or more grooves 68 of the hub 60 thus facilitating ease during securement.

Alternatively, the one or more protrusions 30 can be replaced with one or more interior grooves. For example, the one or more protrusions 30 can be replaced with one, two, three, four, or five, six, seven, or eight or more grooves. For example, the one or more protrusions 30 can be replaced with two grooves extending along an interior surface of the cover 20 that are adjacent to one another and/or atop each other. For example, the one or more protrusions 30 can be replaced with one groove. Such interior grooves can secure to at least a portion of the hub 60. For example, such interior grooves can secure to a protrusion appearing on the hub 60. Such securement can occur by a snap-fit, press fit, friction-fit, and/or other configuration. Thus, the cover 20 can secure to the hub 60 by insertion of a protrusion located on the cover 20 into a groove located on the hub 60, and/or by accepting a protrusion located on the hub 60 into a groove located on the cover 20.

In some configurations, a seal is formed such that the cover 20 does not allow external air and/or contaminants from entering the enclosed internal volume of the catheter housing 10. For example, the cover 20 can engage the hub 60 to form a closed and/or isolated atmosphere, which encloses the insertion site. In such configurations, the catheter insertion site can advantageously be sterilized by inert gas as described above. Similarly, the cover 20 can advantageously help to inhibit or prevent microbe contaminate and help to lower contamination vulnerability. The cover 20 can also be configured to prevent the joint 66 (See FIG. 4A) from separating while the catheter housing 10 is in use.

The cover 20 can comprise one or more walls. For example, the cover can comprise one, two, three, four, or five walls. As shown in FIGS. 2E-2L, the cover 20 can have two walls. For example, the cover 20 can have an outer wall 28 and an inner wall 29. As shown, the one or more protrusions 30 can be located on an interior surface of the inner wall 29 of the cover 20. As also shown, the one or more slots 23 discussed above can be located on the outer wall 28. The dual wall design can provide a number of advantages. For example, the inner wall 29 of the cover 20 can secure to the hub 60 and the space between the inner wall 29 and the outer wall 28 can accommodate the tubing 41, which can provide the advantages discussed above. Further, the tubing 41 can be secured in this space while the inner wall 29 securement to the hub 60 can provide a seal (such as a hermetic seal) around the catheter insertion site. When the cover 20 is secured to the hub 60 via the one or more protrusions 30 of the inner wall 30, the outer wall 28 can rest on a portion of the hub 60, for example, the membrane of the hub 60. For example, as shown by FIG. 1A, a bottoms surface of the outer wall 28 can be flush with a top surface of the membrane of the hub 60. Thus, where tubing 41 is secured through the one or more slots 23 of the cover 20, the tubing 41 can be enclosed by the inner wall 29, outer wall 28, and the membrane of the hub 60. As discussed above, the cover 20 can have one or more strap hoops 22 that can be used along with one or more fastening straps 80 to secure the catheter housing 10 to a patient. The one or more strap hoops can have a bottom surface that is flat or substantially flat (see FIG. 2F, for example). This can ensure that the one or more strap hoops 22 are flush with a top surface of the membrane of the hub 60 when the cover 20 is secured to the hub 60 and/or the catheter housing 10 is secured to a patient. The one or more fastening straps 80 can ensure little or no movement of the cover 20 and/or the hub 60. Additionally or alternatively, as discussed herein the catheter housing 10 can include anti-slip material, such as on a bottom surface of catheter housing 10, which can ensure little or no movement of the cover 20 and/or the hub 60. Additionally or alternatively, as discussed herein the catheter housing 10 can include anti-slip material, such as on a bottom surface of catheter housing 10, which can ensure little or no movement of the cover 20 and/or the hub 60. Thus, the catheter housing 10 and the components secured thereto (for example, the catheter 42, catheter device 40, and tubing 41) can be firmly secured to a patient.

As shown in FIGS. 2E-2F, the cover 20 can have a port 21 on a side of the cover 20, such as a front side of the cover 20. The port 21 can extend outwardly from the front side of the cover 20 and can extend through the outer wall 28 and inner wall 29 of the cover 20. This can enable gases flowing through the port 21 to enter an interior of the catheter housing 10, as discussed above.

As discussed above, the cover 20 can have one or more openings 32 to permit tubing 41 to pass through the cover 20 and into the interior of the cover 20. As shown in FIGS. 2F and 2G, the inner wall 29 and the outer wall 28 can have openings 32*a*, 32*b* that allow tubing 41 connected to the catheter device 40 to exit the cover 20. The openings 32*a*, 32*b* can be proximate to a lock 26 discussed herein. The openings 32*a*, 32*b* can align with a recess in a back wall 26*b* of the lock 26. This can allow tubing 41 connected to a catheter device 40 to maintain a straight configuration from a region of the tubing 41 extending from the catheter device 40 and to the openings 32*a*, 32*b*. The openings 32*a*, 32*b* can be sized and shaped to accommodate various sizes and/or shapes of tubing 41.

The cover 20 can include a lock 26 that can secure the catheter device 40, catheter 42, and/or tubing 41 connected to the catheter device before, during, and/or after a catheter 42 is inserted into a patient at an insertion site. The lock 26 can include one or more walls configured to secure to a catheter device 40 or a portion thereof. For example, the lock 26 can include one, two, three, four, five, six, seven, or eight walls configured to secure to a catheter device 40 or a portion thereof. As shown by FIGS. 2F-2G, the lock 26 can include two side walls 26*a* and a back wall 26*b*. The side walls 26*a* can be sized, shaped, and/or oriented to accommodate and/or secure to portions of catheter devices 40 of any size and/o shape. The side walls 26*a* can be parallel or substantially parallel. Alternatively, the side walls 26*a* can be nonparallel. The side walls 26*a* can be rounded, curved, circular or partially circular, among other shapes. The side walls 26*a* can be spaced to accommodate various sizes of catheter devices 40. For example, the side walls can be spaced in order to accommodate various diameters of cylindrical catheter devices 40 or portions thereof. The side walls 26*a* can have exterior surfaces which face the inner wall 29 of the cover 20 and can have interior surfaces which face towards each other and/or contact the catheter device 40 when the catheter device 40 is secured by the lock 26. The interior surfaces of the walls 26*a* can be straight. Alternatively, the interior surfaces of the walls 26*a* can be curved or partially curved to conform to a portion of a catheter device 40. The interior surfaces of the walls 26*a* can be shaped to surround or partially surround a portion of a catheter device 40. The interior surfaces of the side walls 26*a* can have a smooth surface which can enable the catheter device 40 to slide and fit between the side walls 26*a* easily. Alternatively, interior surfaces of the side walls 26*a* can have a rough surface which can provide more frictional resistance. The interior surfaces of the side walls 26*a* can have a combination of smooth and rough surface. The side walls 26*a* can prevent sideways movement, micro-movement, and/or erosion of the catheter device 40 (or a portion thereof) when the catheter device 40 is secured to the side walls 26*a*.

Figure 2K:
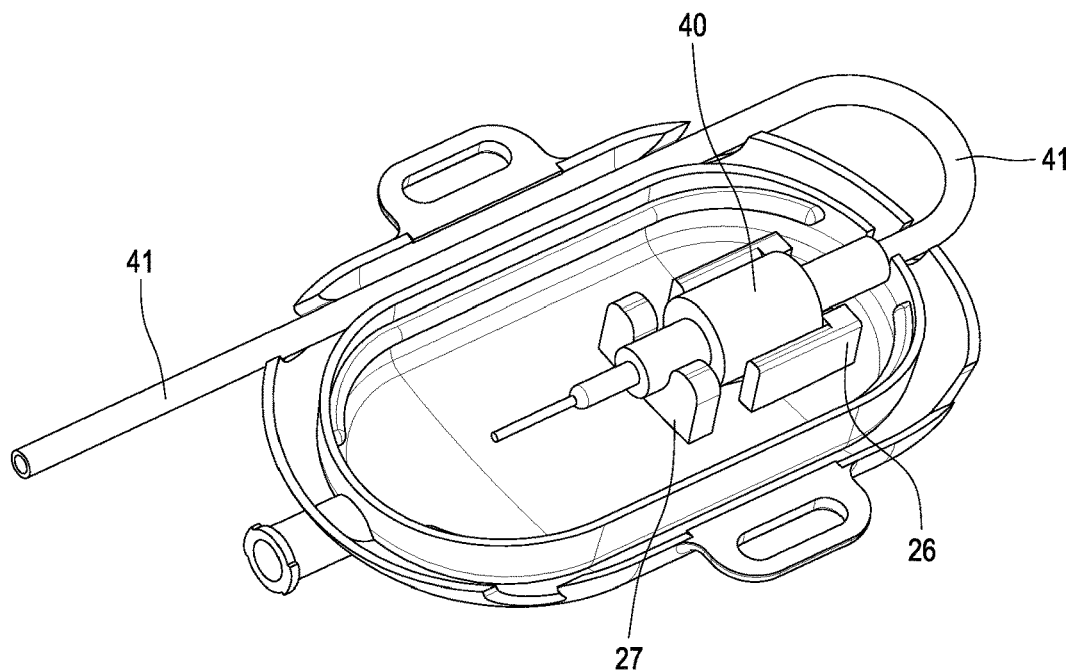
FIG. 2K illustrates a bottom perspective view of the cover of FIG. 2A where a catheter device is secured to the lock of the cover of FIG. 2A in accordance with aspects of this disclosure.
Figure 2L:
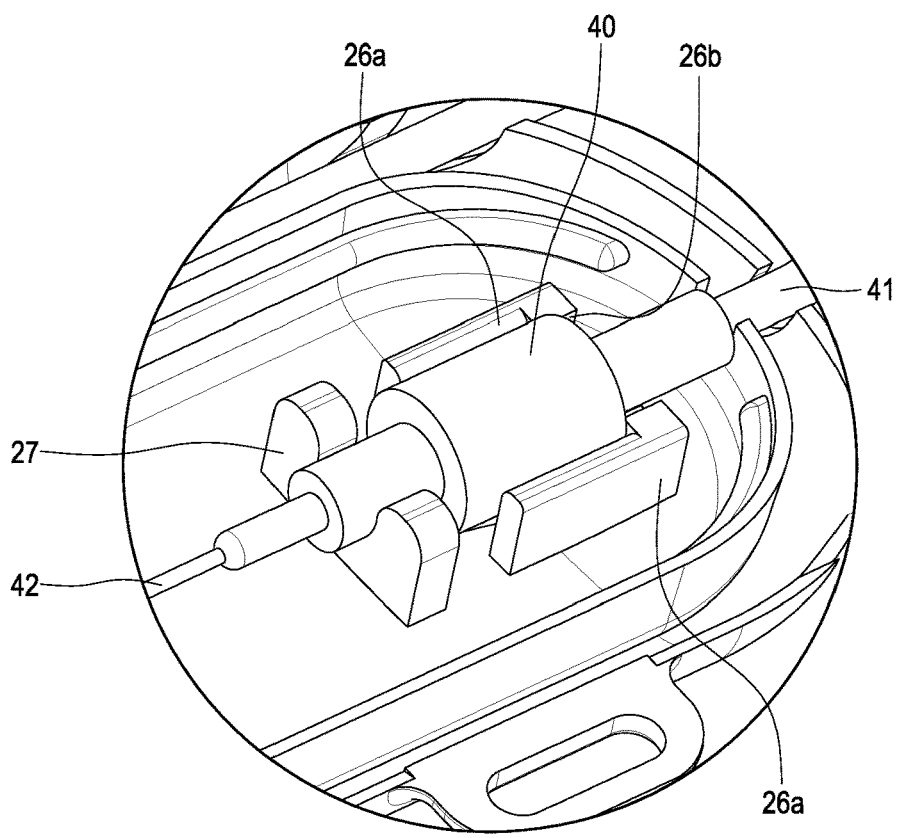
FIG. 2L illustrates a close-up bottom perspective view of the cover of FIG. 2A where a catheter device is secured to the lock of the cover of FIG. 2A in accordance with aspects of this disclosure.

The back wall 26*b* of lock 26 can be sized and/or shaped to accommodate the catheter device 40 or a portion thereof, tubing 41, as shown by FIGS. 2K-2L. The back wall 26b of lock 26 can be sized and/or shaped to accommodate connectors, extensions, adapters, and/or male luers or portions thereof, among others for example. For example, as shown in FIGS. 2G-2L, the back wall 26b can have a recess with a width W1 that is sized and shaped to accommodate and/or secure to a portion of a male luer connector (such as a portion of a male luer connector that directly connects and/or surrounds a portion of an end of tubing 41). FIG. 2I illustrates a front view of the lock 26 and also illustrates the recess of the back wall 26b. The recess can be rounded. Alternatively, the recess can be non-rounded. The recess can be circular. Alternatively, the recess can be non-circular. The recess can comprise a half-moon shape (see FIG. 2I), or another shape. The recess can comprise a half-circle shape. The back wall 26b can have a width W2 that is greater than the width W1 of the recess. This can advantageously prevent the catheter device 40 (or a portion thereof) from being dislodged when tubing 41 is pulled. For example, where the catheter device 40 is secured to the lock 26, if the tubing 41 is pulled, the remaining portion of the back wall 26b between width W1 and width W2 can act to support a side or end of the catheter device 40 (such as a side and/or end of a male luer connector) so that the catheter device 40 does not move or become dislodged.

The securement of catheter 42, catheter device 40, and/or tubing 41 by or with the lock 26 can be a physical locking, holding, stabilizing without locking, retaining, stabilizing to prevent or reduce the likelihood of movement, stabilizing to minimize movement, or another type of securement. The lock 26 can be sized and/or shaped to secure any type of catheter 42, catheter device 40, and/or tubing 41. For example, a catheter device 40 can be secured by a first wall 26a, a second wall 26a, and a back wall 26b. The lock 26 can secure catheter device 40 and a catheter 42 coupled to the catheter device 40 in a proper orientation relative to the patient's skin and/or the catheter insertion site. This can advantageously enable a catheter tip or rim to be secured at a final resting angle or inclination angle that approximates the angle at which a needle is inserted into a vein of a patient. As discussed previously, this is beneficial because it reduces the chance of injury and/or other complications that can result when the catheter moves or is secured at an angle that damages the vein wall or nearby area. For example, the final resting angle or inclination angle can be between 1 and 45 degrees. The inclination angle can also be between 1 and 10 degrees, between 10 and 20 degrees, or between 20 and 30 degrees. The inclination angle can be more than 45 degrees as well, depending on the implementation of the catheter housing 10 or components thereof (such as the cover 20 and/or hub 60). The inclination angle can also be at a very small angle, such as between 0 and 1 degrees. Current techniques for securing a catheter to a patient can result in dislodgment, inappropriate angle of the catheter, or twisting or other movement while the catheter is inserted into a patient. However, the lock 26 described herein, which can accommodate any type of catheter device design and/or catheter coupled thereto, can secure the catheter device and catheter in a position that provides for a normal or optimal angle. This can help to limit or prevent irritation and/or cannula tip erosion caused by contacting of the cannula tip with vein lumen sides. Thus, unlike conventional catheter stabilization methods where securing the catheter typically results in disrupting the natural angle of the catheter, awkward angling of the catheter against the wall of the vein, and/or in which pressure is applied on the a portion of the catheter device 40 in order to secure it to a patient, the securement angle of the catheter device 40 and/or catheter 42 with the lock 26 can preserve the integrity of the connection of the catheter 42 within the vein.

The cover 20 can include a bridge 27 that can help secure, guide, and/or align the catheter device 40 and catheter 42, fluid tube 41, and/or other devices or components connected thereto (such as other adapters or connectors). The bridge 27 can extend from a top interior portion of the cover 20. The bridge 27 can extend a distance from the top interior of the cover 20 a distance equal or substantially equal to a distance that the lock 26 extends from the top interior of the cover 20. Alternatively, the bridge 27 can extend a distance from the top interior of the cover 20 a distance unequal to a distance that the lock 26 extends from the top interior of the cover 20.

The bridge 27 can be positioned proximate to the lock 26 along an interior portion of the cover 20. For example, the bridge 27 can be positioned proximate to the lock 26 and can be closer to catheter insertion site than the lock 26. The bridge 27 can comprise a recess that is sized and/or shaped to accommodate a portion of the catheter device 40. For example, the bridge 27 can have a recess that can accommodate a tip or end of a portion of the catheter device 40 (for example, a cylindrical portion of catheter device 40 as shown in FIG. 2J). The recess of the bridge 27 can be smooth, or alternatively, can be rough. The recess of the bridge 27 can be rounded. The recess of the bridge 27 can comprise a half-moon, half-circle shape, half-square, half-rectangle, or other shapes, for example. The bridge 27 can have a height H1 (extending from a top interior surface of the cover 20) at the recess that is less than a height H2 at a non-recessed portion of the bridge 27. The height H1 can be equal or unequal to a height H3 of the recess of the back wall 26b of the lock 26. For example, the height H1 of the bridge 27 recess can be greater than the height H3 of the recess of the back wall 26b. This can allow a tip of the catheter device 40 to be inclined at a natural inclination angle when the catheter device 40 is secured by the lock 26. This can also enable the bridge 27 to push a portion of the catheter device 40 down to properly position the catheter device 40 and connected catheter 42 when the cover 20 is placed over the catheter device 40 and/or over the hub 60. The bridge 27 can also prevent the lifting, flattening, or inclining of the catheter device 40 and catheter 42 when the catheter housing 10 secures the catheter device 40, catheter 42, and/or tubing 41. The bridge 27 can also prevent the catheter device 40 and catheter 42 from straightening out, moving away from the catheter insertion site, and/or rotating about the lock 26.

The catheter housing 10 can secure a catheter device 40 connected to a catheter 42 without contacting the catheter 42. For example, as shown in FIGS. 2J-2L, the lock 26 and/or bridge 27 can secure one or more portions of the catheter device 40 without touching or contacting the catheter 42. This can advantageously limit prevent or limit movement of the catheter 42 when inserted within a patient's vein. This in turn can prevent or limited problems associated with such movement discussed above (for example, damage to the patient's vein and/or to the catheter insertion site and areas nearby). Additionally, as also shown by these figures, when the catheter device 40 (or one or more portions thereof) is secured by the lock 26, bridge 27, and/or other components of housing 10 (such as an interior surface of cover 20), the catheter 42 can be straight (for example, not bent, not kinked, not twisted, not wrapped, and/or not contorted). This can advantageously ensure that the catheter 42 is able to deliver fluids appropriate to the patient.

As shown in FIGS. 2A-2G, the cover 20 can have a recess 25 sized and shaped to accommodate a portion of the catheter device 40 when the catheter device 40 is secured by the lock 26. The recess 25 can be located between the two sidewalls 26a of the lock 26, for example. The recess 25 can be located between the two sidewalls 26a and the back wall 26b of the lock 26 and the bridge 27. The surface of the recess 25 can be smooth or alternatively rough. The surface of the recess 25 can be rounded, or alternatively non-rounded. The surface of the recess can be shaped to accommodate a cylindrical portion of a catheter device 40. The recess 25 can be conical, as shown in FIG. 2A-2B, for example. For example, the recess 25 can comprise a conical groove for fitting a rear part of a male Luer spiral connector of a catheter device 40. As another example, the recess 25 can comprise a dome shape, arc shape, or another shape for fitting a rear part of a male Luer spiral connector of a catheter device 40.

The recess 25 can taper from a first end to a second end. For example, the recess 25 can taper from a first end at or proximate to the back wall 26b of the lock 26 to a second end at or proximate to the bridge 27. The tapering of the recess 25 can conform to the size and or shape of the catheter device 40 or a portion thereof as the catheter device 40 is angled towards the catheter insertion site. For example, as discussed above, the lock 26 and/or the bridge can secure, align, and/or position the catheter device 40 so that the catheter 42 remains inserted into the patient at a natural or appropriate angle. As such, the catheter device 40 can be inclined while secured to the lock 26 and/or bridge 27. The recess 25 of the cover 20 can taper along a vertical axis 300 (see FIG. 2D) and/or taper along a horizontal axis 302 (see FIG. 2E) according to the position of the catheter device 40 when secured by or with the lock 26 and/or the bridge 27. This can advantageously minimize the overall height of the cover 20 in areas of the cover 20, for example, other than the recess 25.

Figure 3A:
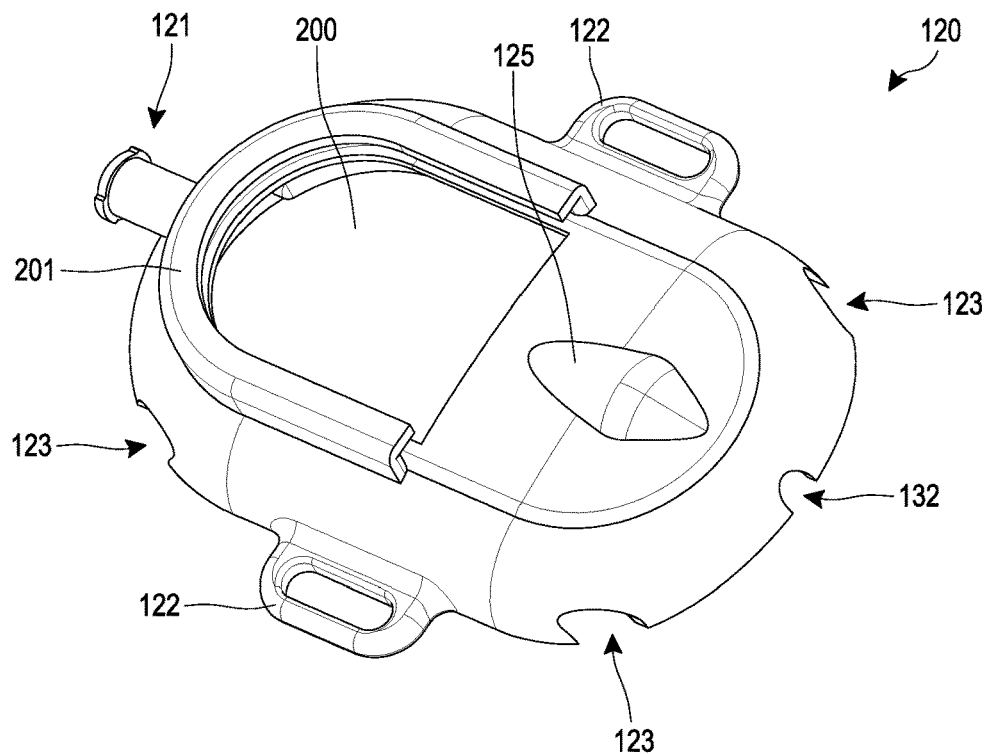
FIG. 3A illustrates a perspective view of an alternative design for a cover of the catheter housing of FIG. 1A.
Figure 3B:
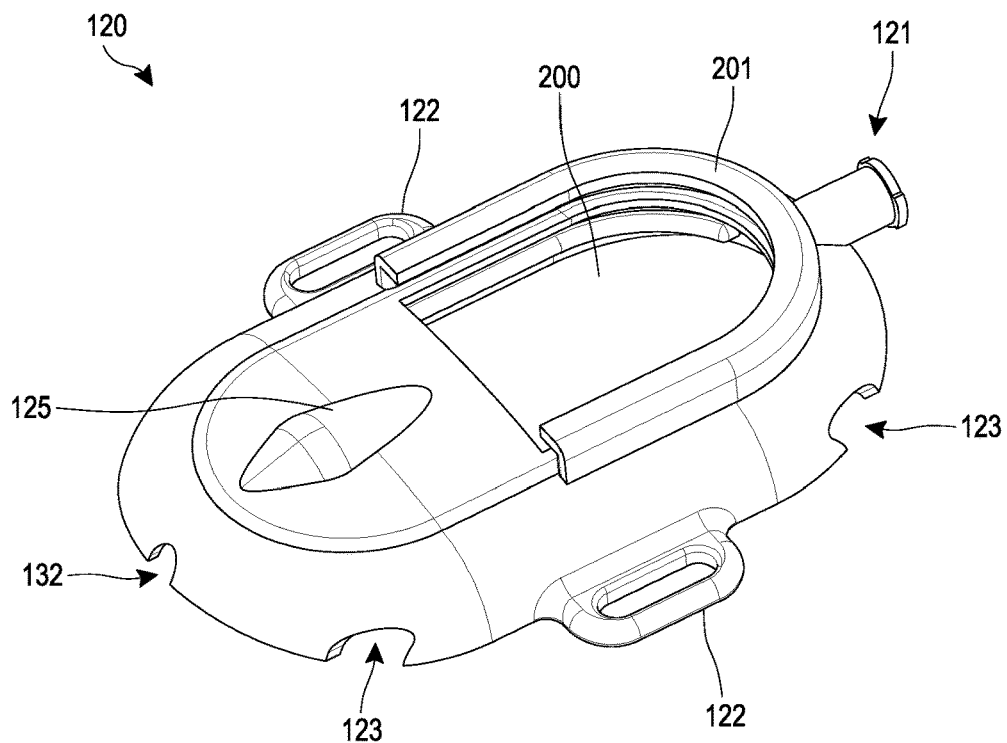
FIG. 3B illustrates another perspective view of the cover of FIG. 3A.
Figure 3C:
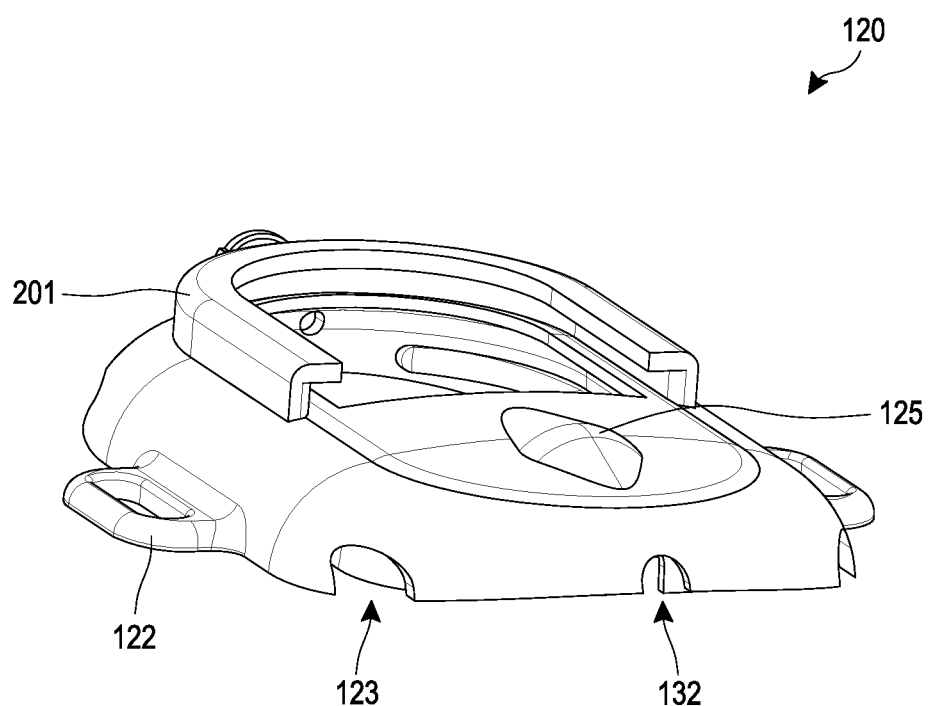
FIG. 3C illustrates another perspective view of the cover of FIG. 3A.

FIGS. 3A-3H illustrates an alternative design for a cover 120 for a catheter housing 10 having a roof 201 with an opening 200 configured to be covered by a transparent window. Cover 120 can allow a transparent window to slide in an out of the roof 201. The roof 201, opening 200, and transparent window can allow for greater visibility to interior portions of the catheter housing 10 and/or the catheter insertion site when the catheter housing 10 is secured to the patient. The transparent window can be permanent, for example, fixed to the roof 201 and/or cover 120. Alternatively, the transparent window can be removable from the roof 201 and/or cover 120. Removing the window from the roof 201 can provide access to interior portion of the catheter housing 10 and/or the catheter insertion site without having to remove the catheter housing 10 from the patient. As shown in FIGS. 3A-3C, the roof 201 can comprise a certain amount of a top portion of the cover 120. For example, the roof 201 can comprise approximately half of a top portion of the cover 120. Alternatively, the roof 201 can comprise more than half of the top portion of the cover 120. For example, where the cover 120 does not have a recess 25 or recess 125 (FIG. 3G), the roof 201 can extend around the entirety of the top portion of the cover 120, and the opening 200 and the transparent window can be sized and/or shaped accordingly. The roof 201 can comprise a variety of cross-sections. For example, the roof 201 can comprise an L-shaped cross section as shown in FIGS. 3A-3C. The transparent window can be sized and/or shape to fit within the L-shaped cross section of the roof 201. Where the transparent window is removable form the roof 201, edges of the transparent window can be configured to secure to the cross section of the roof 201 in a snap-fit, a press fit, a friction fit, and/or other type of configuration. As discussed above, the catheter housing 10 can form a hermetic seal over the catheter insertion site. For example, the cover 20 can secure to the hub 60 and form a hermetic seal around the catheter insertion site. Cover 120 can also secure to the hub 60 and form a hermetic seal around the catheter insertion site. Further, while the transparent window can be removable form the roof 201, the transparent window can secure to the roof 201 and be configured to form a hermetic seal as well.

Cover 120 can be the same in some or many respects as cover 20. For example, cover 120 can be identical to cover 20 except that cover 120 can include an opening 200 and/or a roof 201 as discussed further below.

FIGS. 3A-3B illustrate various perspective view of the cover 120. As discussed herein, the cover 120 can be secured to hub 60. The cover 120 can be made of transparent material. Alternatively, the cover 120 can be made of non-transparent material. Additionally, the cover 120 can be comprise both transparent and nontransparent material. For example, the portions of the cover 120 can be made of transparent material where it is advantageous to be able to see through the cover 120 in order to observe the other components of the catheter housing 10. For example, the portions of the cover can be made of transparent material where it is advantageous to be able to see through the cover 120 in order to observe the other components of the catheter housing 10, and/or observe, access, and/or inspect the puncture site without removing the catheter housing 10 or components thereof. The cover 120 can be made of substantially shockproof and/or durable material. This is advantageous because the catheter housing 10 and/or the cover 120 can be subjected to impact during installation or use. The cover 120 can also be made of substantially waterproof material. This is advantageous because the catheter housing 10 and/or the cover 120 can be subjected to water or other liquids when the device is in use. The cover 120 can comprise plastic, rubber, and/or silicone, among other materials, or a combination of such materials. The cover 120 can comprise of a soft, pliable material, such as medical grade silicone. Alternatively, the cover 120 can comprise harder silicone, or rubber can be used.

The cover 120 can be configured to form a closed environment over a site where an intravenous catheter is inserted into a patient. Such a closed environment can aid in keeping the site free from contamination, as discussed herein. As discussed above, the cover 120 can be made of at least partially transparent material so as to allow a caregiver or other person to examine the catheter insertion site and/or other portions of the catheter housing 10 (for example, the hub 60) while the cover 120 is secured to the hub 60.

The cover 120 can include one or more openings 132 to permit tubing 41 to pass through the cover 120 and into and interior of the cover 120, such as one or more, two or more, three or more, four or more, five or more, or six or more openings 132. For example, as discussed herein, such openings 132 can align with one or more openings in the hub 60 (such as opening 65) that can allow tubing 41 to pass through the housing 10 and to a catheter device 40 when the catheter device 40 is secured to lock 126 of cover 120. The cover 120 can have a rounded shape. Alternatively, the cover 120 can have a non-round shape, for example, a rectangular shape. Alternatively, the cover 120 can be approximately trapezoidal, rectangular, square, oval and/or circular in shape, among other shapes. For example, where the catheter housing 10 includes a hub 60 and a wall 61 of the hub 60 shaped like a stadium, the cover 120 can have a shape that accommodates the stadium shape of wall 61. The cover 120 can comprise a single, continuous piece. Alternatively, the cover 120 can comprise more than one piece.

As illustrated in at least FIGS. 3A-3D, the cover 120 can have one or more ports 121, which can be used to insert sterilizing and/or anesthetic gas into the catheter housing 10. For example, the cover 120 can have one, two, three, four, five, six, seven, eight, nine, ten, eleven or more ports 121. The one or more ports 121 can be located on a side of the cover 120. Alternatively, the one or more ports 121 can be located on a top portion of the cover 120. The one or more ports 121 can be used to provide sterilization and/or antiseptic gases (among others), such as ethylene oxide gas, nitrogen gas, or other sterilizing, antiseptic, and/or anesthetic gases. For example, the cover 120 can include a port 121 for providing sterilizing gases, and a separate port for providing anesthetic gases. The one or more ports 121 can comprise an opening and a port rim. The opening of the port 121 can extend outwardly from the cover 120. The port rim can extend radially outward from the opening of the port 121. The port rim can be configured to secure to a portion of a gas tube in a snap-fit, a press fit, and/or a friction fit configuration. For example, the port rim can comprise a female Luer connector.

Figure 3D:
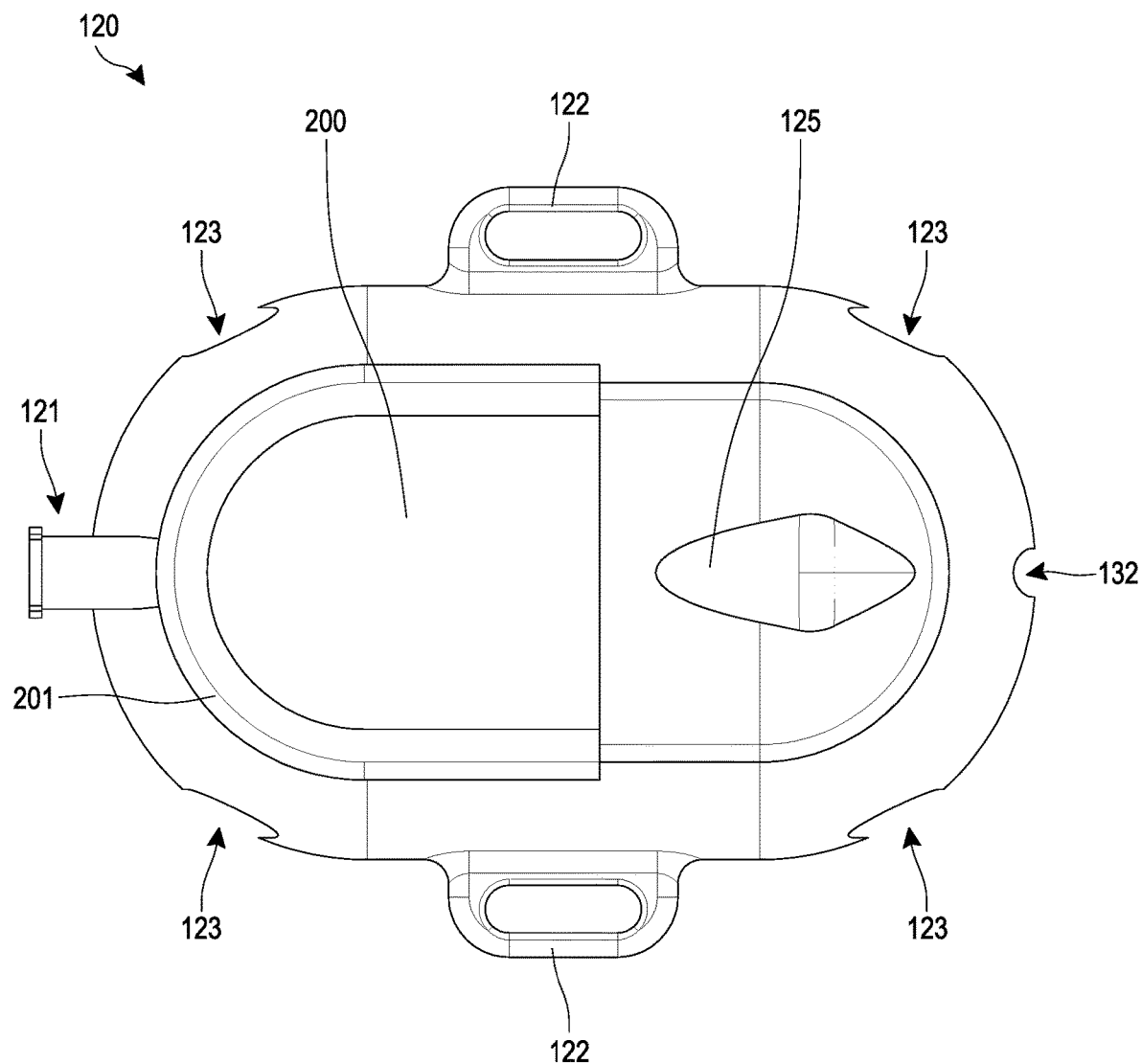
FIG. 3D illustrates a top view of the cover of FIG. 3A.
Figure 3E:
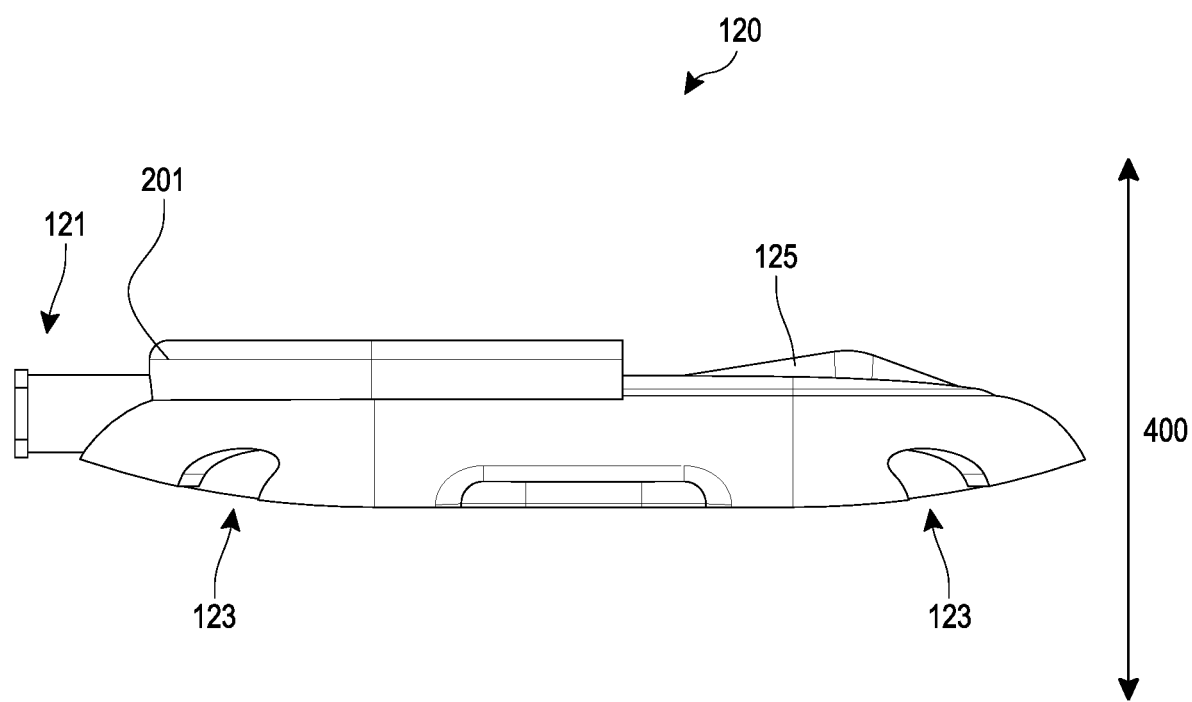
FIG. 3E illustrates a side view of the cover of FIG. 3A.

The one or more ports 121 can be substantially cylindrical, rectangular, or another shape. The one or more ports 121 can include a gas opening which permits sterilizing gas, anesthetic gas, or other gases, to flow into the catheter housing 10. The one or more ports 121 can include a port rim that extends at least partially around an exterior portion of the one or more ports 121. The port rim can extend radially outward from the one or more ports 121. The port rim can be located at an end of the one or more ports 121 (as shown in FIG. 3D) or, alternatively, at another region along the one or more ports 121. The one or more ports 121 can extend outwardly from the cover 120. The port rim can be configured to secure to gas tubes or other devices that provide gas to the catheter housing 10. For example, the port rim can contain one or more threads by which a gas tube or other device can screw into. Alternatively, the port rim can comprise a snap mechanism that can secure to a gas tube or other device, whereby a portion of such tube or other device can be configured to snap into or around the snap mechanism of the port rim. Other alternative methods of securing a gas tube or other device to the port rim of the one or more ports 121 exist. The one or more ports 121 can also include one or more valves, such as a control valve and/or a multi-valve.

The one or more ports 121 of the cover 120 can be configured to align with a gas inlet 67 of the hub 60 (see FIG. 4A). For example, when the cover 120 is secured to the hub 60, the one or more ports 121 of the cover 120 can align with the gas inlet 67 of a wall 61 of the hub 60 to allow gases to flow into the interior of the hub 60 and/or to the catheter insertion site.

The catheter housing 10, including the hub 60 and cover 120 discussed herein, can be coated with anti-microbial coating to aid with disinfection and/or sterilization near the catheter insertion site and/or in or around the catheter housing.

The cover 120 can include one or more slots 123 that can allow tubing 41 connected to the catheter device 40 to pass therethrough and be secured to a portion of the catheter housing 10. For example, as shown in at least FIG. 2J, when a catheter 42 and catheter device 40 are secured to the catheter housing 10 by, for example, the cover 120, tubing 41 connected to the catheter device 40 can pass through an opening in the cover 120, curve around a portion of the cover 120 and pass through one or more slots 123 in the cover. Such configuration can form a J-loop, for example, where the tubing 41 curves around a portion of the cover 40 after exiting an opening in the cover and passes through one or more slots on a side of the cover 120. In the configuration illustrated in FIG. 3I, the tubing 41 exits an opening in the cover 120, curves at an approximate 180 degree angle, passes through two slots 123 on the cover 120 and exits out in a direction opposite to the direction that the tubing 41 initially exited the cover 120. However, the cover 120 can have more than two slots 123, for example, the cover 120 can have four slots 123. In such cases, the tubing 41 can be configured to pass though more all four slots, wrap around substantially all of a portion of the cover 120 and, for example, exit out in a the same direction as the tubing 41 initially exited the cover 120. As discussed herein, the cover 120 can have one or more walls, such as an inner wall 129 and an outer wall 128. The one or more slots 123 can be disposed on the outer wall 128. In such configurations, the space between the inner wall 129 and the outer wall 128 can define an interior passage for the tubing 41 to pass through and/or be housed within. Placing a portion of the tubing 40 through such interior passage can provide the benefits discussed herein, such as mechanically decoupling the tubing 41 from the insertion site and/or the catheter device 40, for example.

Regardless of the placement and/or amount of the one or more slots 123, the one or more slots 123 can allow a caregiver to conveniently and safely wrap and/or secure the tubing 41 to the catheter housing 10. This can provide a number of advantages. The one or more slots 123 can allow the insertion site or portions of the catheter housing (such as the lock discussed herein) to be mechanically decoupled from the tubing 41. Thus, if the tubing 41 gets pulled, caught, or snagged, the force will not affect the insertion site, catheter 42, catheter device 40, and/or portions of the catheter housing 10 (such as the lock 126). For example, such wrapping and/or securement of the tubing 41 to the catheter housing 10 can reduce the likelihood that the tubing will get pulled or caught on clothing or other items. Such wrapping and/or securement can also prevent the tubing 41 from sticking out in a direction and/or area that is inconvenient for caregivers or physicians. For example, where a patient is undergoing surgery, many medical tools devices may be used during the surgery and doctors and nurses may be moving in and around areas nearby a catheter insertion site. In such cases, the one or more slots 123 can significantly reduce the "footprint" of the catheter housing 10 and/or tubing 41. This can reduce the likelihood that the tubing 41 will get tangled or will interfere with activities by such caregivers working in proximity to the catheter insertion site, even within a few feet from the site. The wrapping and/or securement of the tubing 41 to the catheter housing 10 can allow the tubing 41 to be essentially unified with the catheter housing 10, and can eliminate the need for a caregiver to secure the tubing 41 in a J-loop configuration with an adhesive applied directly to the patient's skin. The one or more slots 123 can provide securement the tubing 41 without having the tubing 41 touch the patient's skin, increasing patient comfort and potential rashes or other skin irritation and/or skin trauma issues resulting from such contact. The one or more slots 123 also can provide securement to the tubing 41 which prevents the tubing 41 from getting pulled out and/or from impacting the securement of the catheter device 40 and/or catheter 42. For example, the one or more slots 123 can resist forces applied if the tubing 41 is moved and can significantly reduce or entirely eliminate the force applied to the catheter device 40 and/or catheter 42 if such movement occurs. This provides a significant advantage since significant damage can occur at the vein and/or the catheter insertion site in traditional devices and methods of catheter securement.

As illustrated in at least FIGS. 3A-3D and as discussed above, the cover 120 can include one more strap hoops 122 that can facilitate securement of the catheter housing 10 to a patient using the fastening straps 80. The cover 120 can include, for example, one, two, three, four, five, or six strap hoops. For example, the cover 120 can include a first strap hoop on a first side of the cover 120 and a second strap hoop on a second side of the cover 120 opposite the first side. A fastening strap 80 can pass through the first strap hoop, secure to a itself, wrap around a portion of a patient (such as an arm), pass through the second strap hoop and secure again to itself, using for example Velcro (see FIGS. 1A and 1C). Additionally or alternatively, the cover can have just one strap hoop and/or the fastening strap can secure to a portion of the catheter housing 10 instead of having to loop through a second strap hoop of the cover 120. For example, the fastening strap 80 can pass through the first strap hoop, secure to itself, wrap around a portion of a patient, and secure to the hub 60, thus securing the catheter housing 10 to a patient.

The one or more strap hoops 122 can be sized and shaped to receive a portion of a fastening strap 80. The one or more strap hoops 122 can comprise a loop, such as a rounded loop. The one or more strap hoops 122 can be circular, trapezoidal, rectangular, square, and/or oval. The one or more strap hoops 122 can have a width that is sized to accommodate a width of the fastening strap 80 and can have a depth that is sized to accommodate a thickness of the fastening strap 80. The one or more strap hoops 122 can have one or more slits configured to allow a fastening strap 80 to be inserted into the one or more strap hoops 122 by feeding a side of the one or more fastening straps 80 therethrough.

The cover 120 can have, for example, a first strap hoop 122 on a first side of the cover 120 and a second strap hoop 122 on a second side of the cover 120 that is opposite to the first side. The first strap hoop 122 can be aligned with the second strap hoop 122. The one or more fastening straps 80 can include an adhesive and/or a non-adhesive that enables them to secure to themselves and/or to the catheter housing 10.

As discussed herein, the one or more strap hoops 122 and the one or more fastening straps 80 can be used to provide securement of the catheter housing 10 to the patient. The one or more strap hoops 122 and the one or more fastening straps 80 can fully seal the catheter housing 10 so that the catheter housing 10 is difficult if not impossible to take off by the patient. For example, depending on the location of the catheter housing 10 on the patient's body, the patient may only be able to utilize one hand in attempting to remove the catheter housing 10. In some situations, it can be advantageous to prevent a patient from removing a catheter from themselves. For example, patient's often wake up in a drowsy or non-cognizant state and attempt to remove catheters out of fear or confusion. Thus, utilizing the one or more strap hoops 122 and the one or more fastening straps 80 can advantageously prevent such behavior.

Figure 3F:
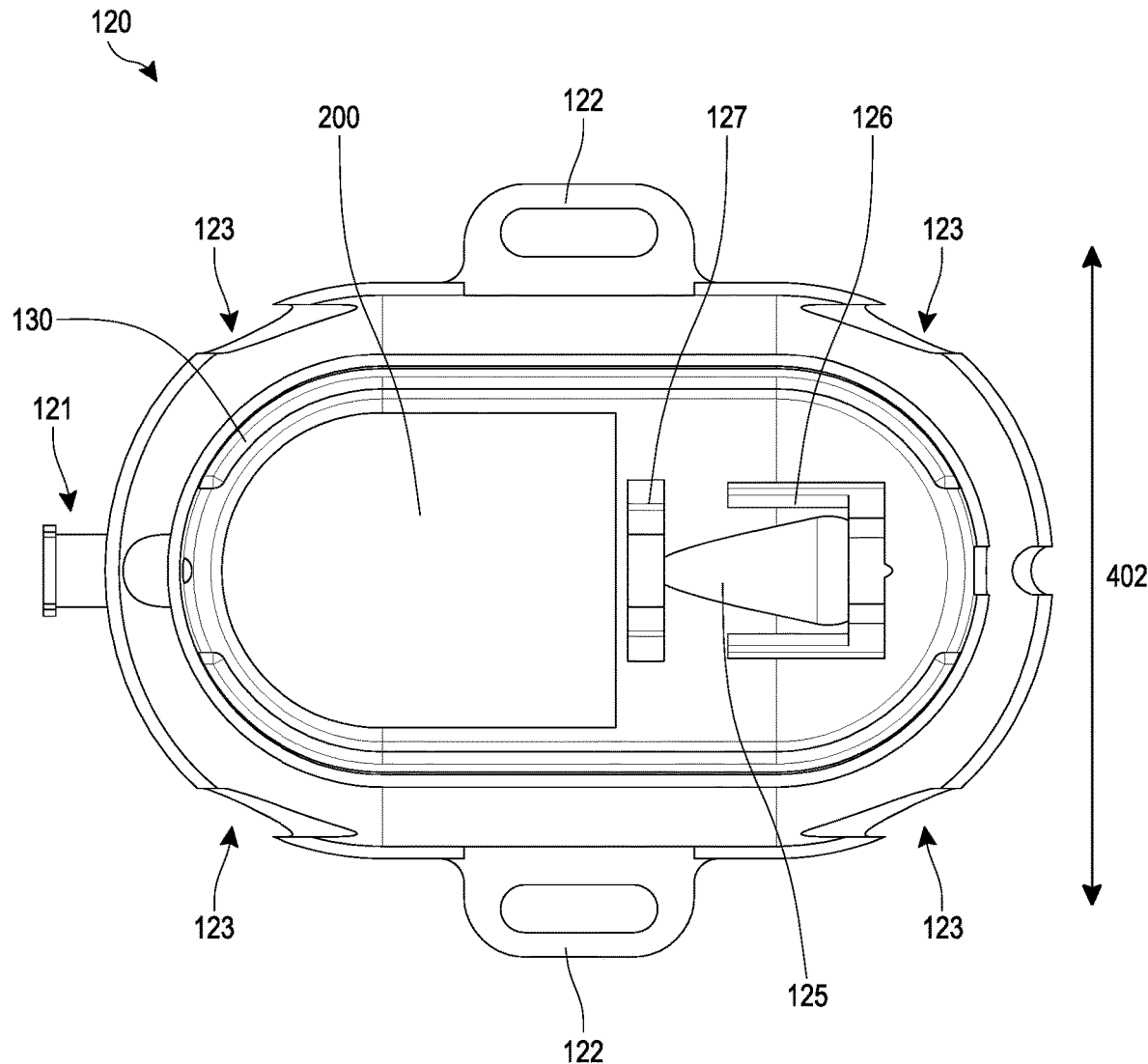
FIG. 3F illustrates a bottom view of the cover of FIG. 3A.
Figure 3G:
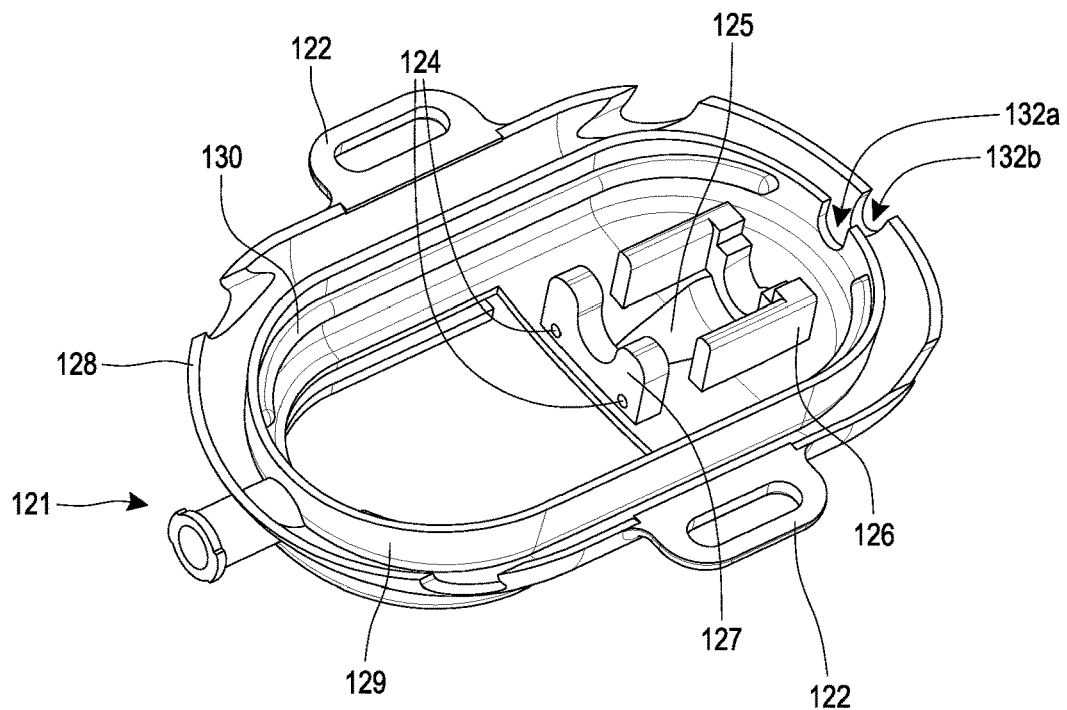
FIG. 3G illustrates a bottom perspective view of the cover of FIG. 3A.
Figure 3H:
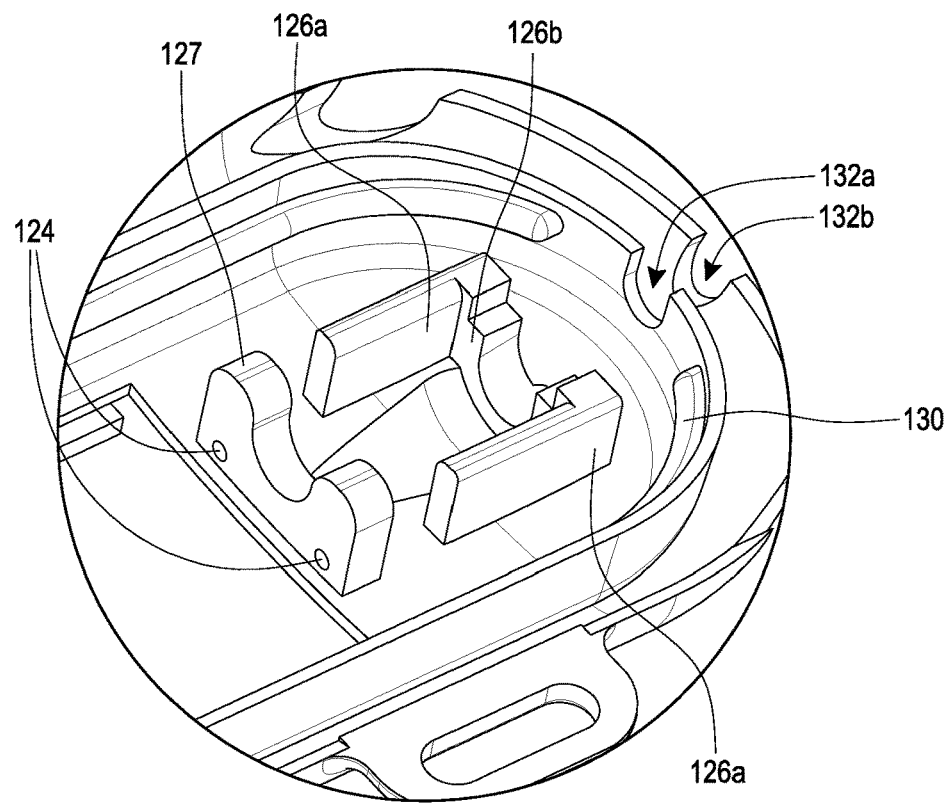
FIG. 3H illustrates a close-up bottom perspective view of the cover of FIG. 3A.

As shown in FIGS. 3F-3H, the cover 120 can include one or more protrusions 130 (also referred herein as "tongues 130"). For example, the cover 120 can include one, two, three, four, or five or more protrusions 130. The one or more protrusions 130 can extend along an interior portion of the cover 120, for example. The one or more protrusions 130 can be located at a lower interior portion of the cover 120, or alternatively, the protrusion 130 can be located at a middle or higher interior portion of the cover 120. The one or more protrusions 130 can be substantially continuous, or alternatively, can be non-continuous, intermittent or exist in sections. The one or more protrusions 130 can extend from an interior of the cover 120. The one or more protrusions 130 can extending along substantially all of an interior of the cover 120. The one or more protrusions 130 can extend around an interior of the cover 120 and be continuous except at and/or near openings in the cover 120. For example, as shown in FIG. 3F-3H, the one or more protrusions 130 can comprise two protrusions 130 that extend along an interior of a first side of the cover 120 and an interior of a second side of the cover 120 and extend partially along a front side of the cover proximate to the region where tubing 41 exits the cover 120 when catheter device 40 is secured by the cover (for example with the lock 126) and extend partially along a back side of the cover 120 proximate to a port 121. Having the one or more protrusions 130 arranged in the configuration can provide strong securement between the cover 120 and the hub 60 when the protrusion 130 are secured to the groove 68 of the hub 60, while also not interfering with the operation and/or use of the lock 126, tubing 41, and/or port 121.

The one or more protrusions 130 can be configured to secure to a portion of the hub 60. For example, such securement can occur when the cover 120 is placed over and/or secure to the hub 60, whereby the one or more protrusions 130 can secure to one or more grooves 68 of the hub 60 (see FIG. 4A). The one or more protrusions 130 can secure to the one or more grooves 68 by a snap-fit, press fit, friction-fit, and/or other configuration for securely connecting the cover 120 to the hub 60. The surface of the one or more protrusions 130 can be rounded (see FIG. 3H). Such a rounded shape can advantageously help the one or more protrusions slide into the one or more grooves 68 of the hub 60 thus facilitating ease during securement.

Alternatively, the one or more protrusions 130 can be replaced with one or more interior grooves. For example, the one or more protrusions 130 can be replaced with one, two, three, four, or five, six, seven, or eight or more grooves. For example, the one or more protrusions 130 can be replaced with two grooves extending along an interior surface of the cover 120 that are adjacent to one another and/or atop each other. For example, the one or more protrusions 130 can be replaced with one groove. Such interior grooves can secure to at least a portion of the hub 60. For example, such interior grooves can secure to a protrusion appearing on the hub 60. Such securement can occur by a snap-fit, press fit, friction-fit, and/or other configuration. Thus, the cover 120 can secure to the hub 60 by insertion of a protrusion located on the cover 120 into a groove located on the hub 60, and/or by accepting a protrusion located on the hub 60 into a groove located on the cover 120.

In some configurations, a seal is formed such that the cover 120 does not allow external air and/or contaminants from entering the enclosed internal volume of the catheter housing 10. For example, the cover 120 can engage the hub 60 to form a closed and/or isolated atmosphere, which encloses the insertion site. In such configurations, the catheter insertion site can advantageously be sterilized by inert gas as described above. Similarly, the cover 120 can advantageously help to inhibit or prevent microbe contaminate and help to lower contamination vulnerability. The cover 120 can also be configured to prevent the joint 66 (see FIG. 4A) from separating while the catheter housing 10 is in use.

The cover 120 can comprise one or more walls. For example, the cover can comprise one, two, three, four, or five walls. As shown in FIGS. 3F-3G, the cover 120 can have two walls. For example, the cover 120 can have an outer wall 128 and an inner wall 129. As shown, the one or more protrusions 130 can be located on an interior surface of the inner wall 129 of the cover 120. As also shown, the one or more slots 123 discussed above can be located on the outer wall 128. The dual wall design can provide a number of advantages. For example, the inner wall 129 of the cover 120 can secure to the hub 60 and the space between the inner wall 129 and the outer wall 128 can accommodate the tubing 41, which can provide the advantages discussed above. Further, the tubing 41 can be secured in this space while the inner wall 129 securement to the hub 60 can provide a seal (such as a hermetic seal) around the catheter insertion site. When the cover 120 is secured to the hub 60 via the one or more protrusions 130 of the inner wall 130, the outer wall 128 can rest on a portion of the hub 60, for example, the membrane of the hub 60. For example, a bottom surface of the outer wall 128 can be flush with a top surface of the membrane of the hub 60. Thus, where tubing 41 is secured through the one or more slots 123 of the cover 120, the tubing 41 can be enclosed by the inner wall 129, outer wall 128, and the membrane of the hub 60. As discussed above, the cover 120 can have one or more strap hoops 122 that can be used along with one or more fastening straps 80 to secure the catheter housing 10 to a patient. The one or more strap hoops can have a bottom surface that is flat or substantially flat (see FIG. 3F, for example). This can ensure that the one or more strap hoops 122 are flush with a top surface of the membrane of the hub 60 when the cover 120 is secured to the hub 60 and/or the catheter housing 10 is secured to a patient. The one or more fastening straps 80 can ensure little or no movement of the cover 120 and/or the hub 60. Additionally or alternatively, as discussed herein the catheter housing 10 can include anti-slip material, such as on a bottom surface of catheter housing 10, which can ensure little or no movement of the cover 120 and/or the hub 60. Thus, the catheter housing 10 and the components secured thereby (for example, catheter device 40, catheter 42, and/or tubing 41) can be firmly secured to a patient.

As shown by FIGS. 3A-3B, the cover 120 can have a port 121 on a side of the cover 120, such as a front side of the cover 120. The port 121 can extend outwardly from the front side of the cover 120 and can extend through the outer wall 128 and inner wall 129 of the cover 120. This can enable gases flowing through the port 121 to enter an interior of the catheter housing 10, as discussed above.

As discussed above, the cover 120 can have one or more openings 132 to permit tubing 41 to pass through the cover 120 and into the interior of the cover 120. As shown in FIGS. 3G and 3H, the inner wall 129 and the outer wall 128 can have openings 132a, 132b that allow tubing 41 connected to the catheter device 40 to exit the cover 120. The openings 132a, 132b can be proximate to a lock 126 discussed herein. The openings 132a, 132b can align with a recess in a back wall 126b of the lock 126. This can allow tubing 41 connected to a catheter device 40 to maintain a straight configuration from a region of the tubing 41 extending from the catheter device 40 and to (and/or through) the openings 132a, 132b. The openings 132a, 132b can be sized and shaped to accommodate various sizes and/or shapes of tubing 41.

The cover 120 can include a lock 126 that can secure the catheter device 40, catheter 42, and/or tubing 41 connected to the catheter device before, during, and/or after a catheter 42 is inserted into a patient at an insertion site. The lock 126 can include one or more walls configured to secure to a catheter device 40 or a portion thereof. For example, the lock 126 can include one, two, three, four, five, six, seven, or eight walls configured to secure to a catheter device 40 or a portion thereof. As shown by FIGS. 3G-3H, the lock 126 can include two side walls 126a and a back wall 126b. The side walls 126a can be sized, shaped, and/or oriented to accommodate and/or secure to portions of catheter devices 40 of any size and/or shape. The side walls 126a can be parallel or substantially parallel. Alternatively, the side walls 126a can be nonparallel. The side walls 126a can be rounded, curved, circular or partially circular, among other shapes. The side walls 126a can be spaced to accommodate various sizes of catheter devices 40. For example, the side walls can be spaced in order to accommodate various diameters of cylindrical catheter devices 40 or portions thereof (for example, a male luer connector). The side walls 126a can have exterior surfaces which face the inner wall 129 of the cover 120 and can have interior surfaces which face towards each other and/or contact the catheter device 40 when the catheter device 40 is secured to the lock 126. The interior surfaces of the walls 126a can be straight. Alternatively, the interior surfaces of the walls 126a can be curved or partially curved to conform to a portion of a catheter device 40. The interior surfaces of the walls 126a can be shaped to surround or partially surround a portion of a catheter device 40 (for example, a male luer connector of a catheter device 40). The interior surfaces of the side walls 126a can have a smooth surface which can enable the catheter device 40 or a portion thereof to slide and fit between the side walls 126a easily. Alternatively, interior surfaces of the side walls 126a can have a rough surface which can provide more frictional resistance. The interior surfaces of the side walls 126a can have a combination of smooth and rough surface. The side walls 126a can prevent sideways movement, micro-movement, and/or erosion of the catheter device 40 when the catheter device 40 is secured to the side walls 126a.

The back wall 126b of lock 126 can be sized and/or shaped to accommodate the catheter device 40 or a portion thereof, and/or tubing 41. The back wall 126b of lock 126 can be sized and/or shaped to accommodate connectors, extensions, adapters, and/or male luers, or portions thereof, among others, for example. For example, the back wall 126b can have a recess with a width that is sized and shaped to accommodate and/or secure to a portion of a male luer connector (such as a portion of a male luer connector that directly connects and/or surrounds a portion of an end of tubing 41). The recess can be rounded. Alternatively, the recess can be non-rounded. The recess can be circular. Alternatively, the recess can be non-circular. The recess can comprise a half-moon shape, or another shape. The recess can comprise a half-circle shape. The back wall 126b can have a width that is greater than the width of the recess. This can advantageously prevent the catheter device 40 (or a portion thereof) from being dislodged when tubing 41 is pulled. For example, where the catheter device 40 is secured by the lock 126, if tubing 41 is pulled, the remaining portion of the back wall 126b between the two widths can act to support a side or end of the catheter device 40 so that the catheter device 40 does not move or become dislodged.

The securement of catheter 42, catheter device 40, and/or tubing 41 by or with the lock 126 can be a physical locking, holding, stabilizing without locking, retaining, stabilizing to prevent or reduce the likelihood of movement, stabilizing to minimize movement, or another type of securement. The lock 126 can be sized and/or shaped to secure any type of catheter 42, catheter device 40, and/or tubing 41. For example, a catheter device 40 (or a male luer connector thereof) can be secured by a first wall 126a, a second wall 126a, and a back wall 126b. The lock 126 can secure catheter device 40 and a catheter 42 in a proper orientation relative to the patient's skin and/or the catheter insertion site. This can advantageously enable a catheter tip or rim to be secured at a final resting angle or inclination angle that approximates the angle at which a needle is inserted into a vein of a patient. As discussed previously, this is beneficial because it reduces the chance of injury and/or other complications that can result when the catheter moves or is secured at an angle that damages the vein wall or nearby area. For example, the final resting angle or inclination angle can be between 1 and 45 degrees. The inclination angle can also be between 1 and 10 degrees, between 10 and 20 degrees, or between 20 and 30 degrees. The inclination angle can be more than 45 degrees as well, depending on the implementation of the catheter housing 10 or components thereof (such as the cover 120 and/or hub 60). The inclination angle can also be at a very small angle, such as between 0 and 1 degrees. Current techniques for securing a catheter to a patient can result in dislodgment, inappropriate angle of the catheter, or twisting or other movement while the catheter is inserted into a patient. However, the lock 126 described herein, which can accommodate any type of catheter device design and/or catheter coupled thereto, can secure the catheter device and catheter in a position that provides for a normal or optimal angle. This can help to limit or prevent irritation and/or cannula tip erosion caused by contacting of the cannula tip with vein lumen sides. Thus, unlike conventional catheter stabilization methods where securing the catheter typically results in disrupting the natural angle of the catheter, awkward angling of the catheter against the wall of the vein, and/or in which pressure is applied on the a portion of the catheter device 40 in order to secure it to a patient, the securement angle of the catheter device 40 and/or catheter 42 with the lock 126 can preserve the integrity of the connection of the catheter 42 within the vein.

The cover 120 can include a bridge 127 that can help secure, guide, and/or align the catheter device 40 and catheter 42, fluid tube 41, and/or other devices or components connected thereto (such as other adapters or connectors). The bridge 127 can extend from a top interior portion of the cover 120. The bridge 127 can extend a distance from the top interior of the cover 120 a distance equal or substantially equal to a distance that the lock 126 extends from the top interior of the cover 120. Alternatively, the bridge 127 can extend a distance from the top interior of the cover 120 a distance unequal to a distance that the lock 126 extends from the top interior of the cover 120.

Figure 3I:
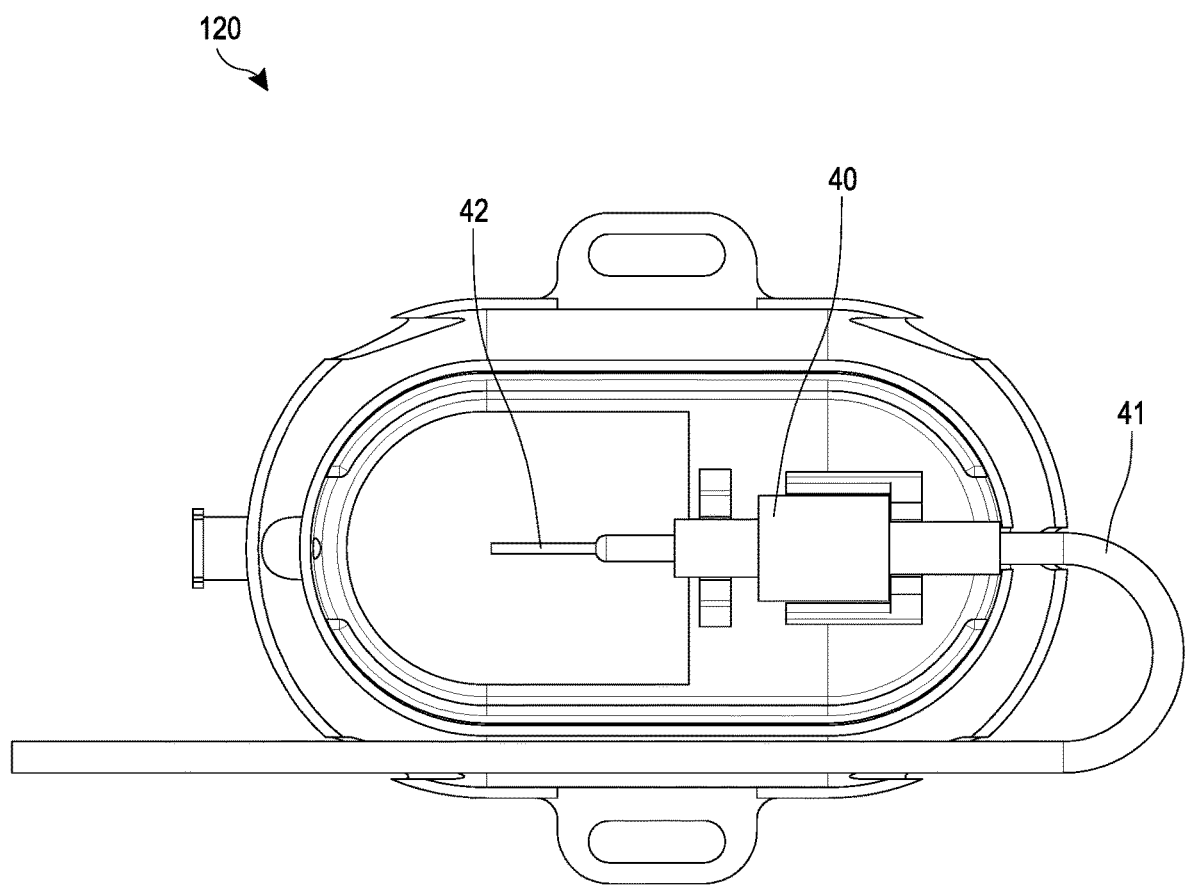
FIG. 3I illustrates a bottom view of the cover of FIG. 3A where a catheter device is secured to a lock of the cover of FIG. 3A in accordance with aspects of this disclosure.

The bridge 127 can be positioned proximate to the lock 126 along an interior portion of the cover 120. For example, the bridge 127 can be positioned proximate to the lock 126 and can be closer to catheter insertion site than the lock 126. The bridge 127 can comprise a recess that is sized and/or shaped to accommodate a portion of the catheter 42 and/or catheter device 40. For example, the bridge 127 can have a recess that can accommodate a tip or end of a portion of the catheter device 40 (for example, a cylindrical portion of catheter device 40 as shown in FIG. 3I). The recess of the bridge 127 can be smooth, or alternatively, can be rough. The recess of the bridge 127 can comprise a half-moon, half-circle shape, half-square, half-rectangle, or other shapes, for example. The bridge 127 can have a height (extending from a top interior surface of the cover 120) at the recess that is less than a height at a non-recessed portion of the bridge 127. The height at the recess can be equal or unequal to a height of the recess of the back wall 126b of the lock 126. For example, the height of the bridge 127 recess can be greater than the height of the recess of the back wall 126b. This can allow a tip of the catheter device 40 to be inclined at a natural inclination angle when the catheter device 40 is secured by the lock 126. This can also enable the bridge 127 to push a portion of the catheter device 40 down to properly position the catheter device 40 and connected catheter 40 when the cover 120 is placed over the catheter device 40 and/or over the hub 60. The bridge 127 can also prevent the lifting, flattening, or inclining of the catheter device 40 and catheter 42 when the catheter housing 10 secures the catheter device 40, catheter 42, and/or tubing 41. The bridge 127 can also prevent the catheter device 40 and catheter 42 from straightening out, moving away from the catheter insertion site, and/or rotating about the lock 126.

Figure 3J:
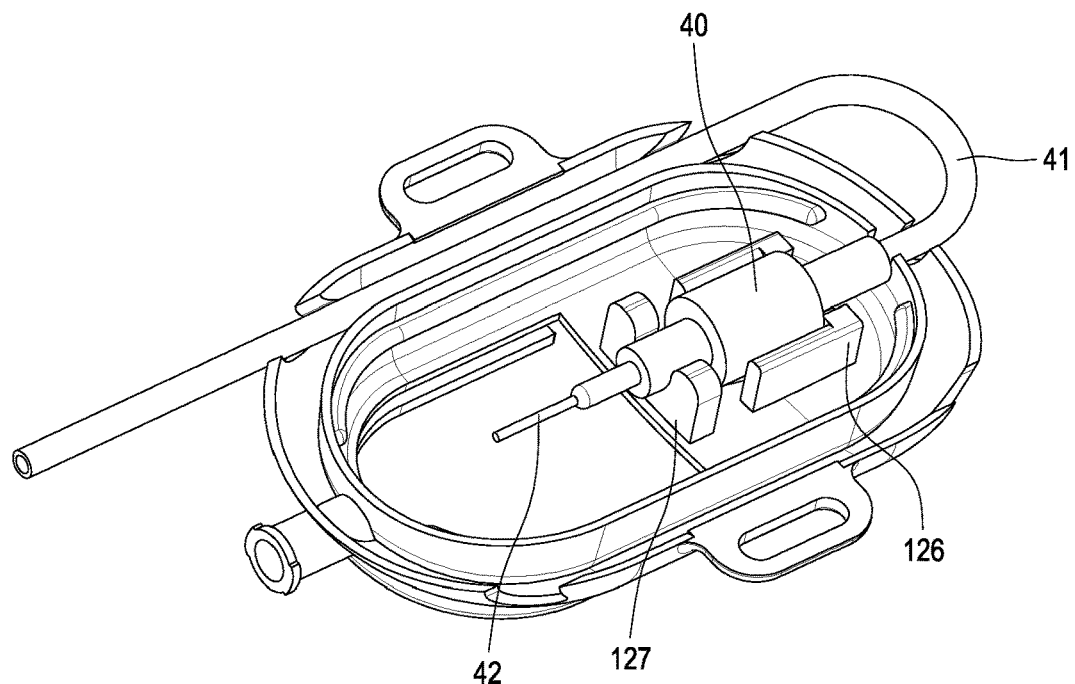
FIG. 3J illustrates a bottom perspective view of the cover of FIG. 3A where a catheter device is secured to the lock of the cover of FIG. 3A in accordance with aspects of this disclosure.
Figure 3K:
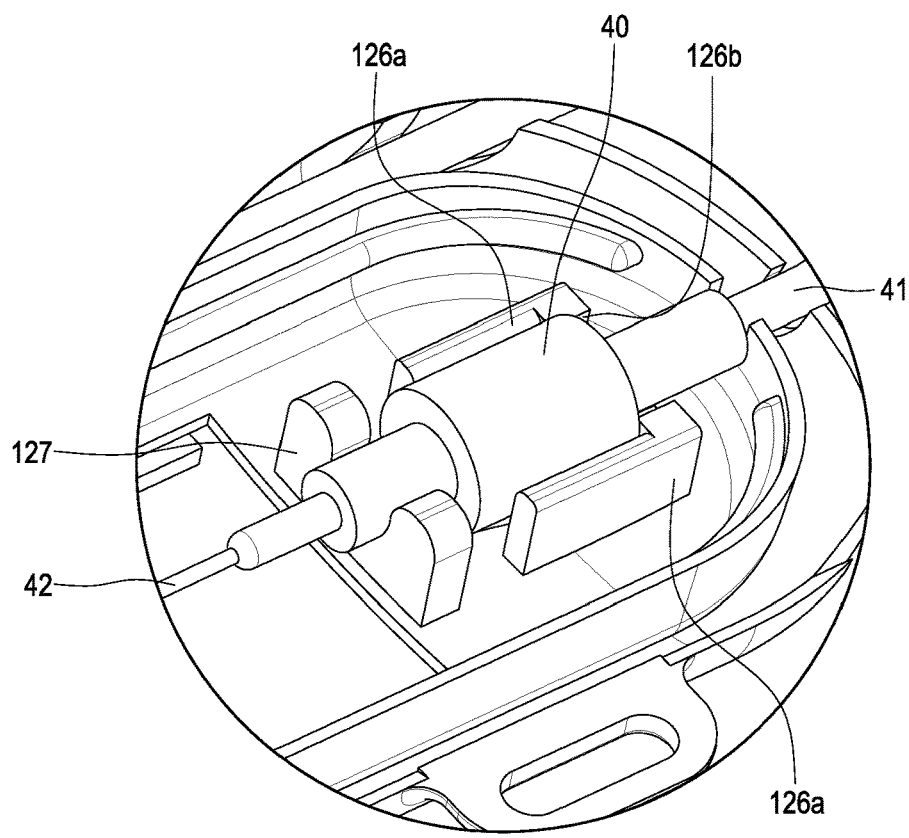
FIG. 3K illustrates a close-up bottom perspective view of the cover of FIG. 3A where a catheter device is secured to the lock of the cover of FIG. 3A.

The catheter housing 10 can secure a catheter device 40 connected to a catheter 42 without contacting the catheter 42. For example, as shown in FIGS. 3I-3K, the lock 126 and/or bridge 127 can secure one or more portions of the catheter device 40 without touching or contacting the catheter 42. This can advantageously limit prevent or limit movement of the catheter 42 when inserted within a patient's vein. This in turn can prevent or limited problems associated with such movement discussed above (for example, damage to the patient's vein and/or to the catheter insertion site and areas nearby). Additionally, as also shown by these figures, when the catheter device 40 (or one or more portions thereof) is secured by the lock 126, bridge 127, and/or other components of housing 10 (such as an interior surface of cover 120), the catheter 42 can be straight (for example, not bent, not kinked, not twisted, not wrapped, and/or not contorted). This can advantageously ensure that the catheter 42 is able to deliver fluids appropriate to the patient.

As shown in FIGS. 3A-3H, the cover 120 can have a recess 125 sized and shaped to accommodate a portion of the catheter device 40 when the catheter device 40 is secured to the lock 126 (such as a portion of a male luer connector of catheter device 40). The recess 125 can be located between the two sidewalls 126a of the lock 126, for example. The recess 125 can be located between the two sidewalls 126a and the back wall 126b of the lock 126 and the bridge 127. The surface of the recess 125 can be smooth or alternatively rough. The surface of the recess 125 can be rounded, or alternatively non-rounded. The surface of the recess can be shaped to accommodate a cylindrical portion of a catheter device 40. The recess 125 can be conical, for example. For example, the recess 125 can comprise a conical groove for fitting a rear part of a male Luer spiral connector of a catheter device 40. As another example, the recess 125 can comprise a dome shape, arc shape, or another shape for fitting a rear part of a male Luer spiral connector of a catheter device 40.

The recess 125 can taper from a first end to a second end. For example, the recess 125 can taper from a first end at or proximate to the back wall 126b of the lock 126 to a second end at or proximate to the bridge 127. The tapering of the recess 125 can conform to the size and or shape of the catheter device 40 or a portion thereof as the catheter device 40 is angled towards the catheter insertion site. For example, as discussed above, the lock 126 and/or the bridge 127 can secure, align, and/or position the catheter device 40 so that the catheter 42 remains inserted into the patient at a natural or appropriate angle. As such, the catheter device 40 can be inclined while secured to the lock 126 and/or bridge 127. The recess 125 of the cover 120 can taper along a vertical axis 400 (see FIG. 3E) and/or taper along a horizontal axis 402 (see FIG. 3F) according to the position of the catheter device 40 when secured by or with the lock 126 and/or the bridge 127. This can advantageously minimize the overall height of the cover 120 in areas of the cover 120, for example, other than the recess 125.

Figure 4B:
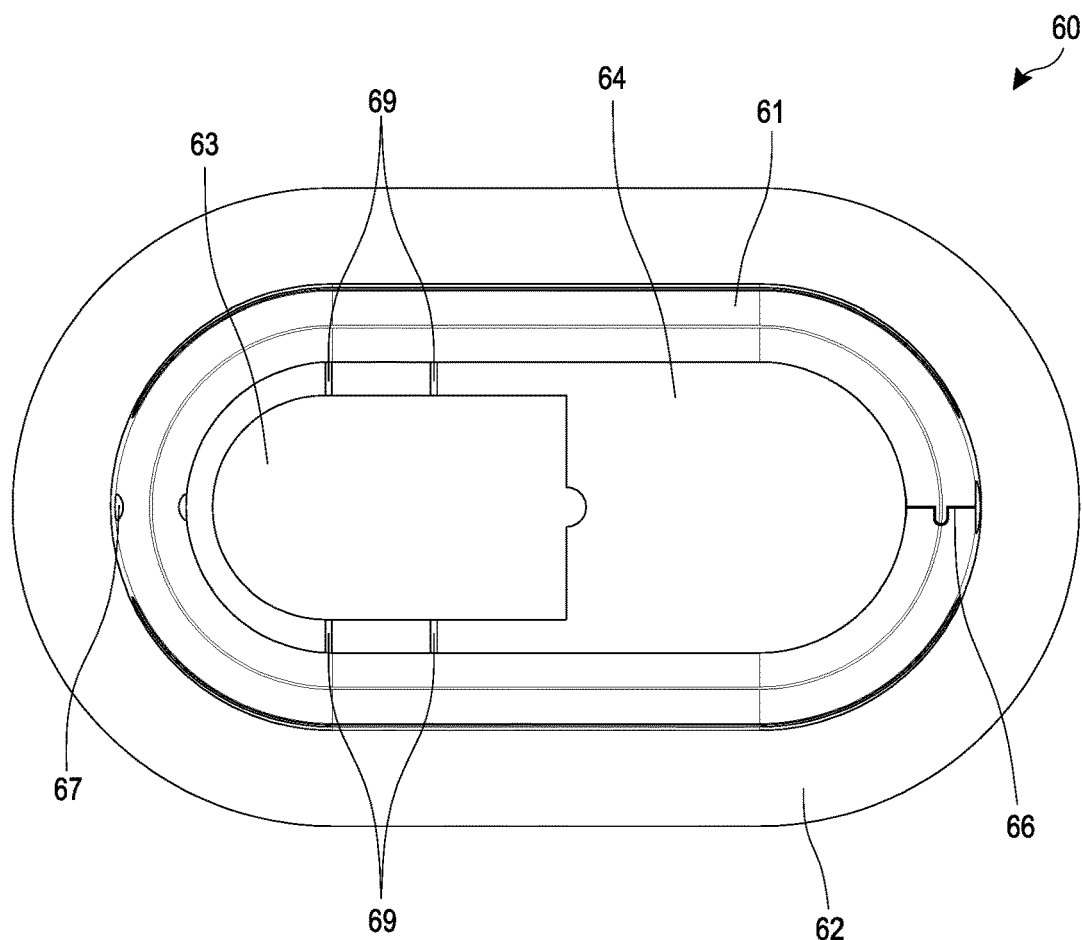
FIG. 4B illustrates a top view of the hub of FIG. 4A.
Figure 4C:
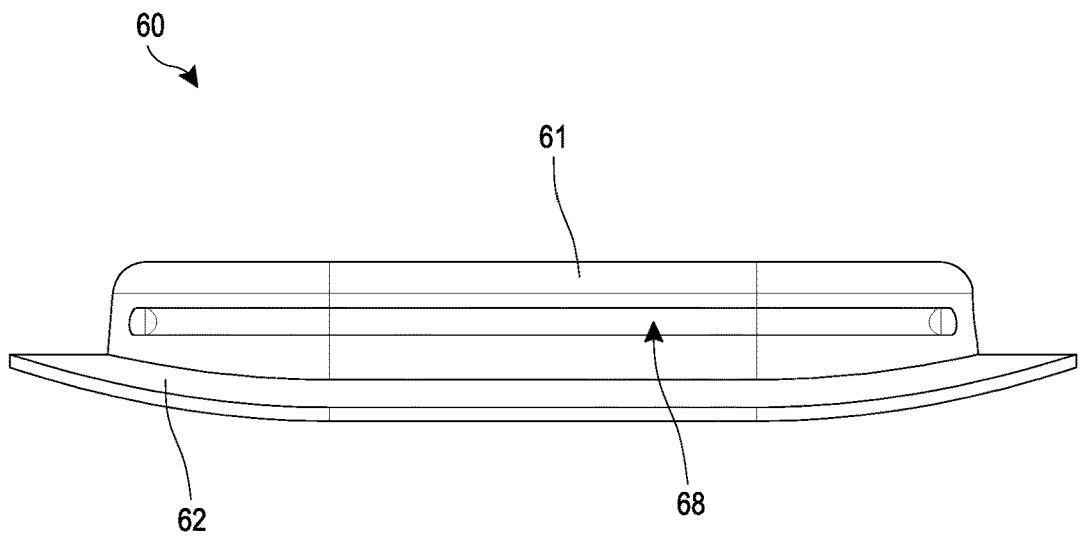
FIG. 4C illustrates a side view of the hub of FIG. 4A.

FIGS. 4A-4C illustrates different views of the hub 60. As shown in FIG. 4A, the hub 60 can include a wall 61 and a membrane 62. A caregiver can attach, adhere, secure, and/or write patient information on the one or more fastening straps 80, hub 60 or a portion of the hub 60. Such patient information can include the insertion date and/or time, the patient's identification, and other information.

The hub 60, and/or components thereof, such as the wall 61 and/or the membrane 62, can comprise plastic, rubber, and/or silicone, among other materials. The hub 60 can comprise a transparent material. Alternatively, the hub 60 can be made of a nontransparent material. Additionally, the hub 60 can comprise both transparent and nontransparent material. For example, portions of the hub 60 can be made of transparent material where it is advantageous to be able to see through a portion of the hub 60 in order to observe other components of the catheter housing 10. The hub 60 can be made of substantially shockproof and/or durable material. This is advantageous because the catheter housing 10 and/or the hub 60 can be subjected to impact during implementation of the device onto, for example, patients in a hospital. The hub 60 can comprise substantially waterproof material. This is advantageous because the catheter housing 10 and the hub 60 can be subjected to water or other liquids when the device is in use.

The wall 61 can include a top surface. The top surface can be concave or convex. Additionally, the top surface can be substantially flat. The top surface can be smooth and/or rounded.

As illustrated in FIGS. 4A and 4B, the hub 60 can contain an opening 63 in the membrane 62. This opening 63 can be positioned over a site where a catheter needle is to be inserted into a patient. The opening 63 can be sized and shaped to fit within the wall 61 (see FIG. 4B). For example, the opening 63 can be generally egg-shaped, trapezoidal, rectangular, square, oval, and/or circular in shape, among other shapes. Additionally, the opening 63 can be a combination of these described shapes. For example, as shown in FIG. 4B, the opening 63 can have a rounded end and a substantially straight end. Additionally, the opening 63 can be bell-shaped, or can contain a rounded end and a substantially straight end with a round recess in the substantially straight end (see, e.g., FIG. 4B) so as to accommodate a portion of a catheter 42, needle, and/or portion of a catheter device 40 to advantageously lay.

As also illustrated in FIG. 4B, the membrane 62 can extend around the opening 63 in a region defined within the wall 61 and surrounding an insertion site. Such configurations can confine the insertion site to within the boundaries of the wall 61 and can thus advantageously reduce and/or elimination ingress of pathogens to the insertion site. The membrane 62 can include a thin silicone membrane. The membrane 62 can surround the needle and/or the insertion site. This can advantageously help to ensure that the hub 60 is secured and/or sealed to a patient's skin. For example, the membrane 62 can surround at least a portion of the insertion site and/or needle to provide a hermetic sealing isolation state between the hub 60 and the patient's skin. Accordingly, the membrane 62 can help to inhibit or prevent air and/or gases from an outside environment from entering the insertion site. Such configurations can also inhibit or prevent lower edges of a catheter device or portion thereof from contacting skin underneath. This can help to inhibit or prevent skin abrasions, ulcers, and/or irritation caused by contact between the catheter device or portion thereof and the patient's skin.

The hub 60 can include one or more markers or indicators 69 located on a portion of the wall 61 and/or the membrane 62, near the opening 63. For example, the hub 60 can include one, two, three, four, five, six, or seven or more markers or indicators 69. For example, the hub 60 can have four markers 69, two of which are disposed proximate to a first side of the opening 63 and two of which are disposed proximate to a second side of the opening 63. The one or more markers 69 can help a caregiver position and align the hub 60 over an insertion site where the catheter and/or needle has been already inserted. Alternatively, the one or more markers 69 can help provide an indication as to where a needle should be inserted into a patient. This can greatly aid caregivers in determining where the optimal insertion location should be so as to correspond with the position of a catheter device 40 when it is engaged and secured by the lock 26, 126 of the cover 20, 120. The one or more markers 69 can be located on a portion of the wall 61 and/or the membrane 62 proximate to the opening 63 (see FIG. 4B). For example, the one or more markers 69 can be located on a portion of the membrane 62 near a side of the wall 61 (see FIG. 4B). The one or more markers 69 can comprise a line, dot, or other indicator, for example.

As illustrated in FIG. 4A-4B, the membrane 62 of the hub 60 can include an inner membrane portion 64. The inner membrane portion 64 can be proximate to the opening 63 and can be contained within the boundaries of the wall 61. The inner membrane portion 64 can provide a platform for the catheter or portion thereof to rest or lay on when the catheter and/or needle is inserted into the patient. For example, the catheter or portion thereof can be inserted into the patient and can rest on the inner membrane portion 64, the lock 26, 126 of the cover 20, 120 and can be placed over a catheter device 40 and/or tubing 41 that rests on the inner membrane portion 64 and can secure the catheter device 40 and/or tubing 41 to prevent movement of the catheter 42, catheter device, 40, and/or tubing 41.

As shown in FIGS. 4A-4B, the wall 61 can extending upwards and/or around a portion of or all of the catheter insertion site. The wall 61 can comprise a variety of shapes egg-shaped, trapezoidal, rectangular, square, oval, and/or circular in shape, among other shapes. The wall 61 or portions thereof can be rounded or alternatively non-rounded. For example, the wall 61 can have a top surface that is rounded. The wall 61 or portions thereof can have a smooth surface, or alternatively, a rough surface. The wall 61 can be a stadium wall. For example, the wall 61 can extend upwards and around a portion of the catheter insertion site like a stadium.

The wall 61 can include one or more grooves 68. For example, wall 61 can include one, two, three, four, five, six, or seven or more peripheral grooves 68. As discussed previously, the one or more grooves 68 can be configured to accommodate one or more protrusions 30, 130 on the cover 20, 120. The one or more grooves 68 of the wall 61 can be continuous around the perimeter of the wall 61. Alternatively, the one or more peripheral grooves 68 can be non-continuous. For example, as shown in FIGS. 4A and 4C, the one or more peripheral grooves 68 can extend along a portion of the perimeter of the wall 61, but not extend continuously around the entire perimeter of the wall 61. For example, the one or more peripheral grooves 68 can extend along a perimeter of the wall 61 proximate to the inlet 67, but terminate at a location before reaching the inlet 67. Additionally or alternatively, the one or more peripheral grooves 68 can extend along a perimeter of the wall 61 proximate to the tube opening 65 and/or joint 66, but terminate at a location before reaching the tube opening 65 and/or joint 66. The wall 61 can include more than one peripheral groove 68 that extend along the perimeter of the wall 61, which secure to one or more protrusions 30, 130 on the cover 20, 120. As discussed previously, the one or more protrusions 30, 130 can secure to the one or more peripheral grooves 68 by a snap-fit, press fit, and/or other configuration for securely connecting the cover 20, 120 to the hub 60.

As illustrated in FIG. 4A, the wall 61 can include one or more joints 66 that can be pulled apart or pushed together, to allow for a needle, fluid tube, or catheter device or portion thereof to more easily pass through the tube opening 65. For example, the wall 61 can include one, two, three, four, five, six, or seven or more joints 66. The wall 61 can include one joint 66. The joint 66 can be proximate to the tube opening 65. Thus, the joint 66 can provide a mechanism whereby a needle, fluid tube, or catheter device or portion thereof can be accommodated by the wall 61 so as to be able to pass into and through the wall 61 with relative ease and in a short timeframe. The joint 66 can be configured to hermetically close the wall 61 around the tube opening 65, and can form a seal in the wall 61 and the hub 60. The joint 66 can permit the wall 61 to be spaced apart, pulled apart, pushed apart, and/or otherwise partially separated. Alternatively, the joint 66 can extend down an entire side portion of the wall 61 so that the joint 66 separates an entire cross-section of the side portion of the wall 61. Alternatively, the joint 66 can separate at least in part by flexing the wall 61.

The membrane 62 of the hub 60 can be sized and shaped to accommodate a patient's arm, leg, appendage, or other portion of a patient's body. The membrane 62 can have rounded edges or alternatively, non-rounded edges. The membrane 62 can be rectangular in shape. Alternatively, the membrane 62 can be egg-shaped, trapezoidal, square, oval, and/or circular in shape, among other shapes. Additionally, the membrane 62 can comprise a combination of these described shapes.

The membrane 62 can be integrally formed with the wall 61. For example, the membrane 62 can be molded with the wall 61. The wall 61 can be pressed onto, adhered to, and/or otherwise attached to a portion of the membrane 62. The membrane 62 can include a recessed portion to accommodate the wall 61. For example, the membrane 62 can contain a recessed portion that surrounds the opening 63 and allows a portion of the wall 61 to sit within or be accommodated by the recessed portion of the membrane 62. Additionally, the membrane 62 can contain a recessed portion to accommodate other portions of the catheter housing 10, such as the cover 20, 120 or a portion of the catheter device 40 and/or tubing 41. The membrane 62 can include one or more different materials. Additionally, the membrane 62 can comprise one material. The wall 61 and the membrane 62 can include the same material. Alternatively, the wall 61 and the membrane 62 can include different materials. The membrane 62 can comprise silicone, plastic, and/or rubber, among other materials. The membrane 62 can comprise, at least in part, biocompatible materials.

The membrane 62 can extend outwardly from a base of the wall 61 (see FIG. 4B). For example, the membrane 62 can be coupled with an outer edge of the base of the wall 61. A bottom surface of the base of the wall 61 can be coupled with the membrane 62. A portion of the membrane 62 can extend inwardly from the wall 61 (see, e.g., FIG. 4B). The membrane 62 can surround at least a portion of a perimeter of the wall 61. Thus, the membrane 62 can surround all or a portion of a perimeter of an inner edge and/or an outer edge of the base of the wall 61.

The membrane 62 can have a top surface comprising a plurality of hook and loop structures, buckles, fungi-like attachment, and/or other attachment structures or methods. For example, the top surface of the membrane 62 can comprise Velcro. The top surface of the membrane 62 can facilitate connection of the one or more fastening straps 80, as discussed above. For example, the one or more fastening straps 80 can couple to the cover 20, 120, wrap around a portion of a patient's body, and secure to a portion of the top surface of the membrane 62.

Figure 4D:
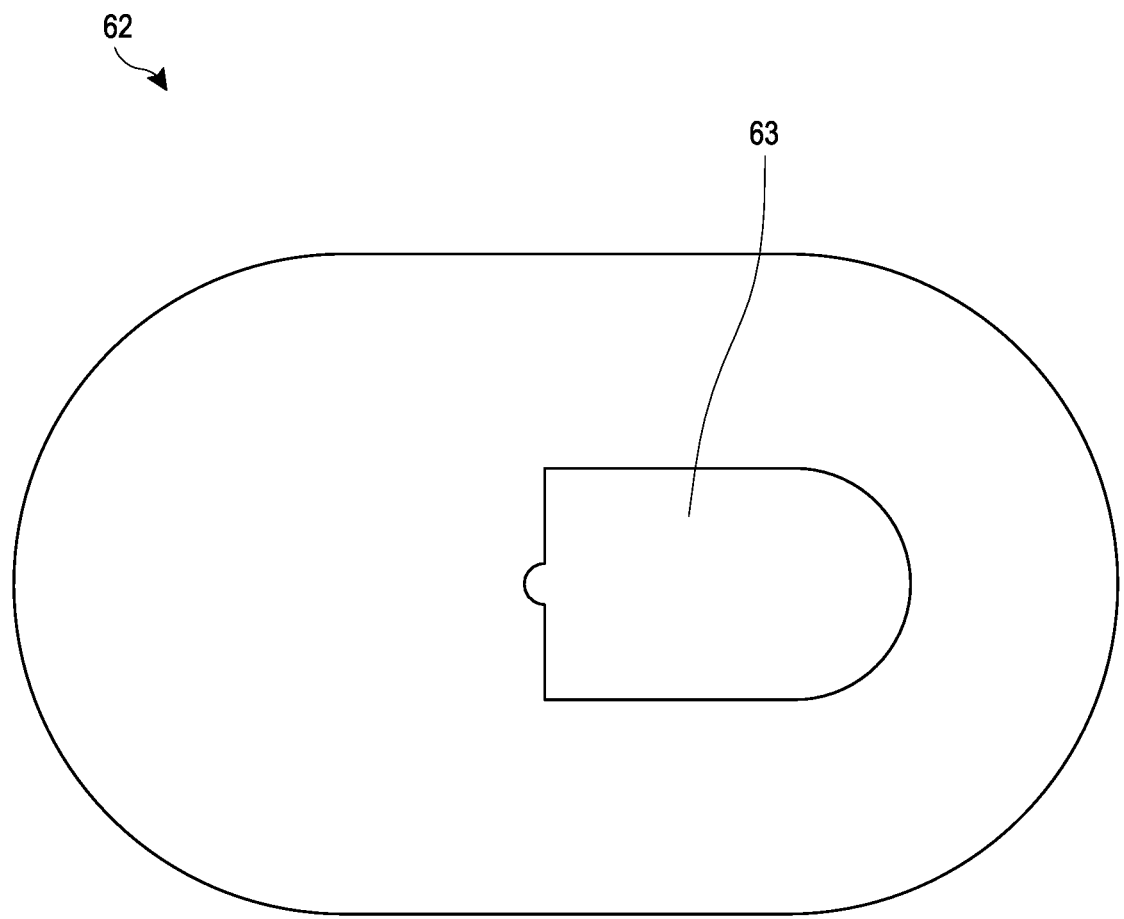
FIG. 4D illustrates a bottom view of the hub of FIG. 4A.
Figure 4E:
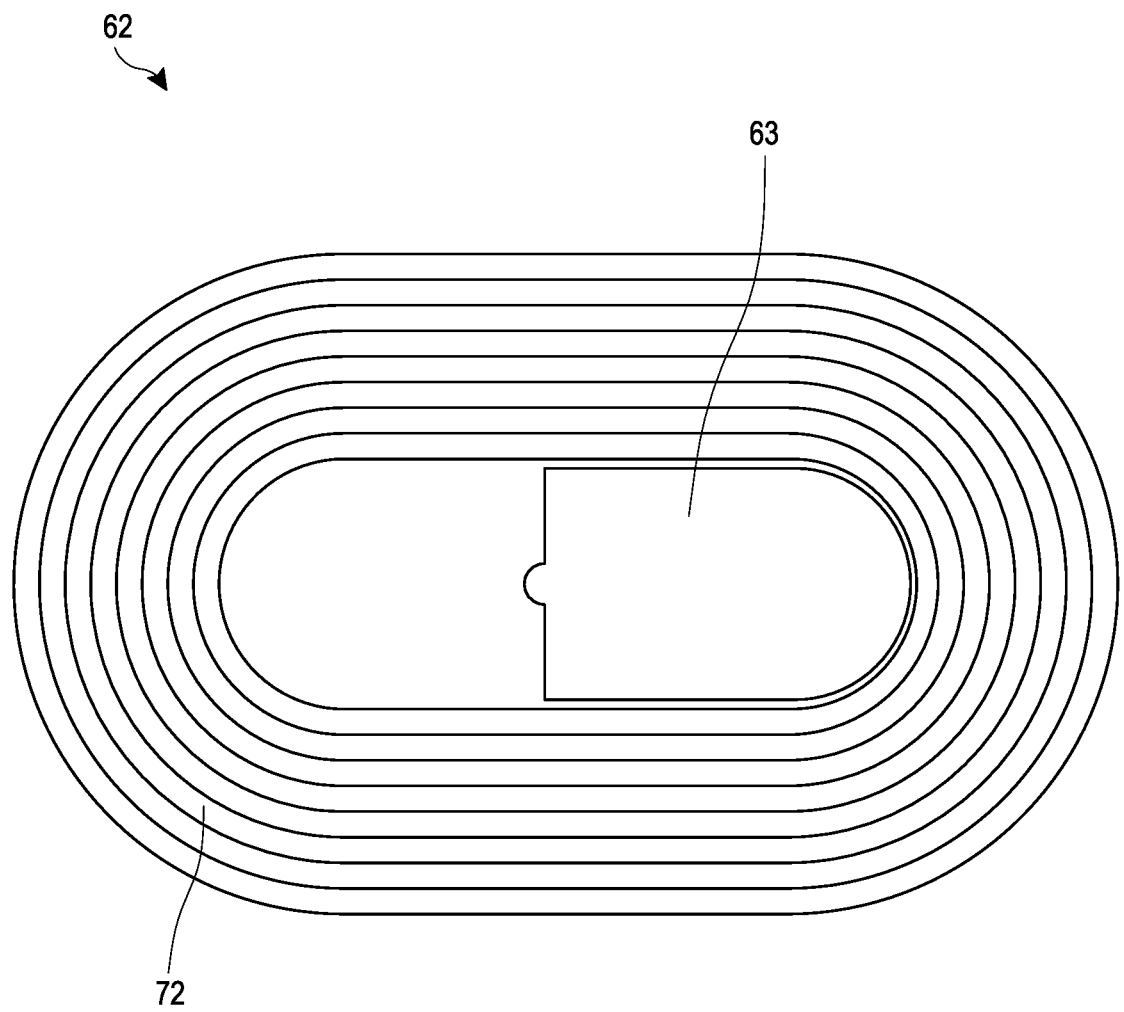
FIG. 4E illustrates a bottom view of the hub of FIG. 4A having anti-slip rings on a bottom surface of the hub.
Figure 4F:
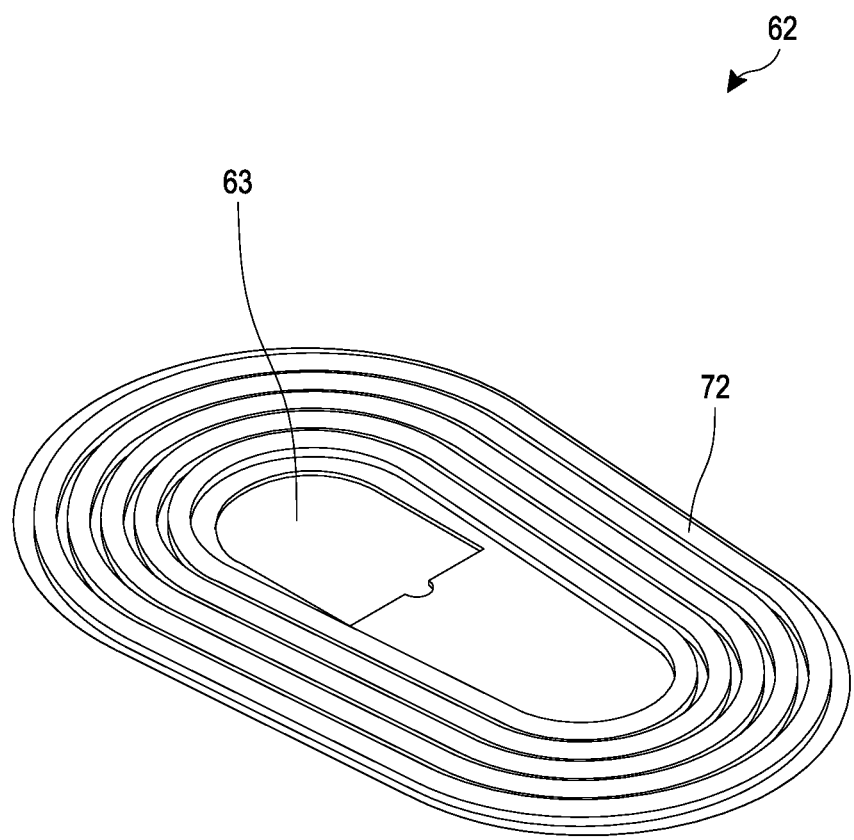
FIG. 4F illustrates a bottom perspective view of the hub of FIG. 4E having anti-slip rings on a bottom surface of the hub.

The membrane 62 can have a bottom surface including an anti-slip material configured to secure the catheter housing device, or a portion thereof such as the hub 60, to a patient's skin (see FIG. 4D). The bottom surface of the membrane 62 can comprise silicon-adhesive, sticky material, rubber compound, biocompatible high-tack anti-slip coating, adhesive, or other types of anti-slip material and/or methods that can prevent slipping or movement of the hub 60 and/or catheter housing 10 when secured to a patient's skin. The bottom surface can comprise a silicone or regular adhesive, for example. The bottom surface can comprise an anti-microbial coating. The bottom surface can comprise anti-slip material in the form of layers, circuits, circles, strips, coatings, and/or rings. For example, as shown in FIGS. 4E and 4F, the bottom surface of the membrane 62 can include one or more anti-slip rings 72, such as one or more, two or more, three or more, four or more, five or more, six or more, seven or more, or eight or more anti-slip rings 72. The anti-slip rings 72 can be, for example, silicon adhesive rings. The anti-slip rings 72 can be substantially cylindrical, circular, square, or rectangular, among other shapes. The anti-slip rings 72 can also comprise a combination of these shapes. The anti-slip rings 72 can have rounded or partially rounded cross-sections. The anti-slip rings 72 can be sized, shaped, and/or spaced apart to accommodate ventilation or for other reasons. For example, the anti-slip rings 72 can provide spacing to allow air to flow between the anti-slip rings 72 and a patient's skin. Thus, even if the hub 60 and/or the catheter housing 10 is secured to a patient, the patient can still benefit from ventilation to the region in and around the insertion site without comprising a hermetic sealing of the insertion site. The anti-slip rings 72 can be arranged adjacent to one another so that they at least partially surround the opening 63 in the membrane 62 (see FIG. 4E). The anti-slip rings 72 can be continuous or non-continuous. Alternatively, the anti-slip rings 72 can be non-continuous—for example, they can terminate at two ends.

At least a portion of the membrane 62 can be used for fixing various peripheral tools, such as a catheter tube, an LCD monitor of a micro-processor, and/or a metallic ampule of the soothing and sterilizing gas. Such peripheral tools can be fixed or secured to at least a portion of the membrane 62 through hook and loop structures, buckles, fungi-like attachment, and/or other attachment structures or methods.

The membrane 62 of the hub 60 can have a bottom surface that comprises a corrugated structure. The corrugated structure can be substantially cylindrical, circular, square, or rectangular, among other shapes. The corrugated structure can also comprise a combination of these shapes. The corrugated structure can be sized, shaped, and spaced apart to accommodate ventilation or for other reasons. The corrugated structure can provide gaps to allow air to flow between the corrugated structure and contact the patient's skin. Thus, even if the hub 60 and/or the catheter housing 10 is secured to a patient, the patient can still benefit from ventilation to the region/section of the bottom surface that contacts the skin of the patient. The corrugated structure can be one continuous piece, or alternatively, can comprise more than one piece.

The membrane 62 of the hub 60 can have a bottom surface that includes one or more suction cups. For example, the bottom surface can have one or more, two or more, three or more, four or more, five or more, six or more, seven or more, eight or more, nine or more, ten or more, or eleven or more. For example, the bottom surface can have between twenty and fifty suction cups. Alternatively, the bottom surface can have between 50 and a hundred suctions cups. The one or more suction cups can be positioned in one or more rows. The suction cups can be configured to stabilize a connection between the hub 60 and the patient's skin. The hub 60 and/or the membrane 62 can be manually pressed onto the patient's skin to secure the hub 60 to the patient. The suction cups can engage with the patient's skin such that the hub 60 can be at least partially secured to the patient with or without requiring the fastening straps to be connected to the hub 60 and/or wrapped around a portion of the patient's body.

The one or more suction cups can be substantially cylindrical, circular, square, or rectangular, among other shapes. The suction cups can also comprise a combination of these shapes. The suction cups can be sized, shaped, and spaced apart to accommodate ventilation or for other reasons. The suction cups can be spaced to provide gaps to allow air to flow between the suction cups and the patient's skin. Thus, even if the hub 60 and/or the catheter housing 10 is secured to a patient, the patient can still benefit from ventilation to the region/section of the bottom surface that contacts the skin of the patient.

The catheter housing 10 can include one or more light sources, such as one, two, three, four, five, six, seven, eight, or nine or more light sources. The light sources can include LEDs. The light sources can illuminate exterior and/or interior regions at or near the catheter housing 10. For example, the light sources can illuminate interior portions of the catheter housing 10 and/or the catheter insertion site to allow such regions to be inspected during the day and/or night. The light sources can also indicate whether cover 20, 120 is secured to the hub 60 and/or indicate whether the lock 26, 126 is secured to the catheter device 40 and/or whether the catheter device 40 is dislodge or moved. For example, the lights can change colors, flash at certain speeds, and/or change brightness to indicate whether cover 20, 120 is secured to the hub 60 and/or indicate whether the lock 26, 126 is secured to the catheter device 40. The light source can include a UV light source to help with disinfecting the catheter and/or hub and/or insertion site. For example, the catheter housing 10 can include a UV Surface Mount LED (SMD LED). The UV SMD LED can provide active sterilization and disinfection to interior regions of the catheter housing 10 and/or the catheter insertion site when the catheter housing 10 is secured to a patient. This can in turn drastically reduce contamination, infections, and/or diseases that can occur with traditional catheter securement devices and methods. One or more UV SMD LEDs can be positioned on interior portions of the catheter housing 10. For example, one or more UV SMD LEDs can be positioned or located within the cover 20, 120, or components of the cover 20, 120. One or more UV SMD LEDs 24, 124 can be positioned on or located within the bridge 27, 127, and can be configured to shine or point at the catheter insertion site (See FIGS. 2F-2G and FIGS. 3G-3H). Alternatively or additionally, one or more UV SMD LEDs can be positioned on or located within the hub 60. For example, one or more UV SMD LEDs can be positioned on or located within the membrane 62 and/or the wall 61. The one or more lights and/or one or more UV SMD LEDs can be electronically coupled to a sensor, wherein the sensor is configured to sense when the tongue of the cover 20, 120 is secured to the groove of the wall 61 of the hub 60 and send a signal to the one or more lights and/or one or more UV SMD LEDs when the tongue of the cover 20, 120 is secured to the groove of the wall 61 of the hub 60. The one or more lights and/or the one or more UV SMD LEDs can be configured to automatically activate when receiving the signal from the sensor. The one or more light sources discussed above can be located on exterior or interior portions or regions of catheter housing 10. For example, the one or more light sources discussed above can be positioned on an exterior-facing surface of cover 20, 120 and/or an exterior facing surface of hub 60.

The catheter housing 10 can include one or more sensors. Additionally, the one or more sensors can be located on various components of the catheter housing 10. For example, the one or more sensors can be located and/or mounted to the cover 20, 120 or portions thereof, the one or more fastening straps 80, and/or the hub 60 or portions thereof (for example, the membrane 62). Additionally, the number of sensors located on and/or mounted to the various components described above can be one, two, three, four, five, six, seven, eight, nine, ten, eleven, twelve, or thirteen or more.

The one or more sensors can be used to measure various physiological parameters or condition of a patient. The one or more sensors can include a temperature sensor (for example, a topical temperature sensor), a blood pressure sensor, a blood oxygen saturation sensor, a sensor for liquid and blood leakage, and/or a skin humidity sensor. The sensors can be located in various locations on the membrane 62.

The one or more sensors can include one or more bio-sensors. The bio-sensors can include a micro-processor. For example, the bio-sensors can include an LCD monitor for detecting, measuring, storing and/or displaying patient vital functions, including venous and arterial blood pressure, heart beats, blood oxygen levels, general and topical temperature, and local tissue humidity, and/or venous blood current speed, among others. The measurements and/or calculations performed and/or taken by the one or more sensors, can be stored on a flash storage memory positioned on one or more of the cover 20, 120 or portions thereof, the one or more fastening straps 80, and/or the hub 60 or portions thereof (for example, the membrane 62). Any of the sensor measurements discussed herein, along with any data associated with the catheter insertion or IV therapy or treatment, can be wirelessly transmitted to a patient monitoring system for analysis, management, organization, and/or display to a care provider or user. Such information and/or data can also be transmitted to a database including patient medical records or electronic patient medical records. Alternatively and/or additionally, such information and/or data can be transmitted to a personal communications device, such as a tablet or smart device, or a software application or website. Transmitting such information and/or data can help a caregiver keep a log for an IV catheter insertion procedure and/or experience for a given patient which can help prevent any issues that might occur in a future IV therapy for the patient.

Figure 5A:
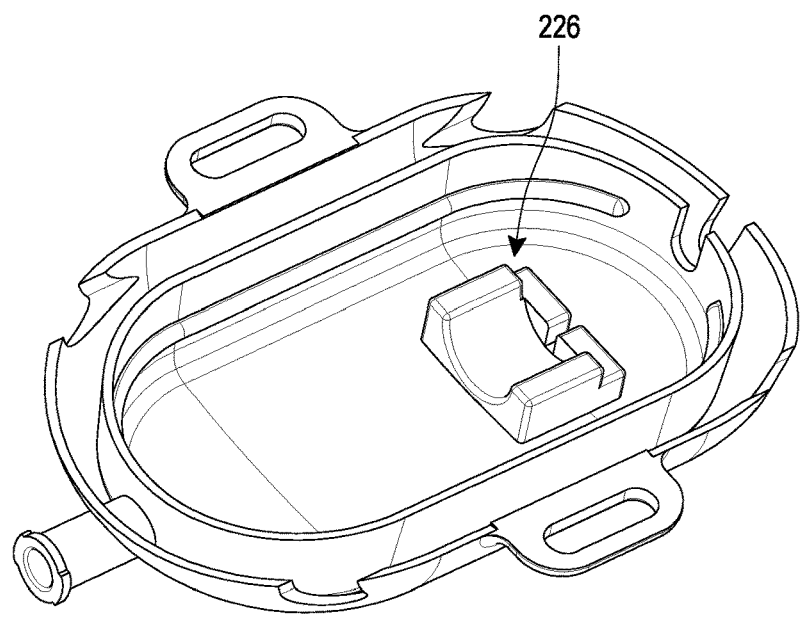
FIG. 5A illustrates a perspective view of an alternative design for a lock for a cover of the catheter housing of FIG. 1A.
Figure 5B:
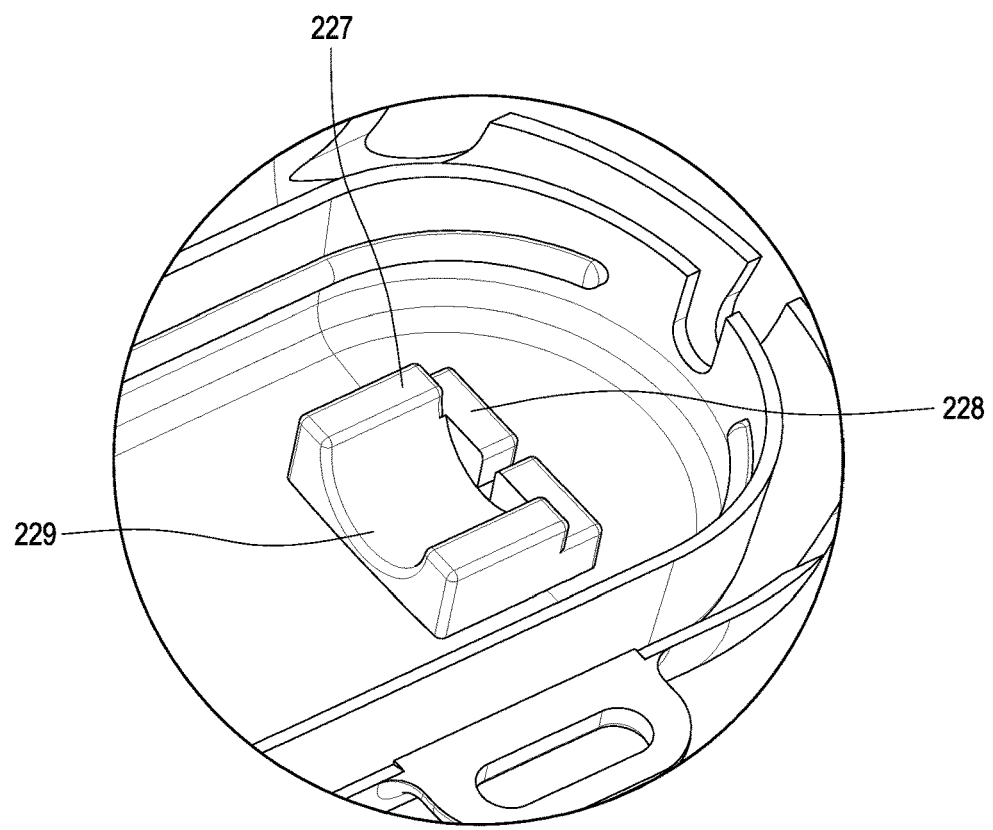
FIG. 5B illustrates a close-up perspective view of the lock of FIG. 5A.
Figure 5C:
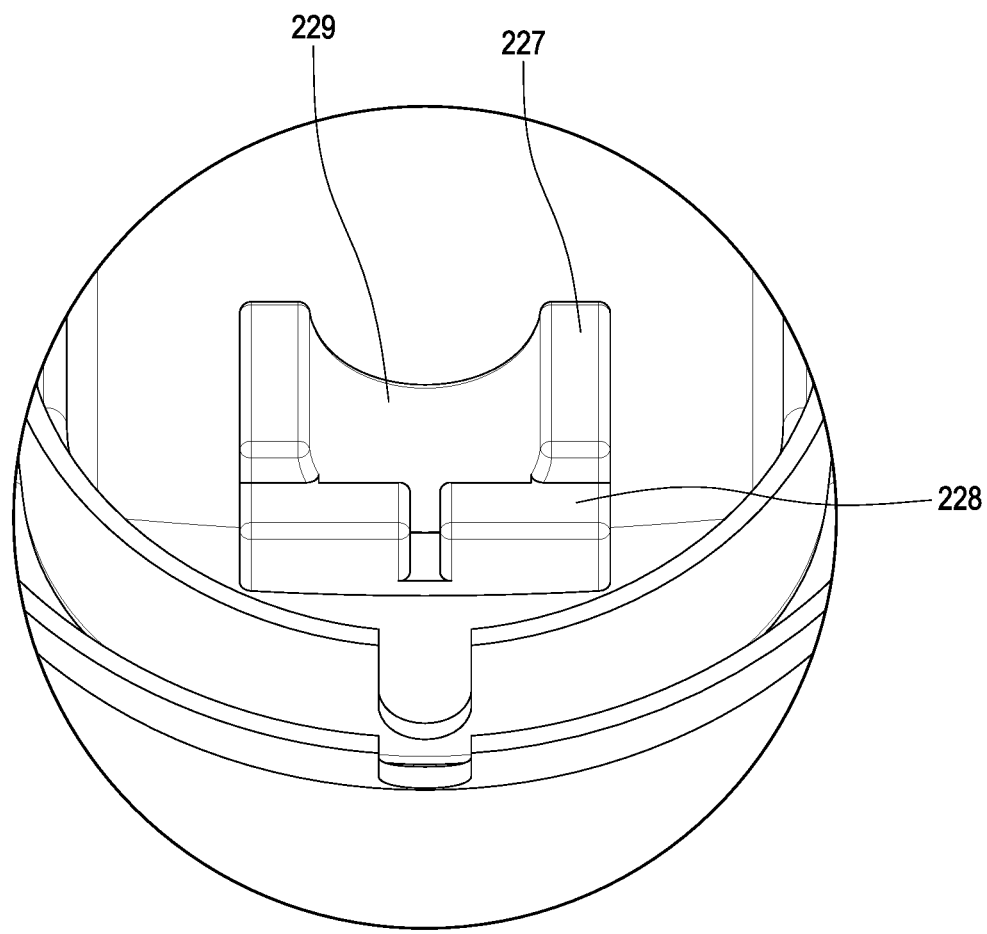
FIG. 5C illustrates another close-up perspective view of the alternative design for the lock of FIG. 5A.

FIGS. 5A-5C illustrate an alternative design for a lock 226 that can be incorporated into the cover 20, 120 of catheter housing 10. Lock 226 can secure the catheter device 40, catheter 42, and/or tubing 41 connected to the catheter device 40, for example, before, during, and/or after a catheter 42 is inserted into a patient at an insertion site. The lock 226 can include one or more walls configured to secure to a catheter device 40 or a portion thereof. For example, the lock 226 can include one, two, three, four, five, six, seven, or eight walls configured to secure to a catheter device 40 or a portion thereof (for example, a male luer connector of catheter device 40). As shown by FIGS. 5A-5B, the lock 226 can include a front piece 227 and a back piece 228. The front piece 227 and back piece 228 can be integral, or alternatively, non-integral. The front piece 227 can be sized, shaped, and/or oriented to accommodate, conform to, and/or secure to portions of catheter devices 40 of any size and/or shape. For example, the front piece 227 can have a recess 229 sized/and/or shaped to accommodate, conform to, and/or secure to portions of catheter devices 40 of any size and/or shape. Recess 229 can be of a variety of shapes. For example, recess 229 can be shaped like an arch, half-circle, half-moon, or can be rectangular, trapezoidal, or square shaped. The dimensions of the recess 229 can be varied to accommodate any size and/or shape of catheter devices 40 (or portions thereof, such as a male luer connector) or portions connected thereto. For example, the recess 229 can be shaped like a half-circle with a radius equal or substantially equal to a radius of a catheter device 40 having a circular cross-section. The front piece 227 can have exterior surfaces which face the inner wall 29, 129 of the cover 20, 120 and can have interior surfaces which face towards each other or partially toward each other and/or contact the catheter device 40 when the catheter device 40 is secured to the lock 226. The interior surfaces of the front piece 227 can be straight. Alternatively, the interior surfaces of the front piece 227 can be curved or partially curved to conform to a portion of a catheter device 40, as shown by FIGS. 5A-5B. The interior surfaces of the front piece 227 can be shaped to surround or partially surround a portion of a catheter device 40. The interior surfaces of the front piece 227 can have a smooth surface which can enable the catheter device 40 to slide into the front piece 227 easily. Alternatively, interior surfaces of the front piece 227 can have a rough surface which can provide more frictional resistance. The interior surfaces of the front piece 227 can have a combination of smooth and rough surface. The front piece 227 can prevent sideways movement, micro-movement, and/or erosion of the catheter device 40 when the catheter device 40 is secured to the front piece 227.

The back piece 228 of the lock 226 can be sized and/or shaped to accommodate the catheter device 40 or a portion thereof, tubing 41, connectors, extensions, and/or adapters coupled to such components, for example. For example, the back piece 228 can have a recess with a width that is sized and shaped to accommodate and/or secure to tubing 41 or a portion of a catheter device 40 (such as a stem or other portion of a male luer connector). The recess can be rounded. Alternatively, the recess can be non-rounded. The recess can be circular. Alternatively, the recess can be non-circular. The recess can comprise a half-moon shape or another shape. The recess can comprise a half-circle shape. The recess can be square shaped or rectangular shaped (See FIGS. 5A-5C). The back piece 228 can be positioned adjacent to the front piece 227 and/or the recess 229 of the front piece 227 and can prevent of the catheter device 40 or a portion thereof from being dislodged when tubing 41 is pulled. For example, where the catheter device 40 is secured to the lock 226, if the tubing 41 is pulled, a portion of the back piece 228 that extends adjacent to a side of the front piece 227 and/or the recess 229 of the front piece 227 can act to support a side or end of the catheter device 40 so that the catheter device 40 does not move or become dislodged (see FIGS. 5A-5B).

The securement of catheter 42, catheter device 40, and/or tubing 41 by or with the lock 226 can be a physical locking, holding, stabilizing without locking, retaining, stabilizing to prevent or reduce the likelihood of movement, stabilizing to minimize movement, or another type of securement. The lock 226 can be sized and/or shaped to secure any type of catheter 42, catheter device 40, and/or tubing 41. For example, a catheter device 40 can be secured by the front piece 227 (including the recess 229 of the front piece 227) and/or the back piece 228. The lock 226 can secure catheter device 40 and/or a catheter 42 in the proper orientation relative to the patient's skin and/or the catheter insertion site. This can advantageously enable a catheter tip or rim to be secured at a final resting angle or inclination angle that approximates the angle at which a needle is inserted into a vein of a patient. As discussed previously, this is beneficial because it reduces the chance of injury and/or other complications that can result when the catheter moves or is secured at an angle that damages the vein wall or nearby area. For example, the final resting angle or inclination angle can be between 1 and 45 degrees. The inclination angle can also be between 1 and 10 degrees, between 10 and 20 degrees, or between 20 and 30 degrees. The inclination angle can be more than 45 degrees as well, depending on the implementation of the catheter housing 10 or components thereof (such as the cover 20 and/or hub 60). The inclination angle can also be at a very small angle, such as between 0 and 1 degrees. Current techniques for securing a catheter to a patient can result in dislodgment, inappropriate angle of the catheter, or twisting or other movement while the catheter is inserted into a patient. However, the lock 226 described herein, which can accommodate any type of catheter device design and/or catheter coupled thereto, can secure the catheter device and catheter in a position that provides for a normal or optimal angle. This can help to limit or prevent irritation and/or cannula tip erosion caused by contacting of the cannula tip with vein lumen sides. Thus, unlike conventional catheter stabilization methods where securing the catheter typically results in disrupting the natural angle of the catheter, awkward angling of the catheter against the wall of the vein, and/or in which pressure is applied on the a portion of the catheter device 40 in order to secure it to a patient, the securement angle of the catheter device 40 and/or catheter 42 with the lock 226 can preserve the integrity of the connection of the catheter 42 within the vein.

The cover 20, 120 can include a lock 226 alone or in combination with the bridge 27, 127 discussed above with regard to cover 20, 120. For example, the cover 20, 120 can include a bridge 27, 127 that can, along with the lock 226, help secure, guide, and/or align a catheter 42, catheter device 40, and/or connectors, extensions, adapters, and/or other devices or components connected thereto. The cover 20, 120 can include a lock 226 alone or in combination with the recess 25, 125 discussed above with regard to cover 20, 120.

Alternative Design for Catheter Housing

Figure 6A:
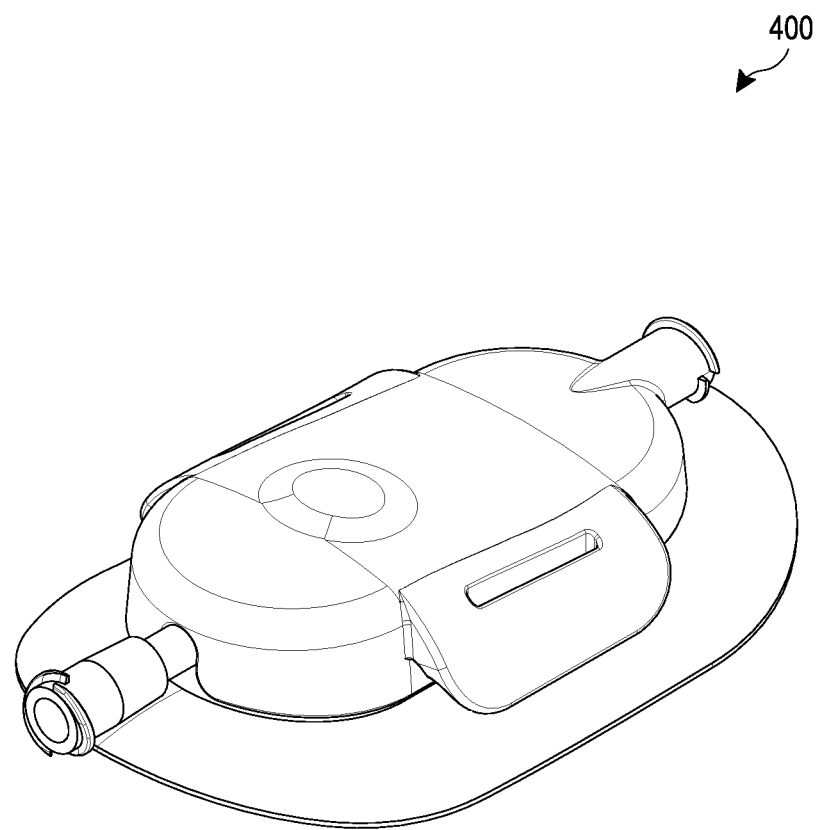
FIG. 6A illustrates a perspective view of an assembly of an alternative design for a catheter housing in accordance with aspects of this disclosure.

FIG. 6A illustrates a perspective view of a fully assembled catheter housing 400 that can be placed on and/or over any portion of a human body. For example, the catheter housing 400 can be secured to an arm, hand, or leg of a patient, and can be secured to the arm, hand, or leg with the use of an anti-slip material on a bottom surface of the catheter housing (or hub or membrane of the hub) around the insertion site without requiring fastening straps. For example, as discussed further below, the bottom surface or a portion thereof can comprise an adhesive material and a release liner, and, when the release liner is pulled off the adhesive bottom surface, the bottom surface of the catheter housing device can be secured to a patient.

Figure 6B:
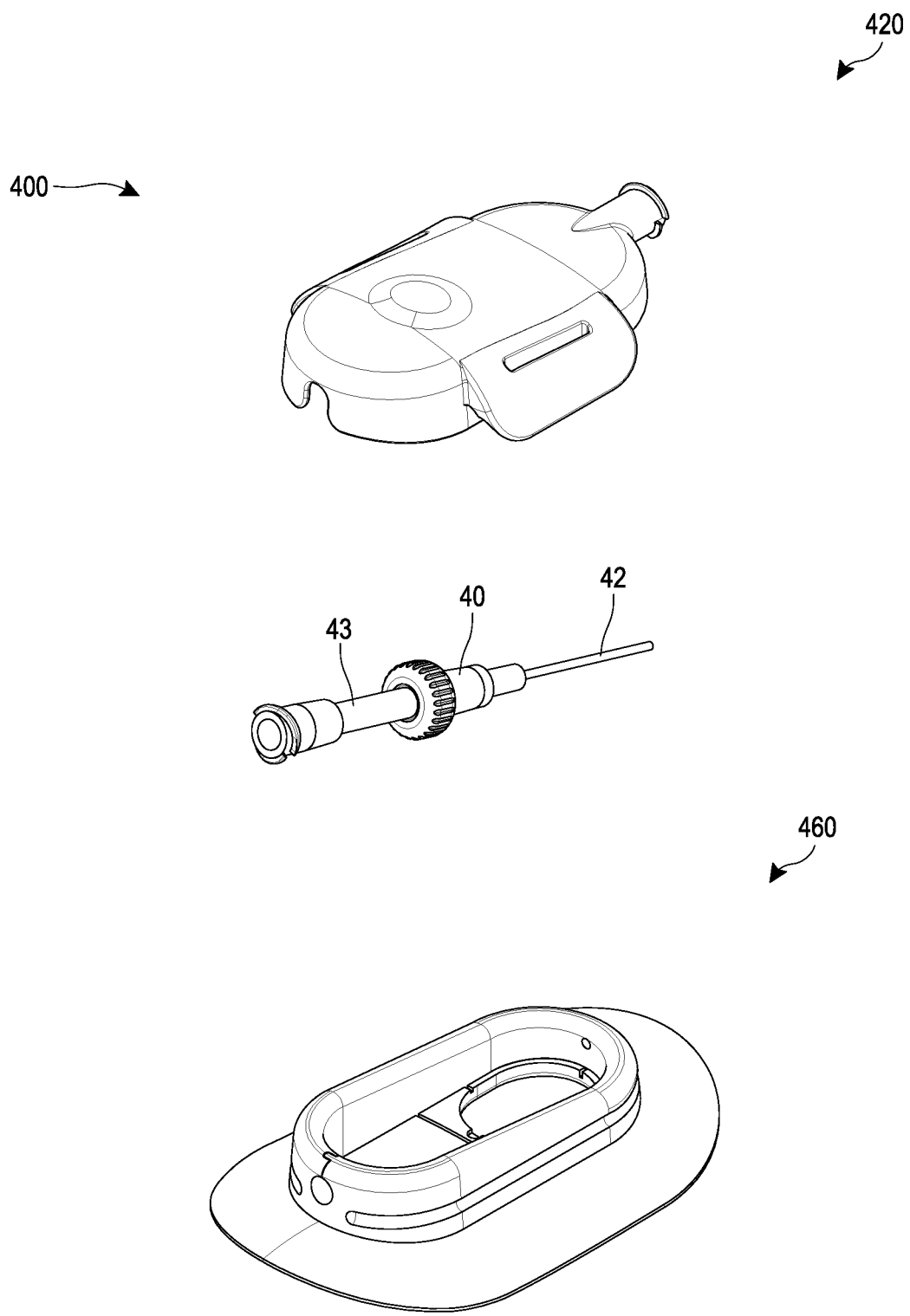
FIG. 6B illustrates an exploded view of the catheter housing of FIG. 6A along with a catheter, catheter device, and an extension set in accordance with aspects of this disclosure.

FIG. 6B illustrates an exploded view of the catheter housing 400 of FIG. 6A. The catheter housing 400 can have a cover 420 and a hub 460. As discussed herein, the catheter housing 400 can secure catheter device coupled to the catheter and the catheter. For example, the catheter housing 400 can secure a catheter device 40 coupled to the catheter 42. One advantage of the catheter housing 400 is that it can comprise of small number of components or parts, which allow for simple assembly and securement of any type of catheter device 40 and/or components connected thereto. While the catheter housing 400 discussed herein can include the cover 420 and hub 460 as separate components, the cover 420 and the hub 460 can comprise a unitary structure, and one of skill in the art will recognize that the features discussed herein with respective to the cover 420 and the hub 460 can be incorporated in some, many, or all respects into a unitary catheter housing.

Figure 6C:
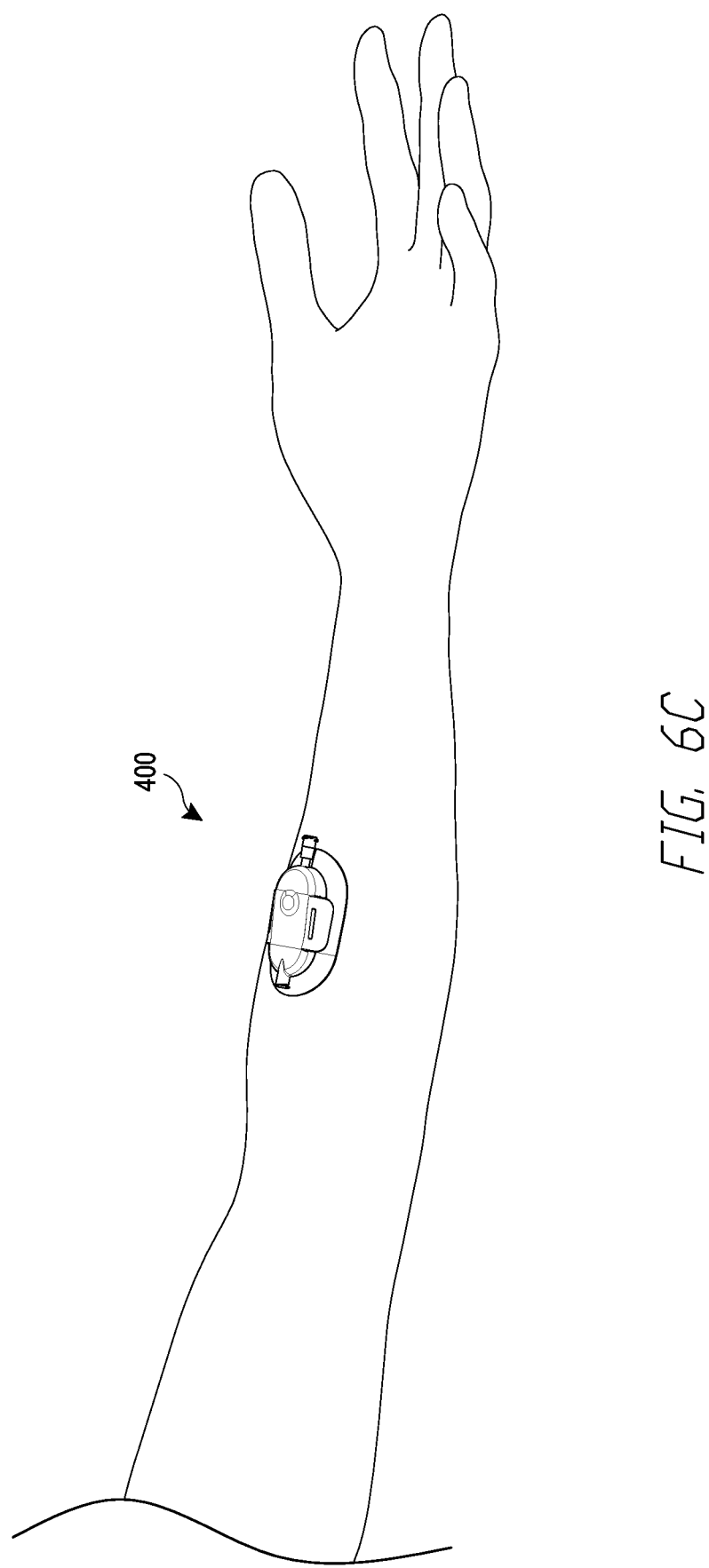
FIG. 6C illustrates a perspective view of the catheter housing of FIG. 6A in an assembled form on a human arm.
Figure 6D:
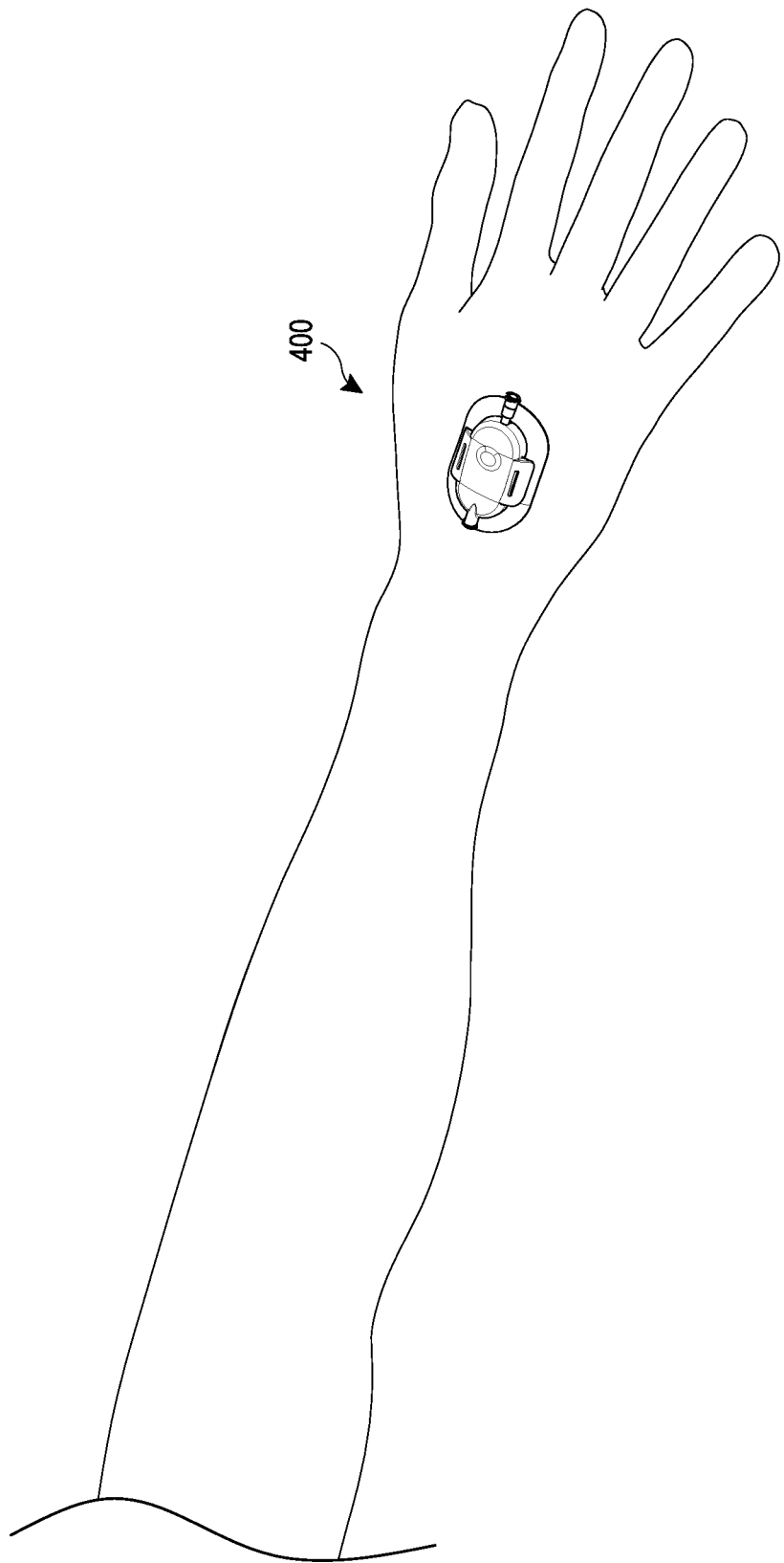
FIG. 6D illustrates a perspective view of the catheter housing of FIG. 6A in an assembled form on a human hand.

As discussed below, the cover 420 can be secured to the hub 460 and/or the hub 460 can be secured to the cover 420. As illustrated in FIGS. 6A and 6C, when the catheter housing 400 is assembled, the cover 420 can substantially surround or enclose the hub 460 and/or a portion thereof. The hub 460 can have an opening in a wall of the hub 460 that allows the catheter device 40 and/or tubing 43 coupled to catheter device 40 to pass therethrough and/or be inserted into an interior of the hub 460. The hub 460 can also have an opening in a membrane of the hub 460 that allows a catheter to remain inserted in a patient while the hub 460 is secured to at least a portion of the catheter housing 400, such as the cover 420. The catheter housing 400 can secure to a patient with the use of an anti-slip surface, mechanism, ring, or protrusion on a bottom surface of the membrane of the hub 460, as discussed below. As also discussed below, hub 460 can include one or more lips on a bottom surface which help to seal a catheter insertion site in case the integrity of the adhesive bottom surface of the hub 460 is lost or degraded in portions thereof.

FIG. 6C illustrates a perspective view of an assembled catheter housing 400 secured to a human arm. As discussed above, catheter housing 400 can also be attached to other locations on a human body, such as on a thigh, foot, calf, ankle, arm, leg, hand, hand, and/or neck, among other body parts. For example, the catheter housing 400 can be attached to various body parts and surround catheter insertion sites located in different regions on a human body, such as a portion of an underside of an arm, among other areas. The catheter housing 400 can be positioned and/or secured at and/or near any location where an IV can be inserted into a patient. The catheter housing 400 can be secured to a portion of a patient's body without the use of a fastening strap. As discussed herein, the catheter housing 400 can include an anti-slip surface, mechanism, ring, or protrusion on a portion of the catheter housing 400 that can contact a patient. The catheter housing 400 and/or components thereof can be made from a variety of material or combination of materials. For example, the catheter housing 400 and/or components thereof (such as the cover 420 and/or the hub 460) can comprise silicone, plastic, and/or rubber. The catheter housing 400 and/or components thereof (such as the cover 420 and/or the hub 460) can comprise appropriate biocompatible materials. The catheter housing 400 and/or components thereof (such as the cover 420 and/or the hub 460) can comprise medical grade soft silicone material. The catheter housing 400 and/or components thereof (such as the cover 420 and/or the hub 460) can be substantially waterproof, durable, and/or washable. The catheter housing 400 and/or components thereof (such as the cover 420 and/or the hub 460) can be disposable, which can advantageously allow the catheter housing 400 and/or components thereof to be thrown away after use with a patient. The catheter housing 400 and/or components thereof (such as the cover 420 and/or the hub 460) can be include or contain information regarding a patient, such as name, birthdate, and other information. Such information can also be, for example, information relating to the catheter insertion and/or information relating to inspection by a caregiver. The catheter housing 400 and/or components thereof (such as the cover 420 and/or the hub 460) can comprise can be biocompatible and/or recyclable.

The catheter housing 400 and/or components thereof (such as the cover 420 and/or the hub 460) can be sized depending on the patient's characteristics (for example, arm thickness). As discussed herein, the catheter housing 400 can have a low-profile shape and structure and can secure to a portion of a patient and have a minimal "footprint." Thus, the catheter housing 400 can advantageously secure catheter device, a catheter coupled to the catheter device, and/or tubing while taking up minimal space on a portion of a patient's body when secured thereto. In some cases, the total height of the catheter housing 400 can be less than 1 cm, for example. In some cases, the total length of the catheter housing 400 can be between 3 cm and 6 cm, for example. In some cases, the total width of the catheter housing 400 can be between 3 cm and 5 cm, for example.

Figure 7A:
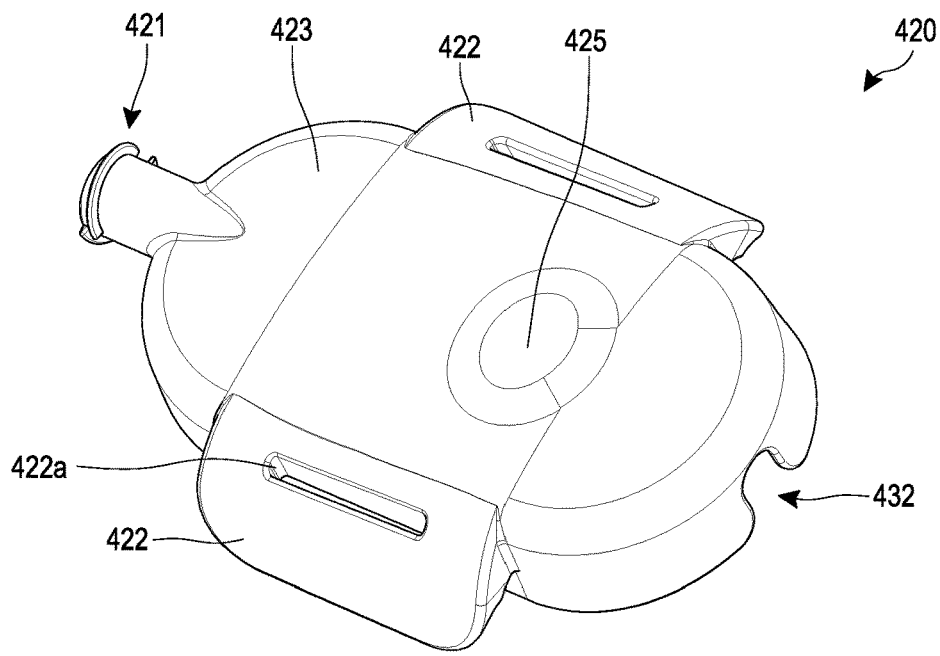
FIG. 7A illustrates a perspective view of a cover of the catheter housing of FIG. 6A.
Figure 7B:
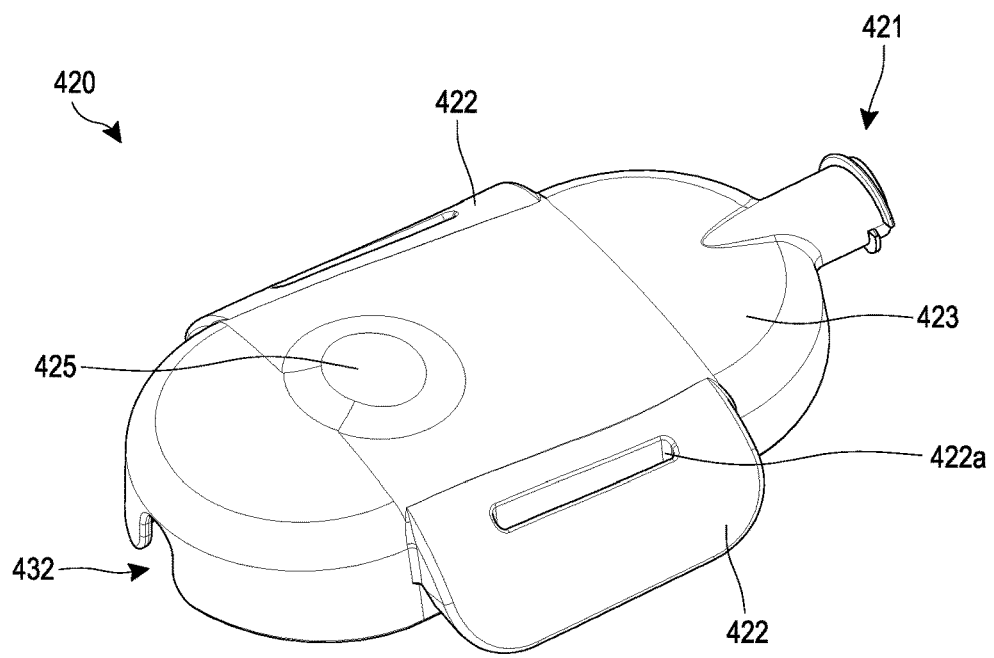
FIG. 7B illustrates another perspective view of the cover of FIG. 7A.
Figure 7C:
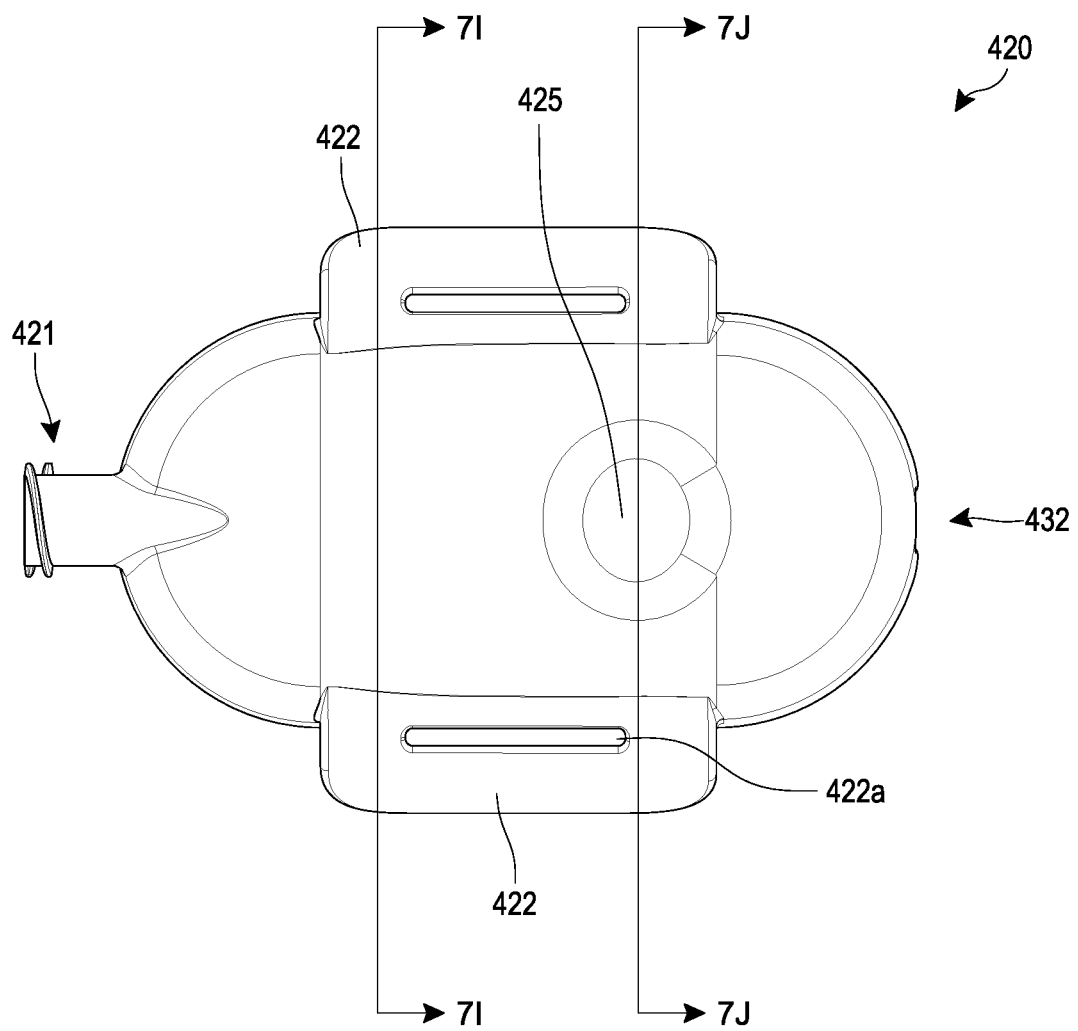
FIG. 7C illustrates a top view of the cover of FIG. 7A.

FIGS. 7A-7B illustrate various perspective views of the cover 420. As discussed herein, the cover 420 can be secured to the hub 460. The cover 420 can be made of transparent material. Alternatively, the cover can be made of nontransparent material. Additionally, the cover 420 can comprise both transparent and nontransparent material. For example, the portions of the cover 420 can be made of transparent material where it is advantageous to be able to see through the cover in order to observe the other components of the catheter housing 400, and/or observe, access, and/or inspect the puncture site without removing the catheter housing 400 or components thereof. The cover 420 can be made of substantially shockproof and/or durable material. This is advantageous because the catheter housing 400 and/or the cover 420 can be subjected to impact during installation or use. The cover 420 can also be made of substantially waterproof material. This is advantageous because the catheter housing 400 and/or the cover 420 can be subjected to water or other liquids when the device is in use. The cover 420 can comprise plastic, rubber, and/or silicone, among other materials, or a combination of such materials. The cover 420 can comprise of a soft, pliable and/or flexible material, such as medical grade silicone. Alternatively, the cover 420 can comprise harder silicone, or rubber can be used. The cover 420 can be made of a transparent and flexible plastic material.

The cover 420 can be configured to form a closed environment over a site where an intravenous catheter is inserted into a patient. Such a closed environment can aid in keeping the site free from contamination, as discussed herein. As discussed above, the cover 420 can be made of at least partially transparent material so as to allow a caregiver or other person to examine the catheter insertion site and/or other portions of the catheter housing 400 (for example, the hub 460) while the cover 420 is secured to the hub 460.

The cover 420 can include one or more openings 432 to permit tubing 41 to pass through the cover 420 and into and interior of the cover 420, such as one or more, two or more, three or more, four or more, five or more, or six or more openings 432. For example, as discussed herein, such openings can align with one or more openings in the hub 460 (such as opening 465) that can allow tubing to pass through the housing 400 and to a catheter device 40 when the catheter device 40 is secured to lock 426 of cover 420. The cover 420 can have a rounded shape. A rounded shape can be advantageously to reduce interference from caregivers or physicians with edges or corners of the cover 420 and can also reduce discomfort associated with patient contact with edges or corners of the cover 420. Alternatively, the cover 420 can have a non-round shape, for example, a rectangular shape. Alternatively, the cover 420 can be approximately trapezoidal, rectangular, square, oval and/or circular in shape, among other shapes. For example, where the catheter housing 400 includes a hub 460 and a wall 461 of the hub 460 shaped like a stadium, the cover 420 can have a shape that accommodates the stadium shape of wall 461. The cover 420 can comprise a single, continuous piece which may advantageously minimize the amount of parts of the catheter housing 400 and can increase ease of assembly and/or securement of the catheter housing 400 on the patient. Alternatively, the cover 420 can comprise more than one piece.

As illustrated in at least FIGS. 7A-7D, the cover 420 can have one or more ports 421, which can be used to insert sterilizing and/or anesthetic gas into the catheter housing 400. For example, the cover 420 can have one, two, three, four, five, six, seven, eight, nine, ten, eleven or more ports 421. The one or more ports 421 can be located on a side of the cover 420. Alternatively, the one or more ports 421 can be located on a top portion of the cover 420. The one or more ports 421 can be located on a front portion of the cover 420 and/or a back portion of the cover 420. For example, where the cover 420 includes a slot 432 on a front portion of the cover 420, a port 421 can be located on a back portion of the cover 420 opposite to the front portion so that anesthetic and/or sterilizing gases can flow in a direction opposite to the direction that catheter tubing is inserted into the housing 400. The one or more ports 421 can be used to provide sterilization and/or antiseptic gases (among others), such as ethylene oxide gas, nitrogen gas, or other sterilizing, antiseptic, and/or anesthetic gases. For example, the cover 420 can include a port 421 for providing sterilizing gases, and a separate port for providing anesthetic gases. Additionally or alternatively, the port 421 can be utilized by caregivers to spray gases and/or liquid into the port 421. The one or more ports 421 can comprise an opening and a port rim. The opening of the port 421 can extend outwardly from the cover 420. The port rim can extend radially outward from the opening of the port 421. The port rim can be configured to secure to a portion of a gas tube in a snap-fit, a press fit, and/or a friction fit configuration. For example, the port rim can comprise a female Luer connector. Additionally or alternatively, the one or more ports 421 can comprise a threaded portion (see FIGS. 7A-7C) which can advantageously allow a gas line or an adapter coupled thereto to connect to the one or more ports 421. The threaded portion can extend along an outside surface of the one or more ports 421 between a free end of the port 421 and a connected end of the port 421.

The one or more ports 421 can be substantially cylindrical, rectangular, or another shape. The one or more ports 421 can include a gas opening which permits sterilizing gas, anesthetic gas, or other gases, to flow into the catheter housing 400. The one or more ports 421 can include a port rim that extends at least partially around an exterior portion of the one or more ports 421. The port rim can extend radially outward from the one or more ports 421. The port rim can be located at an end of the one or more ports 421 or, alternatively, at another region along the one or more ports 421. The one or more ports 421 can extend outwardly from the cover 420. The port rim can be configured to secure to gas tubes or other devices that provide gas to the catheter housing 400. The port rim can comprise a snap mechanism that can secure to a gas tube or other device, whereby a portion of such tube or other device can be configured to snap into or around the snap mechanism of the port rim. Other alternative methods of securing a gas tube or other device to the port rim of the one or more ports 421 exist. The one or more ports 421 can also include one or more valves, such as a control valve, check valve, relief valve, and/or a multi-valve.

Figure 8A:
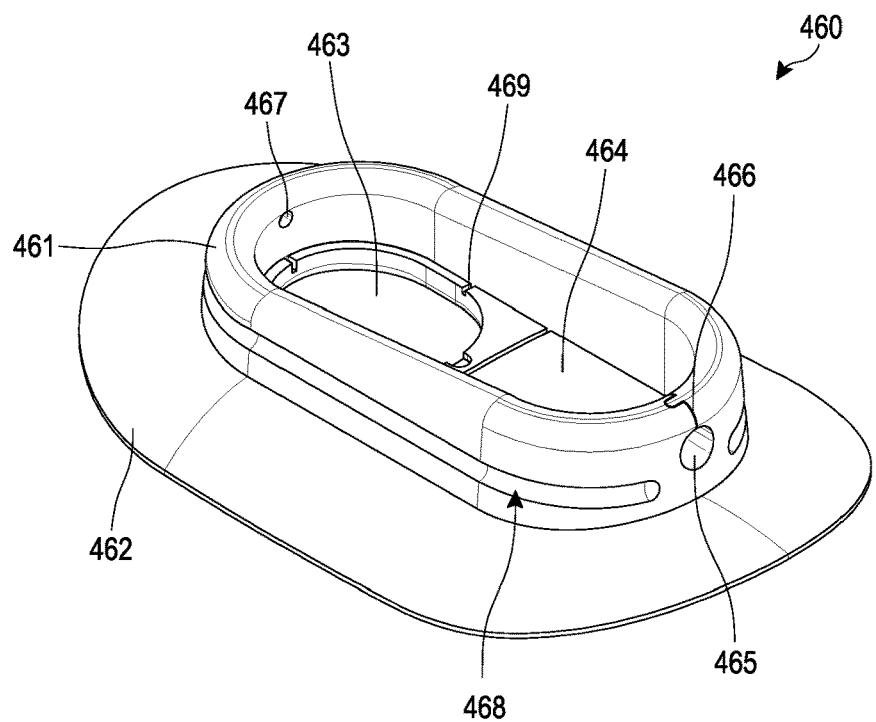
FIG. 8A illustrates a perspective view of a hub of the catheter housing of FIG. 6A.

The one or more ports 421 of the cover 420 can be configured to align with a gas inlet 467 of the hub 460 (see FIG. 8A). For example, when the cover 420 is secured to the hub 460, the one or more ports 421 of the cover 420 can align with the gas inlet 467 of a wall 461 of the hub 460 to allow gases to flow into the interior of the hub 460 and/or to the catheter insertion site.

The catheter housing 400, including the hub 460 and cover 420 discussed herein, can be coated with anti-microbial coating to aid with disinfection and/or sterilization near the catheter insertion site and/or in or around the catheter housing.

Figure 9A:
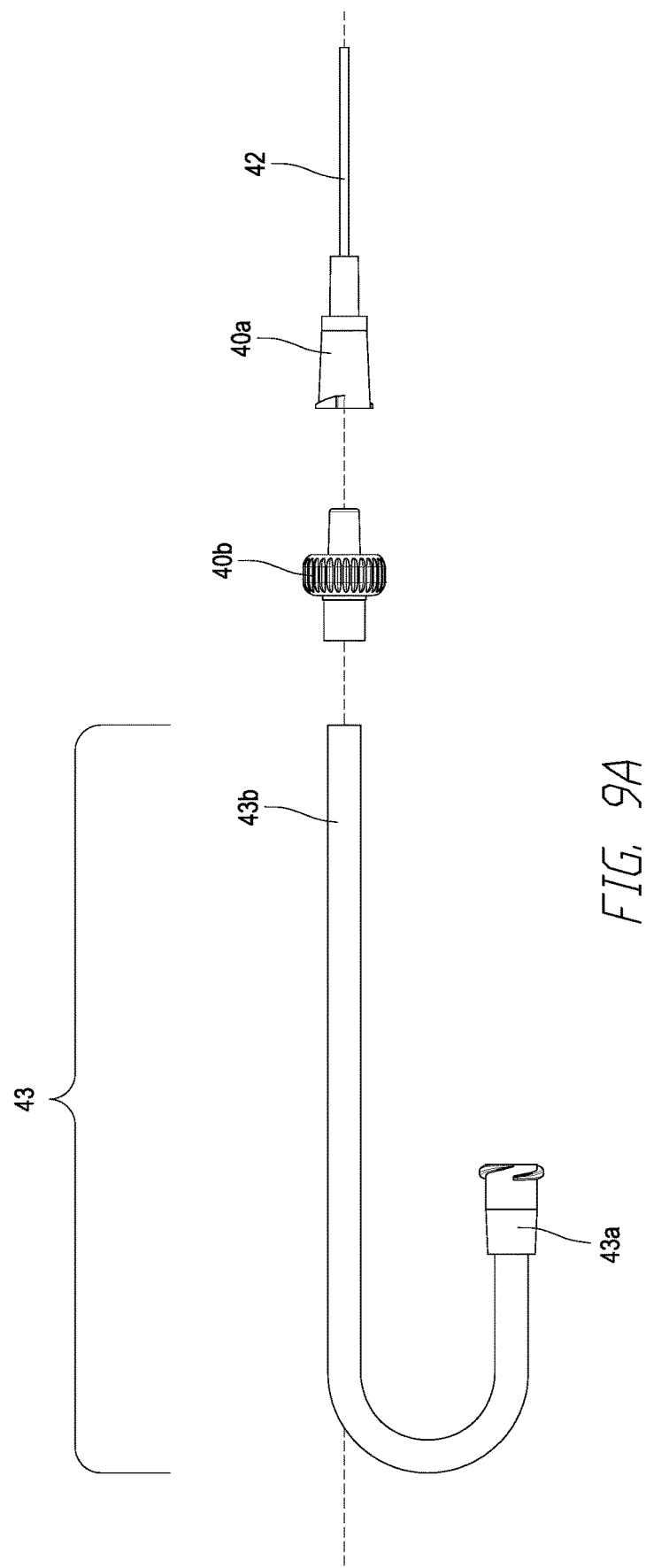
FIG. 9A illustrates an exploded view of a catheter, catheter device, and an extension set in accordance with aspects of this disclosure.

The cover 420 can include one or more wings 422 (which can also be referred to herein as "arms") that can allow tubing connected to the catheter device 40 to pass therethrough and/or underneath and be secured to a portion of the catheter housing 400. For example, as shown in at least FIG. 7K, when a catheter 42 and catheter device 40 are secured by the catheter housing 400 (for example, by cover 420), tubing connected to the catheter device 40 (such as tubing 43b as shown in FIG. 9A) can pass through an opening 432 in the cover 420, curve around a portion of the cover 420 and pass through and/or underneath one or more wings 422 in the cover 420. Such configuration can form a J-loop, for example, where the tubing curves around a portion of the cover 40 after exiting an opening 432 in the cover 420 and passes through one or more wings 422 on a side of the cover 420. In the configuration illustrated in FIGS. 7K-7M, tubing coupled to the catheter device 40 exits an opening 432 in the cover 420, curves at an approximate 180 degree angle, passes through a wing 422 on a side of the cover 420 and exits out in a direction opposite to the direction that the tubing initially exited the cover 420 through opening 432. The cover 420 can have more than one wing 422. For example, the cover 420 can have a wing 422 on a first side of the cover 420 and a second wing 422 on a second side of the cover 420 opposite to the first site of the cover 420. Including a wing 422 on each of two opposite sides of cover 420 can advantageously provide flexibility for a caregiver to secure the tubing to the cover 420 in a J-loop configuration on either side of the cover 420. Such flexibility can allow the tubing to be secured to the cover 420 in a configuration which minimizes interference of the tubing with other tubing, wiring, or other equipment nearby the securement location and/or may reduce discomfort to the patient in some circumstances. In some cases, having a wing 422 on either side of the cover 420 can allow tubing coupled to the catheter device 40 and/or catheter 42 to be wrapped around substantially all of the cover 420 and secured within and/or underneath each of the two wings 422 and, for example, exit out in the same direction as the tubing initially exited the cover 420 (through opening 432). Placing a portion of the tubing through and/or underneath wings 422 can provide the benefits discussed herein, such as mechanically decoupling the tubing from the insertion site and/or the catheter device 40, for example.

Figure 7D:
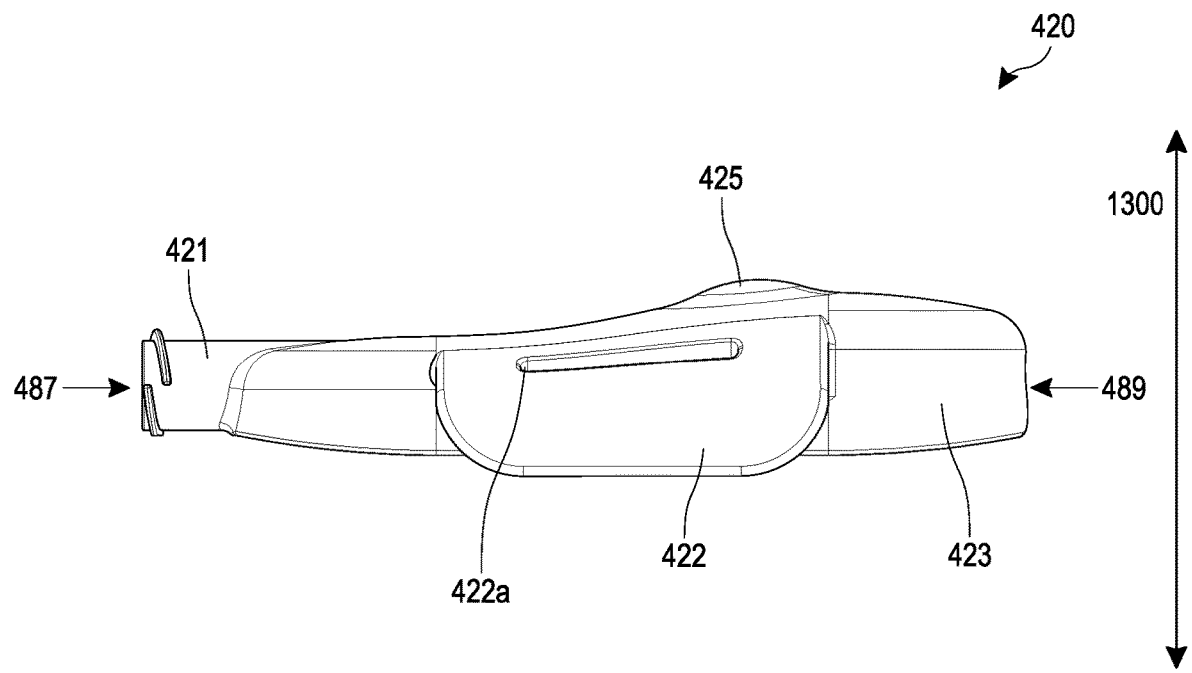
FIG. 7D illustrates a side view of the cover of FIG. 7A.

The cover 420 can comprise a main body 423 (FIG. 7A-7B). The one or more wings/arms 422 can extend from sides of the main body 423 of the cover 420. As shown by at least FIGS. 7A-7B and 7E, wings 422 can extend outward from sides of the main body 423 of the cover 423 and curve in a direction parallel to a vertical axis 1300 (FIG. 7D). For example, the wings 422 can extend outward from the main body 423 of the cover 420 at least partially in a direction that is generally perpendicular to a side of the main body 423 and/or cover 420. The size and/or shape of wings 422 can correspond to the size and/or shape of tubing coupled to the catheter, and the curvature of the wings 422 can be shaped to correspond the curvature and/or shape of the tubing (such as tubing 43b as shown in FIG. 9A). The wings 422 can extend outward from the main body 423 of the cover 420 and can curve in a direction towards the patient when the catheter housing 400 is secured to the patient. For example, the wings 422 can extend outward and curve downward in a direction along vertical axis 1300 such that a free end of the wings 422 contacts a bottom or skin-contacting portion of the catheter housing 400 (such as the hub 460 or membrane 462). The wings 422 can extend outward and curve downward so that there is little or no gap between the free end of the wings 422 and a bottom portion of the catheter housing 400 or the skin of the patient such that tubing passing through and/or secured by the wings 422 trapped and/or held between a top surface of the hub 460 (such as the membrane 462) and interior surface(s) of the wings 422.

Figure 7E:
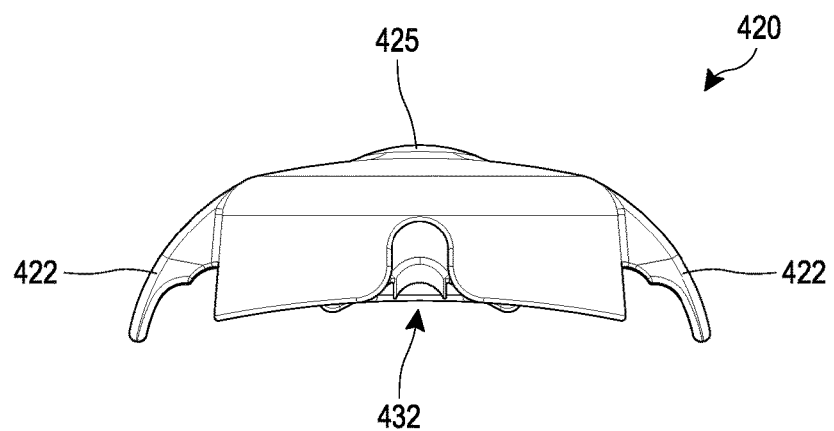
FIG. 7E illustrates a front view of the cover of FIG. 7A.

When the cover 420 is secured to the hub 460, the wings 422 of the main body 423 of the cover 420 can curve in a direction toward the hub 420 and/or the membrane 462 of the hub 460. Interior surfaces of the wings 422 can be smooth, which can advantageously allow tubing to more easily slide therethrough. Alternatively, interior surface of the wings 422 can be rough, which can advantageously reduce the ability of tubing coupled to the catheter device 40 and/or the catheter 42 to slide outside or become disconnected to the wings 422. Interior surfaces of the wings 422 (for example, the surfaces facing the patient when the catheter housing 400 is secured to a patient) can be sized and/or shaped to correspond to a size and/or shape of tubing that the wings 422 are intended to secure and/or guide. For example, as shown in FIG. 7E, a surface along an interior of the wings 422 that faces a direction toward the patient can have one or more curvatures from a portion proximate to the main body 423 of the cover 420 to a free end of the wings 422. As shown in FIG. 7E, the interior surfaces of the wings 422 can include two curved portions. The size and/or shape of the interior surface of the wings 422 can be sized to match the shape of a portion of tubing that is secured and/or guided by the wings 422. For example, a curvature of the interior surface of the wings 422 can correspond with a diameter of tubing coupled to the catheter device 40. Further, the interior surfaces of the wings 422 can have one or more curved portions to correspond to one or more sized and/or shapes of tubing. For example, where the cover 420 includes port 421, tubing secured to the port 421 can be wrapped around a portion of the catheter housing 400 (such as the cover 420) and can be held and/or secured by a first curved portion of the interior surface of the wings 422, and tubing 41 coupled to the catheter 422, catheter device 40, and/or adapter 43 that exits through opening 432 and is wrapped around a portion of the catheter housing 400 (such as cover 420) can also be held and/or secured by a second curved portion of the interior surface of the wings 422. The first and second curved portions can be proximate and/or adjacent to one another such that the tubing coupled to the port 421 and the tubing coupled to the catheter device 40 are adjacent to each other. For example, when the tubing coupled to the port 421 and the tubing coupled to the catheter device 40 are secured to the first and second curved portions of the interior surface of the wings 422, the tubing coupled to the port 421 can be above or below (vertically) the tubing coupled to the catheter device 40 with reference to a vertical axis, such as vertical axis 1300 (see FIG. 7D), As another example, when the tubing coupled to the port 421 and the tubing coupled to the catheter device 40 are secured to the first and second curved portions of the interior surface of the wings 422, the tubing coupled to the port 421 can be closer or further from a bottom surface of the catheter housing 400 (such as the hub 460 or membrane 462 of the hub 460). Thus, the wings 422 can hold, secure, and/or guide one or more tubes/tubing coupled to the catheter housing 400, the catheter device 40, and/or the catheter 42.

Regardless of the placement and/or amount of the one or more wings 422, the one or more wings 422 can allow a caregiver to conveniently and safely wrap and/or secure tubing to the catheter housing 400. This can provide a number of advantages. The one or more wings 422 can allow the insertion site or portions of the catheter housing (such as the lock) to be mechanically decoupled from tubing. Thus, if the tubing gets pulled, caught, or snagged, the force will not affect the insertion site, catheter 42, catheter device 40, and/or portions of the catheter housing 400 (such as the lock 426). Such wrapping and/or securement of the tubing to the catheter housing 400 can also reduce the likelihood that the tubing will get pulled or caught on clothing or other items. Such wrapping and/or securement can also prevent the tubing from sticking out in a direction and/or area that is inconvenient for caregivers or physicians. For example, where a patient is undergoing surgery, many medical tools devices may be used during the surgery and doctors and nurses may be moving in and around areas nearby a catheter insertion site. In such cases, the one or more wings 422 can significantly reduce the "footprint" of the catheter housing 400 and/or tubing coupled to the catheter device 40 and/or the port 421. This can reduce the likelihood that the tubing will get tangled or will interfere with activities by such caregivers working in proximity to the catheter insertion site, even within a few feet from the site. The wrapping and/or securement of the tubing to the catheter housing 400 can allow the tubing to be essentially unified with the catheter housing 400, and can eliminate the need for a caregiver to secure the tubing in a J-loop configuration with an adhesive applied directly to the patient's skin. The one or more wings 422 can provide securement for the tubing without having the tubing touch the patient's skin, increasing patient comfort and potential rashes or other skin irritation issues resulting from such contact. The one or more wings 422 also can provide securement to the tubing which prevents the tubing from getting pulled out and/or from impacting the securement of the catheter 42 and/or catheter device 40. For example, the one or more wings 422 can resist forces applied if the tubing is moved and can significantly reduce or entirely eliminate the force applied to the catheter device 40 and/or catheter 42 if such movement occurs. This provides a significant advantage since significant damage can occur at the vein and/or the catheter insertion site in traditional devices and methods of catheter securement.

As shown in at least FIGS. 7A-7D, the wings 422 can include a slot or opening 422a. Slot 422a can advantageously allow inspection of the tubing coupled to the catheter device 40 and/or the port 421 when it is secured by the wings 422. For example, as discussed above, the tubing can be secured by placement under the wings 422 and/or between the wings 422 and a portion of the hub 460 (such as the membrane 462 of the hub 460. Such inspection can be important because it can allow a caregiver to evaluate whether gas and/or liquid is flowing through the tubing and in turn to the catheter 42 and the patient. For example, such slot 422a allows a caregiver to examine whether medicinal or other fluid are being properly delivered through the tubing and to the catheter 42 and the patient. Alternatively, the slots 422a can allow fastening straps to pass therethrough and secure the catheter housing 400 to the patient. The discussion of the fastening straps 80 with reference to catheter housing 10, cover 20, 120, and/or strap hoops 22, 122 above is applicable with reference to slots 422a and catheter housing 400. As discussed herein, catheter housing 400 can be secured to a patient without fastening straps.

Figure 7F:
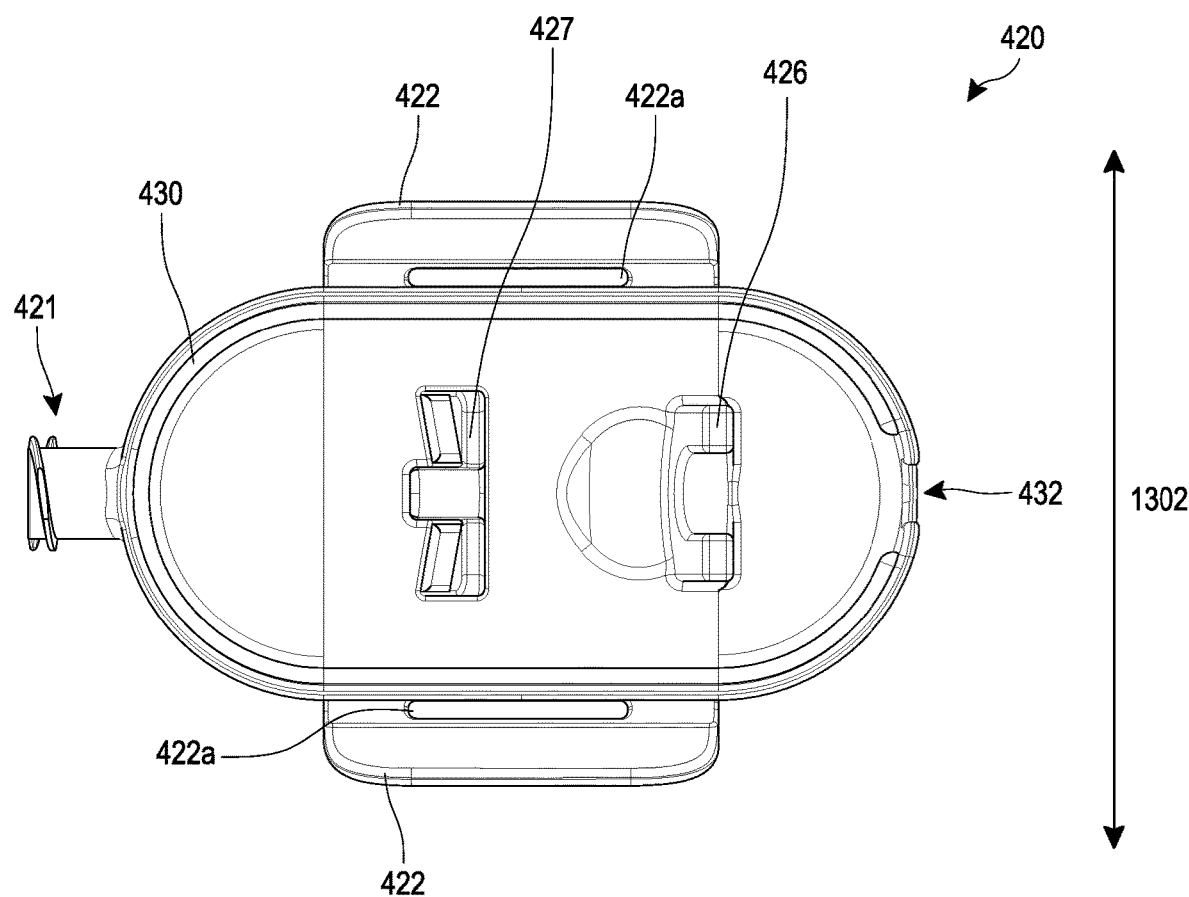
FIG. 7F illustrates a bottom view of the cover of FIG. 7A.
Figure 7G:
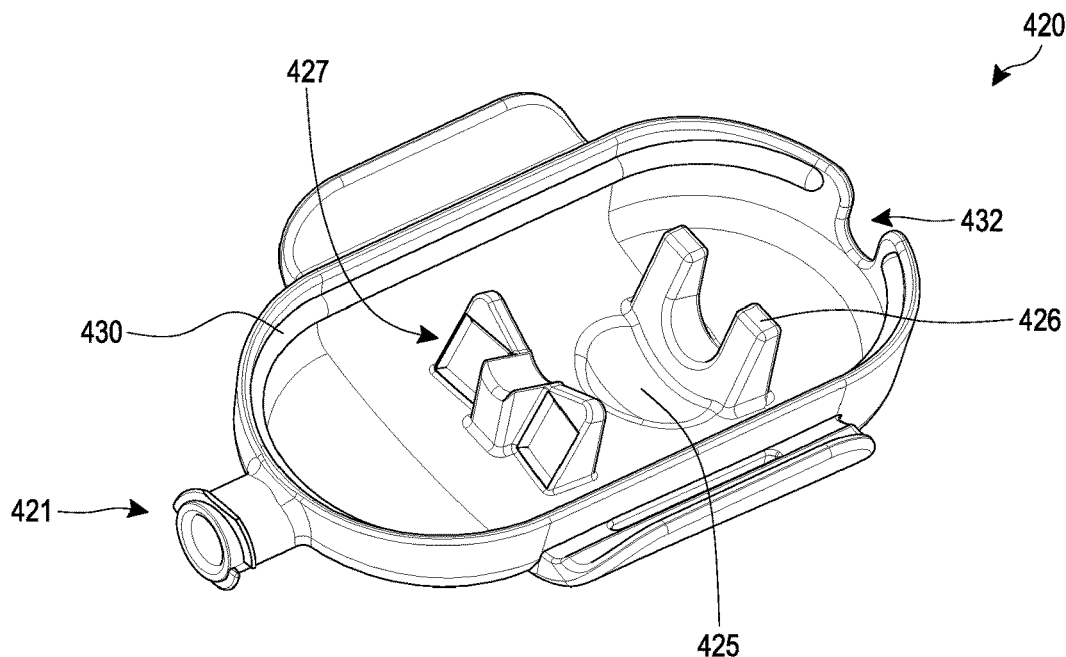
FIG. 7G illustrates a bottom perspective view of the cover of FIG. 7A.

As shown in FIGS. 7F-7G, the cover 420 can include one or more protrusions 430 (also referred herein as "tongues 430"). For example, the cover 420 can include one, two, three, four, or five or more protrusions 430. The one or more protrusions 430 can extend along an interior portion of the cover 420, for example. The one or more protrusions 430 can be located at a lower interior portion of the cover 420, or alternatively, the protrusion 430 can be located at a middle or higher interior portion of the cover 420. The one or more protrusions 430 can be substantially continuous, or alternatively, can be non-continuous, intermittent or exist in sections. The one or more protrusions 430 can extend from an interior of the cover 420. The one or more protrusions 430 can extending along substantially all of an interior of the cover 420. The one or more protrusions 430 can extend around an interior of the cover 420 and be continuous except at and/or near openings in the cover 420. For example, as shown in FIGS. 7F-7G, the one or more protrusions 430 can comprise a single protrusion 430 that extends along an interior of a first side of the cover 420, an interior of a second side of the cover 420, a back portion of the cover 420 (for example, adjacent to the port 421) and partially along a front side of the cover 420 proximate to the region where tubing exits the cover 420 when a catheter 41 and/or catheter device 40 is secured to the cover (for example with the lock 426). Having the one or more protrusions 430 can provide strong securement between the cover 420 and the hub 460 when the protrusion 430 are secured to the groove 468 of the hub 460, while also not interfering with the operation and/or use of the lock 426, tubing coupled to the catheter device 40 and/or the port 421.

The one or more protrusions 430 can be configured to secure to a portion of the hub 460. For example, such securement can occur when the cover 420 is placed over and/or secured to the hub 460, whereby the one or more protrusions 430 can secure to one or more grooves 468 of the hub 460 (see FIG. 8A). The one or more protrusions 430 can secure to the one or more grooves 468 by a snap-fit, press fit, friction-fit, and/or other configuration for securely connecting the cover 420 to the hub 460. The surface of the one or more protrusions 430 can be rounded (see FIG. 7G). Such a rounded shape can advantageously help the one or more protrusions 430 slide into the one or more grooves 468 of the hub 460, thus facilitating ease during securement. The securement between the protrusions 430 of the cover 420 and the grooves 468 of the hub 460 can advantageously ensure a tight, secure fit therebetween, and make it very difficult for a patient to remove and/or disassemble the device when secured to the patient, especially where the catheter housing 400 is adhered, strapped, and/or otherwise secured to the patient.

Alternatively, the one or more protrusions 430 can be replaced with one or more interior grooves. For example, the one or more protrusions 430 can be replaced with one, two, three, four, or five, six, seven, or eight or more grooves. For example, the one or more protrusions 430 can be replaced with two grooves extending along an interior surface of the cover 420 that are adjacent to one another each other. As another example, the one or more protrusions 430 can be replaced with one groove. Such interior grooves can secure to at least a portion of the hub 460. For example, such interior grooves can secure to a protrusion appearing on the hub 460. Such securement can occur by a snap-fit, press fit, friction-fit, and/or other configuration. Thus, the cover 420 can secure to the hub 460 by insertion of a protrusion located on the cover 420 into a groove located on the hub 460, and/or by accepting a protrusion located on the hub 460 into a groove located on the cover 420.

In some configurations, a seal is formed such that the cover 420 does not allow external air and/or contaminants from entering the enclosed internal volume of the catheter housing 400. For example, the cover 420 can engage the hub 460 to form a closed and/or isolated atmosphere, which encloses the insertion site. In such configurations, the catheter insertion site can advantageously be sterilized by inert gas as described above. Similarly, the cover 420 can advantageously help to inhibit or prevent microbe contaminate and help to lower contamination vulnerability. The cover 420 can also be configured to prevent the joint 466 (see FIG. 8A) from separating while the catheter housing 400 is in use.

As shown in FIGS. 7A-7D, the cover 420 can have a port 421 on a side of the cover 420, such as a front side of the cover 420. The port 421 can extend outwardly from the front side of the cover 420 and can extend through the main body 423 of the cover 420. This can enable gases flowing through the port 421 to enter an interior of the catheter housing 400, as discussed above.

As also discussed above, the cover 420 can have one or more openings 432 to permit tubing to pass through the cover 420 and into the interior of the cover 420. The opening 432 can be proximate to a lock 426 discussed herein. The openings 432 can align with the lock 426. This can allow tubing connected to a catheter device 40 to maintain a straight configuration from a region of the tubing extending from the catheter device 400 and to the opening 432. The openings 432 can be sized and shaped to accommodate various sizes and/or shapes of tubing.

Figure 7H:
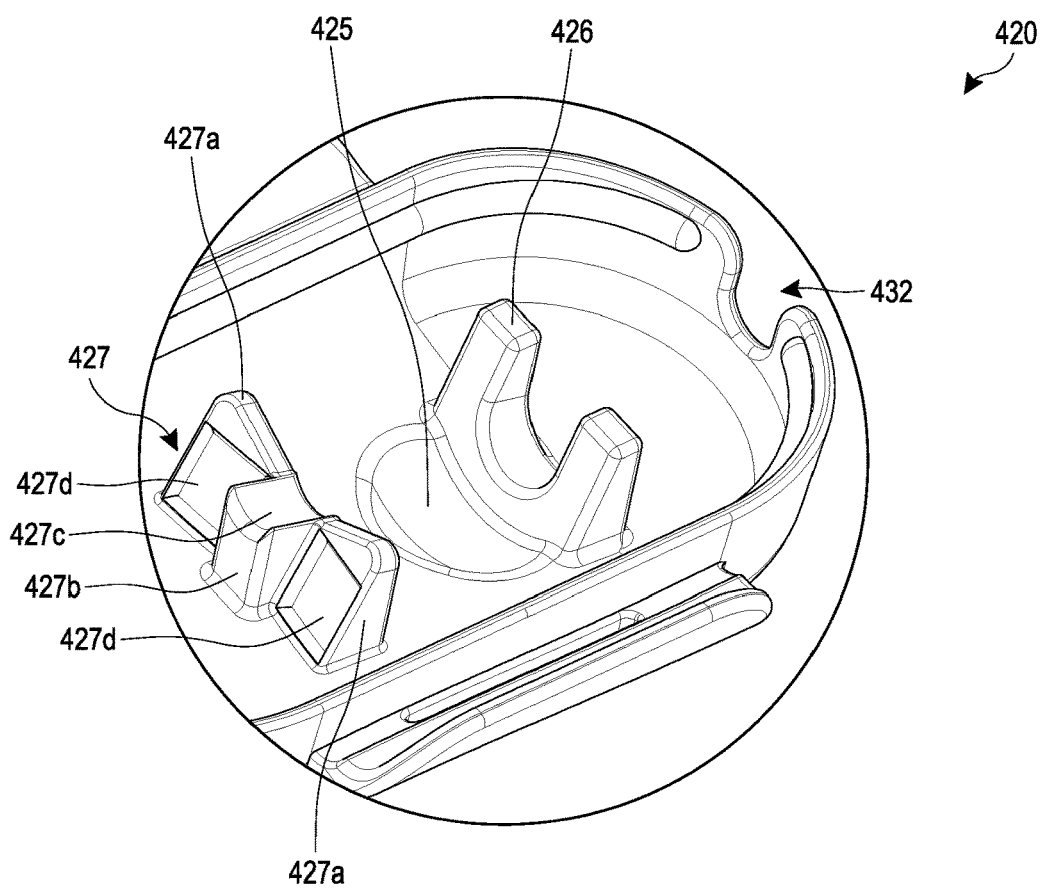
FIG. 7H illustrates a close-up bottom perspective view of the cover of FIG. 7A.
Figure 7I:
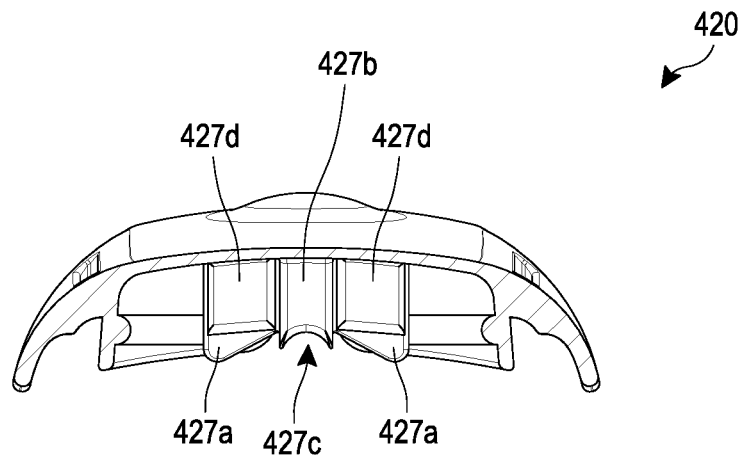
FIG. 7I illustrates a bridge of the cover of FIG. 7A.
Figure 7J:
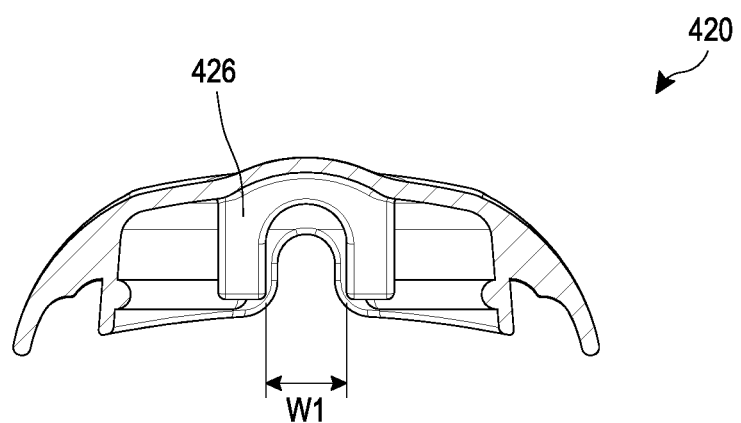
FIG. 7J illustrates a lock of the cover of FIG. 7A.

As shown in FIGS. 7G-7H, the cover 420 can include a lock 426 that can secure the catheter device 40, catheter 42, and/or tubing connected to the catheter device 40 before, during, and/or after a catheter 42 is inserted into a patient at an insertion site. The lock 426 can extend outward and/or downward from an interior surface of the cover 420. Lock 426 can have a recess with a width W1 that is sized and shaped to accommodate and/or secure a catheter device 40 or portions thereof (see FIG. 7J). FIG. 7J illustrates a cross section through cover 420 and shows a close up view of the lock 426 with the recess. The recess can be rounded. Alternatively, the recess can be non-rounded. The recess can be circular and/or partially circular. Alternatively, the recess can be non-circular. The recess can comprise an arch shaped, horseshoe shaped, a half-moon shape, half-circle shape, or another shape. The lock 426 can advantageously reduce the likelihood that the catheter device 40 will be dislodged when tubing coupled to the catheter device 40 is pulled. For example, where the catheter device 40 is secured to the lock 426, if the tubing is pulled, the lock 426 can hold the catheter device 40 so that it does not move or become dislodged. As another example, a male luer connector of catheter device 40 can contact and be prevented from moving towards opening 432 because of lock 426 (see FIGS. 7K and 7F).

The securement of the catheter 42 and/or catheter device 40 by or with the lock 426 can be a physical locking, holding, stabilizing without locking, retaining, stabilizing to prevent or reduce the likelihood of movement, stabilizing to minimize movement, or another type of securement. The lock 426 can be sized and/or shaped to secure any type of catheter device 40 or portion thereof. For example, a male luer connector of catheter device 40 can be secured by lock 426.

As also shown in FIGS. 7G-7H, the cover 420 can include a bridge 427 that can help secure, guide, and/or align catheter device 40, catheter 42, and/or connectors, extensions, adapters, and/or other devices or components connected thereto. The bridge 427 can extend from a top interior portion of the cover 420. The bridge 427 can extend a distance from the top interior of the cover 420 a distance equal or substantially equal to a distance that the lock 426 extends from the top interior of the cover 420. Alternatively, the bridge 427 can extend a distance from the top interior of the cover 420 a distance unequal to a distance that the lock 426 extends from the top interior of the cover 420.

Figure 7K:
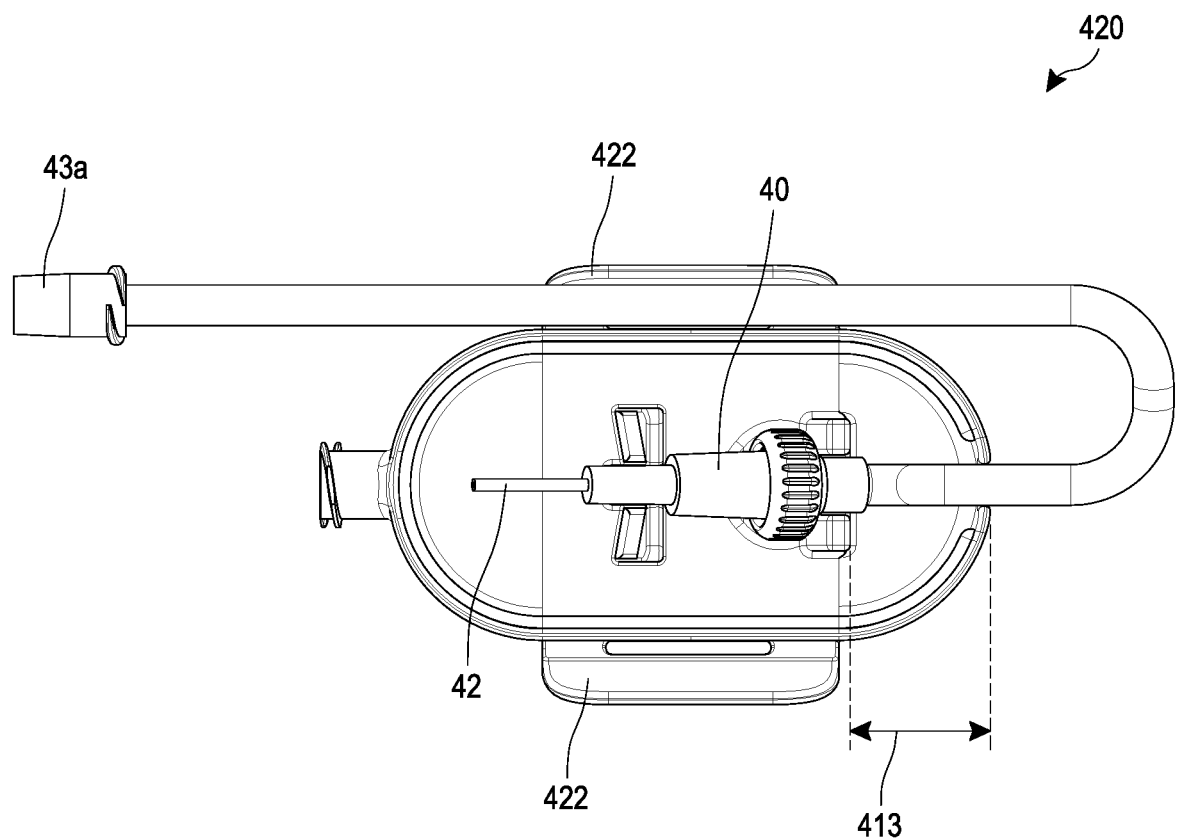
FIG. 7K illustrates a bottom view of the cover of FIG. 7A where a catheter device is secured to the lock of the cover of FIG. 7A in accordance with aspects of this disclosure.
Figure 7L:
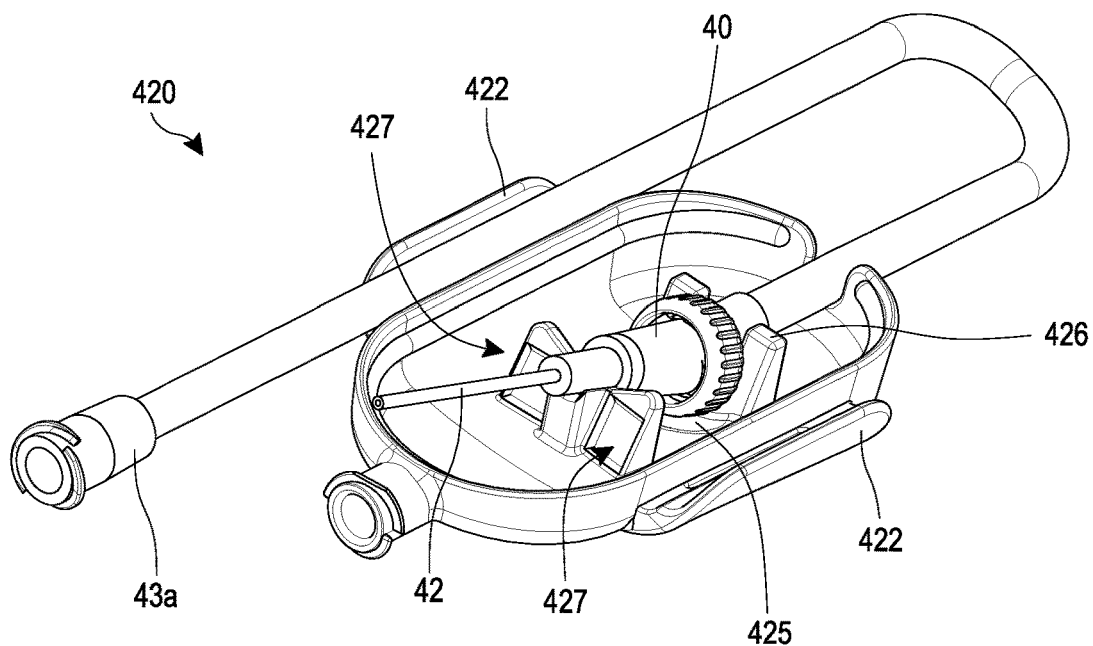
FIG. 7L illustrates a bottom perspective view of the cover of FIG. 7A where a catheter device is secured to the lock of the cover of FIG. 7A in accordance with aspects of this disclosure.
Figure 7M:
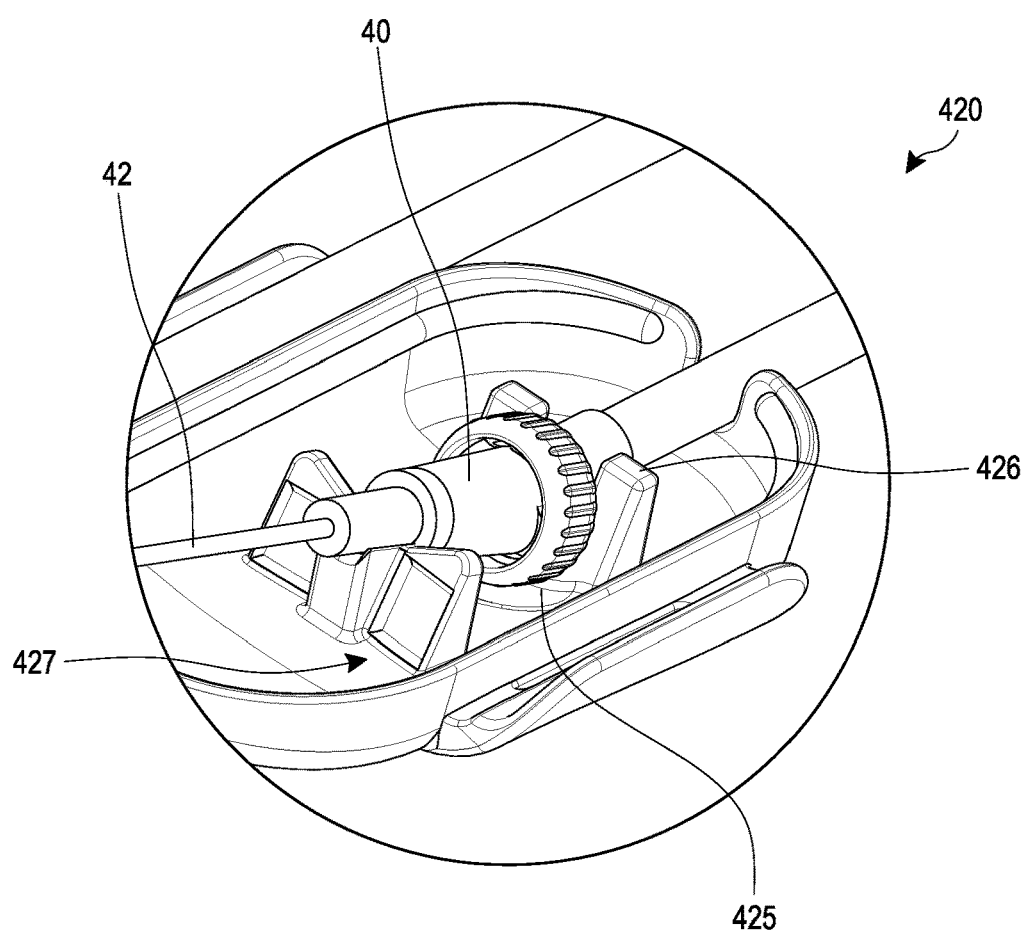
FIG. 7M illustrates a close-up bottom perspective view of the cover of FIG. 7A where a catheter device is secured to the lock of the cover of FIG. 7A.

The bridge 427 can be positioned proximate to the lock 426 along an interior portion of the cover 420. For example, the bridge 427 can be positioned proximate to the lock 426 and can be closer to the catheter insertion site than the lock 426. The bridge 427 can comprise two side walls 427a and a stem 427b located between the two side walls 427a (see FIG. 7H). The stem 427b can comprise a recess 427c on a free or extending end of the stem 427b. Recess 427c can be sized and/or shaped to accommodate a portion of the catheter 42 and/or catheter device 40. For example, the recess 427c can accommodate a portion of the catheter device 40 (for example, a cylindrical portion of catheter device 40 as shown in FIGS. 7L-7M). The recess 427c of the bridge 427 can be smooth, or alternatively, can be rough. The recess 427c of the bridge 427 can be rounded. The recess 427c of the bridge 427 can comprise a half-moon, half-circle shape, half-square, half-rectangle, or other shapes, for example. The bridge 427 can have a height H1 (extending from a top interior surface of the cover 420) at the recess 427c that is less than a height H2 at a non-recessed portion of the bridge 427. The height H1 can be equal or unequal to a height H3 of the recess of the lock 426. For example, the height H1 of the bridge 427 recess can be greater than the height H3 of the recess of the lock 426 (see FIGS. 7I-7J). This can allow a portion (for example tip) of the catheter device 40 to be inclined at a natural inclination angle when the catheter device 40 is secured by the lock 426. This can also enable the bridge 427 to push a portion of the catheter device 40 (or a device or component coupled thereto) down to properly position the catheter device 40 and connected catheter 40 when the cover 420 is placed over the catheter device 40 and/or over the hub 460. The bridge 427 can also prevent the lifting, flattening, or inclining of the catheter 42 and/or catheter device 40 when the catheter housing 400 secures the catheter device 40. The bridge 427 can also prevent the catheter device 40 and/or catheter 42 from straightening out, moving away from the catheter insertion site, and/or rotating about the lock 426.

The catheter housing 400 can secure a catheter device 40 connected to a catheter 42 without contacting the catheter 42. For example, as shown in FIGS. 7K-7M, the lock 426 and/or bridge 427 can secure one or more portions of the catheter device 40 without touching or contacting the catheter 42. This can advantageously limit prevent or limit movement of the catheter 42 when inserted within a patient's vein. This in turn can prevent or limited problems associated with such movement discussed above (for example, damage to the patient's vein and/or to the catheter insertion site and areas nearby). Additionally, as also shown by these figures, when the catheter device 40 (or one or more portions thereof) is secured by the lock 426, bridge 427, and/or other components of housing 400 (such as an interior surface of cover 420), the catheter 42 can be straight (for example, not bent, not kinked, not twisted, not wrapped, and/or not contorted). This can advantageously ensure that the catheter 42 is able to deliver fluids appropriate to the patient.

As discussed herein, the lock 426 and bridge 427 can independently and/or together secure a catheter device 40 (or portions thereof) and prevent movement of the catheter device 40 in any direction. Catheter devices typically have one or more cylindrical cross section portions which couple to a catheter cannula. For example, catheter device 40 can have a first, smaller diameter cylindrical cross section portion and a second, larger diameter cylindrical cross section portion (see FIGS. 7L-7M). The spacing between the bridge 427 and the lock 426 can correspond to a length of one of the two cross sectional portions and a length of male luer connector (see FIG. 7K). When the catheter device 40 is secured by the lock 426 and the bridge 427, a larger diameter cylindrical portion and male luer of the catheter device 40 can extend between a face of the bridge 427 and a face of the lock 426, thus preventing the catheter device 40 from moving forward or backward within the cover 420. In such configuration, the smaller diameter cross section portion of the catheter device 40 can fit at least partially within the recess 427c of the bridge 427. With the catheter device 40 secured by the lock 426 and the bridge 427 in such manner, movement of the catheter device 40 can be prevented in any direction, especially when a bottom or skin-facing surface of the catheter device 40 is contacted by the patient's skin or a portion of the hub 460 (such as the inner membrane portion 464 as discussed below). Such prevention of movement of the catheter device 40 in turn prevents movement of the catheter 42, which prevents injury and/or damage to the patient and/or catheter insertion site as discussed above.

The side walls 427a of the bridge 427 can extend along each side of stem 427b. Side wall 427a can provide structural support for the stem 427b. Side walls 427a can have inclined or sloped surfaces at free ends thereof, as shown by FIGS. 7G-7H. The surfaces of the free ends of the side walls 427a can slope downward toward the stem 427b and/or the recess 427c of the stem 427b. Such inclination or sloping can help placement and/or alignment of a catheter device 40 or portion thereof. For example, when the cover 420 is placed over the top of a catheter device 40 and/or the hub 460, the sloped surfaces of the ends of the side walls 427a help move, force, and/or position a tip of the catheter device 40 into the recess 427c so as to obtain the proper placement and/or inclination angle of the catheter coupled to the catheter device 40.

The side walls 427a of the bridge 427 can have recessed faces 427d on a surface of the side walls 427a, as shown by FIGS. 7G-7H. Such recessed faces 427d can advantageously allow one or more lights to be placed therewithin. When placed within the recessed faces 427d, one or more lights can have surfaces that are flush with the surrounding non-recessed surface of the sidewalls 427a. The one or more lights placed within the recessed faces 427d can be LED or UV. The one or more lights positioned within the recessed faces 427d can advantageously illuminate the catheter insertion site and help a caregiver inspect the site. Where the one or more lights comprise UV, such light sources can help disinfect the catheter, catheter device, catheter insertion site, and/or components of the interior of the catheter housing 500 (such as the cover 420 and/or hub 460). The one or more lights can be a UV Surface Mount LED (SMD LED) that can provide active sterilization and disinfection. This can in turn drastically reduce contamination, infections, and/or diseases that can occur with traditional catheter securement devices and methods. The one or more lights and/or one or more UV SMD LEDs can be electronically coupled to a sensor, wherein the sensor is configured to sense when the tongue 430 of the cover 420 is secured to the groove 468 of the wall 461 of the hub 460 and send a signal to the one or more lights and/or one or more UV SMD LEDs when the tongue 430 of the cover 420 is secured to the groove 468 of the wall 461 of the hub 460. The one or more lights and/or the one or more UV SMD LEDs can be configured to automatically activate when receiving the signal from the sensor. The one or more lights can contain an independent battery/power source, or can be coupled to a power source away from the side walls 427a and/or bridge 427.

As shown in FIGS. 7F-7H, the cover 420 can have a recess 425 sized and shaped to accommodate a portion of the catheter device 40 when the catheter device 40 is secured to the lock 426. The recess 425 can be located proximate to the lock 426, for example (see FIG. 7F). The recess 425 can be located between the lock 426 and the bridge 427 (see FIG. 7F). The surface of the recess 425 can be smooth or alternatively rough. The surface of the recess 425 can be rounded, or alternatively non-rounded. The surface of the recess 425 can be shaped to accommodate a portion of a catheter device 40, such as a cylindrical portion of a catheter device 40. The recess 425 can be circular when viewed from a bottom and/or top of the cover 420 (see FIGS. 7C and 7F), for example. The recess 425 can be partially circular when viewed from a bottom and/or top of the cover 420 (see FIGS. 7C and 7F), for example, a front portion of the recess 425 can comprise a tip or point (see FIG. 7F). The recess 425 can comprise a circular or partially circular shape for fitting a rear part of a male Luer spiral connector of a catheter device 40. As another example, the recess 425 can comprise a dome shape, arc shape, or another shape for fitting a rear part of a male luer spiral connector of a catheter device 40.

Advantageously, the shape, size, and/or orientation of the recess 425 can conform to the size and or shape of the catheter device 40 or a portion thereof as the catheter device 40 is angled towards the catheter insertion site. For example, as discussed above, the lock 426 and/or the bridge 427 can secure, align, and/or position the catheter device 40 so that the catheter 42 remains inserted into the patient at a natural or appropriate angle. As such, the catheter device 40 can be inclined while secured to the lock 426 and/or bridge 427. The recess 425 of the cover 420 can be shaped, sized, and/or oriented according to the position of the catheter device 40 when secured by or with the lock 426 and/or the bridge 427. This can advantageously minimize the overall height of the cover 420 in areas of the cover 420, for example, other than the recess 425.

The bridge 427 and/or lock 426 can secure a catheter 42 and/or catheter device 40 or a portion thereof in the proper orientation relative to the patient's skin and/or the catheter insertion site. This can advantageously enable a catheter tip or rim to be secured at a final resting angle or inclination angle that approximates the angle at which a needle is inserted into a vein of a patient. As discussed previously, this is beneficial because it reduces the chance of injury and/or other complications that can result when the catheter moves or is secured at an angle that damages the vein wall or nearby area. For example, the final resting angle or inclination angle can be between 1 and 45 degrees. The inclination angle can also be between 1 and 10 degrees, between 10 and 20 degrees, or between 20 and 30 degrees. The inclination angle can be more than 45 degrees as well, depending on the implementation of the catheter housing 10 or components thereof (such as the cover 20 and/or hub 60). The inclination angle can also be at a very small angle, such as between 0 and 1 degrees. Current techniques for securing a catheter to a patient can result in dislodgment, inappropriate angle of the catheter, or twisting or other movement while the catheter is inserted into a patient. However, the lock 426 and/or bridge 427 described herein, which can accommodate any type of catheter device design and/or catheter coupled thereto, can secure the catheter device and catheter in a position that provides for a normal or optimal angle. This can help to limit or prevent irritation and/or cannula tip erosion caused by contacting of the cannula tip with vein lumen sides. Thus, unlike conventional catheter stabilization methods where securing the catheter typically results in disrupting the natural angle of the catheter, awkward angling of the catheter against the wall of the vein, and/or in which pressure is applied on the a portion of the catheter device 40 in order to secure it to a patient, the securement angle of the catheter device 40 and/or catheter 42 with or by the lock 426 and/or bridge 427 can preserve the integrity of the connection of the catheter 42 within the vein.

As discussed above, the shape and structure of the catheter housing device 400 can minimize the overall height and/or footprint of the housing 400. FIG. 7D illustrates a side view of the cover 420 of the catheter housing 400. As shown, a height of the cover 420 at a front portion 489 can be greater than a height of the cover 420 at a back portion 487. The greater height at the front portion 489 allow the cover 420 to accommodate portions of the catheter device 40 when secured to the cover 420. The height of the cover 420 can taper from a larger height at the front portion 489 to a smaller height at the back portion 487 so as to minimize the overall height of the catheter housing 400.

FIGS. 8A-8F illustrates different views of the hub 460. As shown in FIG. 4A, the hub 460 can include a wall 461 and a membrane 462. A caregiver can attach, adhere, secure, and/or write patient information on a portion of the hub 460. Such patient information can include the insertion date and/or time, the patient's identification, and other information.

The hub 460, and/or components thereof, such as the wall 461 and/or the membrane 462, can comprise plastic, and/or flexible materials such as rubber and/or silicone, among other materials. The hub 460 can comprise a transparent material. Alternatively, the hub 460 can be made of a nontransparent material. Additionally, the hub 460 can comprise both transparent and nontransparent material. For example, portions of the hub 460 can be made of transparent material where it is advantageous to be able to see through a portion of the hub 460 in order to observe other components of the catheter housing 400. The hub 460 can be made of substantially shockproof and/or durable material. This is advantageous because the catheter housing 400 and/or the hub 460 can be subjected to impact during implementation of the housing 400 onto, for example, patients in a hospital. The hub 460 can comprise substantially waterproof material. This is advantageous because the catheter housing 400 and the hub 460 can be subjected to water or other liquids when the housing 400 is in use.

The wall 461 can include a top surface. The top surface can be concave or convex. Additionally, the top surface can be substantially flat. The top surface can be smooth and/or rounded.

Figure 8B:
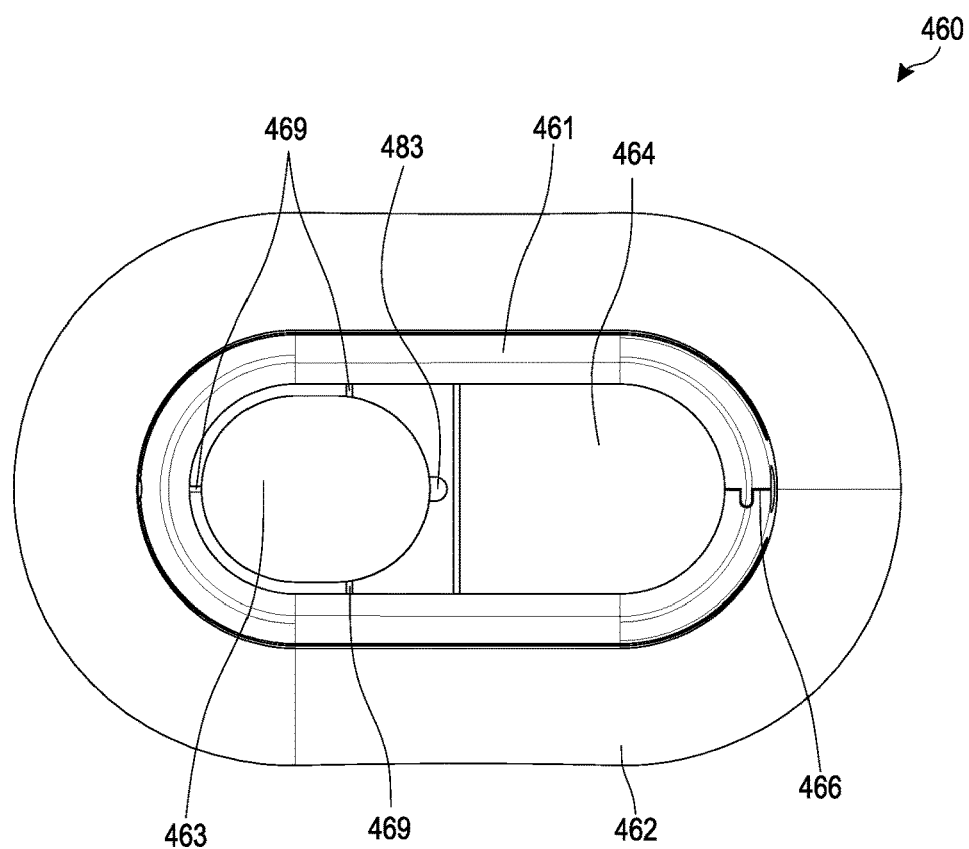
FIG. 8B illustrates a top view of the hub of FIG. 6A.

As illustrated in FIGS. 8A and 8B, the hub 460 can contain an opening 463 in the membrane 462. This opening 463 can be positioned over a site where a catheter needle and/or catheter is to be inserted into a patient. The opening 463 can be sized and shaped to fit within the wall 461 (see FIG. 8B). For example, the opening 463 can be generally egg-shaped, trapezoidal, rectangular, square, oval, and/or circular in shape, among other shapes. Additionally, the opening 463 can be a combination of these described shapes. Additionally, the opening 463 can contain a round recess 483 (see, e.g., FIG. 8B) so as to accommodate a portion of a catheter 42, needle, and/or portion of a catheter device 40.

As also illustrated in FIG. 8B, the membrane 462 can extend around the opening 463 in a region defined within the wall 461 and surrounding an insertion site. Such configurations can confine the insertion site to within the boundaries of the wall 461 and can thus advantageously reduce and/or elimination ingress of pathogens to the insertion site. The membrane 462 can include a thin silicone membrane. The membrane 462 can surround the needle and/or the insertion site. This can advantageously help to ensure that the hub 460 is secured and/or sealed to a patient's skin. For example, the membrane 462 can surround at least a portion of the insertion site and/or needle to provide a hermetic sealing isolation state between the hub 460 and the patient's skin. Accordingly, the membrane 462 can help to inhibit or prevent air and/or gases from an outside environment from entering the insertion site. Such configurations can also inhibit or prevent lower edges of a catheter device or portion thereof from contacting skin underneath. This can help to inhibit or prevent skin abrasions, ulcers, and/or irritation caused by contact between the catheter device or portion thereof and the patient's skin.

The hub 460 can include one or more markers or indicators 469 located on a portion of the wall 461 and/or the membrane 462, near the opening 463. For example, the hub 460 can include one, two, three, four, five, six, or seven or more markers or indicators 469. For example, the hub 460 can have three markers 69, two of which are disposed proximate to sides of the opening 463 and one of which is disposed proximate to a front of the opening 463 (see FIG. 8B). The one or more markers 469 can help a caregiver position and align the hub 460 over an insertion site where the catheter and/or needle has been already inserted. Alternatively, the one or more markers 469 can help provide an indication as to where a needle should be inserted into a patient. This can greatly aid caregivers in determining where the optimal insertion location should be so as to correspond with the position of a catheter device 40 when it is engaged and secured by the lock 426 of the cover 420. The one or more markers 469 can be located on a portion of the wall 461 and/or the membrane 462 proximate to the opening 463 (see FIG. 4B). For example, the one or more markers 469 can be located on a portion of the membrane 462 near a side of the wall 461 (see FIG. 8B). The one or more markers 469 can comprise a line, dot, or other indicator, for example.

As illustrated in FIG. 8A-8B, the membrane 462 of the hub 460 can include an inner membrane portion 464. The inner membrane portion 464 can be proximate to the opening 463 and can be contained within the boundaries of the wall 461. The inner membrane portion 464 can provide a platform for the catheter or portion thereof to rest or lay on when the catheter and/or needle is inserted into the patient. For example, the catheter or portion thereof can be inserted into the patient and can rest on the inner membrane portion 464, the lock 426 of the cover 420 and can be placed over a catheter device 40 that rests on the inner membrane portion 464 and can secure the catheter device 40 to prevent movement of the catheter 42 and/or catheter device 40. The inner membrane portion 464 can prevent a catheter device 40 coupled to the catheter 42 from touching the patient's skin at or near the catheter insertion site and/or opening 463.

As shown in FIGS. 8A-8B, the wall 461 can extend upwards and/or around a portion of or all of the catheter insertion site. The wall 461 can comprise a variety of shapes egg-shaped, trapezoidal, rectangular, square, oval, and/or circular in shape, among other shapes. The wall 461 or portions thereof can be rounded or alternatively non-rounded. For example, the wall 461 can have a top surface that is rounded. The wall 461 or portions thereof can have a smooth surface, or alternatively, a rough surface. The wall 461 can be a stadium wall. For example, the wall 461 can extend upwards and around a portion of the catheter insertion site like a stadium.

Figure 8C:
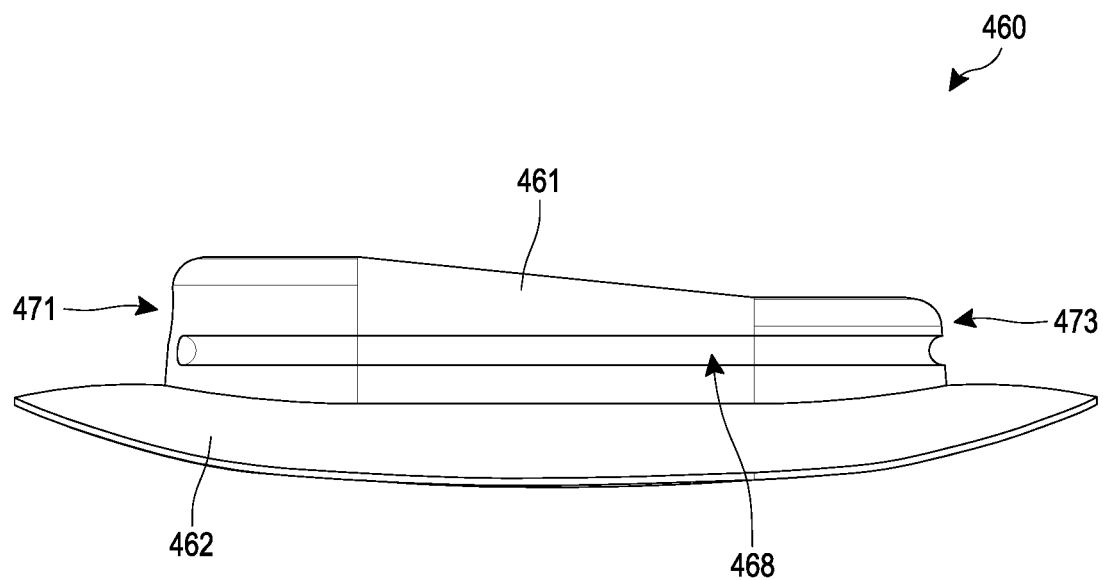
FIG. 8C illustrates a side view of the hub of FIG. 6A.
Figure 8D:
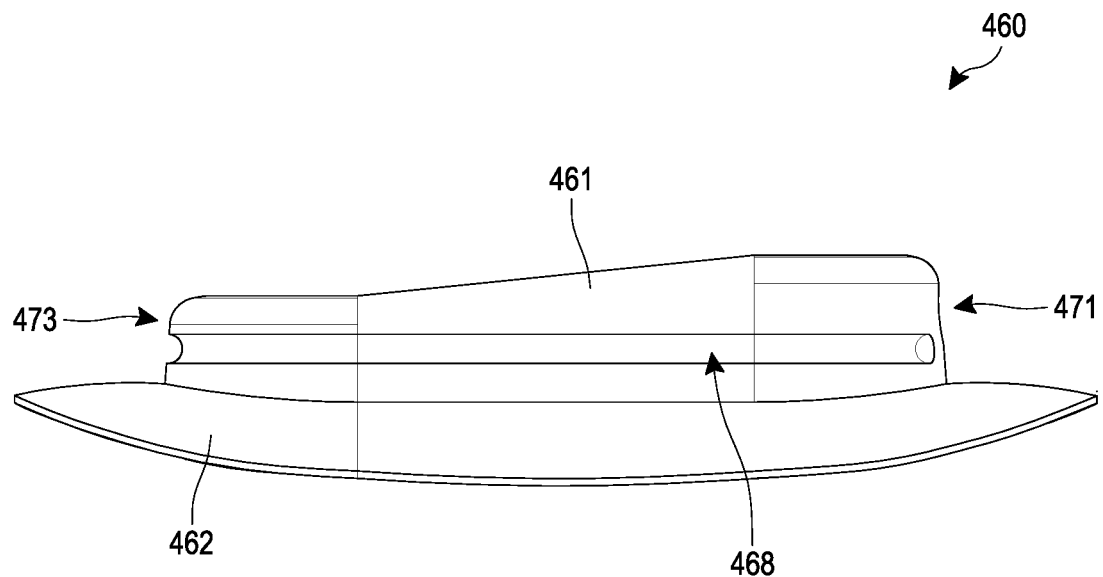
FIG. 8D illustrates another side view of the hub of FIG. 6A.

The wall 461 can include one or more grooves 468. For example, wall 461 can include one, two, three, four, five, six, or seven or more peripheral grooves 468. As discussed previously, the one or more grooves 468 can be configured to accommodate one or more protrusions 430 on the cover 420. The one or more grooves 468 of the wall 461 can be continuous around the perimeter of the wall 461. Alternatively, the one or more peripheral grooves 468 can be non-continuous. For example, as shown in FIGS. 8A and 8C-8D, the one or more peripheral grooves 468 can extend along a portion of the perimeter of the wall 461, but not extend continuously around the entire perimeter of the wall 461. For example, the one or more peripheral grooves 468 can extend along a perimeter of the wall 461 proximate to the inlet 467, but terminate at a location before reaching the inlet 467. Additionally or alternatively, the one or more peripheral grooves 468 can extend along a perimeter of the wall 461 proximate to the opening 465 and/or joint 466, but terminate at a location before reaching the tube opening 465 and/or joint 466. The wall 461 can include more than one peripheral groove 468 that extends along the perimeter of the wall 461, which can secure to one or more protrusions 430 on the cover 420. As discussed previously, the one or more protrusions 430 can secure to the one or more peripheral grooves 468 by a snap-fit, press fit, and/or other configuration for securely connecting the cover 420 to the hub 460.

As illustrated in FIG. 8A, the wall 461 can include one or more joints 466 that can be pulled apart or pushed together, to allow for a needle, fluid tube, or catheter device or portion thereof to more easily pass through the tube opening 465. For example, the wall 461 can include one, two, three, four, five, six, or seven or more joints 466. The wall 461 can include one joint 466. The joint 466 can be proximate to the tube opening 465. Thus, the joint 466 can provide a mechanism whereby a needle, fluid tube, or catheter device or portion thereof can be accommodated by the wall 461 so as to be able to pass into and through the wall 461 with relative ease and in a short timeframe. The joint 466 can be configured to hermetically close the wall 461 around the tube opening 465, and can form a seal in the wall 461 and the hub 460. The joint 466 can permit the wall 461 to be spaced apart, pulled apart, pushed apart, and/or otherwise partially separated. Alternatively, the joint 466 can extend down an entire side portion of the wall 461 so that the joint 466 separates an entire cross-section of the side portion of the wall 461. Alternatively, the joint 466 can separate at least in part by flexing the wall 461.

The membrane 462 of the hub 460 can be sized and shaped to accommodate a patient's arm, leg, appendage, or other portion of a patient's body. The membrane 462 can have rounded edges or alternatively, non-rounded edges. The membrane 462 can be rectangular in shape. Alternatively, the membrane 462 can be egg-shaped, trapezoidal, square, oval, and/or circular in shape, among other shapes. Additionally, the membrane 462 can comprise a combination of these described shapes.

The membrane 462 can be integrally formed with the wall 461. For example, the membrane 462 can be molded with the wall 461. The wall 461 can be pressed onto, adhered to, and/or otherwise attached to a portion of the membrane 462. The membrane 462 can include a recessed portion to accommodate the wall 461. For example, the membrane 462 can contain a recessed portion that surrounds the opening 463 and allows a portion of the wall 461 to sit within or be accommodated by the recessed portion of the membrane 462. Additionally, the membrane 462 can contain a recessed portion to accommodate other portions of the catheter housing 400, such as the cover 420 or a portion of the catheter device 40. The membrane 462 can include one or more different materials. Additionally, the membrane 462 can comprise one material. The wall 461 and the membrane 462 can include the same material. Alternatively, the wall 461 and the membrane 462 can include different materials. The membrane 462 can comprise silicone, plastic, and/or rubber, among other materials. The membrane 462 can comprise, at least in part, biocompatible materials.

The membrane 462 can extend outwardly from a base of the wall 461 (see FIG. 8B). For example, the membrane 462 can be coupled with an outer edge of the base of the wall 461. A bottom surface of the base of the wall 461 can be coupled with the membrane 462. A portion of the membrane 462 can extend inwardly from the wall 461 (see FIG. 8B). The membrane 462 can surround at least a portion of a perimeter of the wall 461. Thus, the membrane 462 can surround all or a portion of a perimeter of an inner edge and/or an outer edge of the base of the wall 461.

As discussed above, the shape and structure of the catheter housing device 400 can minimize the overall height and/or footprint of the housing 400. FIGS. 8C-8D illustrate side views of the hub 460 of the catheter housing 400. As shown, a height of the hub 460 at a front portion 471 can be greater than a height of the hub 460 at a back portion 473. The greater height at the front portion 471 allow the hub 460 to accommodate portions of the catheter device 40 when secured to the cover 420. The height of the hub 460 can taper from a larger height at the front portion 471 to a smaller height at the back portion 473 so as to minimize the overall height of the hub 460 and/or the catheter housing 400 when the cover 420 is secured to the hub 460. The cover 420 can be secured to the hub 460 so that a front portion 489 of the cover 420 cooperates with and secures to a front portion 471 of the hub 460 and so that a back portion 487 of the cover 420 cooperates with and secures to a back portion 473 of the hub 460.

Figure 8E:
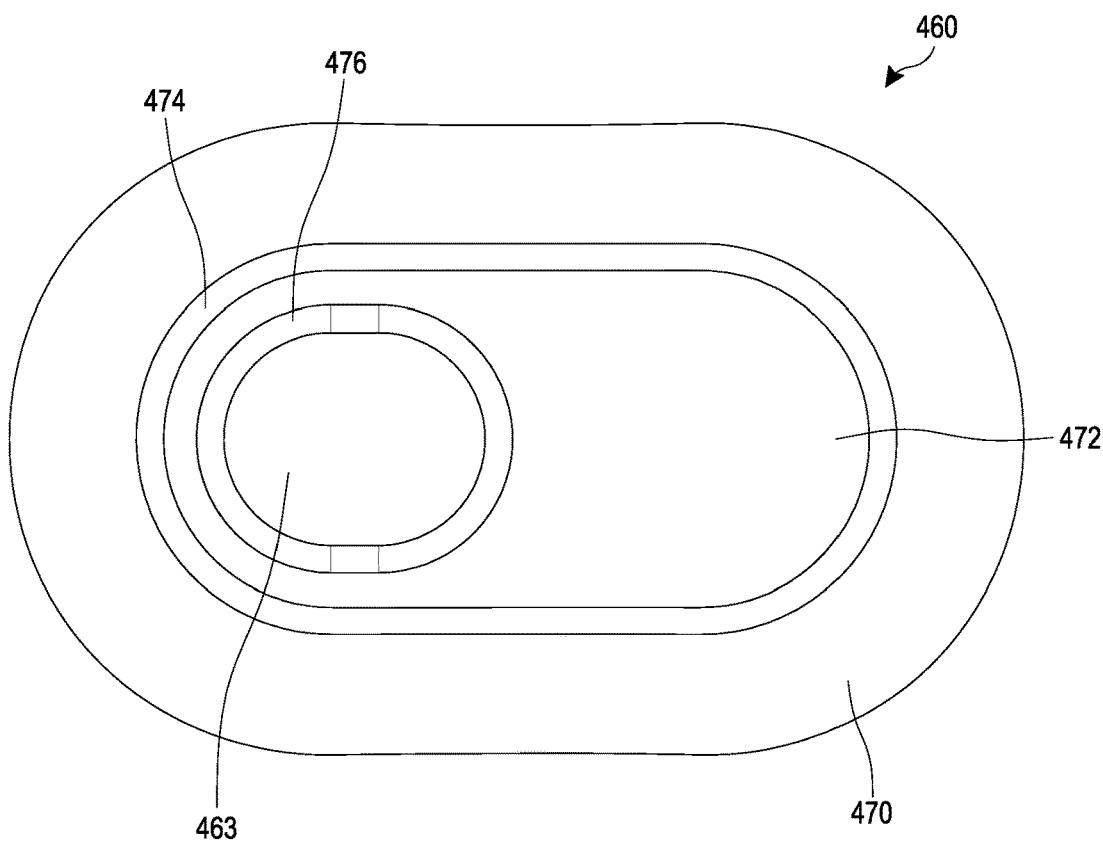
FIG. 8E illustrates a bottom view of the hub of FIG. 6A.
Figure 8F:
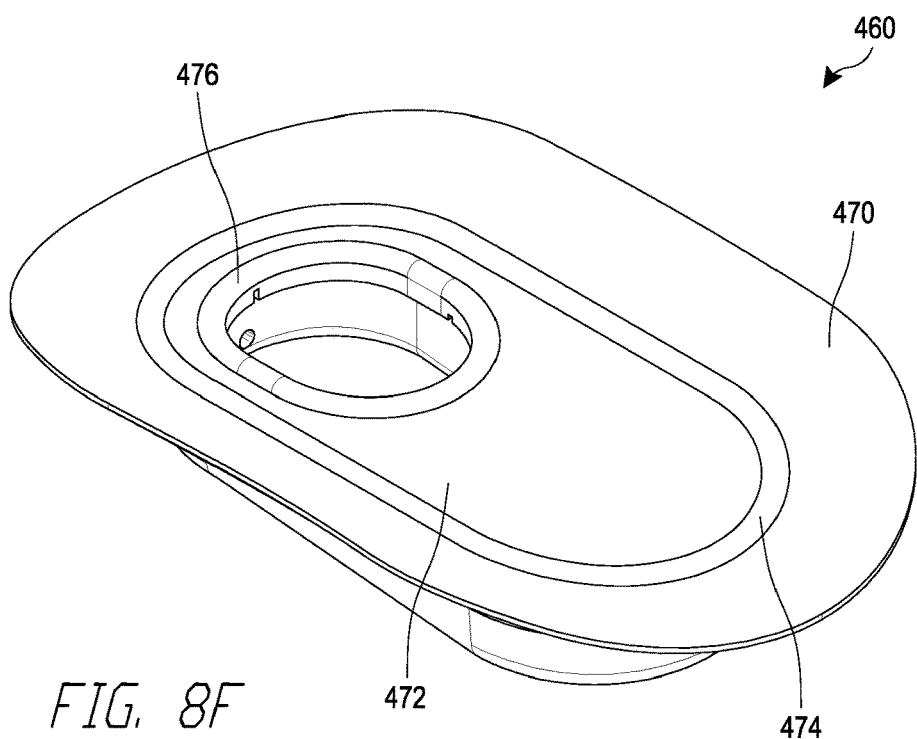
FIG. 8F illustrates a bottom perspective view of the hub of FIG. 6A.

The membrane 462 can have a bottom surface including an anti-slip material configured to secure the catheter housing 400, or a portion thereof such as the hub 460, to a patient's skin (see FIGS. 8E-8F). The bottom surface of the membrane 462 can comprise silicon-adhesive, sticky material, rubber compound, biocompatible high-tack anti-slip coating, adhesive, or other types of anti-slip material and/or methods that can prevent slipping or movement of the hub 460 and/or catheter housing 400 when secured to a patient's skin. The bottom surface can comprise a silicone or regular adhesive, for example. The bottom surface can comprise an anti-microbial coating. The bottom surface can comprise anti-slip material in the form of layers, circuits, circles, strips, coatings, and/or rings. For example, the bottom surface can comprise a transparent adhesive layer that can be permeable, semi-permeable, thin, and/or flexible. The transparent adhesive layer can be similar to an adhesive dressing or tape and can adhere to various portions of skin of a patient.

The bottom surface of the membrane 462 can comprise an inner lip 476 and/or an outer lip 474. The inner and outer lips 476, 474 can extend from the bottom surface of the membrane 462. The bottom surface can comprise an outer portion 470 that extends around the outer lip 474 and/or an inner portion 472 that extends around the inner lip 476 and within the outer lip 474. The inner and outer portions 472, 470 can comprise anti-slip material, such as an adhesive. In some embodiments, the outer portion 470 comprises an adhesive and the inner portion 472 does not comprise an adhesive so as to ensure that adhesive material is not proximate to the catheter insertion site and/or the opening 463. The hub 460 can comprise a release liner that covers the inner and/or outer portions 472, 470 of the bottom surface of the membrane 462 that, when pulled away, allows the inner and/or outer portions 472, 470 to adhere to a portion of the patient's skin.

The hub 460 can comprise a release liner that extends and/or covers the entirety of the outer portion 470. Alternatively, the hub 460 can comprise more than one release liners that are independent from one another. For example, the hub 460 can comprise a release liner that covers a first portion of the outer portion 470 and a second portion of the outer portion 470. The first portion can comprise a greater percentage of the outer portion 470 than the second portion. For example, the hub 460 can comprise a first release liner that covers greater than 50% of the surface area of the outer portion 470 and a second release liner that covers less than 50% of surface area of the outer portion 470. As another example, the hub 460 can comprise a first release liner that covers greater than 80% of the surface area of the outer portion 470 and a second release liner that covers less than 20% of surface area of the outer portion 470.

Where the hub 460 comprises more than one release liner on the outer portion 470, the release liners can be removed sequentially to allow advantageous functionality. For example, where multiple release liners are covering the outer portion 470, one of the release liners can be removed and the catheter housing 400 (or the hub 460 or membrane 462) can be adhered to a patient's skin surface and/or form a seal with the patient's skin while another release liner can be left covering a portion of the outer portion 470 thus permitting the catheter housing 400 (or the hub 460 or membrane 462) contact the patient's skin surface without adhering or forming a seal. Further, where the catheter housing 400 includes a port 421, gas can be inserted into the catheter housing 400 and to the catheter insertion site and/or opening 463. In some cases, when securing the catheter housing 400 to a patient (such as by removing a release liner from a portion of the outer portion 470 and adhering such portion to the patient's skin), it may be desirable to insert an amount of gas into the interior of the catheter housing 400 and/or to the catheter insertion site (for example, to provide an initial sterilization). When such gas is inserted into the catheter housing 400 through the port 421, the non-adhered region of the outer portion 470—where the release liner has not been removed—may lift off the skin surface of the patient temporarily, thus providing an exit pathway for the gas inserted through the port 421 and/or other gases/air previously inside the interior of the catheter housing 400. After the gas is inserted through port 421, the other release liner(s) that were not removed can be removed and the outer portion 470 can be further adhered to the patient's skin. In some cases, remaining release liners can be left un-removed to keep the outer portion 470 un-adhered in some regions. In some cases, the outer portion 470 comprises adhesive and/or a release liner only on a portion (for example, certain percentage) thereof, thus allowing a gas exit pathway when gas is inserted into the catheter housing when a non-adhered portion of a bottom surface of the catheter housing 400 "lifts off". Additionally or alternatively, the catheter housing 400 can include a valve that allows gas to escape from an interior of the catheter housing 400. For example, where the catheter housing 400 forms a hermetic seal over a catheter insertion site, the catheter housing 400 can include a relieve valve that can be activated (for example, opened) when gas is inserted into the gas port 421, thus allowing gas inside the catheter housing 400 to escape to the atmosphere. Such relief valve can be located on the cover 420 and/or the hub 460, for example. For example, the catheter housing 400 can include a cover 420, hub 460, and an adhesive material on a bottom surface of the hub 460 which together form a hermetic seal around the catheter insertion site, and can also include a relief valve which allows gases to exit therethrough. One method of removing the catheter housing 400 from the patient is to peel off the membrane 462 form the skin of the patient. A caregiver may also apply an alcohol-based substance around the outside of the membrane 462 to loosen portions of adhesive on the outer portion 470, for example.

The inner and/or outer lips 476, 474 can help form a seal around the catheter insertion site which may be located within opening 463 of the hub 460. When the inner and/or outer portions 470, 472 comprise an adhesive material and are adhered to skin of the patient, portions of the adhesive material may de-attach from the patient's skin and/or may degrade. In such situations, air and/or contaminants outside the catheter housing 400 may be in fluid communication with the catheter insertion site and/or opening 463, which may be disadvantageous where it is desirable to keep the catheter insertion site sealed off from such outside environment. Inner and/or outer lips 476, 474 can extend outward from the bottom surface of the membrane 462 and can maintain contact with the patient's skin and surround the opening 463 and/or catheter insertion site. Inner lip 476 can be continuous and can extend outwards from the bottom surface of the membrane 462 and surround the opening 463 around a perimeter of the opening 463 (see FIG. 8E). Outer lip 474 can be continuous and can extend outward from the bottom surface of the membrane 462 and surround the opening 463 and can be spaced from the perimeter of the opening 463 and/or the inner lip 476 (see FIG. 8E). Thus, where portions of the adhesive bottom surface of the membrane 462 de-attach from the patient's skin, the outer and/or inner lips 474, 476 can maintain a seal with the patient's skin and can advantageously seal off the catheter insertion site and/or opening 463 from an outside environment and, in turn, contaminants that may be present. The inner and/or outer lips 476, 474 can comprise silicon or another material discussed above. The inner and/or outer lips 476, 474 can be rounded, which can help the lips 476, 474 maintain contact and/or conform to skin of the patient when the catheter housing 400 is secured thereto.

At least a portion of the membrane 462 can be used for fixing various peripheral tools, such as a catheter tube, an LCD monitor of a micro-processor, and/or a metallic ampule of the soothing and sterilizing gas. Such peripheral tools can be fixed or secured to at least a portion of the membrane 462 through hook and loop structures, buckles, fungi-like attachment, and/or other attachment structures or methods.

The membrane 462 of the hub 460 can have a bottom surface that comprises a corrugated structure. The corrugated structure can be substantially cylindrical, circular, square, or rectangular, among other shapes. The corrugated structure can also comprise a combination of these shapes. The corrugated structure can be sized, shaped, and spaced apart to accommodate ventilation or for other reasons. The corrugated structure can provide gaps to allow air to flow between the corrugated structure and contact the patient's skin. Thus, even if the hub 460 and/or the catheter housing 400 is secured to a patient, the patient can still benefit from ventilation to the region/section of the bottom surface that contacts the skin of the patient. The corrugated structure can be one continuous piece, or alternatively, can comprise more than one piece.

The membrane 462 of the hub 460 can have a bottom surface that includes one or more suction cups. For example, the bottom surface can have one or more, two or more, three or more, four or more, five or more, six or more, seven or more, eight or more, nine or more, ten or more, or eleven or more suction cups. For example, the bottom surface can have between twenty and fifty suction cups. Alternatively, the bottom surface can have between 50 and a hundred suctions cups. The one or more suction cups can be positioned in one or more rows. The suction cups can be configured to stabilize a connection between the hub 460 and the patient's skin. The hub 460 and/or the membrane 462 can be manually pressed onto the patient's skin to secure the hub 460 to the patient. The suction cups can engage with the patient's skin such that the hub 460 can be at least partially secured to the patient with or without requiring the fastening straps to be connected to the hub 460 and/or wrapped around a portion of the patient's body.

The one or more suction cups can be substantially cylindrical, circular, square, or rectangular, among other shapes. The suction cups can also comprise a combination of these shapes. The suction cups can be sized, shaped, and spaced apart to accommodate ventilation or for other reasons. The suction cups can be spaced to provide gaps to allow air to flow between the suction cups and the patient's skin. Thus, even if the hub 460 and/or the catheter housing 400 is secured to a patient, the patient can still benefit from ventilation to the region/section of the bottom surface that contacts the skin of the patient.

The catheter housing 400 can include one or more light sources, such as one, two, three, four, five, six, seven, eight, or nine or more light sources. The light sources can include LEDs. The light sources can illuminate exterior and/or interior regions at or near the catheter housing 400. For example, the light sources can illuminate interior portions of the catheter housing 400 and/or the catheter insertion site to allow such regions to be inspected during the day and/or night. The light sources can also indicate whether cover 420 is secured to the hub 460 and/or indicate whether the lock 426 is secured to the catheter device 40 and/or whether the catheter device 40 is dislodge or moved. For example, the lights can change colors, flash at certain speeds, and/or change brightness to indicate whether cover 420 is secured to the hub 460 and/or indicate whether the lock 426 is secured to the catheter device 40. The light source can include a UV light source to help with disinfecting the catheter and/or hub and/or insertion site. For example, the catheter housing 400 can include a UV Surface Mount LED (SMD LED). The UV SMD LED can provide active sterilization and disinfection to interior regions of the catheter housing 400 and/or the catheter insertion site when the catheter housing 400 is secured to a patient. This can in turn drastically reduce contamination, infections, and/or diseases that can occur with traditional catheter securement devices and methods. One or more UV SMD LEDs can be positioned on interior portions of the catheter housing 400. For example, one or more UV SMD LEDs can be positioned or located within the cover 420 or components of the cover 420. One or more UV SMD LEDs can be positioned on or located within the bridge 427 as discussed above, and can be configured to shine or point at the catheter insertion site. Alternatively or additionally, one or more UV SMD LEDs can be positioned on or located within the hub 460. For example, one or more UV SMD LEDs can be positioned on or located within the membrane 462 and/or the wall 461. The one or more lights and/or one or more UV SMD LEDs can be electronically coupled to a sensor, wherein the sensor is configured to sense when the tongue 430 of the cover 420 is secured to the groove of the wall 461 of the hub 460 and transmit a signal to the one or more lights and/or one or more UV SMD LEDs when the tongue 460 of the cover 420 is secured to the groove 468 of the wall 461 of the hub 460. The one or more lights and/or the one or more UV SMD LEDs can be configured to automatically activate when receiving the signal from the sensor.

The catheter housing 400 can include one or more sensors. Additionally, the one or more sensors can be located on various components of the catheter housing 400. For example, the one or more sensors can be located and/or mounted to the cover 420 or portions thereof, and/or the hub 460 or portions thereof (for example, the membrane 462). Additionally, the number of sensors located on and/or mounted to the various components described above can be one, two, three, four, five, six, seven, eight, nine, ten, eleven, twelve, or thirteen or more.

The one or more sensors can be used to measure various physiological parameters or condition of a patient. The one or more sensors can include a temperature sensor (for example, a topical temperature sensor), a blood pressure sensor, a blood oxygen saturation sensor, a sensor for liquid and blood leakage, and/or a skin humidity sensor. The sensors can be located in various locations on the membrane 462.

The one or more sensors can include one or more bio-sensors. The bio-sensors can include a micro-processor. For example, the bio-sensors can include an LCD monitor for detecting, measuring, storing and/or displaying patient vital functions, including venous and arterial blood pressure, heart beats, blood oxygen levels, general and topical temperature, and local tissue humidity, and/or venous blood current speed, among others. The measurements and/or calculations performed and/or taken by the one or more sensors, can be stored on a flash storage memory positioned on one or more of the cover 420 or portions thereof, and/or the hub 460 or portions thereof (for example, the membrane 462). Any of the sensor measurements discussed herein, along with any data associated with the catheter insertion or IV therapy or treatment, can be wirelessly transmitted to a patient monitoring system for analysis, management, organization, and/or display to a care provider or user. Such information and/or data can also be transmitted to a database including patient medical records or electronic patient medical records. Alternatively and/or additionally, such information and/or data can be transmitted to a personal communications device, such as a tablet or smart device, or a software application or website. Transmitting such information and/or data can help a caregiver keep a log for an IV catheter insertion procedure and/or experience for a given patient which can help prevent any issues that might occur in a future IV therapy for the patient.

FIG. 9A illustrates an exploded view of the catheter 42, catheter device 40, and an extension set 43. The extension set 43 can include a female connector 43a and a tube 43b coupled thereto. An end of tube 43b can couple to and/or be received within a portion of a catheter device 40, such as the catheter device 40 discussed above. For example, an end of tube 43b can couple to a portion (such as a stem portion) of a male luer 40b of a catheter device 40. The male connector 43c can be connected to a female end of a cylindrical portion 40a of the catheter device 40 which can have one or more protrusions along a portion thereof (for example, with reference to FIG. 9A, a left end of the cylindrical portion 40a can have a protrusion on a top and on a bottom along a perimeter edge). The male luer connector 40b can comprise an outer ring or annular portion sized and/or shaped to accommodate the female end of cylindrical portion 40a. The outer ring of the male luer connector 40b can have threads on an interior thereof, such as an interior perimeter and/or surface of the outer ring of the male luer connector 40b. The threads can spiral around an interior of the outer ring of the male luer connector 40b, which can help the outer ring secure to the one or more protrusions on the female end of the cylindrical portion 40a. The outer ring of the male luer connector 40b can have ridges and/or protrusions along an exterior perimeter of the outer ring (see FIG. 9A), which can advantageously aid a user or caregiver in threading or securing a portion 40a of catheter device 40 to the male luer connector 40b. Male luer connector 40b can be configured to rotate or alternatively can be configured to be static. Male luer connector 40b can also comprise a stem extending through the outer ring (see FIG. 9A). The stem and outer ring of the male luer connector 40b can be integral, or alternatively, non-integral. The stem of the male luer connector 40b can have a male end sized and/or shaped to fit within a portion of the female end of the portion 40a and can have a male end sized and/or shaped to receive an end of tubing 43b.

Female luer connector 43a can be sized and/or shaped to receive an end of the tubing 43b. The female luer connector 43a can have protrusions and/or threading on an end thereof, which help it to secure to threading of a male connector, such as male connector coupled to a fluid bag where IV fluids are stored. When assembled, extension set 43 (and components thereof), male connector 40b, cylindrical portion 40a, and catheter 42 can be in fluid communication.

Extension set 43 advantageously can connect to a fluid supply (such as an IV fluid supply) at a location outside the catheter housing 400. This can allow caregivers to disconnect/connect a fluid line to the catheter device 40 (and catheter 42) without having to remove the catheter housing 400 or portions thereof. For example, where the catheter housing 400 includes a cover 420 that is secured to the hub 460 and the hub 460 is secured (for example, adhered) to the patient, the caregiver can disconnect/connect a fluid line to the extension set 43 (or female luer 43a of the extension set 43) without having to remove the cover 420 from the hub 460 and/or the hub 460 from the patient. This benefit is further realized where the catheter housing 400 forms a hermetic seal over the catheter insertion site and the caregiver wishes to remove, replace, or connect tubing without disturbing the integrity of the hermetic seal.

The tubing 43b can have a length customized as desired by the caregiver or physician. The tubing 43b can advantageously provide a connection point with a fluid line outside an exterior of the catheter housing 400 (such as outside an exterior of the main body 423 of the cover 420 or an exterior of the hub 460). The tubing 43b can have a length that allows it to wrap around a portion of the catheter housing 400 and/or secure to the wings 422 (see FIG. 7K, for example). Alternatively, the tubing 43a can have a shorter length. For example, the tubing 43b can have a length that is greater than a distance from a face of the lock 426 and an end of the main body 423 of the cover 420, but shorter than the length as shown in FIG. 7K. As another example, the tubing 43b can have a length that is greater than a distance 413 from a face of the lock 426 and opening 432 (see FIG. 7K). The tubing 43b can have a length that is greater than a distance 413 from a face of the lock 426 and opening 432 so that when an end of tubing 43b is coupled to female connector 43a, the female connector 43a is separated from an exterior surface of the main body 423 of the cover 420 by a gap. Such gap can be altered by modifying the length of the tubing 43b. Where it is desired to have a greater gap and/or extend the location where a fluid line couples to the extension set 43 (such as female connector 43b), the length of the tubing 43b can be increased. Alternatively, where it is desired to have a smaller gap between the location where a fluid line couples to the extension set 43 (such as female connector 43b), and an exterior of the catheter housing 400, the length of the tubing 43b can be sized to be greater than the distance 413 between the lock 426 and the opening 423 by a small amount. For example, in some cases, it may be desirable for the gap to be small so and a fluid line can be connected to female connector 43a nearby opening 432 of the cover 420. In such cases, the fluid line coupled to the extension set 43 can be secured to the catheter housing 400 via the wings 422 in as discussed above.

The extension set 43 not only allows a fluid line to be coupled to the catheter device 40 and catheter 42 at a location outside the catheter housing 400, but it also can advantageously act as a universal connection interface for coupling other catheter device (for example, outside the catheter housing 400) and/or a fluid line. The dimensions and/or configuration (for example, threading) of the female connector 43a and/or male connector 43c can be sized and/or shaped to secure to catheter hubs 40, male/female connectors, and/or fluid lines of any sizes. Tubing 43b can be flexible. Tubing 43b can alternatively be rigid. For example, tubing 43b can have a length that is sufficient to position female connector 43a away from opening 432 by a gap and can be rigid so that tubing 43b (and therefore connected components such as catheter device 40) do not move if an external fluid line or connector is secured to female connector 43a. While extension set 43 is shown and described as having tubing 43b and female luer 43a, extension set 43 can additionally include a male luer, such as the male luer 40b. In such cases, the catheter device 40 can not include a male luer 40b but can include one or more cylindrical portions 40a.

Alternative Design for Catheter Housing

Figure 10A:
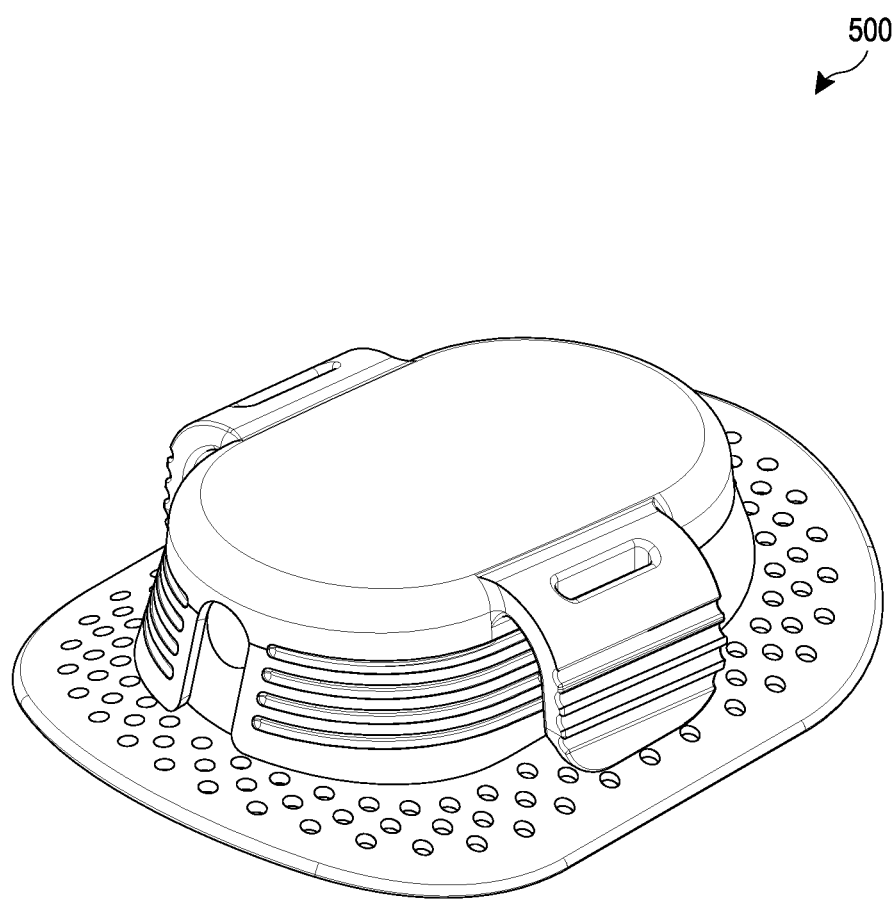
FIG. 10A illustrates a perspective view of an assembly of an alternative design for a catheter housing.

FIG. 10A illustrates a perspective view of a fully assembled catheter housing 500 that can be placed on and/or over any portion of a human body. FIGS. 10A, 10C, and 10D illustrate catheter housing 500 without also showing a catheter 542, catheter device 540, and tubing 541. The catheter housing 500 can be secured to an arm, hand, or leg of a patient, and can be secured to the arm, hand, or leg with the use of an anti-slip material on a bottom surface of the catheter housing 500 (or hub 560 or membrane 562 of the hub 560 which are each further described herein) around a catheter insertion site without requiring fastening straps. For example, as discussed further below, the bottom surface or a portion thereof can comprise an adhesive material and a release liner, and, when the release liner is pulled off the adhesive bottom surface, the bottom surface of the catheter housing device can be secured to a patient.

Figure 10B:
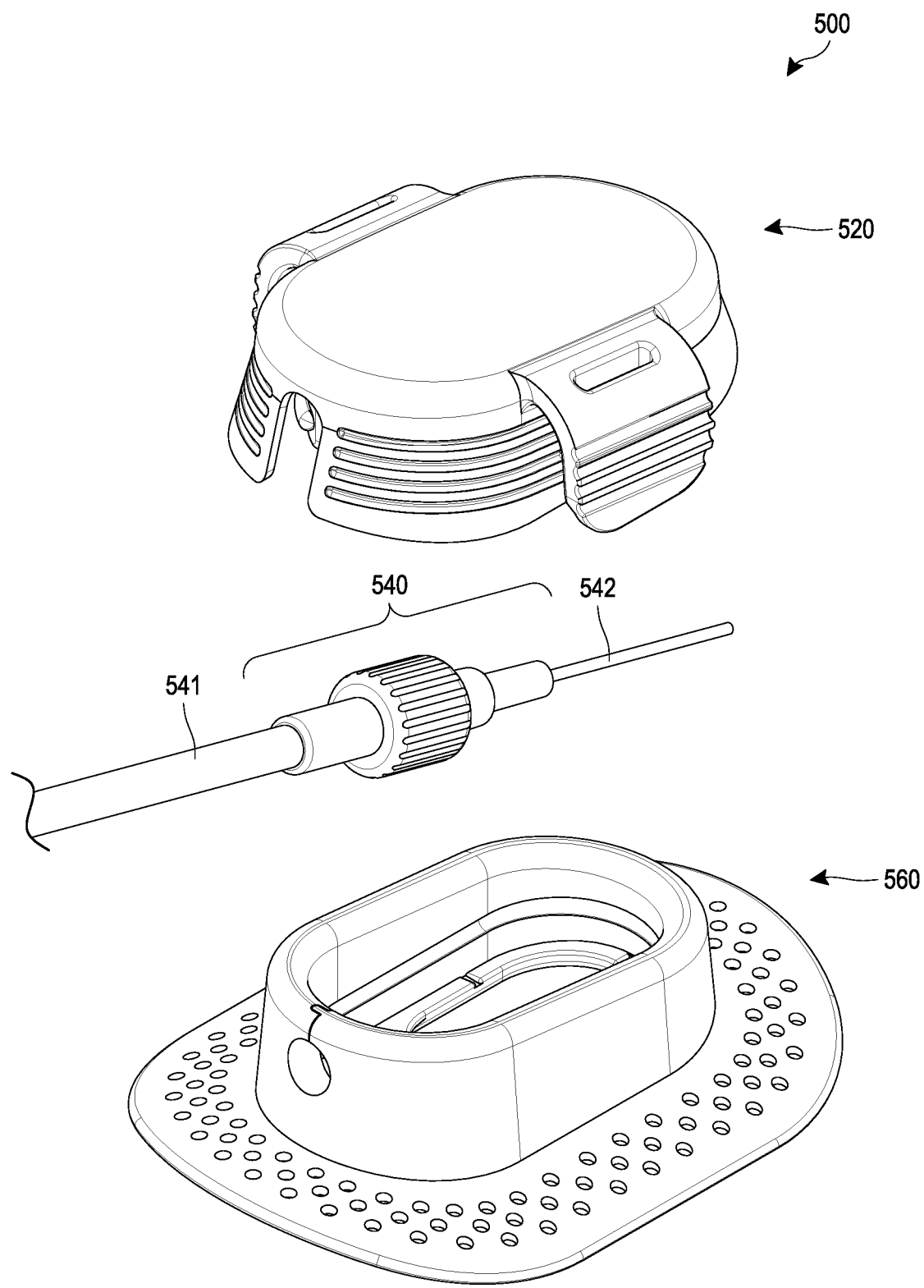
FIG. 10B illustrates an exploded view of the catheter housing of FIG. 10A along with a catheter, catheter device, and a fluid tube in accordance with aspects of this disclosure.
Figure 10C:
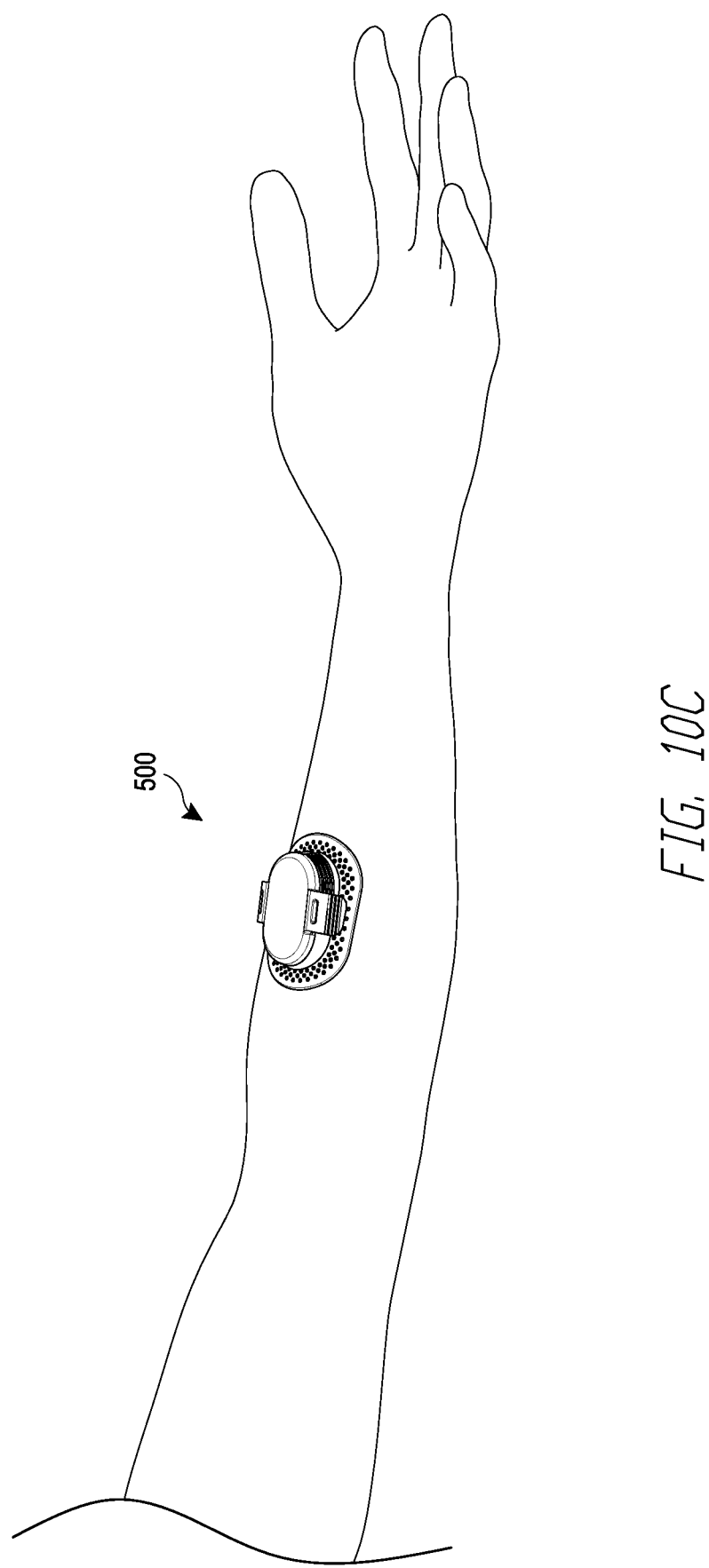
FIG. 10C illustrates a perspective view of the catheter housing of FIG. 10A in an assembled form on a human arm.
Figure 10D:
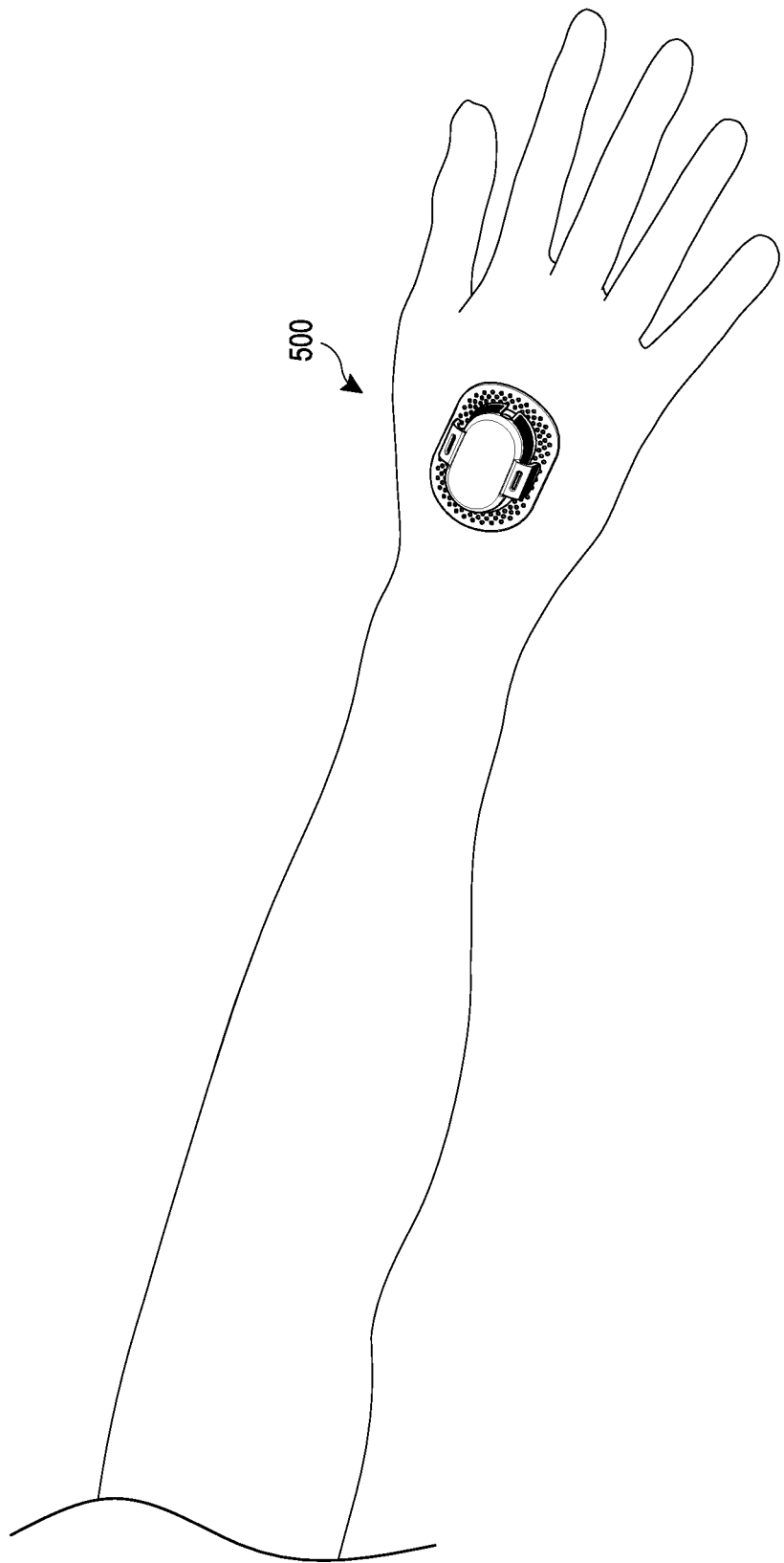
FIG. 10D illustrates a perspective view of the catheter housing of FIG. 6A in an assembled form on a human hand.
Figure 13A:
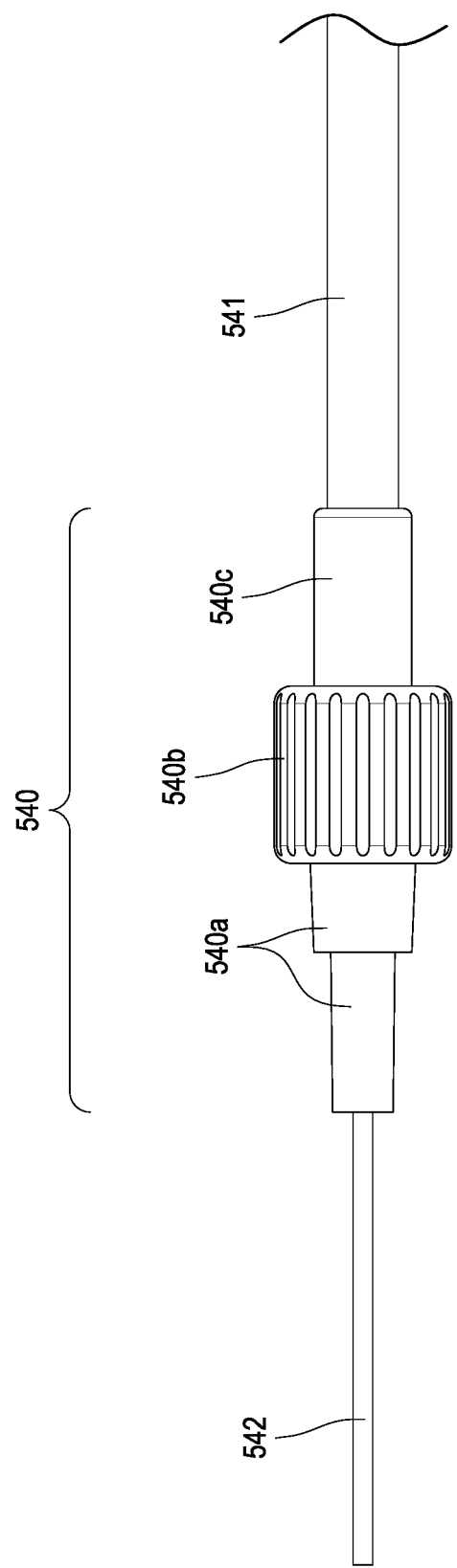
FIG. 13A illustrates an exploded view of a catheter, catheter device, and a fluid tube in accordance with aspects of this disclosure.

FIG. 10B illustrates an exploded view of the catheter housing 500 of FIG. 10A along with a catheter 542, catheter device 540, and tubing 541. The catheter housing 500 can include a cover 520 and a hub 560. As discussed herein, the catheter housing 500 can secure a catheter device (or portion thereof) and/or a catheter coupled to the catheter device. For example, the catheter housing 500 can secure a catheter device 540 coupled to a catheter 542. Similar to as discussed above, catheter device 540 can be any device that couples to a catheter cannula and/or a fluid tube. For example, catheter device 540 can include one or more cylindrical portions 540a and/or a male luer connector 540b (see FIG. 13A). Additionally, similar to as discussed above, the one or more cylindrical portions 540a can directly connect to catheter 542 and the male luer connector 540b, and the male luer connector 540b can directly connect to tubing 541. For example, male luer connector 540b can include an annular ring and a stem portion 540c that connects to one or both of the tubing 541 and the one or more cylindrical portions 540a (for example, with opposite ends of the stem portion 540c). Stem portion 540c can be integral or non-integral with male luer connector 540b. One advantage of the catheter housing 500 is that it can comprise a small number of components or parts, which can allow for simple assembly and securement of any type of catheter device and/or catheter. While the catheter housing 500 discussed herein can include the cover 520 and hub 560 as separate components, the cover 520 and the hub 560 can comprise a unitary or integral structure, and one of skill in the art will recognize that the features discussed herein with respective to the cover 520 and the hub 560 can be incorporated in some, many, or all respects into a unitary or integral catheter housing.

As discussed below, the cover 520 can be secured to the hub 560 and/or the hub 560 can be secured to the cover 520. As illustrated in FIGS. 10A and 10C, when the catheter housing 500 is assembled, the cover 520 can substantially surround or enclose the hub 560 or can partially surround or partially enclose the hub 560. The hub 560 can have an opening in a wall of the hub 560 that allows tubing 541 to fit within and/or pass therethrough into an interior of the hub 560. The hub 560 can also have an opening in a membrane of the hub 560 (such as membrane 562) that allows a catheter to be inserted into a patient while the hub 560 is secured to at least a portion of the catheter housing 500, such as the cover 520. The catheter housing 500 can secure to a patient with the use of an anti-slip surface, mechanism, ring, or protrusion on a bottom surface of a membrane of the hub 560, as discussed below. As also discussed below, hub 560 can include one or more lips on a bottom surface which help to seal a catheter insertion site in case the integrity of the adhesive bottom surface of the hub 560 is lost or degraded in portions thereof.

FIGS. 10C-10D illustrate a perspective view of an assembled catheter housing 500 secured to a human arm. As discussed above, the catheter housing 500 can also be attached to other locations on a human body, such as on a thigh, foot, calf, ankle, arm, leg, hand, hand, and/or neck, among other body parts. For example, the catheter housing 500 can be attached to various body parts and surround catheter insertion sites located in different regions on a human body, such as a portion of an underside of an arm, among other areas. The catheter housing 500 can be positioned and/or secured at and/or near any location where an IV can be inserted into a patient. The catheter housing 500 can be secured to a portion of a patient's body without the use of a fastening strap. As discussed herein, the catheter housing 500 can include an anti-slip surface, mechanism, ring, or protrusion on a portion of the catheter housing 500 that can contact a patient. The catheter housing 500 and/or components thereof can be made from a variety of materials or combination of materials. For example, the catheter housing 500 and/or components thereof (such as the cover 520 and/or the hub 560) can comprise silicone, plastic, and/or rubber. The catheter housing 500 and/or components thereof (such as the cover 520 and/or the hub 560) can comprise appropriate biocompatible materials. The catheter housing 500 and/or components thereof (such as the cover 520 and/or the hub 560) can comprise medical grade soft silicone material. The catheter housing 500 and/or components thereof (such as the cover 520 and/or the hub 560) can be substantially waterproof, durable, and/or washable. The catheter housing 500 and/or components thereof (such as the cover 520 and/or the hub 560) can be disposable, which can advantageously allow the catheter housing 500 and/or components thereof to be thrown away after use with a patient. The catheter housing 500 and/or components thereof (such as the cover 520 and/or the hub 560) can include or contain information regarding a patient, such as name, birthdate, and other information. Such information can also be, for example, information relating to the catheter insertion and/or information relating to inspection by a caregiver. The catheter housing 500 and/or components thereof (such as the cover 520 and/or the hub 560) can be biocompatible and/or recyclable.

The catheter housing 500 and/or components thereof (such as the cover 520 and/or the hub 560) can be sized depending on the patient's characteristics (for example, arm thickness). As discussed herein, the catheter housing 500 can have a low-profile shape and structure and can secure to a portion of a patient and have a minimal "footprint." Thus, the catheter housing 500 can advantageously secure a catheter device (such as catheter device 540) coupled to a catheter 542, a catheter 542, and/or connected tubing 541 while taking up minimal space on a portion of a patient's body when secured thereto. In some cases, the total height of the catheter housing 500 can be less than 1 cm, for example. In some cases, the total length of the catheter housing 500 can be between 3 cm and 10 cm, for example. In some cases, the total width of the catheter housing 500 can be between 3 cm and 5 cm, for example.

Figure 11A:
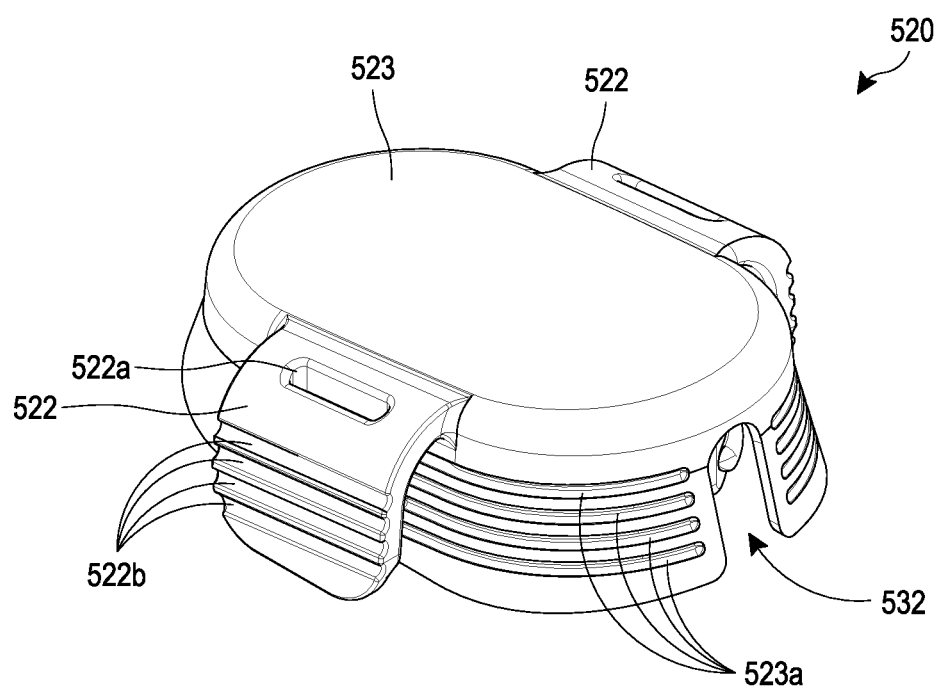
FIG. 11A illustrates a perspective view of a cover of the catheter housing of FIG. 10A.
Figure 11B:
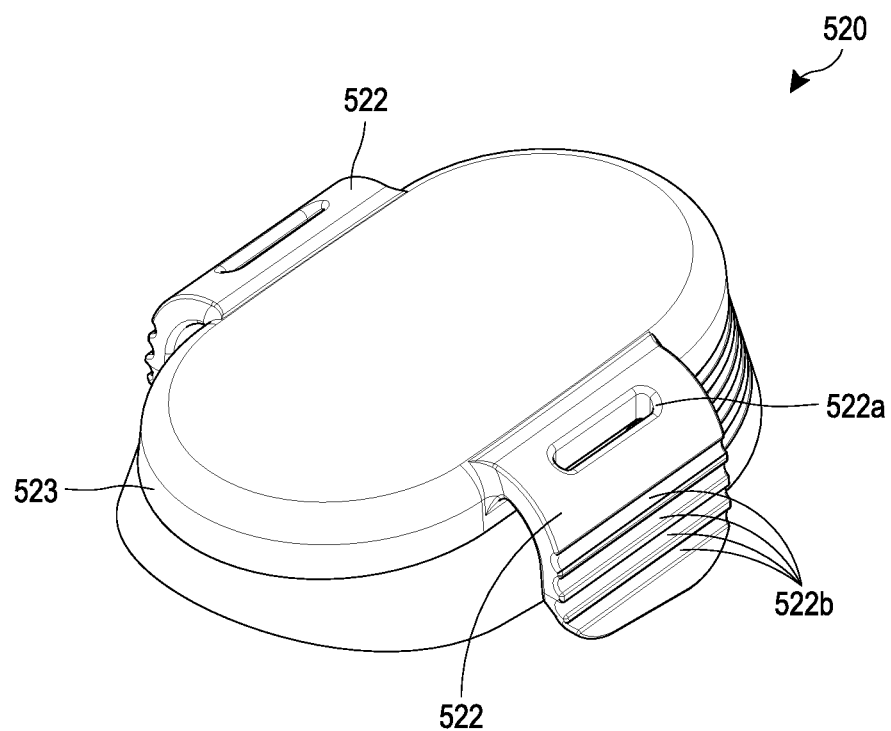
FIG. 11B illustrates another perspective view of the cover of FIG. 11A.
Figure 11C:
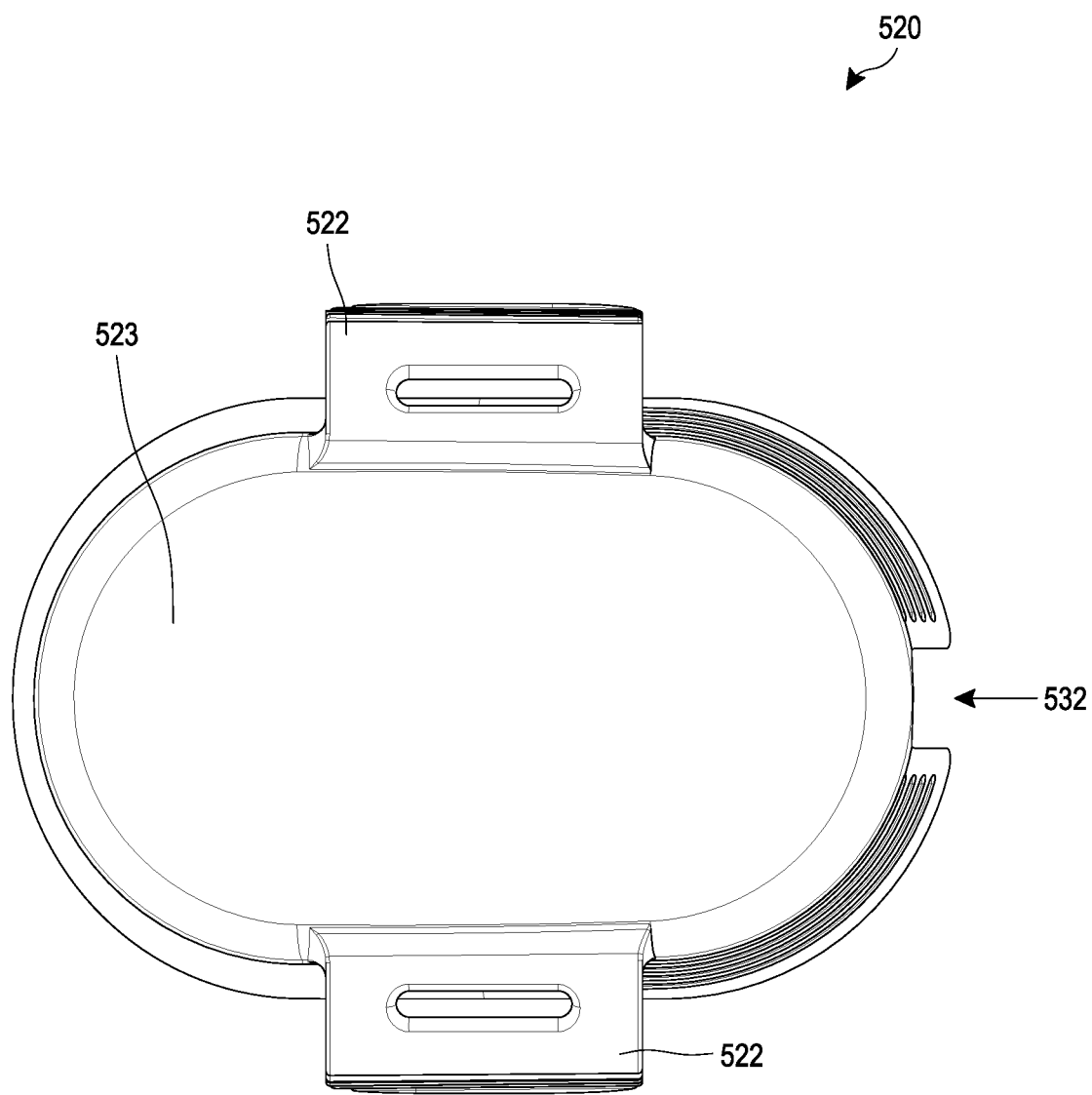
FIG. 11C illustrates a top view of the cover of FIG. 11A.

FIGS. 11A-11B illustrate various perspective views of the cover 520. As discussed herein, the cover 520 can be secured to the hub 560. The cover 520 can be made of transparent material. Alternatively, the cover can be made of nontransparent material. Additionally, the cover 520 can comprise both transparent and nontransparent material. For example, the portions of the cover 520 can be made of transparent material where it is advantageous to be able to see through the cover in order to observe the other components of the catheter housing 500, and/or observe, access, and/or inspect the puncture site without removing the catheter housing 500 or components thereof. The cover 520 can be made of substantially shockproof and/or durable material. This is advantageous because the catheter housing 500 and/or the cover 520 can be subjected to impact during installation or use. The cover 520 can also be made of substantially waterproof material. This is advantageous because the catheter housing 500 and/or the cover 520 can be subjected to water or other liquids when the device is in use. The cover 520 can comprise plastic, rubber, and/or silicone, among other materials, or a combination of such materials. The cover 520 can comprise a soft, pliable and/or flexible material, such as medical grade silicone. Alternatively, the cover 520 can comprise harder silicone, or rubber can be used. The cover 520 can be made of a transparent and flexible plastic material.

The cover 520 can be configured to form a closed environment over a site where an intravenous catheter is inserted into a patient. Such a closed environment can aid in keeping the site free from contamination, as discussed herein. As discussed above, the cover 520 can be made of at least partially transparent material so as to allow a caregiver or other person to examine the catheter insertion site and/or other portions of the catheter housing 500 (for example, the hub 560) while the cover 520 is secured to the hub 560. Such examination can allow a caregiver to verify that the insertion site is free from contamination and/or if portions of the skin or the catheter housing 500 near the site need to be cleaned, for example.

The cover 520 can include one or more openings 532 to permit tubing 541 or a portion of catheter device 540 (such as a stem portion 540c) to fit within and/or pass through the cover 520 and into an interior of the cover 520. For example, cover 520 can include one or more, two or more, three or more, four or more, five or more, or six or more openings 532. As discussed herein, such openings 532 can align with one or more openings in the hub 560 (such as opening 565) that can be sized and/or shaped to receive tubing 541 or a portion of catheter device 540 (such as stem portion 540c) when the catheter device 540 is secured to a portion of the cover 520 (such as lock 526 and/or bridge 527 of cover 520 further described below). The cover 520 can have a rounded shape. A rounded shape can be advantageously to reduce interference from caregivers or physicians with edges or corners of the cover 520 and can also reduce discomfort associated with patient contact with edges or corners of the cover 520. Alternatively, the cover 520 can have a non-round shape, for example, a rectangular shape. Alternatively, the cover 520 can be approximately trapezoidal, rectangular, square, oval and/or circular in shape, among other shapes. For example, where the catheter housing 500 includes a hub 560 and a wall 561 of the hub 560 shaped like a stadium, the cover 520 can have a shape that accommodates the stadium shape of wall 561. The cover 520 can comprise a single, continuous piece which may advantageously minimize the amount of parts of the catheter housing 500 and can increase ease of assembly and/or securement of the catheter housing 500 on the patient. Alternatively, the cover 520 can comprise more than one piece.

The catheter housing 500, including the hub 560 and cover 520 discussed herein, can be coated with an antimicrobial coating to aid with disinfection and/or sterilization near the catheter insertion site and/or in or around the catheter housing.

Figure 11D:
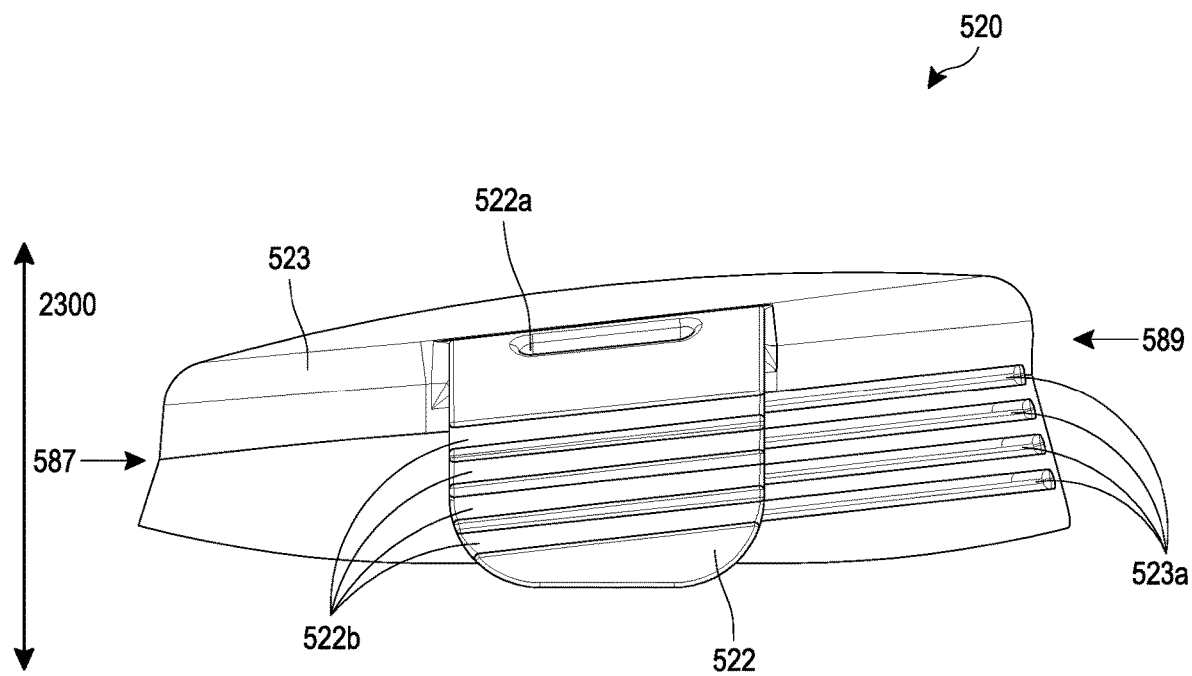
FIG. 11D illustrates a side view of the cover of FIG. 11A.

The cover 520 can include one or more wings 522 (which can also be referred to herein as "arms") that can allow tubing connected to the catheter device 540 to fit within and/or pass therethrough or underneath, so as to be secured to a portion of the catheter housing 500. For example, as shown in at least FIG. 11K, when a catheter device 540 is secured by the catheter housing 500 (for example, by cover 520), tubing 541 connected to the catheter device 540 can pass through an opening 532 (and/or both of openings 532a, 532b described below) in the cover 520, curve around a portion of the cover 520 and pass through and/or underneath one or more wings 522 of the cover 520. Where catheter device 540 includes a male luer connector 540b and a stem portion 540c which is received by opening 532 (or openings 532a, 523b), tubing 541 can extend from a such stem portion 540c proximate such opening 532 (or openings 532a, 523b) and can curve around a portion of the cover 520 and pass through and/or underneath one or more wings 522 of the cover 520. Such configuration can form a J-loop, for example, where the tubing 541 curves around a portion of the cover 520 after exiting an opening 532 (and/or both of openings 532a, 532b described below) in the cover 520 and passes through wing 522 on a side of the cover 520. In the configuration illustrated in FIG. 11K, tubing 541 coupled to the catheter device 540 exits at or near opening 532 in the cover 520, curves at an approximate 180 degree angle, passes through a wing 522 on a side of the cover 520 and exits out in a direction opposite to the direction that the tubing initially exited the cover 520 through opening 532. The cover 520 can have more than one wing 522. For example, the cover 520 can have a wing 522 on a first side of the cover 520 and a second wing 522 on a second side of the cover 520 opposite to the first site of the cover 520. Including a wing 522 on each of two opposite sides of cover 520 can advantageously provide flexibility for a caregiver to secure the tubing to the cover 520 in a J-loop configuration on either side of the cover 520. Such flexibility can allow the tubing 541 to be secured to the cover 520 in a configuration which minimizes interference of the tubing with other tubing, wiring, or other equipment nearby the securement location and/or may reduce discomfort to the patient in some circumstances. In some cases, having a wing 522 on either side of the cover 520 can allow tubing 541 coupled to the catheter device 540 to be wrapped around substantially all of the cover 520 and secured within and/or underneath each of the two wings 522 and, for example, exit out in the same direction as the tubing initially exited the cover 520 (through opening 532 and/or openings 532a, 532b). Placing a portion of the tubing 541 through and/or underneath wings 522 can provide the benefits discussed herein, such as mechanically decoupling the tubing 541 from the insertion site and/or the catheter device 540, for example.

The cover 520 can comprise a main body 523 (see FIGS. 11A-11B). The one or more wings/arms 522 can extend from sides of the main body 523 of the cover 520. As shown by at least FIGS. 11A-11B and 11E, wings 522 can extend outward from sides of the main body 523 of the cover 523 and curve in a direction parallel to a vertical axis 2300 (see FIG. 11D). For example, the wings 522 can extend outward from the main body 523 of the cover 520 at least partially in a first direction that is generally perpendicular to a side of the main body 523 and/or cover 520 and extend in a second direction that is generally perpendicular to the first direction. The size and/or shape of wings 522 can correspond to the size and/or shape of tubing coupled to the catheter device, and the curvature of the wings 522 can be shaped to correspond the curvature and/or shape of the tubing (such as tubing 543). The wings 522 can extend outward from the main body 523 of the cover 520 and can curve in a direction towards the patient when the catheter housing 500 is secured to the patient. For example, the wings 522 can extend outward and curve downward in a direction along vertical axis 2300 such that a free end of the wings 522 contacts a bottom or skin-contacting portion of the catheter housing 500 (such as the hub 560 or membrane 562). The wings 522 can extend outward and curve downward so that there is little or no gap between the free end of the wings 522 and a bottom portion of the catheter housing 500 or the skin of the patient such that tubing passing through and/or secured by the wings 522 trapped and/or held between a top surface of the hub 560 (such as the membrane 562) and interior surface(s) of the wings 522 (an interior surface of the wings 522 can be a surface that faces toward the main body 523).

Figure 11E:
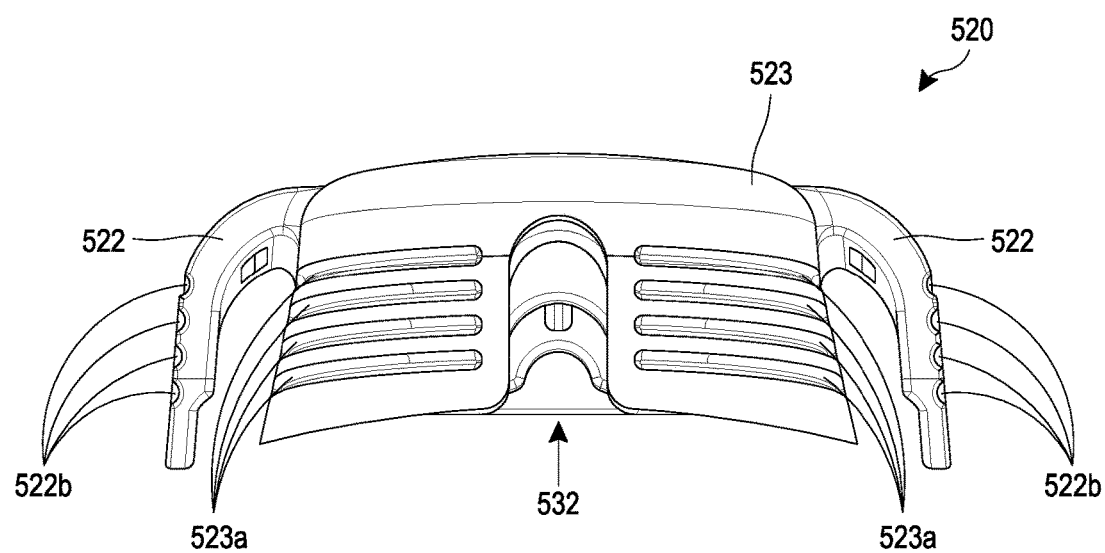
FIG. 11E illustrates a front view of the cover of FIG. 11A.

When the cover 520 is secured to the hub 560, the wings 522 of the main body 523 of the cover 520 can curve in a direction toward the hub 520 and/or the membrane 562 of the hub 560. Interior surfaces of the wings 522 can be smooth, which can advantageously allow tubing to more easily slide therethrough and/or within. Alternatively, an interior surface of the wings 522 can be rough, which can advantageously reduce the ability of tubing 541 coupled to the catheter device 540 to slide outside or become disconnected from the wings 522. Interior surfaces of the wings 522 (for example, the surfaces at least partially facing the patient when the catheter housing 500 is secured to a patient) can be sized and/or shaped to correspond to a size and/or shape of tubing 541 that the wings 522 are intended to secure and/or guide. For example, as shown in FIG. 11E, a surface along an interior of the wings 522 that faces a direction at least partially toward the patient or the main body 523 can have one or more curvatures from a portion proximate to the main body 523 of the cover 520 to a free end of the wings 522. The size and/or shape of the interior surface of the wings 522 can be sized to match the shape of a portion of tubing 541 that is secured and/or guided by the wings 522. For example, a curvature of the interior surface of the wings 522 can correspond with a diameter of tubing coupled to the catheter device 540. Further, the interior surfaces of the wings 522 can have one or more curved portions to correspond to one or more sized and/or shapes of tubing. For example, where the cover 520 includes a port (such as port 521), tubing secured to the port can be wrapped around a portion of the catheter housing 500 (such as the cover 520) and can be held and/or secured by a first curved portion of the interior surface of the wings 522, and tubing 541 coupled to the catheter 542, and/or catheter device 540 that exits through opening 532 and is wrapped around a portion of the catheter housing 500 (such as cover 520) can also be held and/or secured by a second curved portion of the interior surface of the wings 522. The first and second curved portions can be proximate and/or adjacent to one another such that the tubing coupled to the port and the tubing coupled to the catheter device 540 are adjacent to each other. For example, when the tubing coupled to the port and the tubing coupled to the catheter device 540 are secured to the first and second curved portions of the interior surface of the wings 522, the tubing coupled to the port can be above or below (vertically) the tubing coupled to the catheter device 540 with reference to a vertical axis, such as vertical axis 2300 (see FIG. 11D), As another example, when the tubing coupled to the port and the tubing coupled to the catheter device 540 are secured to the first and second curved portions of the interior surface of the wings 522, the tubing coupled to the port can be closer or further from a bottom surface of the catheter housing 500 (such as the hub 560 or membrane 562 of the hub 560). Thus, the wings 522 can hold, secure, and/or guide one or more tubes/tubing coupled to the catheter housing 500, the catheter device 540, and/or the catheter 42. The one or more wings 522 can have a tapered free end, and/or can have a free end that has a smaller thickness than another portion of the wings 522 (see FIG. 11E). Such configuration can help initial alignment and/or positioning of a tube within the space defined between the one or more wings 522 and the main body 523 of the cover 520 prior to securing the tube in such space.

Regardless of the placement and/or amount of the one or more wings 522, the one or more wings 522 can allow a caregiver to conveniently and safely wrap and/or secure tubing to the catheter housing 500. This can provide a number of advantages. The one or more wings 522 can allow the insertion site or portions of the catheter housing 500 (such as the lock 526) to be mechanically decoupled from tubing. Thus, if the tubing gets pulled, caught, or snagged, the force will not affect the insertion site, catheter 542, catheter device 540, and/or portions of the catheter housing 500 (such as the lock 526). Such wrapping and/or securement of the tubing to the catheter housing 500 can also reduce the likelihood that the tubing will get pulled or caught on clothing or other items. Such wrapping and/or securement can also prevent the tubing from sticking out in a direction and/or area that is inconvenient for caregivers or physicians. For example, where a patient is undergoing surgery, many medical tools devices may be used during the surgery and doctors and nurses may be moving in and around areas nearby a catheter insertion site. In such cases, the one or more wings 522 can significantly reduce the "footprint" of the catheter housing 500 and/or tubing coupled to the catheter device 540 and/or a port of the housing 500. This can reduce the likelihood that the tubing will get tangled or will interfere with activities by such caregivers working in proximity to the catheter insertion site, even within a few feet from the site. The wrapping and/or securement of the tubing to the catheter housing 500 can allow the tubing to be essentially unified with the catheter housing 500, and can eliminate the need for a caregiver to secure the tubing in a J-loop configuration with an adhesive applied directly to the patient's skin. The one or more wings 522 can provide securement for the tubing without having the tubing touch the patient's skin, increasing patient comfort and potential rashes or other skin irritation issues resulting from such contact. The one or more wings 522 also can provide securement to the tubing which prevents the tubing from getting pulled out and/or from impacting the securement of the catheter 542 and/or catheter device 540. For example, the one or more wings 522 can resist forces applied if the tubing is moved and can significantly reduce or entirely eliminate the force applied to the catheter device 540 and/or catheter 542 if such movement occurs. This provides a significant advantage since significant damage can occur at the vein and/or the catheter insertion site in traditional devices and methods of catheter securement.

As shown in at least FIGS. 11A-11D, the wings 522 can include a slot or opening 522*a*. Slot 522*a* can advantageously allow inspection of the tubing coupled to the catheter device 540 and/or an optional port(s) of the housing 500 when it is secured by the wings 522. For example, as discussed above, the tubing can be secured by placement under the wings 522 and/or between the wings 522 and a portion of the hub 560 (such as the membrane 562 of the hub 560). Such inspection can be important because it can allow a caregiver to evaluate whether gas and/or liquid is flowing through the tubing and in turn to the catheter 542 and the patient. For example, such slot 522*a* allows a caregiver to examine whether medicinal or other fluid are being properly delivered through the tubing and to the catheter 542 and the patient while the tubing is secured to the one or more wings 522 (for example, to ensure that the securement of the tubing to the wings 522 is not pinching the tubing). Alternatively, the slots 522*a* can allow fastening straps to pass therethrough and secure the catheter housing 500 to the patient. The discussion of the fastening straps 80 with reference to catheter housing 10, cover 20, 120, and/or strap hoops 22, 122 above is applicable with reference to slots 522*a*, cover 520, and catheter housing 500. As discussed herein, catheter housing 500 can be secured to a patient without fastening straps.

As shown in at least FIGS. 11A-11E, the one or more wings 522 can include one or more indents 522*b* along a surface thereof. The one or more indents 522*b* can be recessed from a surface of the one or more wings 522 (such as an exterior surface of the one or more wings 522) and can extend along a portion of the surface. For example, the one or more wings 522 can include one or more indents 522*b* that extend along a portion of an exterior surface thereof and are spaced apart from one another, for example, along a height or length of the one or more wings 522. For example, the one or more wings 522 can include four indents 522*b* that are vertically spaced (with respect to axis 2300 in FIG. 11D). The indents 522*b* can extend along a portion of a width of a side of the one or more wings 522 (for example, an entire width of the side of the wing 522). The one or more indents 522*b* can aid a user in gripping and/or handling the cover 520 and/or the wings 522, which can advantageously help in securing the cover 520 to the hub 560 and/or a patient. Alternative to the one or more indents 522*b*, cover 520 can include one or more ribs which protrude from a surface of the one or more wings 522. Such one or more ribs can be positioned as shown with respect to the one or more indents 522*b*, and can extend along and/or be positioned in a manner identical to that which is described with reference to the one or more indents 522*b* above. Similar to the one or more indents 522*b*, such one or more ribs can aid a user in gripping and/or handling the cover 520, which can advantageously help in securing cover 520 to hub 560 and/or a patient.

Figure 11F:
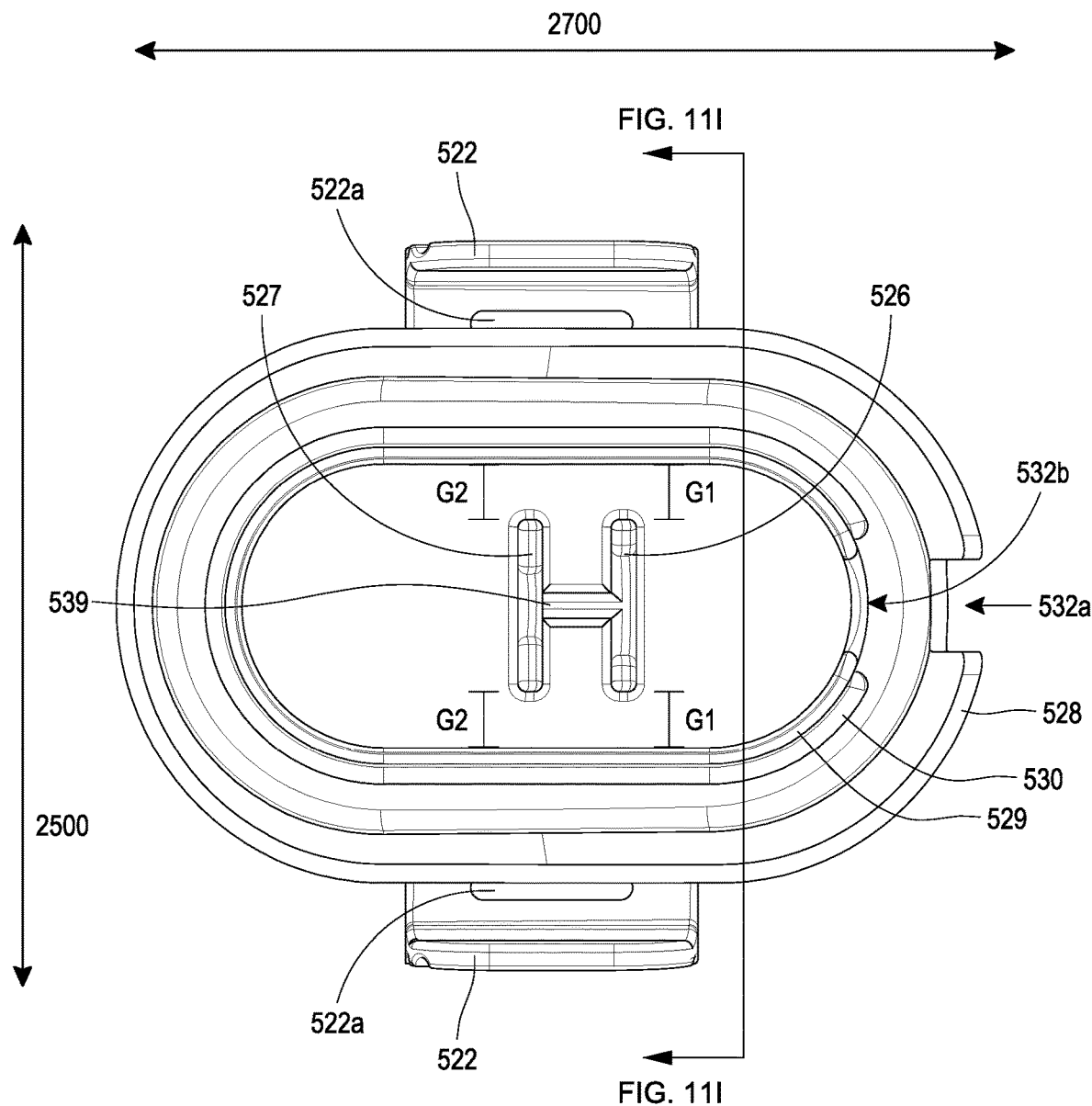
FIG. 11F illustrates a bottom perspective view of the cover of FIG. 11A.
Figure 11G:
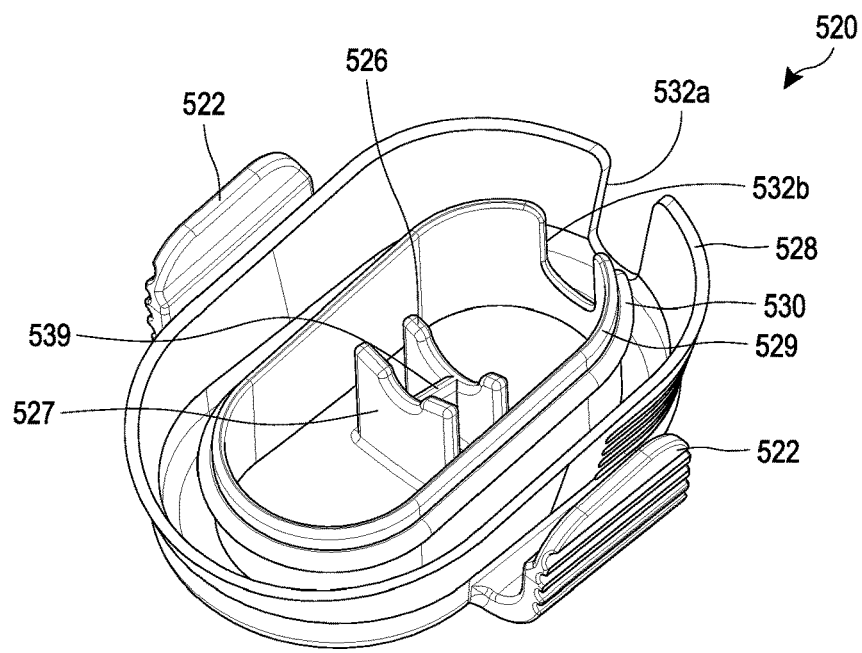
FIG. 11G illustrates a close-up bottom perspective view of the cover of FIG. 11A.
Figure 11H:
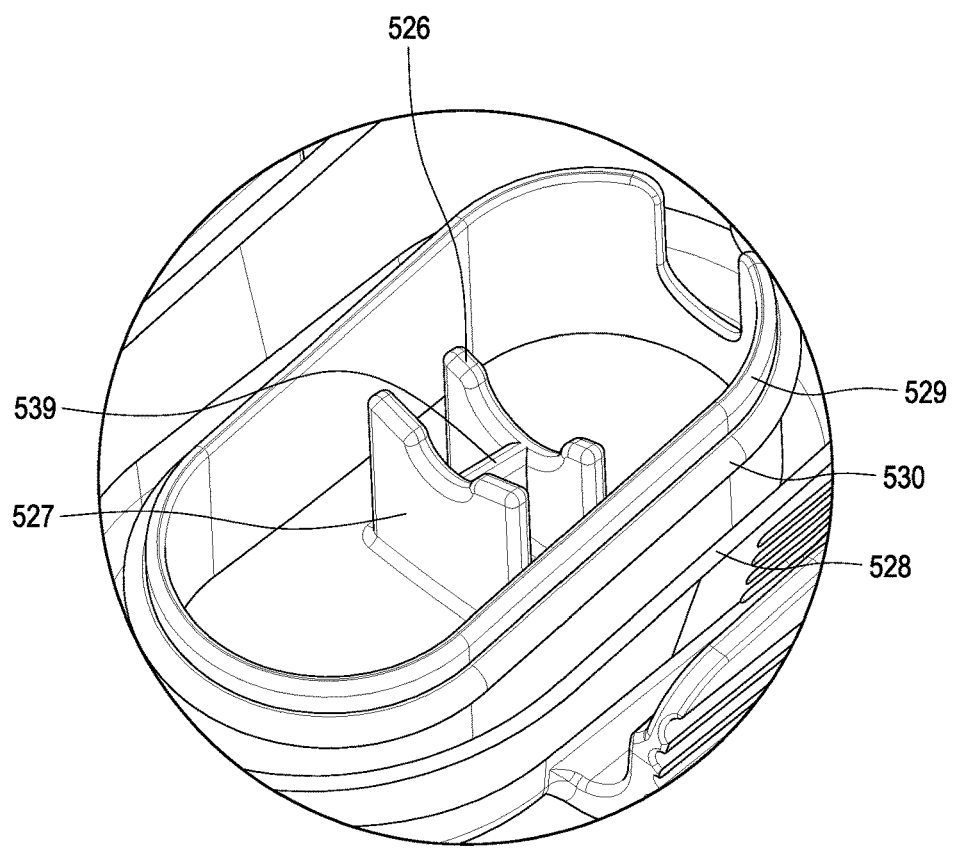
FIG. 11H illustrates a bridge of the cover of FIG. 11A.

As shown in FIGS. 11F-11G, cover 520 can include one or more protrusions 530 (also referred herein as "tongues 530"). For example, the cover 520 can include one, two, three, four, or five or more protrusions 530. The one or more protrusions 530 can extend along an interior portion of the cover 520, for example. The one or more protrusions 530 can be located at a lower interior portion of the cover 520, or alternatively, the protrusion 530 can be located at a middle or higher interior portion of the cover 520. The one or more protrusions 530 can be substantially continuous, or alternatively, can be non-continuous, intermittent or can exist in sections. The one or more protrusions 530 can extend outward from an interior of the cover 520. The one or more protrusions 530 can extend along substantially all of an interior surface of the cover 520. The one or more protrusions 530 can extend around an interior of the cover 520 and be continuous except at and/or near openings in the cover 520. For example, as shown in FIG. 11F, the one or more protrusions 530 can comprise a protrusion 530 that extends along an exterior surface of an inner wall 529 of the cover 520 and stop at or near an opening 532b in the inner wall 529. Having the one or more protrusions 530 arranged in such configuration can provide strong securement between the cover 520 and the hub 560 when the protrusion 530 is secured to the groove 568 of the hub 560, while also not interfering with the operation and/or use of the lock 526, bridge 527, and/or tubing 541.

The one or more protrusions 530 can be configured to secure to a portion of the hub 560. For example, such securement can occur when the cover 520 is placed over a portion of the hub 560, whereby the one or more protrusions 530 can secure to one or more grooves 568 of the hub 560 (see FIG. 12A). The one or more protrusions 530 can secure to the one or more grooves 568 by a snap-fit, press fit, friction-fit, and/or other configuration for securely connecting the cover 520 to the hub 560. The surface of the one or more protrusions 530 can be rounded (see, for example, FIG. 11G). Such a rounded shape can advantageously help the one or more protrusions 530 slide into the one or more grooves 568 of the hub 560 thus facilitating ease of securement and/or removal if sufficient force is applied. In some cases, the one or more protrusions 530 and the one or more grooves 568 can be tightly secured such that removal of the hub 560 and the cover 520 from one another requires two hands.

Alternatively, the one or more protrusions 530 can be replaced with one or more interior grooves. For example, the one or more protrusions 530 can be replaced with one, two, three, four, or five, six, seven, or eight or more grooves. For example, the one or more protrusions 530 can be replaced with one or more grooves extending along an interior surface of the cover 520 that are adjacent to one another and/or atop each other. For example, the one or more protrusions 530 can be replaced with one continuous groove. Such interior grooves can secure to at least a portion of the hub 560. For example, such interior grooves can secure to a protrusion appearing on the hub 560 which can replace the groove 568 that is shown and described with respect to hub 560 below. Such securement can occur by a snap-fit, press fit, friction-fit, and/or other configuration. Thus, the cover 520 can secure to the hub 560 by insertion of a protrusion located on the cover 520 into a groove located on the hub 560, and/or by accepting a protrusion located on the hub 560 into a groove located on the cover 520.

In some configurations, a seal is formed such that the cover 520 does not allow external air and/or contaminants from entering the enclosed internal volume of the catheter housing 500. For example, the cover 520 can engage the hub 560 to form a closed and/or isolated environment, which encloses the insertion site. In such configurations, the catheter insertion site can advantageously be sterilized by inert gas as described above. Similarly, the cover 520 can advantageously help to inhibit or prevent microbe contaminate and help to lower contamination vulnerability. The cover 520 can also be configured to prevent the joint 566 (see FIGS. 12A-12B) from separating while the catheter housing 500 is in use.

The cover 520 can comprise one or more walls. For example, the cover 520 can comprise one, two, three, four, or five walls. As shown in FIGS. 11F-11G, the cover 520 can have two walls. For example, the cover 520 can have an outer wall 528 and an inner wall 529. As shown, the one or more protrusions 530 can be located on an exterior surface of the inner wall 529 of the cover 520. The exterior surface of the inner wall 529 can face towards the outer wall 528 and the interior surface of the inner wall 529 can face at least partially towards the catheter insertion site. The interior surface of the inner wall 529 is opposite the exterior surface of the inner wall 529.

As discussed above, the cover 520 can have one or more openings 532 to accommodate, receive, and/or secure tubing 541 and/or a portion of catheter device 540 (for example stem portion 540c). As shown in FIG. 11F, the inner wall 529 and the outer wall 528 can have openings 532a, 532b that allow tubing 541 connected to the catheter device 540 to exit the cover 520. Such openings 532a, 532b can be additionally or alternatively be sized and/or shaped to accommodate, receive, and/or secure stem portion 540c. The openings 532a, 532b can be aligned with and/or proximate to a lock 526 and/or the bridge 527 discussed herein. The openings 532a, 532b can align with a recess in the lock 526 and/or the bridge 527. This can allow tubing 541 and/or a portion of catheter device 540 (such as stem portion 540c) to maintain a straight configuration through the openings 532a, 532b. The openings 532a, 532b can be sized and shaped to accommodate various sizes and/or shapes of tubing 541 and/or various sizes and/or shaped of catheter devices 540 (or portions thereof, such as stem portion 540c).

As shown in at least FIGS. 11A-11E, cover 520 can include one or more indents 523a along a surface thereof. The one or more indents 523a can be recessed from a surface of the cover 520 (such as an exterior surface of cover 520) and can extend along a portion of the surface. For example, the main body 523 of cover 520 can include one or more indents 523a that extend along a portion of an exterior surface thereof and are spaced apart from one another, for example, along a height of the cover 520. For example, the cover 520 can include four indents 523a that are vertically spaced (with respect to axis 2300 in FIG. 11D). The indents 523a can extend around an entire perimeter of a surface of cover 520 or less than the entire perimeter of a surface of the cover 520. For example, the indents 523a can extend along less than half of a perimeter of the cover 520. The one or more indents 523a can aid a user in gripping and/or handling the cover 520, which can advantageously help in securing cover 520 to hub 560 and/or a patient. Alternative to the one or more indents 523b, cover 520 can include one or more ribs which protrude from a surface of the cover 520 (such as an exterior surface). Such one or more ribs can be positioned as shown with respect to the one or more indents 523b, and can extend along and/or be positioned in a manner identical to that which is described with reference to the one or more indents 523b above. Similar to the one or more indents 523b, such one or more ribs can aid a user in gripping and/or handling the cover 520, which can advantageously help in securing cover 520 to hub 560 and/or a patient.

Figure 11I:
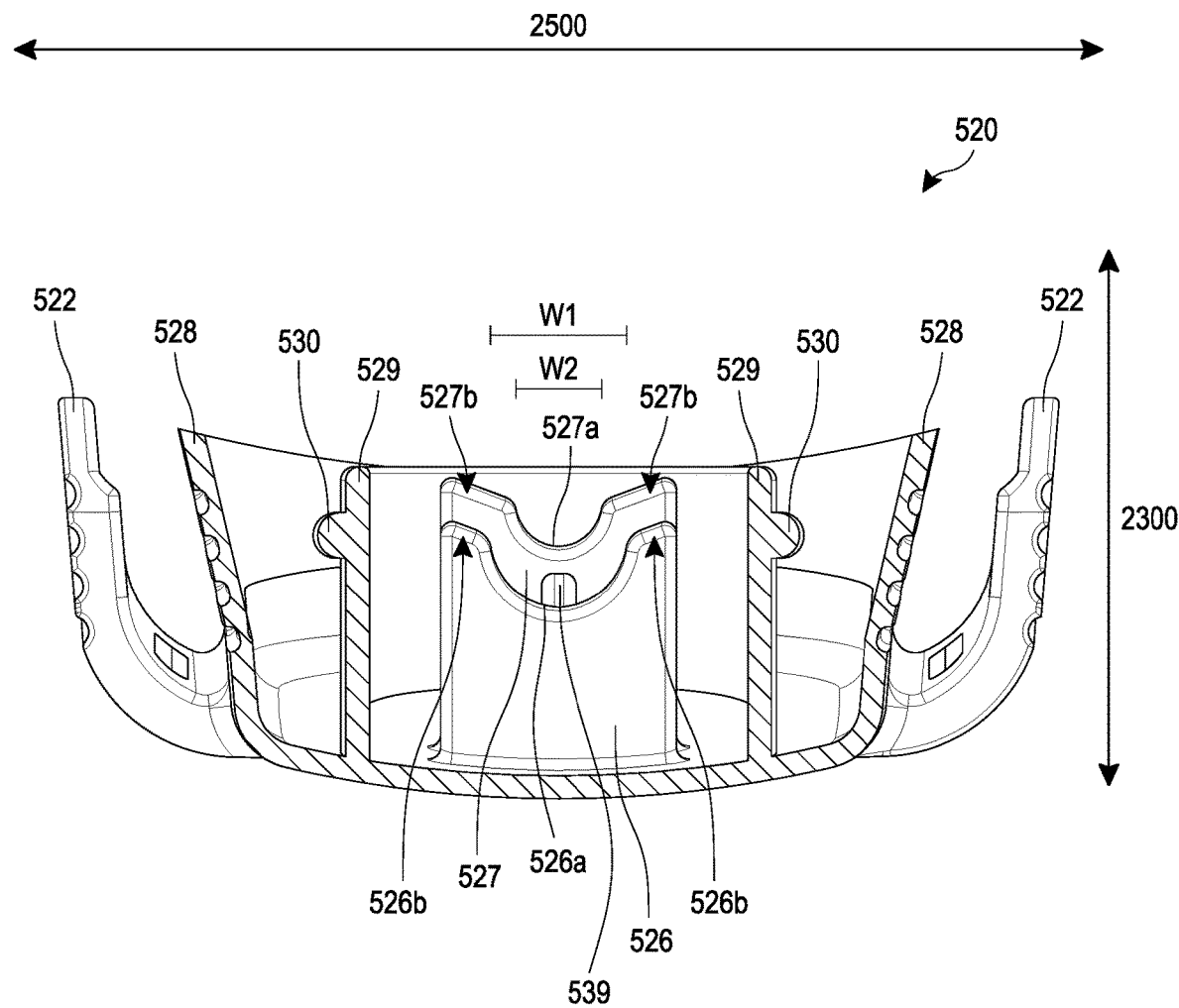
FIG. 11I illustrates a lock of the cover of FIG. 11A.
Figure 11J:
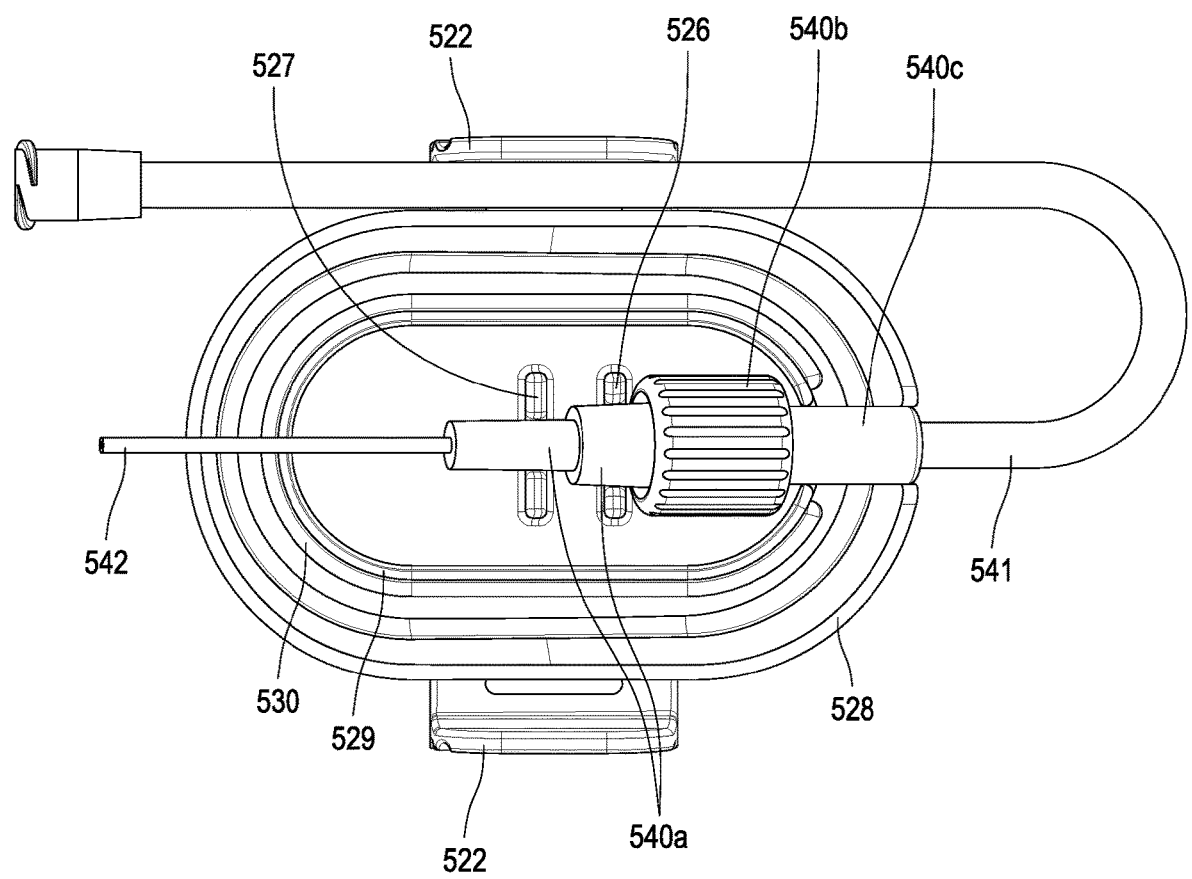
FIG. 11J illustrates a bottom view of the cover of FIG. 11A where a catheter device is secured by the cover of FIG. 11A in accordance with aspects of this disclosure.
Figure 11K:
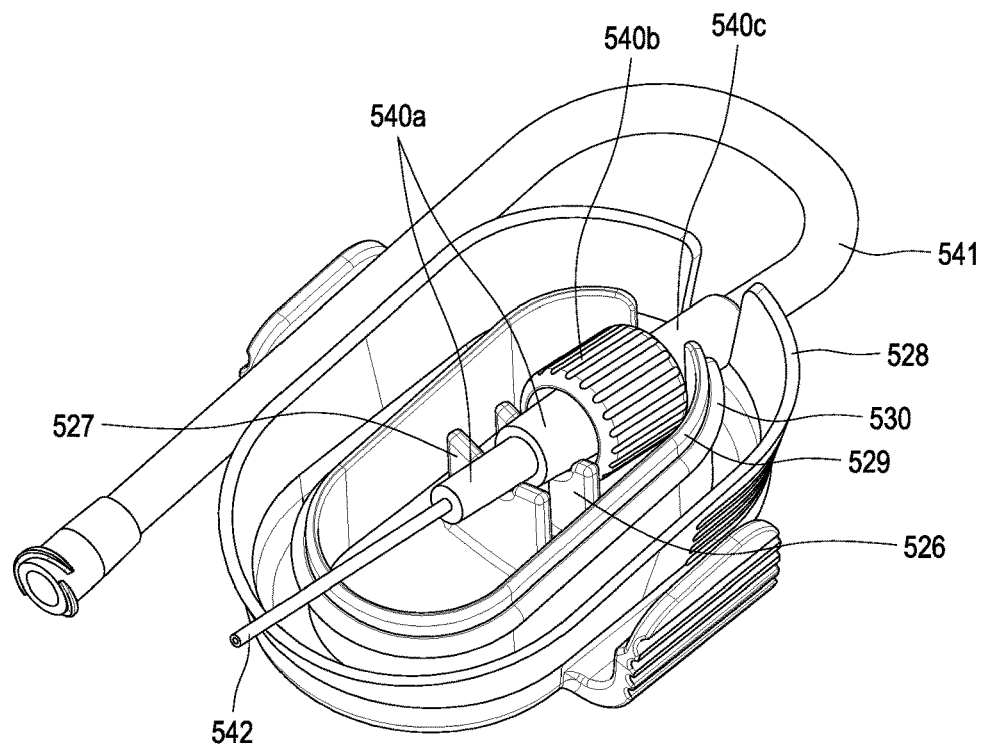
FIG. 11K illustrates a bottom perspective view of the cover of FIG. 11A where a catheter device is secured by the cover of FIG. 11A in accordance with aspects of this disclosure.
Figure 11L:
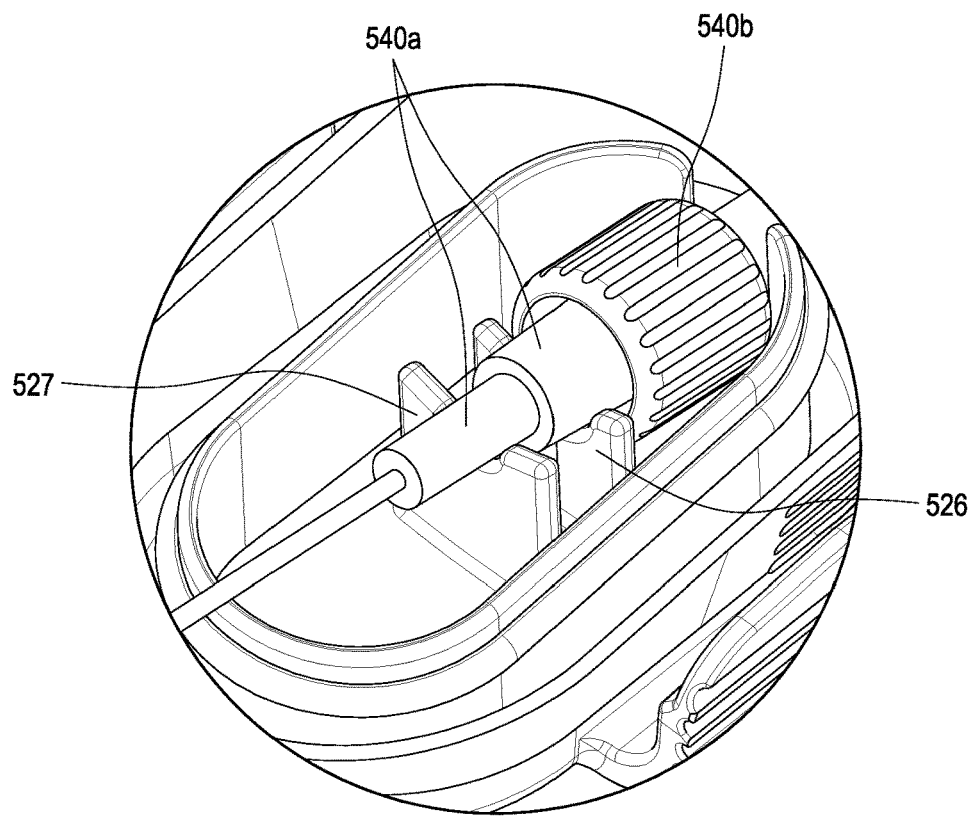
FIG. 11L illustrates a close-up bottom perspective view of the cover of FIG. 11A where a catheter device is secured by the cover of FIG. 11A in accordance with aspects of this disclosure.

As shown in at least FIG. 11I, outer wall 528 of cover 520 can be flared. For example, outer wall 528 can have a first portion that is generally parallel to the inner wall 529 and a second portion that is angled with respect to the first portion and/or with respect to the inner wall 529. At least a portion of the outer wall 528 can flare and/or extend away from the inner wall 529. Such configuration can help guide a portion of the hub 560 when the cover 520 is secured (or is being secured) to hub 560. For example, with reference to FIG. 11M, wall 561 of hub 560 can more easily align with, slide with, and/or secure in between outer and inner walls 528, 529 of cover 520 where the outer wall 528 has a flared or partially flared portion.

As shown in at least FIGS. 11F-11L, cover 520 can include a lock 526 that can secure the catheter device 540, the catheter 542, and/or tubing 541 connected to the catheter device 540 before, during, and/or after a catheter 542 is inserted into a patient at an insertion site. Lock 526 can extend outward and/or downward from an interior surface of the cover 520 (see FIG. 11G). Lock 526 can have a recess 526*a* with a width W1 that is sized and shaped to accommodate and/or secure to a catheter device 540 or a portion thereof (see FIG. 11I). For example, recess 526*a* can be sized and/or shaped to retain and/or surround a cylindrical portion 540*a* of catheter device 540 (see FIG. 11J-11L). FIG. 11I illustrates a cross section through cover 520 and shows a close up view of the lock 526. The recess 526*a* can be rounded. Alternatively, the recess 526*a* can be non-rounded. The recess 526*a* can be circular and/or partially circular. Alternatively, the recess 526*a* can be non-circular. The recess 526*a* can comprise an arch shape, a half-moon shape, half-circle shape, or another shape. The lock 526 can advantageously reduce the likelihood that the catheter device 540 or a portion thereof will be dislodged when tubing 541 coupled to the catheter device 540 is moved (for example, snagged or jiggled). For example, as illustrated in at least FIG. 11J, the catheter device 540 can comprise two cylindrical portions 540*a* with different cross-sectional areas. In such case, the lock 526 can retain and/or surround a portion of one of the cylindrical portions 540*a*, for example.

The securement of the catheter device 540 (or a portion thereof) by or with the lock 526 can be a physical locking, holding, stabilizing without locking, retaining, stabilizing to prevent or reduce the likelihood of movement, stabilizing to minimize movement, or another type of securement. The lock 526 can be sized and/or shaped to secure any type of catheter device 540 (or portion thereof). The recess 526*a* of the lock 526 can be sized and/or shaped to receive and/or surround a portion of a perimeter of the catheter device 540 or a portion thereof. For example, the recess 526*a* of the lock 526 can be sized and/or shaped to surround ¼, ½, or ¾ of the perimeter of the catheter device 540 or a portion thereof, or any fractions or percentages therebetween, or any ranges bounded by any combination of these percentages, although other values can be used in some implementations. Where catheter device 540 includes a male luer 540*b* as shown in FIGS. 11J-11M), cover 520 can secure the male luer 540*b* between lock 526 and another portion of cover 520. For example, male luer 540*b* can be secured between lock 526 and a wall of cover 520 (such as inner wall 529 of cover 520). Lock 526 can be spaced away from a wall of cover 520 (such as inner wall 529 of cover 520) a distance that is equal to a length of male luer 540*b*. In such configurations, male luer 540*b* can be secured between a wall of cover 520 (such as inner wall 529) and lock 526 such that catheter device 540 is prevented from moving in a direction parallel to an axis running through the lock 526, catheter device 540, male luer 540*b*, and/or catheter 542. Such axis can be aligned with an axis running through openings 532, 532*a*, 532*b* discussed above. Such securement of the male luer 540*b* by lock 526 and a portion of cover 520 (for example, inner wall 529) can prevent movement of catheter device 540 and catheter 542 if tubing 541 is pulled, which can advantageously prevent dislodgement of catheter 542 and/or catheter device 540 and also injury resulting from movement of the catheter 542 with respect to a patient's vein.

When a catheter device 540 is secured by catheter housing 500, opposite ends of a male luer connector 540*b* (of catheter device 540) can be positioned between (and/or can be in contact with) lock 526 and another portion of cover 520 (such as a wall of cover 520). For example, when a catheter device 540 is secured by catheter housing 500, opposite ends of a male luer connector 540*b* can be positioned between (and/or can be in contact with) lock 526 and an inner wall 529 or outer wall 528 of cover 520. Additionally, when a catheter device 540 is secured by catheter housing 500, opposite ends of a male luer connector 540*b* can be positioned between (and/or can be in contact with) lock 526 and a wall of cover 520 (such as inner wall 529 or outer wall 528) and an opening in such wall of cover 520 (for example, openings 532, 532*a*, 532*b*). When male luer connector 540*b* is secured in such manner by catheter housing 540 (or portions thereof), the male luer connector 540*b* can be prevented from moving in a direction parallel along an axis running along a length of the connector 540*b* between such opposite ends (see FIG. 11J).

Lock 526 can comprise one or more tapered portions 526*b* proximate the recess 526*a*. As shown in FIG. 11I, lock 526 can include a first end connected to a portion of the cover 520 (such as an interior surface of the cover 520) and a second end opposite the first end that is cantilevered or free. The free end of the lock 526 can comprise recess 526*a* and a tapered portion 526*b* on one or both sides of recess 526*a*. Tapered portions 526*b* can help alignment of the catheter device 540 (or a portion thereof, such as cylindrical portions 540*a*) within recess 526*a* when retained and/or secured by lock 526. Tapered portions 526*b* can slope toward the recess 526*a* (for example, downwards towards the recess 526*a*). For example, after a catheter 542 is inserted into the vein and the catheter device 540 is resting on a portion of hub 560 (for example inner membrane 562*b*), cover 520 can be placed overtop and/or secured to hub 560 and a cylindrical portion 540*a* of catheter device 540 can be guided into recess 526*a* by the tapering portions 526*b*.

Lock 526 can extend from a surface of the cover 520 (such as the interior surface shown in FIG. 11G) from a first, connected end, to a second, free end, and can have a length between the first and second ends. The length can extend parallel to axis 2300 in FIGS. 11I and 11D. The lock 526 can have a cross section having a width or thickness (in a direction parallel to axis 2700 in FIG. 11I) and a height (in a direction parallel to axis 2500 in FIGS. 11F and 11I). The width of lock 526 can be smaller than the height. For example, the lock 526 can have a rectangular cross section where the width is smaller than the height. Lock 526 can have a rounded cross section. For example, lock 526 can have a rectangular cross section (or another shape) having rounded corners. Lock 526 can have cross section that is square among other shapes. Lock 526 can be spaced inward from a perimeter of cover 520. For example, lock 526 can be spaced from a wall of cover 520, such as outer wall 528 and/or inner wall 529. The width and/or height of the cross section of lock 526 can be spaced from a perimeter of cover 520 (for example, from an inner wall 529 of cover 520). Lock 526 can be spaced inward from inner wall 529 by a gap on one or both sides of lock 526. For example, as illustrated in FIG. 11I, lock 526 can have side edges and one or both of the side edges can be spaced from the inner wall 529 by a gap G1. With reference to FIGS. 11D, 11F, and 11I, axis 2300 can correspond with a height of cover 520, axis 2500 can correspond with a width of cover 520, and axis 2700 can correspond with a length of cover 520. For example, a height of cover 520 can extend along axis 2300, a width of cover 520 can extend along axis 2500, and a length of cover 520 can extend along axis 2700.

As also shown in at least FIGS. 11F-11I, cover 520 can include a bridge 527 that can help secure, guide, and/or align the catheter device 540 (or a portion thereof), catheter 542, and/or connectors, extensions, adapters, and/or other devices or components connected thereto. The bridge 527 can extend outward and/or downward from a top interior portion of the cover 520. The bridge 527 can extend from the top interior of the cover 520 a distance equal or substantially equal to a distance that the lock 526 extends from the top interior of the cover 520. Alternatively, the bridge 527 can extend a distance from the top interior of the cover 520 a distance unequal to a distance that the lock 526 extends from the top interior of the cover 520. For example, the bridge 527 can extend from an interior surface of the cover 520 a distance further than the lock 526. The bridge 527 can have a length that is greater than, equal, or smaller than the lock 526.

The bridge 527 can be positioned proximate to the lock 526 along an interior portion of the cover 520. For example, the bridge 527 can be positioned proximate to the lock 526 and can be closer to catheter insertion site than the lock 526. As another example, the lock 526 can be positioned closer to opening of the cover 520 (such as opening 532b in inner wall 529 and/or opening 532a in outer wall 528) than bridge 527.

Bridge 527 can comprise one or more tapered portions 527b proximate the recess 527a. For example, as shown in FIG. 11G-11I, bridge 527 can include a first end connected to a portion of the cover 520 (such as an interior surface of the cover 520) and a second end opposite the first end that is cantilevered or free. The free end of the bridge 527 can comprise recess 527a and a tapered portion 527b on one or both sides of recess 527a. Tapered portions 527b can help alignment of the catheter device 540 (or a portion thereof) when it is placed within and/or secured to the recess 527a of lock 527. Tapered portions 527b can slope toward the recess 527a (for example, downward toward recess 527a). Such tapering or sloping can help placement and/or alignment of a catheter device 540 or portion thereof. For example, when the cover 520 is placed over the top of a catheter device 540 and/or the hub 460, the sloped surfaces 527b can help move, force, and/or position a portion (for example, a cylindrical portion 540a) of the catheter device 540 into the recess 527a so as to obtain the proper placement and/or inclination angle of the catheter 542 coupled to the catheter device 540.

Recess 527a can be sized and/or shaped to accommodate catheter device 540 (or a portion thereof). For example, the recess 527a can accommodate a cylindrical portion 540a of catheter device 540. The portion of the catheter device 540 that the bridge 527 retains and/or secures can be different and/or spaced from the portion of the catheter device 540 that the lock 526 retains and/or secures. The portion of the catheter device 540 that the bridge 527 retains and/or secures can have a smaller cross-sectional area than the portion of the catheter device 540 that the lock 526 retains and/or secures (see FIG. 11J, for example). The recess 527a of the bridge 527 can be smooth, or alternatively, can be rough. The recess 527a can be rounded. The recess 527a can comprise a half-moon, half-circle shape, half-square, half-rectangle, or other shapes, for example. The recess 527a of the bridge 527 can be sized and/or shaped to receive and/or surround a portion of a perimeter of the catheter device 540 or a portion thereof. For example, the recess 527a can be sized and/or shaped to surround ¼, ½, or ¾ of a perimeter of a cylindrical portion 540a of catheter device 540, or any fractions or percentages therebetween, or any ranges bounded by any combination of these percentages, although other values can be used in some implementations.

As discussed above, the bridge 527 can have a different height or length than the lock 526. For example, the bridge 527 can extend outward from an interior surface of cover 520 a greater distance than the lock 527. This can allow a tip or front of the catheter device 540 (and/or catheter 542) to be inclined at a natural inclination angle when the catheter device 540 is secured to the lock 526. This can also enable the bridge 527 to push a portion of the catheter device 540 down to properly position the catheter device 540 and connected catheter 542 when the cover 520 is placed over the catheter device 540 and/or over the hub 460. The bridge 527 can also prevent the lifting, flattening, or inclining of the catheter 542 and/or catheter device 540 when the catheter housing 500 secures the catheter device 540. The bridge 527 can also prevent the catheter device 540 and/or catheter 542 from straightening out, moving away from the catheter insertion site, and/or rotating about the lock 526 when the catheter housing 500 secures the catheter device 540.

The catheter housing 500 can secure a catheter device 540 connected to a catheter 542 without contacting the catheter 542. For example, as shown in FIGS. 11J-11M, the lock 526, bridge 527, and/or other components of housing 500 (such as inner wall 529) can secure to one or more portions of the catheter device 540 without touching or contacting the catheter 542. This can advantageously limit prevent or limit movement of the catheter 542 when inserted within a patient's vein. This in turn can prevent or limited problems associated with such movement discussed above (for example, damage to the patient's vein and/or to the catheter insertion site and areas nearby). Additionally, as also shown by these figures, when the catheter device 540 (or one or more portions thereof) is secured by the lock 526, bridge 527, and/or other components of housing 500 (such as inner wall 529), the catheter 542 can be straight (for example, not bent, not kinked, not twisted, not wrapped, and/or not contorted). This can advantageously ensure that the catheter 542 is able to deliver fluids appropriate to the patient.

As discussed herein, the lock 526 and bridge 527 can independently and/or together secure a catheter device 540 (or a portion thereof) and prevent movement of the catheter device 540 in any direction. As discussed above, catheter device 540 can include one or more cylindrical portions 540a. For example, catheter device 540 can have a first, smaller diameter cylindrical portion 540a and a second, larger diameter cylindrical portion 540b. In such configuration, the smaller diameter cylindrical portion 540a can fit at least partially within the recess 527a of the bridge 527 and the larger diameter cylindrical portion 540b can fit at least partially within the recess 526a of lock 526. Further, as discussed above, a portion of the catheter device 540 (such as male luer 540b) can be secured between lock 526 and another portion of cover 520 (such as inner wall 529 of cover 520). With the catheter device 540 secured in such manner, movement of the catheter device 540 can be prevented in any direction, especially when a bottom or skin-facing surface of the catheter device 540 is contacted by the patient's skin or a portion of the hub 560 (such as the inner membrane portion 562b as discussed below). Such prevention of movement of the catheter device 540 in turn prevents movement of the catheter 542, which prevents or reduces catheter failures, injury, and/or damage to the patient and/or catheter insertion site as discussed above.

Bridge 527 can extend from a surface of the cover 520 (such as the interior surface shown in FIG. 11G) from a first, connected end, to a second, free end, and can have a length between the first and second ends. The length can extend parallel to axis 2300 in FIGS. 11I and 11D. The bridge 527 can have a cross section having a width or thickness (in a direction parallel to axis 2700 in FIG. 11F) and a height (in a direction parallel to axis 2500 in FIGS. 11F and 11I). The width and/or height of the cross section of bridge 527 can be spaced from a perimeter of cover 520 (for example, from an inner wall 529 of cover 520). The width of bridge 527 can be smaller than the height. For example, the bridge 527 can have a rectangular cross section where the width is smaller than the height. Alternatively, bridge 527 can have cross section that is square among other shapes. The bridge 527 can have a rounded cross section. For example, the bridge can have a rectangular shaped cross section and have rounded corners. Bridge 527 can be spaced inward from a perimeter of cover 520. For example, bridge 527 can be spaced from a wall of cover 520, such as outer wall 528 and/or inner wall 529. Bridge 527 can be spaced inward from inner wall 529 by a gap on one or both sides of bridge 527. For example, as illustrated in FIG. 11I, bridge 527 can have side edges and one or both of the side edges can be spaced from the inner wall 529 by a gap G2. With reference to FIGS. 11D, 11F, and 11I, axis 2300 can correspond with a height of cover 520, axis 2500 can correspond with a width of cover 520, and axis 2700 can correspond with a length of cover 520. For example, a height of cover 520 can extend along axis 2300, a width of cover 520 can extend along axis 2500, and a length of cover 520 can extend along axis 2700.

A side surface of the bridge 527 can have a recess that is sized and/or shaped to receive one or more lights. For example, a side surface of the bridge 527 that faces towards the catheter insertion site can have a recess that is sized to fit an LED or UV light. Such a UV light can advantageously illuminate the catheter insertion site and help a caregiver inspect the site, and/or can help disinfect the catheter, catheter device, catheter insertion site, and/or components of the interior of the catheter housing 500 (such as the cover 520 and/or hub 560). The one or more lights can be a UV Surface Mount LED (SMD LED) that can provide active sterilization and disinfection. This can in turn drastically reduce contamination, infections, and/or diseases that can occur with traditional catheter securement devices and methods. The one or more lights and/or one or more UV SMD LEDs can be electronically coupled to a sensor, wherein the sensor is configured to sense when cover 520 is secured to the hub 560 and send a signal to the one or more lights. The one or more lights can be configured to automatically activate when receiving the signal from the sensor. The one or more lights can contain an independent battery/power source, or can be coupled to a power source away from the bridge 527.

Figure 11M:
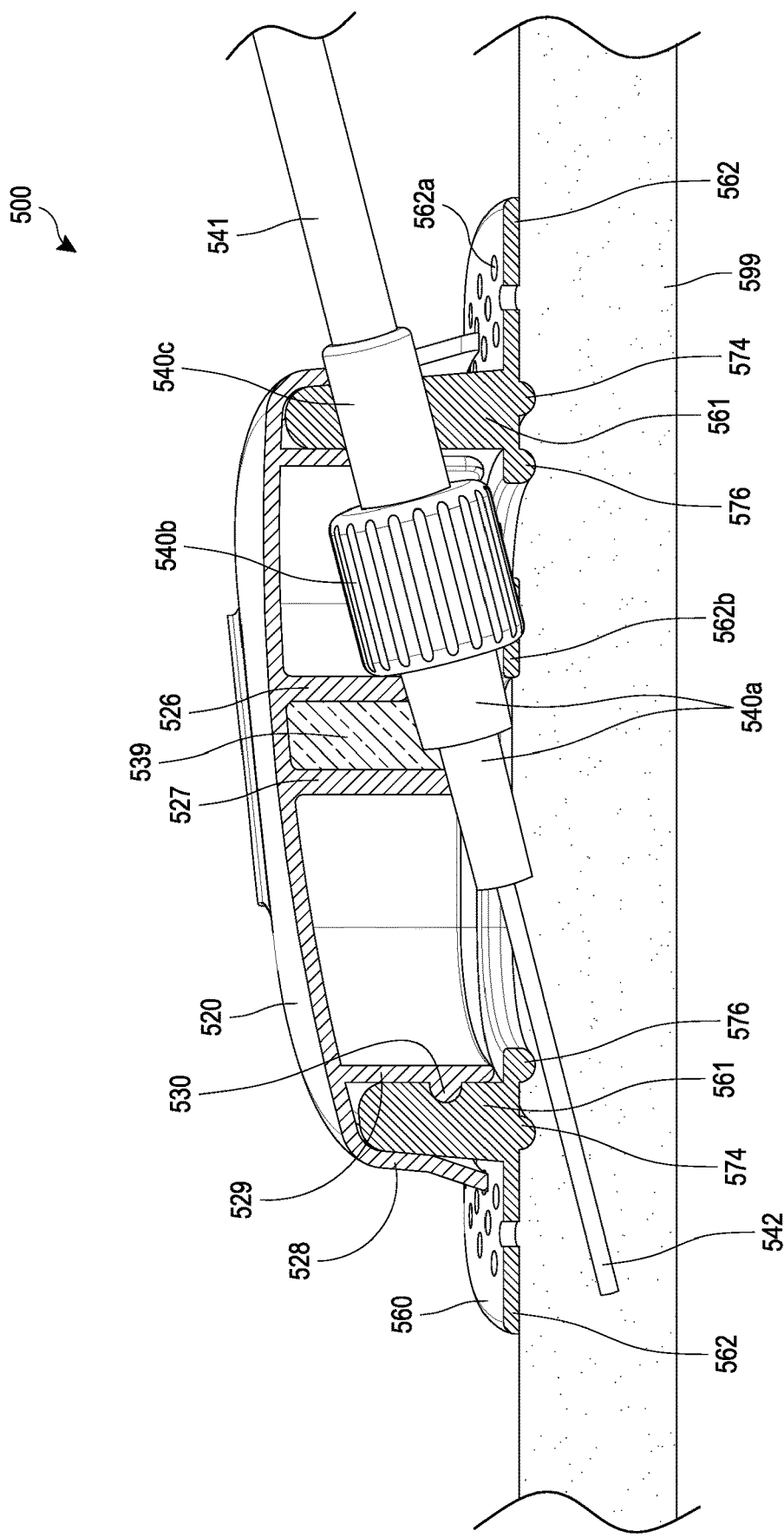
FIG. 11M illustrates a cross-sectional view of the catheter housing of FIG. 10A when placed upon and/or secured to a patient at a catheter insertion site.

Bridge 527 and lock 526 can be integral with one another or alternatively, non-integral with one another. As shown in at least FIGS. 11F-11I, cover 520 can include a stem wall 539. Stem wall 539 can extend outward and/or downward from a surface of cover 520, for example, from an interior surface of cover 520. Stem wall 539 can have a first end connected to the surface of the cover 520 and a second end opposite the first end. Stem wall 539 can have a length that extends between the first and second ends of the stem wall 539 (and along axis 2300). Stem wall 539 can have a height extending along axis 2500 and a width extending along axis 2700 (see FIG. 11F). Stem wall 539 can connect to portions of one or both of the bridge 527 and/or lock 526. For example, as shown in FIG. 11F, stem wall 539 can connect to a side surface of lock 526 and/or connect to a side surface of bridge 527, and the side surfaces of the bridge 527 and lock 526 can face towards each other. Stem wall 539 can connect to an interior or middle portion of the side surfaces of the bridge 527 and/or lock 526. For example, stem wall 539 can connect to the lock 527 near and/or below the recess 526a of lock 526 and/or near and/or below the recess 527a of bridge 527. Stem wall 539 can have a height (or thickness), extending along a direction parallel to axis 2500 in FIG. 11F, that is smaller than a height of a cross section of one or both of the bridge 527 and/or lock 526. For example, as shown in FIG. 11F, stem wall 539 can have a height (or thickness) that is less than a height of a cross section of both of bridge 527 and lock 526 such that the stem wall 539 together with the bridge 527 and lock 526 form an H-shape when the cover 520 is viewed from a bottom (for example, interior) side (see FIG. 11F). Stem wall 539 can connect and/or extend between a portion of lock 526 and a portion of bridge 527 and can have a variable length of extension from an interior surface of cover 520. For example, as shown in FIG. 11M, stem wall 530 can have a first length at a point where stem wall 539 connects to bridge 527 and a second length where stem wall 539 connects to lock 526, and the first and second lengths of stem wall 539 can be different. For example, the first length can be greater than the second length. Such configuration can be present where, as discussed above, the bridge 527 has a length that is greater than the length of the lock 526. The stem wall 539 can have a height that slopes from the first length to the second length or vice versa. Alternatively, the first and second lengths of the stem wall 539 can be equal.

Stem wall 539 can be integral with bridge 527 and/or lock 527. Alternatively, stem wall 539 can be non-integral with bridge 527 and/or lock 526. Stem wall 539 can provide structural support to one or both of the bridge 527 and lock 526.

The bridge 527 and/or lock 526 can secure catheter device 540 (or a portion thereof) in a natural and/or optional orientation relative to the patient's skin and/or the catheter insertion site. For example, as shown in the cross section of the catheter housing 500 in FIG. 11M, catheter housing 500 can secure the catheter device 540 at an angle relative to a patient's skin 599 and/or a vein therein. As described above, such securement can be by a lock 526 and/or a bridge 527 which extend outward (for example, downward in the view of FIG. 11M) from an interior surface of cover 520 and surround portions of the catheter device 540. As discussed above, cover 520 can secure catheter device 540 by positioning male luer 540b between lock 526 and another portion of cover 520 (for example, inner wall 529. Additionally and/or alternatively, catheter device 540 can be at least partially secured by openings 532, 532a, 532b in cover 520 and/or opening 565 in wall 561 of hub 560 (see FIG. 12A). As discussed below, opening 565 in wall 561 of hub 560 can be sized and/or shaped to accommodate, surround, retain, and/or secure a portion of catheter device 540, such as stem portion 540c. Any or all of the securement described above and as that illustrated in FIG. 11M can advantageously enable a catheter device 540 to be secured at a final resting angle or inclination angle that approximates the angle at which a catheter 542 is inserted into a vein of a patient. As discussed previously this is beneficial because it reduces the chance of injury and/or other complications that can result when a catheter 542 moves or is secured at an angle that damages the vein wall or nearby area. Such inclination angle can be between 1 and 45 degrees. The inclination angle can also be between 1 and 10 degrees, between 10 and 20 degrees, or between 20 and 30 degrees. The inclination angle can be more than 45 degrees as well, depending on the implementation of the stabilization device. The inclination angle can also be at a very small angle, such as between 0 and 1 degrees. Current techniques for securing a catheter to a patient can result in dislodgment, inappropriate angle of the catheter, kinking of the catheter, or twisting or other movement while the catheter is inserted into a patient. However, the lock 526 and/or the bridge 527 described herein, alone or in combination with other securement features described above can secure the catheter in a position that provides for a normal, or optimal, catheter angle. This can help to limit or prevent irritation and/or catheter erosion caused by contacting of a catheter's cannula tip with vein lumen sides. Thus, unlike conventional catheter stabilization methods where securing the catheter typically results in disrupting the natural angle of the catheter, awkward angling of the catheter against the wall of the vein, and/or in which pressure is applied on the a portion of the catheter device 540 in order to secure it to a patient, the securement angle of the catheter device 540 and/or catheter 542 with or by the lock 426, bridge 427, and/or other securement features described above can preserve the integrity of the connection of the catheter 542 within the vein. As shown in FIG. 11M, when catheter device 540 is secured by catheter housing 500, catheter device 540 can be spaced from an interior surface of cover 520. For example, when catheter device 540 is secured by lock 526, bridge 527, a wall of cover 520 (such as inner wall 529), openings 532, 532*a*, 532*b*, and/or opening 565 of wall 561 of hub 560, male luer connector 540*b* can be spaced from an interior surface of a top of cover 520 ("top" in view of the orientation shown in FIG. 11M). FIG. 11M also illustrates various other optional components of catheter housing 500 that are discussed elsewhere herein.

As discussed above, the shape and structure of the catheter housing 500 can minimize the overall height and/or footprint of the housing 500. FIG. 11D illustrates a side view of the cover 520 of the catheter housing 500. As shown, a height of the cover 520 at a front portion 589 can be greater than a height of the cover 520 at a back portion 587. The greater height at the front portion 589 allows the cover 520 to accommodate portions of the catheter device 540 when secured to the cover 520. The height of the cover 520 can taper from a larger height at the front portion 589 to a smaller height at the back portion 587 so as to minimize the overall height of the catheter housing 500.

Figure 12A:
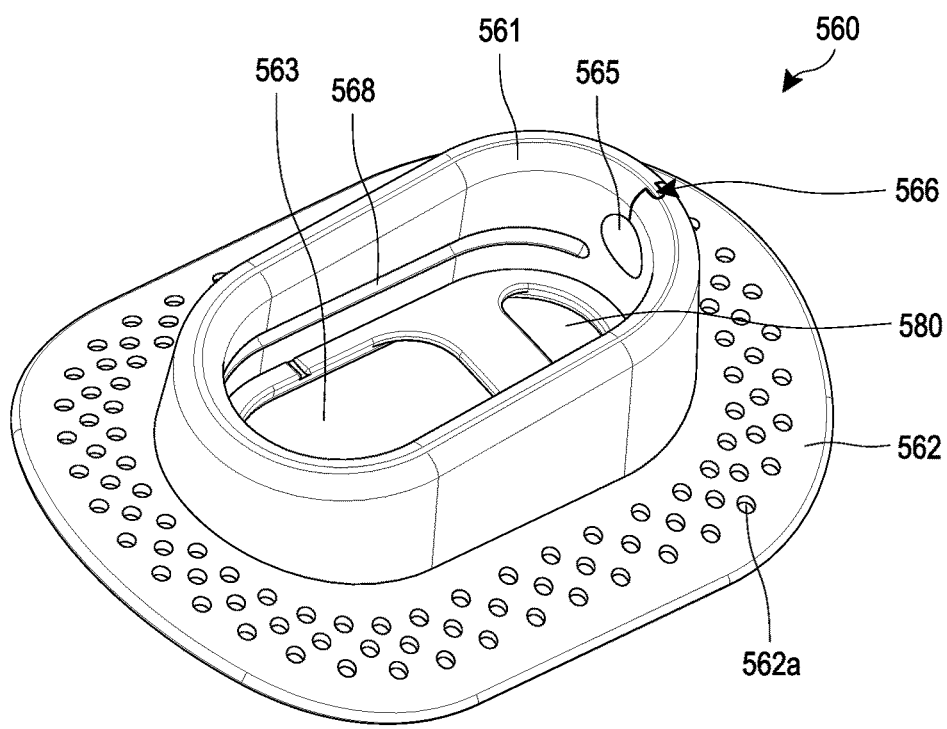
FIG. 12A illustrates a perspective view of a hub of the catheter housing of FIG. 10A in accordance with aspects of this disclosure.

FIGS. 12A-12F illustrate different views of hub 560. As shown in FIG. 12A, hub 560 can include a wall 561 and a membrane 562. A caregiver can attach, adhere, secure, and/or write patient information on a portion of hub 560. Such patient information can include the insertion date and/or time, the patient's identification, and other information.

Hub 560, and/or components thereof, such as the wall 561 and/or the membrane 562, can comprise plastic, and/or flexible materials such as rubber and/or silicone, among other materials. Hub 560 can comprise a transparent material. Alternatively, hub 560 can be made of a nontransparent material. Additionally, hub 560 can comprise both transparent and nontransparent material. For example, portions of hub 560 can be made of transparent material where it is advantageous to be able to see through a portion of hub 560 in order to observe other components of the catheter housing 500. Hub 560 can be made of substantially shockproof and/or durable material. This is advantageous because the catheter housing 500 and/or hub 560 can be subjected to impact during implementation of the housing 500 onto, for example, patients in a hospital. Hub 560 can comprise substantially waterproof material. This is advantageous because the catheter housing 500 and hub 560 can be subjected to water or other liquids when the housing 500 is in use.

The wall 561 can include a top surface. The top surface can be concave or convex. Additionally, the top surface can be substantially flat. The top surface can be smooth and/or rounded.

Figure 12B:
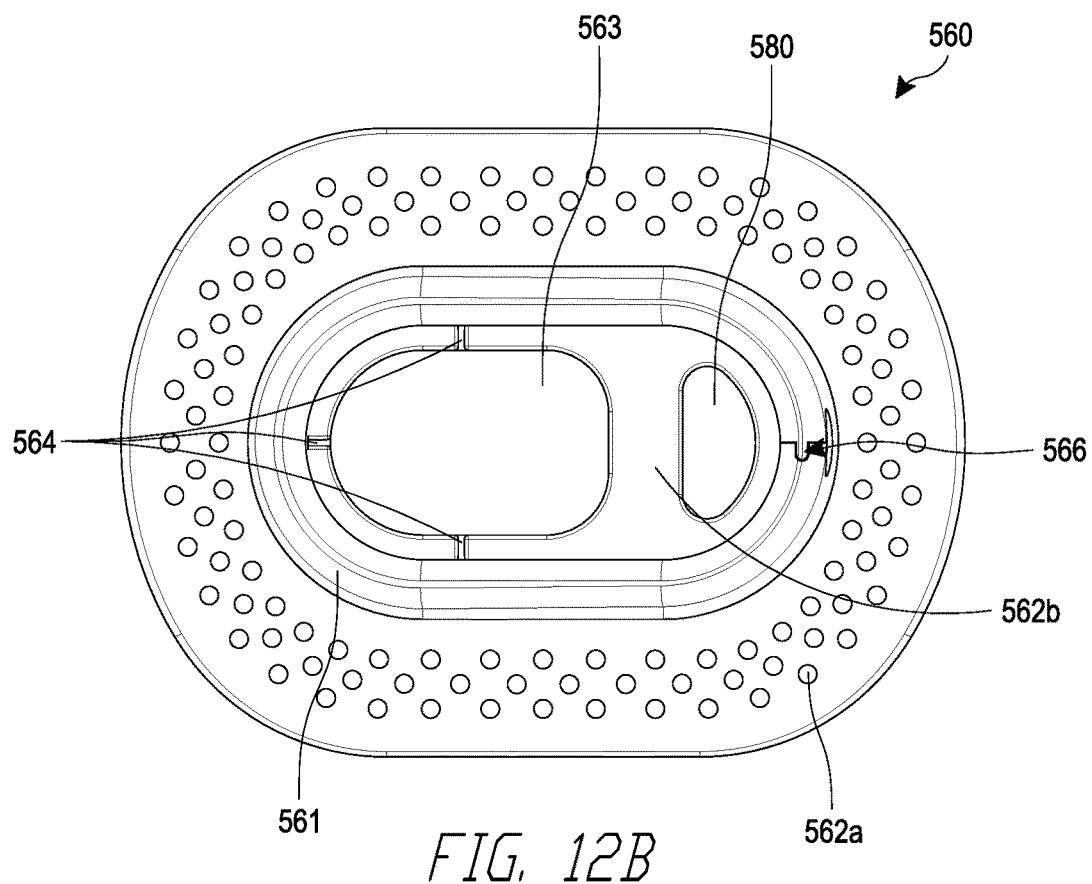
FIG. 12B illustrates a top view of the hub of FIG. 12A.

As illustrated in FIGS. 12A and 12B, hub 560 can contain an opening 563 in the membrane 562. This opening 563 can be positioned over a site where a catheter needle and/or catheter is to be (or has been) inserted into a patient. The opening 563 can be sized and shaped to fit within the wall 561 (see FIG. 12B). For example, the opening 563 can be rounded or non-rounded, and can be generally egg-shaped, trapezoidal, rectangular, square, oval, and/or circular in shape, among other shapes. Additionally, the opening 563 can be a combination of these described shapes. Hub 560 can additionally include an opening 580 separated from opening 563 by an inner portion 562*b* of membrane 560. Opening 580 can be can be sized and shaped to fit within the wall 561 (see FIG. 12B). Opening 580 can be rounded or non-rounded, and can be generally egg-shaped, trapezoidal, rectangular, square, oval, and/or circular in shape, among other shapes. Opening 580 can advantageously enhance breathability of skin of the patient near the catheter insertion site.

As also illustrated in FIG. 12B, membrane 562 can extend around the opening(s) 563 and/or 580 in a region defined within the wall 561 and surrounding an insertion site. Such configurations can confine the insertion site to within the boundaries of the wall 561 and can thus advantageously reduce and/or elimination ingress of pathogens to the insertion site. The membrane 562 can include a thin silicone membrane. The membrane 562 can surround the needle and/or the insertion site. This can advantageously help to ensure that hub 560 is secured and/or sealed to a patient's skin. For example, the membrane 562 can surround at least a portion of the insertion site and/or needle to provide a hermetic sealing isolation state between hub 560 and the patient's skin. Accordingly, the membrane 562 can help to inhibit or prevent air and/or gases from an outside environment from entering the insertion site. Such configurations can also inhibit or prevent lower edges or portions of a catheter device or portion thereof from contacting skin underneath. This can help to inhibit or prevent skin abrasions, ulcers, and/or irritation caused by contact between the catheter device or portion thereof and the patient's skin.

Hub 560 can include one or more markers or indicators 564 located on a portion of the wall 561 and/or the membrane 562, near the opening 563. For example, hub 560 can include one, two, three, four, five, six, or seven or more markers or indicators 564. For example, hub 560 can have three markers 564, two of which are disposed proximate to sides of the opening 563 and one of which is disposed proximate to a front of the opening 563 (see FIG. 12B). The one or more markers 564 can help a caregiver position and align hub 560 over an insertion site where the catheter and/or needle has been already inserted. Additionally, the one or more markers 564 can help provide an indication as to where a needle should be inserted into a patient. This can greatly aid caregivers in determining where the optimal insertion location should be so as to correspond with the position of a catheter device 540 when it is engaged and secured by the lock 526 of the cover 520. The one or more markers 564 can be located on a portion of the wall 561 and/or the membrane 562 proximate to the opening 563 (see FIG. 12B). For example, the one or more markers 564 can be located on a portion of the membrane 562 near a side of the wall 561, such as an interior side of wall 561 that faces at least partially toward the opening 563 (see FIG. 12B). The one or more markers 564 can comprise a line, dot, or other indicator, for example.

As illustrated in FIG. 12A-12B, the membrane 562 of hub 560 can include an inner membrane portion 562b. The inner membrane portion 562b can be proximate and/or between the openings 563, 580 and can be contained within the boundaries of the wall 561. The inner membrane portion 562b can provide a platform for the catheter device 540 or portion thereof to rest or lay on when the catheter and/or needle is inserted into the patient. For example, the catheter or portion thereof can be inserted into the patient and the catheter device 540 can rest on the inner membrane portion 562b, and the lock 526 and/or bridge 527 of cover 520 and can be placed over a catheter device 540 that rests on the inner membrane portion 562b. In such configuration, the lock 526 and/or bridge 527 can secure the catheter device 540 to prevent movement of the catheter device 540 and/or connected catheter 542. The inner membrane portion 562b can prevent a catheter device 540 (or a portion thereof) coupled to the catheter 542 from touching the patient's skin at or near the catheter insertion site and/or openings 563, 580, which advantageously can prevent discomfort and/or irritation. Thus, when the catheter device 540 is secured by the catheter housing 500 (for example, via lock 526 and/or bridge 527), a portion of the catheter device 540 can rest atop the inner membrane portion 562b (see FIG. 11M).

As shown in FIGS. 12A-12B, the wall 561 can extend outward, upwards, and/or around a portion of or all of the catheter insertion site and/or the openings 563 and/or 580 of membrane 562. The wall 561 can comprise a variety of shapes. For example, the wall 561 can be egg-shaped, trapezoidal, rectangular, square, oval, and/or circular in shape, among other shapes. The wall 561 or portions thereof can be rounded or alternatively non-rounded. For example, the wall 561 can have a top surface that is rounded. The wall 561 or portions thereof can have a smooth surface, or alternatively, a rough surface. The wall 561 can be a stadium wall. For example, the wall 561 can extend outwards and around a portion of the catheter insertion site like a stadium. The wall 561 can extend outwards from the membrane 562 at an angle. For example, the wall 561 can extend generally perpendicular from the membrane or can extend outwards at a different angle with respect to a surface of the membrane 562.

The wall 561 can include one or more grooves. For example, wall 561 can include one, two, three, four, five, six, or seven or more peripheral grooves 568. As discussed previously, the one or more grooves 568 can be sized and/or shaped to accommodate one or more protrusions 530 on the cover 520. The one or more grooves 568 of the wall 561 can be continuous around a perimeter of the wall 561 and/or can extend along a surface of the wall 561 (such as an interior surface). Alternatively, the one or more peripheral grooves 568 can be non-continuous. For example, as shown in FIG. 12A, the one or more peripheral grooves 568 can extend along a portion of a perimeter of an interior surface of wall 561, but not extend continuously around the entire perimeter. For example, the one or more peripheral grooves 568 can extend along a perimeter of the interior surface of wall 561 proximate to the opening 565 and/or joint 566, but terminate at a location before reaching the opening 565 and/or joint 566. The wall 561 can include more than one peripheral groove 568 that extends along a perimeter of the wall 561, which can secure to one or more protrusions 530 on the cover 520. As discussed previously, the one or more protrusions 530 can secure to the one or more peripheral grooves 568 by a snap-fit, press fit, and/or other configuration for securely connecting the cover 520 to hub 560.

As illustrated in FIG. 12A, the wall 561 can include one or more joints 566 that can be pulled apart or pushed together, to allow for a needle, fluid tube, or catheter device (or portion thereof) to more easily pass through the opening 565. For example, the wall 561 can include one, two, three, four, five, six, or seven or more joints 566. The wall 561 can include one joint 566. The joint 566 can be proximate to the opening 565. Joint 566 can extend along an entire height of a portion of wall 561 or along less than an entire height of a portion of wall 561. Joint 566 can be positioned adjacent opening 565 proximate to a top surface of wall 561. Joint 561 can be positioned a distance from membrane 562 that is further than a distance that the opening 565 is positioned from membrane 562. Joint 566 can provide a mechanism whereby a needle, fluid tube, or catheter device or portion thereof can be accommodated by the wall 561 so as to be able to pass into and through the wall 561 with relative ease and in a short timeframe. Joint 566 can allow a portion of catheter device 540 (such as stem portion 540c) to be inserted into or through opening 566. The joint 566 can be configured to allow a tube or a portion of catheter device 540 (such as stem portion 540c) to be inserted into opening 565 from a direction that is parallel to an axis running through the opening 565 and/or from a direction that is perpendicular to such axis (for example, inserted from on top the opening 565). The joint 566 can be configured to hermetically close the wall 561 around the opening 565, and can form a seal in the wall 561 and hub 560. The joint 566 can permit the wall 561 to be spaced apart, pulled apart, pushed apart, and/or otherwise partially separated. The joint 566 can separate a portion of the wall 561. Alternatively, the joint 566 can extend down an entire side portion of the wall 561 so that the joint 566 separates an entire cross-section of the side portion of the wall 561. The joint 566 can separate at least in part by flexing the wall 561.

The membrane 562 of hub 560 can be sized and shaped to accommodate a patient's arm, leg, appendage, or other portion of a patient's body. The membrane 562 can have rounded edges or alternatively, non-rounded edges. The membrane 562 can be rectangular in shape. Alternatively, the membrane 562 can be egg-shaped, trapezoidal, square, oval, and/or circular in shape, among other shapes. Additionally, the membrane 562 can comprise a combination of these described shapes.

The membrane 562 can be integrally formed with the wall 561. For example, the membrane 562 can be molded with the wall 561. Alternatively, the membrane 562 can be non-integral with the wall 561. The wall 561 can be pressed onto, adhered to, and/or otherwise attached to a portion of the membrane 562. The membrane 562 can include a recessed portion to accommodate a portion of the wall 561. For example, the membrane 562 can contain a recessed portion that allows a portion of the wall 561 to sit within or be accommodated by the recessed portion of the membrane 562. Additionally, the membrane 562 can contain a recessed portion to accommodate other portions of the catheter housing 500, such as the cover 520 or a portion of the catheter device 40. The membrane 562 can include one or more different materials. Additionally, the membrane 562 can comprise one material. The wall 561 and the membrane 562 can include the same material. Alternatively, the wall 561 and the membrane 562 can include different materials. The membrane 562 can comprise silicone, plastic, and/or rubber, among other materials. The membrane 562 can comprise, at least in part, biocompatible materials.

The membrane 562 can extend outwardly from a base of the wall 561 (see FIG. 12B). For example, the membrane 562 can be coupled with an outer edge of the base of the wall 561. A bottom surface of the base of the wall 561 can be coupled with the membrane 562. A portion of the membrane 562 can extend inwardly from the wall 561 (such as inner portion 526b). The membrane 562 can surround at least a portion of a perimeter of the wall 561. Thus, the membrane 562 can surround all or a portion of a perimeter of an inner edge and/or an outer edge of the base of the wall 561.

Figure 12C:
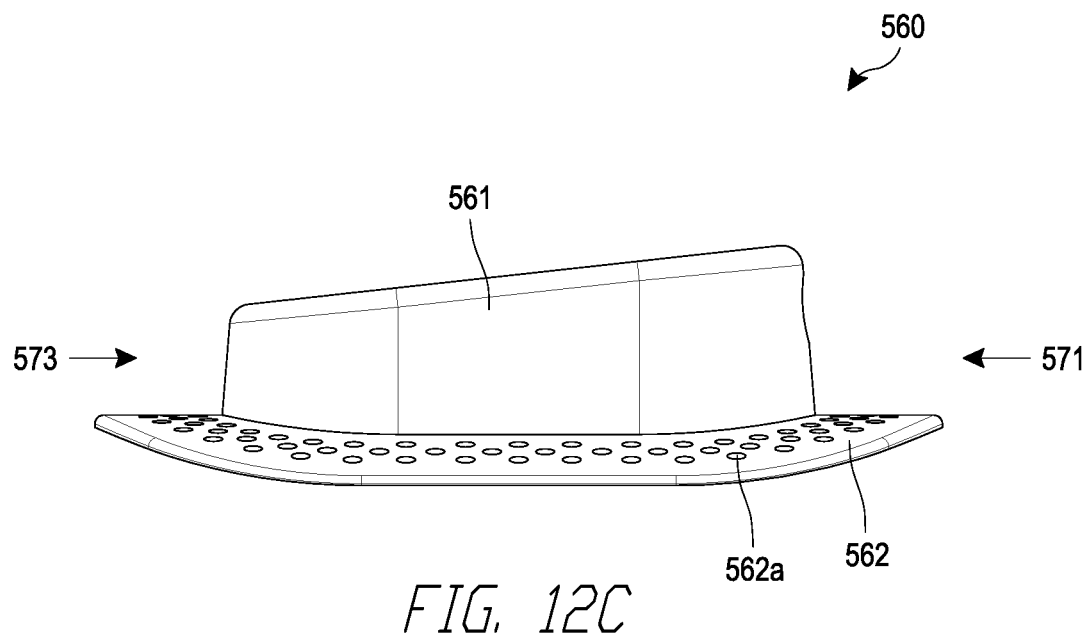
FIG. 12C illustrates a side view of the hub of FIG. 12A.
Figure 12D:
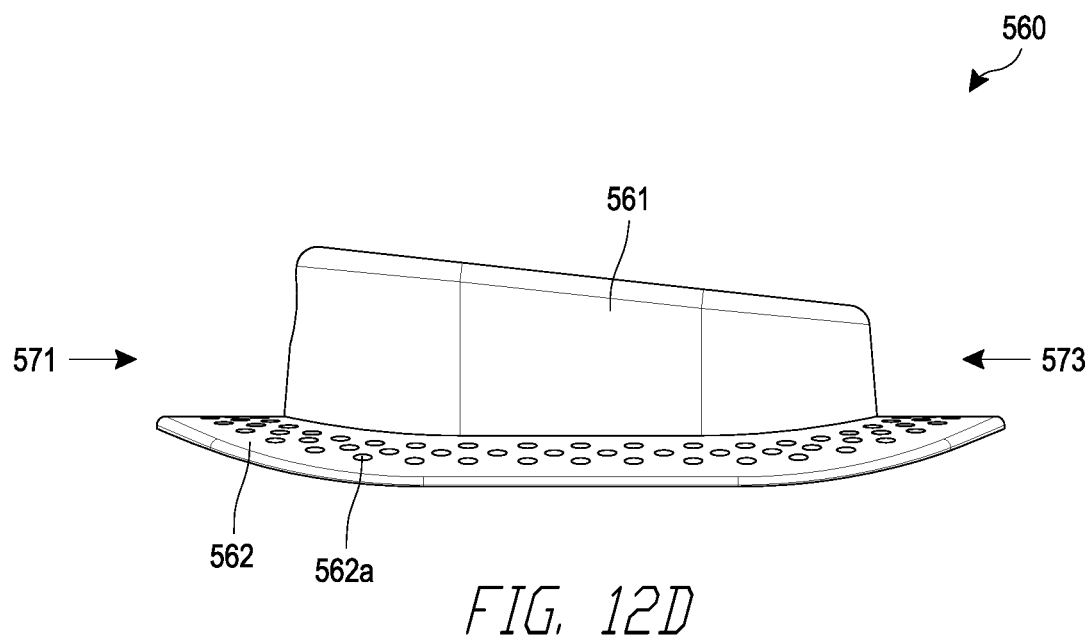
FIG. 12D illustrates another side view of the hub of FIG. 12A.

As discussed above, the shape and structure of the catheter housing device 500 can minimize the overall height and/or footprint of the housing 500. FIGS. 12C-12D illustrate side views of hub 560 of the catheter housing 500. As shown, a height of hub 560 at a front portion 571 can be greater than a height of hub 560 at a back portion 573. The greater height at the front portion 571 allow hub 560 to accommodate portions of the catheter device 540 when secured to the cover 520. The height of hub 560 can taper from a larger height at the front portion 571 to a smaller height at the back portion 573 so as to minimize the overall height of hub 560 and/or the catheter housing 500 when the cover 520 is secured to hub 560. The cover 520 can be secured to hub 560 so that a front portion 589 of the cover 520 cooperates with and secures to a front portion 571 of hub 560 and so that a back portion 587 of the cover 520 cooperates with and secures to a back portion 573 of hub 560. Such configuration of the relative height of front and back portions 571, 573 can advantageously provide for the inclination angle of the catheter device 540 as shown in FIG. 11M when opening 565 is positioned on a taller/longer portion of wall 561.

The membrane 562 can have a bottom surface including an anti-slip material configured to secure the catheter housing 500, or a portion thereof such as hub 560, to a patient's skin. The bottom surface of the membrane 562 can comprise silicon-adhesive, sticky material, rubber compound, biocompatible high-tack anti-slip coating, adhesive, or other types of anti-slip material and/or methods that can prevent slipping or movement of hub 560 and/or catheter housing 500 when secured to a patient's skin. The bottom surface can comprise a silicone or regular adhesive, for example. The bottom surface can comprise an anti-microbial coating. The bottom surface can comprise anti-slip material in the form of layers, circuits, circles, strips, coatings, and/or rings. For example, the bottom surface can comprise a transparent adhesive layer that can be permeable, semi-permeable, thin, and/or flexible. The transparent adhesive layer can be similar to an adhesive dressing or tape and can adhere to various portions of skin of a patient.

The bottom surface of the membrane 562 can comprise an inner lip 576 and/or an outer lip 574. The inner and outer lips 576, 574 can extend from the bottom surface of the membrane 562. The bottom surface can comprise an outer portion 570 that extends around the outer lip 574 and/or an inner portion 572 that extends around the inner lip 576 and within the outer lip 574. The inner and outer portions 572, 570 can comprise anti-slip material, such as an adhesive. The outer portion 570 can comprise an adhesive and the inner portion 572 can comprise a non-adhesive surface so as to ensure that adhesive material is not proximate to the catheter insertion site and/or the opening 563 and/or opening 580. Hub 560 can comprise a release liner that covers the inner and/or outer portions 572, 570 of the bottom surface of the membrane 562 that, when pulled away, allows the inner and/or outer portions 572, 570 to adhere to a portion of the patient's skin. In some configurations, the membrane 562 includes adhesive only on outer portion 570. In some configurations, catheter housing 500 includes adhesive only on outer portion 570.

Hub 560 can comprise a release liner that extends and/or covers the entirety of the outer portion 570. Alternatively, hub 560 can comprise more than one release liners that are independent from one another. For example, hub 560 can comprise a release liner that covers a first portion of the outer portion 570 and another release liner that covers a second portion of the outer portion 570. The first portion can comprise a greater percentage of the outer portion 570 than the second portion. For example, hub 560 can comprise a first release liner that covers greater than 50% of the surface area of the outer portion 570 and a second release liner that covers less than 50% of surface area of the outer portion 570. As another example, hub 560 can comprise a first release liner that covers greater than 80% of the surface area of the outer portion 570 and a second release liner that covers less than 20% of surface area of the outer portion 570.

Where hub 560 comprises more than one release liner on the outer portion 570, the release liners can be removed sequentially to allow advantageous functionality. For example, where multiple release liners are covering the outer portion 570, one of the release liners can be removed and the catheter housing 500 (or hub 560 or membrane 562) can be adhered to a patient's skin surface and/or form a seal with the patient's skin while another release liner can be left covering a portion of the outer portion 570 thus permitting the catheter housing 500 (or hub 560 or membrane 562) contact the patient's skin surface without adhering or forming a seal. Further, where the catheter housing 500 includes one or more ports (such as one or both ports 521a, 521b), gas can be inserted into the catheter housing 500 and to the catheter insertion site and/or openings 563, 580. In some cases, when securing the catheter housing 500 to a patient (such as by removing a release liner from a portion of the outer portion 570 and adhering such portion to the patient's skin), it may be desirable to insert an amount of gas into the interior of the catheter housing 500 and/or to the catheter insertion site (for example, to provide an initial sterilization). When such gas is inserted into the catheter housing 500 through the port 521, the non-adhered region of the outer portion 570—where the release liner has not been removed—may lift off the skin surface of the patient temporarily, thus providing an exit pathway for the gas inserted through the port and/or other gases/air previously inside the interior of the catheter housing 500. After the gas is inserted through port, the other release liner(s) that were not removed can be removed and the outer portion 570 can be further adhered to the patient's skin. In some cases, remaining release liners can be left un-removed to keep the outer portion 570 un-adhered in some regions. In some cases, the outer portion 570 comprises adhesive and/or a release liner only on a portion (for example, certain percentage) thereof, thus allowing a gas exit pathway when gas is inserted into the catheter housing when a non-adhered portion of a bottom surface of the catheter housing 500 "lifts off". Additionally or alternatively, the catheter housing 500 can include a valve that allows gas to escape from an interior of the catheter housing 500. For example, where the catheter housing 500 forms a hermetic seal over a catheter insertion site, the catheter housing 500 can include a relief valve that can be activated (for example, opened) when gas is inserted into the gas port, thus allowing gas inside the catheter housing 500 to escape to the atmosphere. Such relief valve can be located on the cover 520 and/or hub 560, for example. Such relief valve can be incorporated into the gas outlet port 521*b* which is discussed further below. For example, the catheter housing 500 can include a cover 520, hub 560, and an adhesive material on a bottom surface of hub 560 which together form a hermetic seal around the catheter insertion site, and can also include a relief valve which allows gases to exit therethrough. One method of removing the catheter housing 500 from the patient is to peel off the membrane 562 form the skin of the patient. A caregiver may also apply an alcohol-based substance around the outside of the membrane 562 to loosen portions of adhesive on the outer portion 570, for example.

The inner and/or outer lips 576, 574 can help form a seal around the catheter insertion site which may be located within opening 563 of hub 560. When the inner and/or outer portions 570, 572 comprise an adhesive material and are adhered to skin of the patient, portions of the adhesive material may de-attach from the patient's skin and/or may degrade. In such situations, air and/or contaminants outside the catheter housing 500 may be in fluid communication with the catheter insertion site and/or opening 563, 580, which may be disadvantageous where it is desirable to keep the catheter insertion site sealed off from such outside environment. Inner and/or outer lips 576, 574 can extend outward from the bottom surface of the membrane 562 and can maintain contact with the patient's skin and surround the opening 563, 580 and/or catheter insertion site. Inner lip 576 can be continuous and can extend outwards from the bottom surface of the membrane 562 and surround the opening 563 around a perimeter of the opening 563 (see FIG. 12E). Outer lip 574 can be continuous and can extend outward from the bottom surface of the membrane 562 and surround the opening 563 and can be spaced from the perimeter of the opening 563 and/or the inner lip 576 (see FIG. 12E). Thus, where portions of the adhesive bottom surface of the membrane 562 de-attach from the patient's skin, the outer and/or inner lips 574, 576 can maintain a seal with the patient's skin and can advantageously seal off the catheter insertion site and/or opening 563 from an outside environment and, in turn, contaminants that may be present. The inner and/or outer lips 576, 574 can comprise silicon or another material discussed above. The inner and/or outer lips 576, 574 can be rounded, which can help the lips 576, 574 maintain contact and/or conform to skin of the patient when the catheter housing 500 is secured thereto.

At least a portion of the membrane 562 can be used for fixing various peripheral tools, such as a catheter tube, an LCD monitor of a micro-processor, and/or a metallic ampule of the soothing and sterilizing gas. Such peripheral tools can be fixed or secured to at least a portion of the membrane 562 through hook and loop structures, buckles, fungi-like attachment, and/or other attachment structures or methods.

The membrane 562 can have a bottom surface that comprises a corrugated structure. The corrugated structure can be substantially cylindrical, circular, square, or rectangular, among other shapes. The corrugated structure can also comprise a combination of these shapes. The corrugated structure can be sized, shaped, and spaced apart to accommodate ventilation or for other reasons. The corrugated structure can provide gaps to allow air to flow between the corrugated structure and contact the patient's skin. Thus, even if hub 560 and/or the catheter housing 500 is secured to a patient, the patient can still benefit from ventilation to the region/section of the bottom surface that contacts the skin of the patient. The corrugated structure can be one continuous piece, or alternatively, can comprise more than one piece. Such corrugated structures are further shown and described in jointly owned, co-pending application Ser. No. 16/204,689 and U.S. Pat. No. 10,173,035, both of which are incorporated herein in their entirety.

The membrane 562 can have a bottom surface that includes one or more suction cups. For example, the bottom surface can have one or more, two or more, three or more, four or more, five or more, six or more, seven or more, eight or more, nine or more, ten or more, or eleven or more suction cups. For example, the bottom surface can have between twenty and fifty suction cups. Alternatively, the bottom surface can have between 50 and a hundred suctions cups. The one or more suction cups can be positioned in one or more rows. The suction cups can be configured to stabilize a connection between hub 560 and the patient's skin. Hub 560 and/or the membrane 562 can be manually pressed onto the patient's skin to secure hub 560 to the patient. The suction cups can engage with the patient's skin such that hub 560 can be at least partially secured to the patient with or without requiring the fastening straps to be connected to hub 560 and/or wrapped around a portion of the patient's body. The one or more suction cups can be substantially cylindrical, circular, square, or rectangular, among other shapes. The suction cups can also comprise a combination of these shapes. The suction cups can be sized, shaped, and spaced apart to accommodate ventilation or for other reasons. The suction cups can be spaced to provide gaps to allow air to flow between the suction cups and the patient's skin. Thus, even if hub 560 and/or the catheter housing 500 is secured to a patient, the patient can still benefit from ventilation to the region/section of the bottom surface that contacts the skin of the patient. Such Suction cups are further shown and described in jointly owned, application Ser. No. 16/204,689 and U.S. Pat. No. 10,173,035, both of which are incorporated herein in their entirety.

Figure 12E:
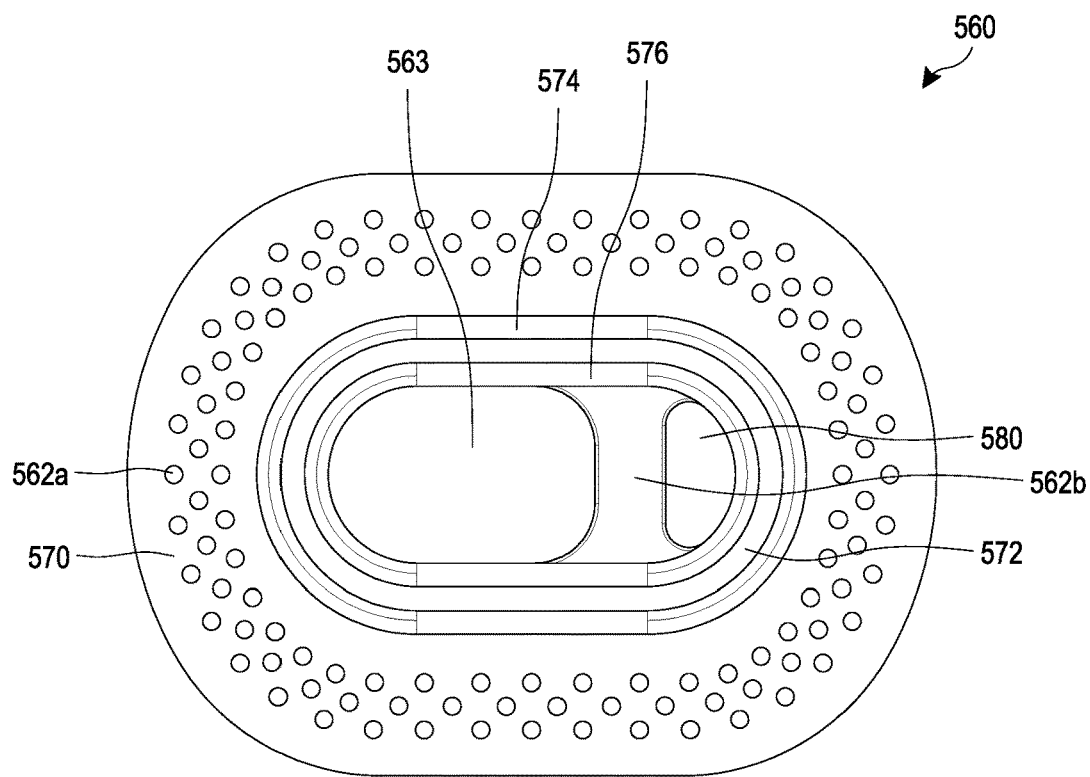
FIG. 12E illustrates a bottom view of the hub of FIG. 12A.
Figure 12F:
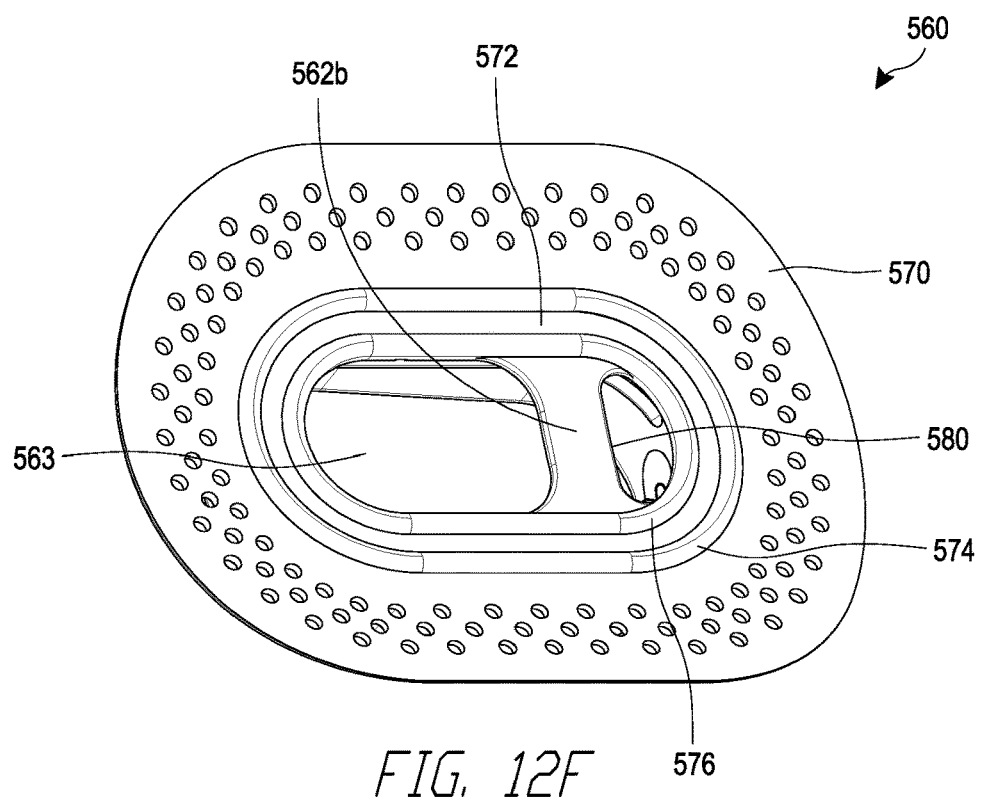
FIG. 12F illustrates a bottom perspective view of the hub of FIG. 12A.

As shown in at least FIGS. 12A and 12E-12F, membrane 562 can have one or more perforations 562*a* extending through a thickness of membrane 562. For example, the membrane 562 can have one or more, two or more, three or more, four or more, five or more, six or more, seven or more, eight or more, nine or more, ten or more, or eleven or more perforations 562*a*. For example, the membrane 562 can have between twenty and fifty perforations 562*a*. Alternatively, the membrane 562 can have between fifty and one hundred perforations 562*a*, although a different amount of perforations 562*a* can be present. The one or more perforations 562*a* can extend around a portion of a perimeter of the wall 561 on the membrane 562. For example, the one or more perforations 562*a* can extend around the entire perimeter of the wall 561 along the membrane 562. The one or more perforations 562*a* can be spaced apart from one another and/or positioned in one or more rows, such as one, two or three rows which extend around a portion of a perimeter of the membrane 562. The one or more perforations 562*a* can increase breathability and comfort of the membrane 562 when secured to a patient. Additionally, the perforations 562*a* can reduce the likelihood that air will be trapped or partially trapped between regions of the bottom surface of the membrane 562 when secured to a patient, which can arise where the bottom surface is adhesive. Utilization of such one or more perforations 562*a* can also reduce the amount of adhesive that is used and/or contacts the patient, which can increase patient comfort and breathability and reduce heat. Such perforations 562a can also allow alcohol (from, for example, an alcohol swab) to pass therethrough to aid removal of membrane 562 from patient where membrane 562 includes adhesive.

The catheter housing 500 can include one or more light sources, such as one, two, three, four, five, six, seven, eight, or nine or more light sources. The light sources can include LEDs. The light sources can illuminate exterior and/or interior regions at or near the catheter housing 500. For example, the light sources can illuminate interior portions of the catheter housing 500 and/or the catheter insertion site to allow such regions to be inspected during the day and/or night. The light sources can also indicate whether cover 520 is secured to hub 560 and/or indicate whether the lock 526 and/or bridge 527 is secured to the catheter device 540 and/or whether the catheter device 540 is dislodged or moved. For example, the lights can change colors, flash at certain speeds, and/or change brightness to indicate whether cover 520 is secured to hub 560 and/or indicate whether the lock 526 is secured to the catheter device 540. The light source can include a UV light source to help with disinfecting the catheter and/or hub and/or insertion site. For example, the catheter housing 500 can include a UV Surface Mount LED (SMD LED). The UV SMD LED can provide active sterilization and disinfection to interior regions of the catheter housing 500 and/or the catheter insertion site when the catheter housing 500 is secured to a patient. This can in turn drastically reduce contamination, infections, and/or diseases that can occur with traditional catheter securement devices and methods. One or more UV SMD LEDs can be positioned on interior portions of the catheter housing 500. For example, one or more UV SMD LEDs can be positioned or located within the cover 520 or components of the cover 520. One or more UV SMD LEDs can be positioned on or located within the bridge 527 as discussed above, and can be configured to shine or point at the catheter insertion site. Alternatively or additionally, one or more UV SMD LEDs can be positioned on or located within hub 560. For example, one or more UV SMD LEDs can be positioned on or located within the membrane 562 and/or the wall 561. The one or more lights and/or one or more UV SMD LEDs can be electronically coupled to a sensor, wherein the sensor is configured to sense when the tongue 530 of the cover 520 is secured to the groove 568 of the wall 561 of hub 560 and transmit a signal to the one or more lights and/or one or more UV SMD LEDs when the tongue 530 of the cover 520 is secured to the groove 568 of the wall 561 of hub 560. The one or more lights and/or the one or more UV SMD LEDs can be configured to automatically activate when receiving the signal from the sensor.

The catheter housing 500 can include one or more sensors. Additionally, the one or more sensors can be located on various components of the catheter housing 500. For example, the one or more sensors can be located and/or mounted to the cover 520 or portions thereof, and/or hub 560 or portions thereof (for example, the membrane 562). Additionally, the number of sensors located on and/or mounted to the various components described above can be one, two, three, four, five, six, seven, eight, nine, ten, eleven, twelve, or thirteen or more. The one or more sensors can be used to measure various physiological parameters or condition of a patient. The one or more sensors can include a temperature sensor (for example, a topical temperature sensor), a blood pressure sensor, a blood oxygen saturation sensor, a sensor for liquid and blood leakage, and/or a skin humidity sensor. The sensors can be located in various locations on the membrane 562.

The one or more sensors can include one or more biosensors. The bio-sensors can include a micro-processor. For example, the bio-sensors can include an LCD monitor for detecting, measuring, storing and/or displaying patient vital functions, including venous and arterial blood pressure, heart beats, blood oxygen levels, general and topical temperature, and local tissue humidity, and/or venous blood current speed, among others. The measurements and/or calculations performed and/or taken by the one or more sensors, can be stored on a flash storage memory positioned on one or more of the cover 520 or portions thereof, and/or hub 560 or portions thereof (for example, the membrane 562). Any of the sensor measurements discussed herein, along with any data associated with the catheter insertion or IV therapy or treatment, can be wirelessly transmitted to a patient monitoring system for analysis, management, organization, and/or display to a care provider or user. Such information and/or data can also be transmitted to a database including patient medical records or electronic patient medical records. Alternatively and/or additionally, such information and/or data can be transmitted to a personal communications device, such as a tablet or smart device, or a software application or website. Transmitting such information and/or data can help a caregiver keep a log for an IV catheter insertion procedure and/or experience for a given patient which can help prevent any issues that might occur in a future IV therapy for the patient.

As discussed above, FIG. 13A illustrates a catheter device 540, catheter 542 coupled to the catheter device 540, and a tube 541 coupled to the catheter device 540. As also discussed above, catheter device 540 can include one or more cylindrical portions 540a, a male luer connector 540b, and/or a stem portion 540c which can be integral or non-integral with male luer connector 540b. Male luer connector 540b can be the same in some, many, or all respects as to male connector 43c described above. For example, male connector 540c can be identical to male connector 43c as described above except that it comprises a larger (for example, wider) outer ring and/or a longer stem portion 540c. The catheter 542 can be identical to the catheter 42 described above. The tube 541 can be a common tube that couples to the catheter device 540 that is configured to deliver fluid (such as fluids from an IV bag) to the catheter 542. The tube 541 can be the same in some, many or all respects as tubing 43b described above. The catheter device 540 can be the same in some, many, or all respects as the catheter device 40 described and shown above.

In contrast to the catheter housing 10, 400 and/or covers 20, 120, 420 which illustrate one or more ports 21, 421 that can be included in the same, as shown in FIGS. 11A-11D, the catheter housing 500 and/or cover 520 can have no ports. However, while catheter housing 500 and cover 520 are not illustrated in some of the figures as having ports, the catheter housing 500 and/or cover 520 can include one or more ports which can be the same in some, many, or all respects as the ports 21, 421 that are described with reference to catheter housing 10, 400 and/or covers 20, 120, 420.

Figure 14A:
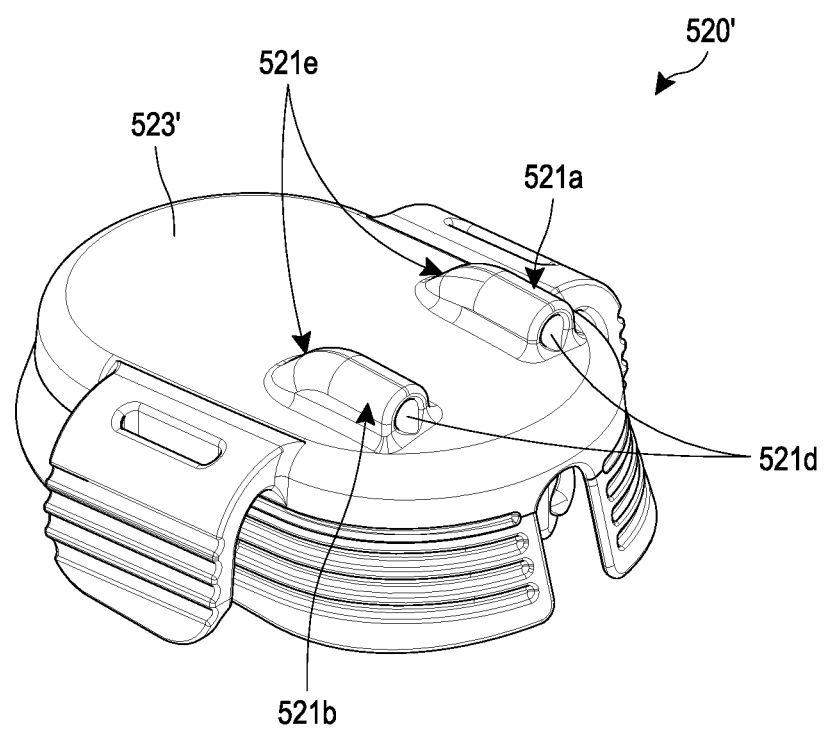
FIGS. 14A-14B illustrate various views of an alternative design for a cover for a catheter housing in accordance with aspects of this disclosure.
Figure 14B:
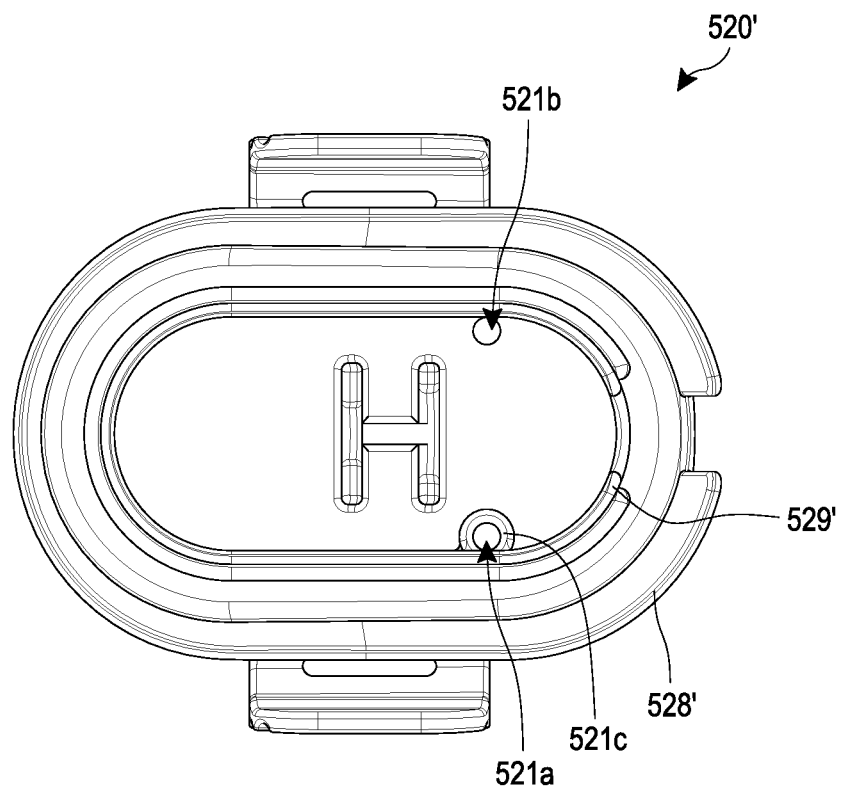

FIGS. 14A-14B illustrates a cover 520' that is identical in every respect to cover 520 as shown and described above, except that cover 520' includes gas ports 521a, 521b. Because cover 520' is identical in these respects to cover 520, cover 520' can be utilized alongside the other components of the catheter housing 500 described and shown above (for example, hub 560). Thus, it is understood that the catheter housing 500 can include cover 520 or cover 520'. Gas ports 521a, 521b can be used to allow gas to flow into and/or out of an interior of the cover 520'. Port 521a can be a gas inlet port configured to secure to a tube to allow gases from the tube to be inserted through a portion of the cover 520' and towards the catheter insertion site. For example, sterilizing and/or anesthetic gas can be inserted through port 521a. Port 521b can be a gas outlet port configured to allow gases to flow out from the catheter housing 500 and through a portion of the cover 520'. Port 521b can include a relief valve that allows gas to escape-from an interior of the cover 520' and/or catheter housing 500, for example, where a certain pressure is attained. The relief valve of can be configured to open when gas is inserted through gas inlet port 521a.

Ports 521a, 521b can extend through various portions of cover 520'. For example, one or both ports 521a, 521b can extend through a top surface of main body 523' of cover 520'. As shown in FIG. 14B, ports 521a, 521b can define an opening on the interior surface of cover 520'. Cover 520' can comprise a wall 521c that surrounds a perimeter of the opening defined by the port 521a. Wall 521c can be cylindrical, for example. One or both of ports 521a, 521b can be positioned proximate the inner wall 529' of cover 520'. Ports 521a, 521b can be positioned proximate opposite sides/surfaces of inner wall 529'. Port 521a and/or port 521b can be configured to secure a tube via a snap fit, friction fit, press fit, or another type of securement.

As shown in FIG. 14A, gas ports 521a, 521b can protrude outward and/or along top surface of main body 523' of cover 520'. Ports 521a, 521b can define a chamber along such length of extension, and the chamber can be sized and/or shaped to receive and/or secure to a tube. Ports 521a, 521b can comprise a rounded shape. Ports 521a, 521b can comprise cylindrical cross section or partially cylindrical cross section along their length. Ports 521a, 521b can have a first end 521d defining an opening and a second end 521e opposite the first end 521d. The second end 521e can slope or taper in cross section so as to transition the fluid passage defined by the ports 521a, 521b to the opening in the portion of the cover 520' (for example, the openings appearing in FIG. 14B). For example, a chamber defined by ports 521a, 521b can transition from a direction parallel to an axis running through openings at ends 521d (see FIG. 14A) to a direction perpendicular to such axis near the openings through the portion of the cover 520' (see FIG. 14B).

While cover 520' illustrations ports 521a, 521b, an alternative amount of ports can be included in cover 520', such as three, four, five, six, seven, eight, nine, ten, eleven or more ports. Additionally, cover 520' can include just one of either port 521a or port 521b. The ports can be used to provide sterilization and/or antiseptic gases (among others), such as ethylene oxide gas, nitrogen gas, or other sterilizing, antiseptic, and/or anesthetic gases. For example, the cover 520' can include a port for providing sterilizing gases, and a separate port for providing anesthetic gases. Additionally or alternatively, the port can be utilized by caregivers to spray gases and/or liquid into the port. One or both of ports 521a, 521b can include a filter configured to filter air and/or gas passing therethrough. Such filter can be positioned within one or both of ports 521a, 521b along a length thereof, and/or can be positioned near one or both openings of ports 521a, 521b.

Terminology

Certain terminology can be used in the following description for the purpose of reference only, and thus are not intended to be limiting. For example, terms such as "above" and "below" refer to directions in the drawings to which reference is made. Terms such as "proximal," "distal," "front," "back," "rear," and "side" describe the orientation and/or location of portions of the components or elements within a consistent but arbitrary frame of reference which is made clear by reference to the text and the associated drawings describing the components or elements under discussion. Such terminology can include the words specifically mentioned above, derivatives thereof, and words of similar import.

It should be emphasized that many variations and modifications can be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein can be combined in different ways to form additional embodiments, all of which fall within the scope of the present disclosure.

Conditional language used herein, such as, among others, "can," "might," "can," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a" and "an" are to be construed to mean "one or more" or "at least one" unless specified otherwise.

Conjunctive language such as the phrase "at least one of X, Y and Z," unless specifically stated otherwise, is otherwise understood with the context as used in general to convey that an item, term, etc. can be either X, Y or Z. Thus, such conjunctive language is not generally intended to imply that certain embodiments require at least one of X, at least one of Y and at least one of Z to each be present.

What is claimed is:

1. A catheter housing configured to surround a catheter insertion site on a patient, the catheter housing comprising:
   a hub configured to surround the catheter insertion site on the patient and secure to the patient; and
   a cover configured to enclose the catheter insertion site, the cover comprising an exterior surface, an interior surface opposite the exterior surface and configured to face toward the catheter insertion site when the catheter housing is in use, a wall defining an exterior perimeter of the cover, and a lock extending outward from the interior surface and configured to extend toward the patient when the catheter housing is in use, the lock comprising a first end connected to the interior surface, a second end opposite the first end, and a length extending between the first and second ends, wherein the second end of the lock comprises a recess configured to retain a first portion of a catheter device coupled to a catheter and position the catheter device away from the interior surface when the catheter housing is in use, wherein the lock is spaced inward from the wall of the cover, and wherein an entirety of the recess is spaced from the interior surface of the cover;

wherein the cover further comprises:
- a bridge extending outward from the interior surface and configured to extend toward the patient when the catheter housing is in use, the bridge spaced from the lock and the wall of the cover, and wherein the bridge is configured to retain a second portion of the catheter device when the catheter housing is in use; and
- a stem wall extending outward from the interior surface of the cover and extending between and connecting the bridge and the lock.

2. The catheter housing of claim 1, wherein:
the bridge comprises a first end connected to the interior surface of the cover, a second end opposite the first end of the bridge, and a length extending between the first and second ends of the bridge, the second end of the bridge comprising a recess sized and shaped to at least partially surround and retain the second portion of the catheter device when the catheter housing is in use.

3. The catheter housing of claim 1, wherein the hub comprises:
- a membrane configured to contact and secure to skin of the patient, the membrane having an opening configured to surround the catheter insertion site when the catheter housing is in use; and
- a hub wall inset from an exterior edge of the membrane and extending outward from the membrane, the hub wall configured to extend around the catheter insertion site when the catheter housing is in use;
wherein the cover is removably connectable to the hub wall.

4. The catheter housing of claim 3, wherein the hub wall comprises a groove along at least a portion of an interior facing side of the hub wall, and wherein the cover further comprises a tongue configured to secure to the groove of the hub wall.

5. A system comprising the catheter housing of claim 1 and the catheter device of claim 1, wherein said catheter device comprises a male luer connector and a catheter hub.

6. The catheter housing of claim 1, wherein said recess is rounded.

7. The catheter housing of claim 1, wherein the hub comprises a membrane configured to secure to skin of the patient around the catheter insertion site when the catheter housing is in use.

8. The catheter housing of claim 1, wherein the recess is configured to surround less than about ½ of a perimeter of the first portion of the catheter device when the first portion of the catheter device is retained by the recess.

9. A catheter housing configured to surround a catheter insertion site on a patient, the catheter housing comprising:
- a hub comprising a membrane configured to secure to skin of the patient around the catheter insertion site when the catheter housing is in use; and
- a cover configured to enclose the catheter insertion site when the catheter housing is in use, the cover comprising a top portion and sides extending outwardly from the top portion and oriented transverse with respect to the top portion, the sides defining an exterior perimeter of the cover, the top portion comprising an exterior surface and an interior surface opposite the exterior surface, the cover further comprising a lock having a first end connected to the interior surface, a second end opposite the first end, and a length extending between the first and second ends, wherein the second end of the lock comprises a recess configured to retain a first portion of a catheter device coupled to a catheter when the catheter housing is in use wherein the cover further comprises:
- a bridge extending outward from the interior surface and configured to extend toward the patient when the catheter housing is in use, the bridge spaced from the lock, wherein the bridge is configured to retain a second portion of the catheter device when the catheter housing is in use;
- a stem wall extending outward from the interior surface of the cover and extending between and connecting the bridge and the lock.

10. The catheter housing of claim 9, wherein said recess is rounded.

11. The catheter housing of claim 9, wherein the second end of the lock comprises tapered portions adjacent the recess, the tapered portions configured to aid positioning of the first portion of the catheter device at least partially within the recess when the catheter housing is in use.

12. The catheter housing of claim 9, wherein the bridge comprises a first end connected to the interior surface, a second end opposite the first end of the bridge, and a length extending between the first and second ends of the bridge, wherein the second end of the bridge comprises a recess configured to retain the second portion of the catheter device when the catheter housing is in use, wherein the bridge is spaced inward from the sides of the cover.

13. The catheter housing of claim 12, wherein the length of the bridge is greater than the length of the lock.

14. The catheter housing of claim 9, wherein the recess is configured to surround less than about ½ of a perimeter of the first portion of the catheter device when the first portion of the catheter device is retained by the recess.

15. The catheter housing of claim 9, wherein the hub further comprises a hub wall connected to the membrane and inset from an exterior edge of the membrane, the hub wall configured to extend around the catheter insertion site when the catheter housing is in use, and wherein the cover is removably connectable to the hub wall.

16. A catheter housing configured to surround a catheter insertion site on a patient, the catheter housing comprising:
- a cover comprising a top portion, a wall extending outwardly from the top portion and defining an exterior perimeter of the cover, and an opening in a portion of the wall that is configured to receive a first portion of a catheter device coupled to a catheter or a tube coupled to the catheter device; and
- a lock extending outward from an interior surface of the top portion of the cover and towards the patient when the catheter housing is in use, the lock comprising a first end connected to the interior surface, a second end opposite the first end, and a length extending between the first and second ends, wherein the second end of the lock comprises a recess configured to retain a second portion of the catheter device when the catheter housing is in use;

wherein the cover further comprises:
- a bridge extending outward from the interior surface and configured to extend toward the patient when the catheter housing is in use, the bridge spaced from the lock and the wall of the cover, and wherein the bridge is configured to retain a third portion of the catheter device when the catheter housing is in use;

a stem wall extending outward from the interior surface of the cover and extending between and connecting the bridge and the lock;

wherein the opening in said portion of the wall of the cover and the recess of the second end of the lock are configured to retain the catheter device in an inclined position relative to skin of the patient when the catheter housing is in use.

17. The catheter housing of claim 16, wherein said recess is rounded.

18. The catheter housing of claim 17, wherein the second end of the lock comprises tapered portions adjacent the recess, the tapered portions configured to aid positioning of the second portion of the catheter device at least partially within the recess when the catheter housing is in use.

* * * * *